United States Patent
Hills et al.

(10) Patent No.: US 7,648,945 B2
(45) Date of Patent: *Jan. 19, 2010

(54) HERBICIDE COMBINATION

(75) Inventors: Martin Hills, Idstein (DE); Erwin Hacker, Hochheim (DE); Hansjörg Krähmer, Hofheim (DE); Christian Waldraff, Bad Vilbel (DE); Hansjörg Dietrich, Hofheim (DE); Klaus Trabold, Heidelberg (DE); Dieter Feucht, Kelkheim (DE); Klaus-Helmut Müller, Düsseldorf (DE); Ulrich Philipp, Lees Summit, MO (US)

(73) Assignee: Bayer CropScience AG (DE)

( * ) Notice: Subject to any disclaimer, the term of this patent is extended or adjusted under 35 U.S.C. 154(b) by 371 days.

This patent is subject to a terminal disclaimer.

(21) Appl. No.: 11/090,374

(22) Filed: Mar. 25, 2005

(65) Prior Publication Data

US 2005/0250647 A1  Nov. 10, 2005

(30) Foreign Application Priority Data

Mar. 27, 2004 (DE) ............. 10 2004 015 140
Jun. 30, 2004 (DE) ............. 10 2004 031 347

(51) Int. Cl.
 C07D 413/10  (2006.01)
 C07D 413/14  (2006.01)
 A01N 43/54  (2006.01)
 A01N 43/88  (2006.01)
 C07D 413/02  (2006.01)
 C07D 413/06  (2006.01)
 A01N 43/72  (2006.01)

(52) U.S. Cl. ..................... 504/223; 544/65
(58) Field of Classification Search ........... 504/239, 504/223; 544/65
 See application file for complete search history.

(56) References Cited

U.S. PATENT DOCUMENTS

| 5,013,659 | A | | 5/1991 | Bedbrook et al. |
| 5,463,081 | A | | 10/1995 | Ort et al. |
| 5,476,936 | A | * | 12/1995 | Philipp et al. ......... 504/223 |
| 5,580,986 | A | | 12/1996 | Dorfmeister et al. |
| 5,990,047 | A | | 11/1999 | Hacker et al. |

FOREIGN PATENT DOCUMENTS

| EP | 0 131 624 | 1/1985 |
| EP | 0 142 924 | 5/1985 |
| EP | 0 193 259 | 9/1986 |
| EP | 0 221 044 | 5/1987 |
| EP | 0 257 993 | 3/1988 |
| EP | 0 663 913 | 7/1995 |
| WO | WO-91/13972 | 9/1991 |
| WO | WO-91/19806 | 12/1991 |
| WO | WO-92/11376 | 7/1992 |
| WO | WO-92/13845 | 8/1992 |
| WO | WO-92/14827 | 9/1992 |
| WO | WO-96/41537 | 12/1996 |

OTHER PUBLICATIONS

U.S. Appl. No. 11/090,985, filed Mar. 25, 2005.
U.S. Appl. No. 11/090,424, filed Mar. 25, 2005.
Worthing, et al.; "The Pesticide Manual;" 10th ed.; World Compendium; Farnham, BCPC, GB; pp. 1335-1341; XP002099499 (1995).

* cited by examiner

*Primary Examiner*—Sreeni Padmanabhan
*Assistant Examiner*—Courtney Brown
(74) *Attorney, Agent, or Firm*—Connolly Bove Lodge & Hutz LLP

(57) ABSTRACT

The present invention relates to a herbicide combination comprising components (A) and (B), where
 (A) is one or more herbicides from the group of the compounds of the formula (I) or salts thereof

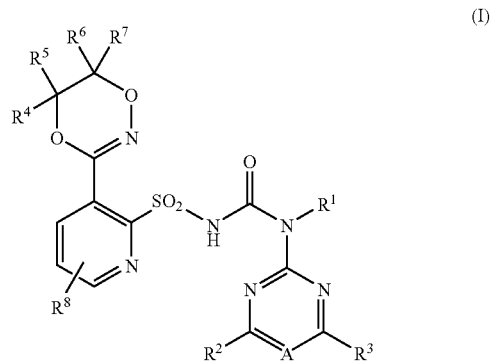

(I)

in which $R^1$, $R^2$, $R^3$, $R^4$, $R^5$, $R^6$, $R^7$, $R^8$ and A are as defined in claim 1; and
 (B) is one or more herbicides different from herbicide (A), preferably from the group of compounds consisting of
  (B1) herbicides which can be employed selectively and which are effective mainly against monocotyledonous and dicotyledonous harmful plants,
  (B2) herbicides which can be employed selectively and which are effective mainly against dicotyledonous harmful plants and
  (B3) herbicides which can be employed selectively and which are effective mainly against monocotyledonous harmful plants,
  (B4) herbicides which can be employed non-selectively and which are effective against monocotyledonous and dicotyledonous harmful plants, for example for use in the non-selective field or in crops which are specifically tolerant.

8 Claims, No Drawings

HERBICIDE COMBINATION

The present invention relates to the technical field of the crop protection compositions which can be used against unwanted vegetation, for example in crop plants. The invention relates in particular to a herbicide combination comprising at least two herbicides and their use for controlling unwanted vegetation.

The publication U.S. Pat. No. 5,476,936 discloses certain herbicidally effective sulfonylureas. The effectiveness of these herbicides against harmful plants is at a high level; however, it depends in general on the application rate, the formulation in question, the harmful plants or the spectrum of harmful plants to be controlled in each case, the climatic and soil conditions, etc. A further criterion is the duration of action, or the rate of degradation of the herbicide. Also to be taken into account are, if appropriate, changes in the susceptibility of harmful plants which may occur on prolonged use of the herbicides or geographically restricted. Activity losses in individual plants can only be compensated to a certain extent by higher application rates of the herbicides, for example because this reduces the selectivity of the herbicides, or an improvement in activity is not observed, not even at a higher application rate.

It was an object of the present invention to provide an improved crop protection composition.

Surprisingly, it has now been found that herbicides from the group of the compounds of the formula (I) or salts thereof interact in a particularly favorable manner in combination with structurally different herbicides, for example when they are used for controlling unwanted vegetation.

Accordingly, the present invention provides a herbicide combination comprising herbicides (A) and (B), where (A) is one or more herbicides from the group of the compounds of the formula (I) or salts thereof

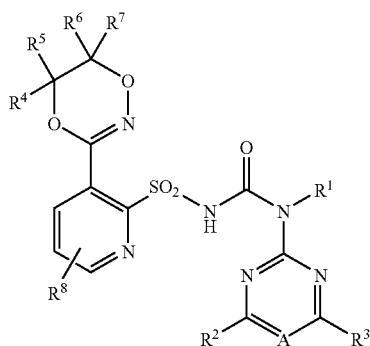

in which

A is nitrogen or a $CR^{11}$ grouping,
   where
   $R^{11}$ is hydrogen, alkyl, halogen and haloalkyl,
$R^1$ is hydrogen or an optionally substituted radical from the group consisting of alkyl, alkoxy, alkoxyalkyl, alkenyl, alkynyl, cycloalkyl, cycloalkylalkyl, aralkyl and aryl,
$R^2$ is hydrogen, halogen or is in each case optionally halogen-substituted alkyl, alkoxy, alkylthio, alkylamino or dialkylamino having in each case 1 to 6 carbon atoms,
$R^3$ is hydrogen, halogen or is in each case optionally halogen-substituted alkyl, alkoxy, alkylthio, alkylamino or dialkylamino having in each case 1 to 6 carbon atoms,
$R^4$-$R^7$ independently of one another are hydrogen, halogen, cyano, thiocyanato or are in each case optionally halogen-substituted alkyl, alkoxy, alkylthio, alkylsulfinyl, alkylsulfonyl, alkylamino, alkylcarbonyl, alkoxycarbonyl, alkylaminocarbonyl having in each case 1 to 3 carbon atoms,
$R^8$ is hydrogen, halogen, cyano, thiocyanato or is in each case optionally halogen-substituted alkyl, alkoxy, alkylthio, alkylsulfinyl, alkylsulfonyl, alkylamino, alkylcarbonyl, alkoxycarbonyl, alkylaminocarbonyl having in each case 1 to 3 carbon atoms, where in the radicals mentioned above the alkyl and alkylene groups may in each case contain 1 to 6 carbon atoms, the alkenyl and alkynyl groups may in each case contain 2 to 6 carbon atoms, the cycloalkyl groups may in each case contain 3 to 6 carbon atoms and the aryl groups may in each case contain 6 or 10 carbon atoms; and (B) is one or more herbicides different from herbicide (A), preferably from the group of compounds consisting of
   (B1) herbicides which can be employed selectively and which are effective mainly against monocotyledonous and dicotyledonous harmful plants,
   (B2) herbicides which can be employed selectively and which are effective mainly against dicotyledonous harmful plants and
   (B3) herbicides which can be employed selectively and which are effective mainly against monocotyledonous harmful plants,
   (B4) herbicides which can be employed non-selectively and which are effective against monocotyledonous and dicotyledonous harmful plants, for example for use in the non-selective field or in crops which are specifically tolerant.

The herbicide combinations according to the invention additionally comprise further components, or example agrochemically active compounds of a different type and/or formulation auxiliaries and/or additives customary in crop protection, or they can be employed together with these.

In a preferred embodiment, the herbicide combinations according to the invention comprise an effective amount of herbicides (A) and (B) and/or have synergistic actions. The synergistic actions can be observed, for example, when the herbicides (A) and (B) are applied together, for example as a coformulation or or as a tank mix; however, they can also be observed when the herbicides are applied at different times (splitting). It is also possible to apply the herbicides or the herbicide combinations in a plurality of portions (sequential application), for example as pre-emergence applications followed by post-emergence applications or as early post-emergence applications followed by medium or late post-emergence applications. Preference is given here to the joint or almost simultaneous application of the active compounds of the combination in question.

The synergistic effects permit a reduction of the application rates of the individual herbicides, a higher efficacy at the same application rate, the control of species which were as yet uncontrolled (gaps), an extension of the period of application and/or a reduction in the number of individual applications required and—as a result for the user—weed control systems which are more advantageous economically and ecologically.

The combination according to the invention of herbicides (A)+(B) permits, for example, synergistic activity increases which exceed the activities achieved with the individual herbicides (A) and (B) by far and in an unexpected manner.

The above formula (I) encompasses all stereoisomers and mixtures thereof, including, in particular, also racemic mixtures and—if enantiomers are possible—the respective biologically active enantiomer.

The compounds of the formula (I) and their salts are known, as is their preparation, for example from U.S. Pat. No. 5,476,936, which is incorporated into the present description by way of reference.

Preferred herbicides (A) are compounds of the formula (I) and salts thereof in which
A is nitrogen or a CH grouping,
$R^1$ is hydrogen or an optionally halogen-substituted radical from the group consisting of alkyl, alkoxy, alkoxyalkyl, alkenyl and alkynyl having in each case up to 3 carbon atoms,
$R^2$ is hydrogen, halogen or is in each case optionally halogen-substituted alkyl, alkoxy, alkylthio, alkylamino or dialkylamino having in each case 1 to 3 carbon atoms in the alkyl radicals,
$R^3$ is hydrogen, halogen or is in each case optionally halogen-substituted alkyl, alkoxy, alkylthio, alkylamino or dialkylamino having in each case 1 to 3 carbon atoms in the alkyl radicals,
$R^4$-$R^7$ independently of one another are hydrogen, halogen, cyano, thiocyanato or are in each case optionally halogen-substituted alkyl, alkoxy, alkylthio, alkylsulfinyl, alkylsulfonyl, alkylamino, alkylcarbonyl, alkoxycarbonyl, or alkylaminocarbonyl having in each case 1 to 3 carbon atoms in the alkyl radicals,
$R^8$ is hydrogen, halogen, cyano, thiocyanato or is in each case optionally halogen-substituted alkyl, alkoxy, alkylthio, alkylsulfinyl, alkylsulfonyl, alkylamino, alkylcarbonyl, alkoxycarbonyl or alkylaminocarbonyl having in each case 1 to 3 carbon atoms in the alkyl radicals.

Preferred herbicides (A) are also salts which are obtained by customary processes from compounds of the formula (I) and bases, such as, for example, sodium hydroxide, sodium hydride, sodium amide and sodium carbonate, potassium hydroxide, potassium hydride, potassium amide and potassium carbonate or calcium hydroxide, calcium hydride, calcium amide and calcium carbonate, sodium $C_1$-$C_4$-alkoxides or potassium $C_1$-$C_4$-alkoxides, ammonia, $C_1$-$C_4$-alkylamines, di-($C_1$-$C_4$-alkyl)amines or tri-($C_1$-$C_4$)amines.

Particularly preferred herbicides (A) are compounds of the formula (I) and salts thereof in which
A is nitrogen or a CH group,
$R^1$ is hydrogen, methyl, ethyl, methoxy, methoxymethyl or ethoxy,
$R^2$ is hydrogen, chlorine, methyl, ethyl, trifluoromethyl, methoxy, ethoxy, difluoromethoxy, methylthio, methylamino or dimethylamino,
$R^3$ is hydrogen, chlorine, methyl, ethyl, trifluoromethyl, methoxy, ethoxy, difluoromethoxy, methylthio, methylamino or dimethylamino,
$R^4$-$R^7$ independently of one another are hydrogen, fluorine, chlorine, cyano, or are in each case optionally fluorine- or chlorine-substituted methyl, methylthio, methylsulfinyl, methylsulfonyl, methoxycarbonyl and ethoxycarbonyl, preferably hydrogen,
$R^8$ is hydrogen, fluorine, chlorine, bromine, cyano, or is in each case optionally chlorine- or fluorine-substituted methyl, methoxy, ethoxy, methylthio, ethylthio, methylsulfinyl, ethylsulfinyl, methylsulfonyl, ethylsulfonyl, methylamino or dimethylamino, preferably hydrogen.

Particularly preferred herbicides (A) are compounds of the formula (I) and salts thereof, in particular their alkali metal salts, in which
A is nitrogen,
$R^1$ is hydrogen or methyl,
$R^2$ is hydrogen, chlorine, methyl, ethyl, trifluoromethyl, methoxy, ethoxy, difluoromethoxy, methylthio, methylamino or dimethylamino,
$R^3$ is hydrogen, chlorine, methyl, ethyl, trifluoromethyl, methoxy, ethoxy, difluoromethoxy, methylthio, methylamino or dimethylamino,
$R^4$-$R^7$ are hydrogen
$R^8$ is hydrogen.

Other particularly preferred herbicides (A) are compounds of the formula (I) and salts thereof, in particular their alkali metal salts, in which
A is a CH grouping,
$R^1$ is hydrogen or methyl,
$R^2$ is hydrogen, chlorine, methyl, ethyl, trifluoromethyl, methoxy, ethoxy, difluoromethoxy, methylthio, methylamino or dimethylamino,
$R^3$ is hydrogen, chlorine, methyl, ethyl, trifluoromethyl, methoxy, ethoxy, difluoromethoxy, methylthio, methylamino or dimethylamino,
$R^4$-$R^7$ are hydrogen,
$R^8$ is hydrogen.

The general or preferred radical definitions given above can be combined with one another as desired, i.e. including combinations between the given preferred ranges.

The hydrocarbon radicals mentioned in the radical definitions, such as alkyl, alkenyl or alkynyl, can be straight-chain or branched even if this is not explicitly stated, including in combinations with heteroatoms, such as in alkoxy, alkylthio, haloalkyl or alkylamino.

If desired salts may be prepared from the compounds of the formula (I), for example metal salts, such as alkali metal (for example Na, K) salts or alkaline earth metal (for example Ca, Mg) salts or ammonium or amine salts. Such salts are obtained in a simple manner by customary methods for forming salts, for example by dissolving or dispersing a compound of the formula (I) in a suitable diluent, such as, for example, methylene chloride, acetone, tert-butyl methyl ether or toluene, and adding a suitable base. The salts can then—if appropriate after prolonged stirring—be isolated by concentration or filtration with suction.

Examples of compounds used as herbicide (A) are mentioned in table 1 below, where the following abbreviations are used:

m.p.=melting point decomp. or d.=with decomposition
(+)=the indicated melting point (m.p.) refers to the respective sodium salt, i.e. the corresponding compound in which the hydrogen of the —$SO_2$—NH— group is replaced by sodium.

TABLE 1

Examples of compounds of the formula (I) where $R^4 = R^5 = R^6 = R^7 = R^8 =$ H:

| Ex. No. | $R^1$ | A | $R^2$ | $R^3$ | m.p. (° C.) |
|---|---|---|---|---|---|
| I-1 | H | CH | $OCH_3$ | $OC_2H_5$ | 154 |
| I-2 | H | CH | $OCH_3$ | $CH_3$ | |
| I-3 | H | CH | $OCH_3$ | $CH_3$ | 180-181$^{(+)}$ |
| I-4 | H | CH | $OCH_3$ | $C_2H_5$ | |
| I-5 | H | CH | $OCH_3$ | $CF_3$ | |

TABLE 1-continued

Examples of compounds of the formula (I) where $R^4 = R^5 = R^6 = R^7 = R^8 = H$:

| Ex. No. | $R^1$ | A | $R^2$ | $R^3$ | m.p. (° C.) |
|---|---|---|---|---|---|
| I-6 | H | CH | OCH$_3$ | OCF$_2$H | |
| I-7 | H | CH | OCH$_3$ | NHCH$_3$ | 199.5 |
| I-8 | H | CH | OCH$_3$ | N(CH$_3$)$_2$ | |
| I-9 | H | CH | OCH$_3$ | Cl | 110-111 |
| I-10 | H | CH | OCH$_3$ | Cl | 175-178$^{(+)}$ |
| I-11 | H | CH | OCH$_3$ | OCH$_3$ | 167-168 |
| I-12 | H | CH | OCH$_3$ | OCH$_3$ | 171-172$^{(+)}$ |
| I-13 | H | CH | OC$_2$H$_5$ | OC$_2$H$_5$ | |
| I-14 | H | CH | OC$_2$H$_5$ | OC$_2$H$_5$ | 152-154$^{(+)}$ |
| I-15 | H | CH | OC$_2$H$_5$ | CH$_3$ | |
| I-16 | H | CH | OC$_2$H$_5$ | C$_2$H$_5$ | |
| I-17 | H | CH | OC$_2$H$_5$ | CF$_3$ | |
| I-18 | H | CH | OC$_2$H$_5$ | OCF$_2$H | |
| I-19 | H | CH | OC$_2$H$_5$ | NHCH$_3$ | |
| I-20 | H | CH | OC$_2$H$_5$ | N(CH$_3$)$_2$ | |
| I-21 | H | CH | OC$_2$H$_5$ | Cl | 158-159 |
| I-22 | H | CH | OC$_2$H$_5$ | Cl | 213$^{(+)}$ |
| I-23 | H | CH | CH$_3$ | CH$_3$ | 153 |
| I-24 | H | CH | CH$_3$ | C$_2$H$_5$ | |
| I-25 | H | CH | CH$_3$ | CF$_3$ | |
| I-26 | H | CH | CH$_3$ | OCF$_2$H | |
| I-27 | H | CH | CH$_3$ | NHCH$_3$ | |
| I-28 | H | CH | CH$_3$ | N(CH$_3$)$_2$ | |
| I-29 | H | CH | CH$_3$ | Cl | 108-109 |
| I-30 | H | CH | CH$_3$ | Cl | >300$^{(+)}$ |
| I-31 | H | CH | C$_2$H$_5$ | C$_2$H$_5$ | |
| I-32 | H | CH | C$_2$H$_5$ | CF$_3$ | |
| I-33 | H | CH | C$_2$H$_5$ | OCF$_2$H | |
| I-34 | H | CH | C$_2$H$_5$ | NHCH$_3$ | |
| I-35 | H | CH | C$_2$H$_5$ | Cl | |
| I-36 | H | CH | CF$_3$ | CF$_3$ | |
| I-37 | H | CH | CF$_3$ | OCF$_2$H | |
| I-38 | H | CH | CF$_3$ | NHCH$_3$ | |
| I-39 | H | CH | CF$_3$ | N(CH$_3$)$_2$ | |
| I-40 | H | CH | CF$_3$ | Cl | |
| I-41 | H | CH | OCF$_2$H | OCF$_2$H | |
| I-42 | H | CH | OCF$_2$H | NHCH$_3$ | |
| I-43 | H | CH | OCF$_2$H | N(CH$_3$)$_2$ | |
| I-44 | H | CH | OCF$_2$H | Cl | |
| I-45 | H | CH | NHCH$_3$ | NHCH$_3$ | |
| I-46 | H | CH | NHCH$_3$ | N(CH$_3$)$_2$ | |
| I-47 | H | CH | NHCH$_3$ | Cl | |
| I-48 | H | CH | N(CH$_3$)$_2$ | N(CH$_3$)$_2$ | |
| I-49 | H | CH | N(CH$_3$)$_2$ | Cl | |
| I-50 | H | CH | Cl | Cl | |
| I-51 | H | N | OCH$_3$ | OCH$_3$ | 255 |
| I-52 | H | N | OCH$_3$ | OCH$_3$ | 159-162$^{(+)}$ |
| I-53 | H | N | OCH$_3$ | OC$_2$H$_5$ | |
| I-54 | H | N | OCH$_3$ | CH$_3$ | |
| I-55 | H | N | OCH$_3$ | C$_2$H$_5$ | |
| I-56 | H | N | OCH$_3$ | CF$_3$ | |
| I-57 | H | N | OCH$_3$ | OCF$_2$H | |
| I-58 | H | N | OCH$_3$ | NHCH$_3$ | |
| I-59 | H | N | OCH$_3$ | N(CH$_3$)$_2$ | |
| I-60 | H | N | OCH$_3$ | N(CH$_3$)$_2$ | 156$^{(+)}$ |
| I-61 | H | N | OCH$_3$ | Cl | |
| I-62 | H | N | OC$_2$H$_5$ | OC$_2$H$_5$ | |
| I-63 | H | N | OC$_2$H$_5$ | CH$_3$ | |
| I-64 | H | N | OC$_2$H$_5$ | C$_2$H$_5$ | |
| I-65 | H | N | OC$_2$H$_5$ | CF$_3$ | |
| I-66 | H | N | OC$_2$H$_5$ | OCF$_2$H | |
| I-67 | H | N | OC$_2$H$_5$ | NHCH$_3$ | |
| I-68 | H | N | OC$_2$H$_5$ | N(CH$_3$)$_2$ | |
| I-69 | H | N | OC$_2$H$_5$ | Cl | |
| I-70 | H | N | OC$_2$H$_5$ | Cl | 213$^{(+)}$ |
| I-71 | H | N | CH$_3$ | CH$_3$ | |
| I-72 | H | N | CH$_3$ | C$_2$H$_5$ | |
| I-73 | H | N | CH$_3$ | CF$_3$ | |
| I-74 | H | N | CH$_3$ | OCF$_2$H | |
| I-75 | H | N | CH$_3$ | NHCH$_3$ | |
| I-76 | H | N | CH$_3$ | N(CH$_3$)$_2$ | |
| I-77 | H | N | CH$_3$ | Cl | |
| I-78 | H | N | C$_2$H$_5$ | C$_2$H$_5$ | |
| I-79 | H | N | C$_2$H$_5$ | CF$_3$ | |
| I-80 | H | N | C$_2$H$_5$ | OCF$_2$H | |
| I-81 | H | N | C$_2$H$_5$ | NHCH$_3$ | |
| I-82 | H | N | C$_2$H$_5$ | Cl | |
| I-83 | H | N | CF$_3$ | CF$_3$ | |
| I-84 | H | N | CF$_3$ | OCF$_2$H | |
| I-85 | H | N | CF$_3$ | NHCH$_3$ | |
| I-86 | H | N | CF$_3$ | N(CH$_3$)$_2$ | |
| I-87 | H | N | CF$_3$ | Cl | |
| I-88 | H | N | OCF$_2$H | OCF$_2$H | |
| I-89 | H | N | OCF$_2$H | NHCH$_3$ | |
| I-90 | H | N | OCF$_2$H | N(CH$_3$)$_2$ | |
| I-91 | H | N | OCF$_2$H | Cl | |
| I-92 | H | N | NHCH$_3$ | NHCH$_3$ | |
| I-93 | H | N | NHCH$_3$ | N(CH$_3$)$_2$ | |
| I-94 | H | N | NHCH$_3$ | Cl | |
| I-95 | H | N | N(CH$_3$)$_2$ | N(CH$_3$)$_2$ | |
| I-96 | H | N | N(CH$_3$)$_2$ | Cl | |
| I-97 | H | N | Cl | Cl | |
| I-98 | CH$_3$ | N | OCH$_3$ | OCH$_3$ | |
| I-99 | CH$_3$ | N | OCH$_3$ | OC$_2$H$_5$ | |
| I-100 | CH$_3$ | N | OCH$_3$ | CH$_3$ | |
| I-101 | CH$_3$ | N | OCH$_3$ | C$_2$H$_5$ | |
| I-102 | CH$_3$ | N | OCH$_3$ | CF$_3$ | |
| I-103 | CH$_3$ | N | OCH$_3$ | OCF$_2$H | |
| I-104 | CH$_3$ | N | OCH$_3$ | NHCH$_3$ | |
| I-105 | CH$_3$ | N | OCH$_3$ | N(CH$_3$)$_2$ | |
| I-106 | CH$_3$ | N | OCH$_3$ | Cl | |
| I-107 | CH$_3$ | N | OC$_2$H$_5$ | C$_2$H$_5$ | |
| I-108 | CH$_3$ | N | OC$_2$H$_5$ | CH$_3$ | |
| I-109 | CH$_3$ | N | OC$_2$H$_5$ | C$_2$H$_5$ | |
| I-110 | CH$_3$ | N | OC$_2$H$_5$ | CF$_3$ | |
| I-111 | CH$_3$ | N | OC$_2$H$_5$ | OCF$_2$H | |
| I-112 | CH$_3$ | N | OC$_2$H$_5$ | NHCH$_3$ | |
| I-113 | CH$_3$ | N | OC$_2$H$_5$ | N(CH$_3$)$_2$ | |
| I-114 | CH$_3$ | N | OC$_2$H$_5$ | Cl | |
| I-115 | CH$_3$ | N | CH$_3$ | CH$_3$ | |
| I-116 | CH$_3$ | N | CH$_3$ | C$_2$H$_5$ | |
| I-117 | CH$_3$ | N | CH$_3$ | CF$_3$ | |
| I-118 | CH$_3$ | N | CH$_3$ | OCF$_2$H | |
| I-119 | CH$_3$ | N | CH$_3$ | NHCH$_3$ | |
| I-120 | CH$_3$ | N | CH$_3$ | N(CH$_3$)$_2$ | |
| I-121 | CH$_3$ | N | CH$_3$ | Cl | |
| I-122 | CH$_3$ | N | C$_2$H$_5$ | C$_2$H$_5$ | |
| I-123 | CH$_3$ | N | C$_2$H$_5$ | CF$_3$ | |
| I-124 | CH$_3$ | N | C$_2$H$_5$ | OCF$_2$H | |
| I-125 | CH$_3$ | N | C$_2$H$_5$ | NHCH$_3$ | |
| I-126 | CH$_3$ | N | C$_2$H$_5$ | Cl | |
| I-127 | CH$_3$ | N | CF$_3$ | CF$_3$ | |
| I-128 | CH$_3$ | N | CF$_3$ | OCF$_2$H | |
| I-129 | CH$_3$ | N | CF$_3$ | NHCH$_3$ | |
| I-130 | CH$_3$ | N | CF$_3$ | N(CH$_3$)$_2$ | |
| I-131 | CH$_3$ | N | CF$_3$ | Cl | |
| I-132 | CH$_3$ | N | OCF$_2$H | OCF$_2$H | |
| I-133 | CH$_3$ | N | OCF$_2$H | NHCH$_3$ | |
| I-134 | CH$_3$ | N | OCF$_2$H | N(CH$_3$)$_2$ | |
| I-135 | CH$_3$ | N | OCF$_2$H | Cl | |
| I-136 | CH$_3$ | N | NHCH$_3$ | NHCH$_3$ | |
| I-137 | CH$_3$ | N | NHCH$_3$ | N(CH$_3$)$_2$ | |
| I-138 | CH$_3$ | N | NHCH$_3$ | Cl | |
| I-139 | CH$_3$ | N | N(CH$_3$)$_2$ | N(CH$_3$)$_2$ | |
| I-140 | CH$_3$ | N | N(CH$_3$)$_2$ | Cl | |
| I-141 | CH$_3$ | N | Cl | Cl | |
| I-142 | H | N | N(CH$_3$)$_2$ | OCH$_2$CF$_3$ | 158 |
| I-143 | H | CH | Cl | OCH$_2$CF$_3$ | 204-205 |
| I-144 | H | CH | Cl | OCH$_2$CF$_3$ | |
| I-145 | H | CH | Cl | OCH$_2$CF$_3$ | 207$^{(+)}$ |

The herbicides (A) inhibit the enzyme acetolactate synthase (ALS) and thus the protein synthesis in plants. The application rate of the herbicides (A) may vary within a wide range, for example between 0.001 g and 500 g of AS/ha (hereinbelow, AS/ha means "active substance per hectare"=based on 100% pure active compound). On applications using application rates of from 0.01 g to 200 g AS/ha of the herbicides (A), preferably of the compounds I-1 to I-145, a relatively broad spectrum of harmful plants, for example annual and perennial monocotyledonous or dicotyledonous weeds and also unwanted crop plants is controlled by the pre-emergence and the post-emergence method. In the combinations according to the invention, the application rates are generally lower, for example in the range from 0.001 g to 100 g of AS/ha, preferably from 0.005 g to 50 g of AS/ha, particularly preferably from 0.01 g to 9 g of AS/ha.

The herbicides (A) are suitable, for example, for controlling harmful plants in crop plants, for example in economically important farm crops, for example monocotyledonous farm crops, such as cereals (for example wheat, barley, rye, oats), rice, corn, millet, or dicotyledonous farm crops, such as sugar beet, oil seed rape, cotton, sunflower and leguminous plants, for example of the genus *Glycine* (for example *Glycine max.* (soybean), such as non-transgenic *Glycine max.* (for example conventional cultivars, such as STS cultivars) or transgenic *Glycine max.* (for example RR soybean or LL soybean) and crossbreeds thereof, *Phaseolus, Pisum, Vicia* and *Arachis*, or vegetable crops from various botanical groups, such as potato, leek, cabbage, carrot, tomato, onion, and also permanent crops and plantation crops, such as pome fruit and stone fruit, berry fruit, grapevines, Hevea, bananas, sugar cane, coffee, tea, citrus fruit, nut plantations, lawn, palm plantations and forest plantations. These crops are also preferred for the application of the herbicide combinations (A)+(B) according to the invention. For the herbicide combinations (A)+(B4), above all mutant crops which are tolerant to the herbicides (B4) and tolerant transgenic crops are of particular interest, preferably corn, rice, cereals, oilseed rape and soybean, in particular soybean, which are resistant to imidazolinone herbicides, glufosinate or glyphosate.

The herbicides (A) can also be employed non-selectively for controlling unwanted vegetation, for example in permanent crops and plantation crops, on roadsides, squares, industrial plants, airports or railway tracks, or for the burn-down application, for example in farm crops, for example monocotyledonous farm crops, such as cereals (for example wheat, barley, rye, oats), rice, corn, millet, or dicotyledonous farm crops, such as sugar beet, oilseed rape, cotton, sunflowers and leguminous plants, for example of the genera *Glycine* (for example *Glycine max.* (soybean), such as non-transgenic *Glycine max* (for example conventional cultivars, such as STS cultivars) or transgenic *Glycine max.* (for example RR soybeans or LL soybeans) and crossbreeds thereof, *Phaseolus, Pisum, Vicia* and *Arachis*, or vegetable crops from various botanical groups, such as potato, leek, cabbage, carrot, tomato, onion.

Suitable herbicides (B) are, for example, the following herbicides different from the herbicides (A), as described, for example, in Weed Research 26, 441-445 (1986), or "The Pesticide Manual", 13th edition, The British Crop Protection Council, 2003, and literature cited therein. The herbicides are referred to either by the "common name" according to the International Organization for Standardization (ISO) or by the chemical name, if appropriate together with a customary code number and in each case include all application forms, such as acids, salts, esters and isomers, such as stereoisomers and optical isomers. One and in some cases a plurality of application forms are mentioned: 2,4-D, acetochlor, acifluorfen, acifluorfen-sodium, aclonifen, alachlor, alloxydim, alloxydim-sodium, ametryn, amicarbazone, amidosulfuron, aminopyralid, amitrole, anilofos, asulam, atrazine, azafenidin, azimsulfuron, beflubutamid, benazolin, benazolin-ethyl, benfuresate, bensulfuron-methyl, bentazone, benzfendizone, benzobicyclon, benzofenap, bifenox, bilanafos, bispyribac-sodium, bromacil, bromobutide, bromofenoxim, bromoxynil, butachlor, butafenacil, butenachlor, butralin, butroxydim, butylate, cafenstrole, carbetamide, carfentrazone-ethyl, chlomethoxyfen, chloridazon, chlorimuron-ethyl, chlornitrofen, chlorotoluron, chlorsulfuron, cinidon-ethyl, cinmethylin, cinosulfuron, clefoxydim, clethodim, clodinafop-propargyl, clomazone, clomeprop, clopyralid, cloransulam-ethyl, cumyluron, cyanazine, cyclosulfamuron, cycloxydim, cyhalofop-butyl, desmedipham, dicamba, dichlobenil, dichlorprop, dichlorprop-P, diclofop-methyl, diclosulam, difenzoquat, diflufenican, diflufenzopyr, dikegulac-sodium, dimefuron, dimepiperate, dimethachlor, dimethametryn, dimethenamid, diquatdibromide, dithiopyr, diuron, dymron, EPTC, esprocarb, ethalfluralin, ethametsulfuron-methyl, ethofumesate, ethoxyfen, ethoxysulfuron, etobenzanid, fenoxaprop-ethyl, fenoxaprop-P-ethyl, fentrazamide, flamprop-M-isopropyl, flamprop-M-methyl, flazasulfuron, florasulam, fluazifop, fluazifop-butyl, fluazolate, flucarbazone-sodium, flucetosulfuron, fluchoralin, flufenacet, flufenpyr, flumetsulam, flumiclorac-pentyl, flumioxazin, fluometuron, fluorochloridone, fluoroglycofen-ethyl, flupoxam, flupyrsulfuron-methyl-sodium, fluridone, fluroxypyr, fluroxypyr-butoxypropyl, fluoxypyr-meptyl, flurprimidol, flurtamone, fluthiacet-methyl, fomesafen, foramsulfuron, glufosinate, glufosinate-ammonium, glyphosate, halosulfuron-methyl, haloxyfop, haloxyfop-ethoxyethyl, haloxyfop-methyl, haloxyfop-P-metyl; hexazinone, imazamethabenz-methyl, imazamox, imazapic, imazapyr, imazaquin, imazethapyr, imazosulfuron, indanofan, iodosulfuron-methyl-natrium, ioxynil, isoproturon, isouron, isoxaben, isoxachlortole, isoxaflutole, ketospiradox, lactofen, lenacil, linuron, MCPA, mecoprop, mecoprop-P, mefenacet, mesosulfuron-methyl, mesotrione, metamifop, metamitron, metazachlor, methabenzthiazuron, methyidymron, metobromuron, metolachlor, metosulam, metoxuron, metribuzin, metsulfuron-methyl, molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, penoxsulam, pentoxazone, pethoxamid, phenmedipham, picloram, picolinafen, pinoxaden, piperophos, pretilachlor, primisulfuron-methyl, profluazol, profoxydim, prometryn, propachlor, propanil, propaquizafop, propisochlor, propoxycarbazone-sodium, propyzamide, prosulfocarb, prosulfuron, pyraclonil, pyraflufen-ethyl, pyrazolate, pyrazosulfuron-ethyl, pyrazoxyfen, pyribenzoxim, pyributicarb, pyridafol, pyridate, pyriftalid, pyriminobac-methyl, pyrithiobac-sodium, quinclorac, quinmerac, quinoclamine, quizalofop-ethyl, quizalofop-P-ethyl, quizalofop-P-tefuryl, rimsulfuron, sethoxydim, simazine, simetryn, S-metolachlor, sulcotrione, sulfentrazone, sulfometuron-methyl, sulfosate, sulfosulfuron, tebuthiuron, tepraloxydim, terbuthylazine, terbutryn, thenylchlor, thiazopyr, thifensulfuron-methyl, thiobencarb, tiocarbazil, tralkoxydim, triallate, triasulfuron, triaziflam, tribenuron-methyl, triclopyr, tridiphane, trifloxysulfuron, trifluralin, triflusulfuron-methyl and tritosulfuron.

Preference is given to herbicides (B) of the following subgroups (B1) to (B4) (most of the herbicides are referred to by the "common name", if possible according to the reference "The Pesticide Manual" British Crop Protection Council, 1997: 11th Ed., abbreviated "PM", or 2003, 13th Ed., abbreviated "PM13"):

(B1) Herbicides which Are Active Against Monocotyledonous and Dicotyledonous Harmful Plants, for Example (B1.1) flufenacet (BAY FOE 5043) (PM, pp. 82-83), 4'-fluoro-N-isopropyl-2-(5-trifluoromethyl-1,3,4-thiadiazol-2-yloxy)acetanilide, (B1.2) metolachlor (PM, pp. 833-834), 2-chloro-N-(2-ethyl-6-methylphenyl)-N-(2-methoxy-1-methylethyl)acetamide, (B1.3) acetochlor (PM, pp. 10-12), 2-chloro-N-(ethoxymethyl)-N-(2-ethyl-6-methylphenyl)acetamide, (B1.4) dimethenamid (PM, pp. 409-410), 2-chloro-N-(2,4-dimethyl-3-thienyl)-N-(2-methoxy-1-methylethyl)acetamide, (B1.5) pethoxamid (AG Chem, New Compound Review (publ. Agranova), Vol. 17, 1999, p. 94, i.e. 2-chloro-N-(2-ethoxyethyl)-N-(2-methyl-1-phenyl-1-propenyl)acetamide, (B1.6) atrazine (PM, pp. 55-57), N-ethyl-N'-isopropyl-6-chloro-2,4-diamino-1,3,5-triazine, (B1.7) simazine (PM, pp. 1106-1108), 6-chloro-N,N-diethyl-2,4-diamino-1,3,5-triazine, (B 1.8) cyanazine (PM, pp. 280-283), 2-(4-chloro-6-ethylamino-1,3,5-triazin-2-ylamino)-2-methylpropionitrile, (B1.9) terbuthylazin (PM, pp. 1168-1170), N-ethyl-N'-tert-butyl-6-chloro-2,4-diamino-1,3,5-triazine, (B1.10) metribuzin (PM, pp. 840-841), 4-amino-6-tert-butyl-3-methylthio-1,2,4-triazin-5(4H)-one, (B1.11) terbutryn (PM, pp. 1170-1172), N-(1,1-dimethylethyl)-N'-ethyl-6-(methylthio)-1,3,5-triazine-2,4-diamine, (B1.12) nicosulfuron (PM, pp. 877-879), 2-(4,6-dimethoxypyrimidin-2-yl)-3-(3-dimethylcarbamoyl-2-pyridylsulfonyl)urea and its salts, (B1.13) rimsulfuron (PM, pp. 1095-1097), 1-(4,6-dimethoxypyrimidin-2-yl)-3-(3-ethylsulfonyl-2-pyridylsulfonyl)urea and its salts, (B1.14) primisulfuron and esters, such as the methyl ester (PM, pp. 997-999), 2-[4,6-bis(difluoromethoxy)pyrimidin-2-ylcarbamoylsulfamoyl]benzoic acid or methyl 2-[4,6-bis(difluoromethoxy)pyrimidin-2-ylcarbamoylsulfamoyl]benzoate, and their salts, (B1.15) halosulfuron (PM, pp. 657-659), 3-chloro-5-(4,6-dimethoxypyrimidin-2-ylcarbamoylsulfamoyl)-1-methylpyrazole-4-carboxylic acid and its esters and salts, preferably the methyl ester, (B1.16) iodosulfuron (PM13, pp. 573-574) and, preferably, esters, such as the methyl ester, and salts thereof (cf. WO 96/41537 which is expressly included herein by way of reference), 4-iodo-2-(4-methoxy-6-methyl-1,3,5-triazin-2-ylcarbamoylsulfamoyl)benzoic acid or methyl 4-iodo-2-(4-methoxy-6-methyl-1,3,5-triazin-2-ylcarbamoylsulfamoyl)benzoate and their salts, such as the sodium salt, known from WO-A-92/13845, which is expressly incorporated herein by way of reference, (B1.17) foramsulfuron and its salts (PM13, pp. 494-495), 1-(4,6-dimethoxypyrimidin-2-yl)-3-[2-(dimethylcarbamoyl)-5-formamidophenylsulfonyl]urea, (B1.18) pendimethalin (PM, pp. 937-939), N-(1-ethylpropyl)-2,6-dinitro-3,4-xylidine, (B1.19) sulcotrione (PM, pp. 1124-1125), 2-(2-chloro-4-mesylbenzoyl)cyclohexane-1,3-dione, (B1.20) dicamba (PM, pp. 356-357), 3,6-dichloro-o-anisic acid and its salts, (B1.21) mesotrione, 2-(4-mesyl-2-nitrobenzoyl)cyclohexane-1,3-dione (ZA 1296, cf. Weed Science Society of America (WSSA) in WSSA Abstracts 1999, Vol. 39, pages 65-66, numbers 130-132), (B1.22) linuron (PM, pp. 751-753), 3-(3,4-dichlorophenyl)-1-methoxy-1-methylurea, (B1.23) isoxachlortole (AG Chem, New Compound Review, publ. Agranova, Vol. 16, 1998, p. 39), i.e. 4-chloro-2-(methylsulfonyl)phenyl 5-cyclopropylisoxazol-4-yl ketone, (B1.24) isoxaflutole (PM, pp. 737-739), (5-cyclopropylisoxazol-4-yl) 2-(methylsulfonyl)-4-(trifluoromethyl)phenyl methanone, (B1.25) metosulam (PM, pp. 836-838), 2',6'-dichloro-5,7-dimethoxy-3'-methyl[1,2,4]triazolo[1,5-a]pyrimidine-2-sulfonamide, (B1.26) flumetsulam (PM, pp. 573-574), 2',6'-difluoro-5-methyl-[1,2,4]triazolo[1,5-a]pyrimidine-2sulfonamide, (B1.27) cloransulam and esters, such as the methyl ester (PM, p. 265), 3-chloro-2-(5-ethoxy-7-fluoro-[1,2,4]triazolo[1,5-c]pyrimidin-2-yl -sulfonamido)benzoic acid and, preferably, the methyl ester, (B1.28) florasulam (Zeitschrift für Pflanzenkrankheiten und Pflanzenschutz, Verlag Eugen Ulmer, Stuttgart, Special Edition XVI, 1998, pp. 527-534), N-(2,6-difluorophenyl)-8-fluoro-5-methoxy(1,2,4)triazolo[1,5-c]pyrimidine-2-sulfonamide, (B1.29) molinate (PM, pp. 847-849), N-(ethylthiocarbonyl)azepan, (B1.30) thiobencarb (PM, pp. 1192-1193), chlorobenzyl N,N-diethylthiocarbamate, (B1.31) quinchlorac (PM, pp. 1078-1080), 3,7-dichloroquinoline-8-carboxylic acid and its salts, (B1.32) propanil (PM, pp -1017-1019), N-(3,4-dichlorophenyl)propanamide, (B1.33) pyribenzoxim, benzophenone O-[2,6-bis[(4,6-dimethoxy-2-pyrimidnyl)oxy]benzoyl]oxime, conference proceedings: The 1997 Brighton Crop Protection Conference, Weeds (publ. British Crop Protection Council) pp. 39-40, (B1.34) butachlor (PM, pp. 159-160), N-(butoxymethyl)-2-chloro-N-(2,6-diethylphenyl)acetamide, (B1.35) pretilachlor (PM, pp. 995-996), N-(2-propoxyethyl)-2-chloro-N-(2,6-diethylphenyl)acetamide, (B1.36) clomazone (PM, pp. 256-257), 2-[(2-chlorophenyl)-4,4-dimethyl-3-isoxazolidinone, (B1.37) oxadiargyl (PM, pp. 904-905), 5-tert-butyl-3-[2,4-dichloro-5-(prop-2-ynyloxy)phenyl]-1,3,4-oxadiazol-2 (3H)-one, (B 1.38) oxaziclomefone, 3-[1-(3,5-dichlorophenyl)-1-methylethyl]-2,3-dihydro-6-methyl-5-phenyl-4H-1,3-oxazin-4-one, conference proceedings: The 1997 Brighton Crop Protection Conference, Weeds (publ. British Crop Protection Council) pp. 73-74, (B1.39) anilofos (PM, pp. 47-48), S-4-chloro-N-isopropylcarbaniloylmethyl O,O-dimethyl phosphorodithioate, (B1.40) cafenstrole (PM, pp. 173-174), 1-diethylcarbamoyl-3-(2,4,6-trimethylphenylsulfonyl)-1,2,4-triazole, (B1.41) thiazopyr (PM, pp. 1185-1187), methyl 2-difluoromethyl-5-(4,5-dihydro-1,3-thiazol-2-yl)-4-isobutyl-6-trifluoromethylnicotinate, (B1.42) triclopyr (PM, pp. 1237-1239), [(3,5,6-trichloro-2-pyridinyl)oxy]acetic acid, preferably as triclopyr, triclopyr-butotyl, triclopyr-triethylammonium, (B1.43) oxadiazone (PM, pp. 905-907), 5-tert-butyl-3-(2,4-dichloro-5-isopropoxyphenyl)-1,3,4-oxadiazol-2(3H)-one, (B1.44) esprocarb (PM, pp. 472-473), S-benzyl 1,2-dimethylpropyl(ethyl)thiocarbamate, (B1.45) pyributicarb (PM, pp 1060-1061) O-3-tert-butylphenyl-6-methoxy-2-pyridyl methylthiocarbamate (TSH-888), (B1.46) azimsulfuron (PM, pp. 63-65) 1-(4,6-dimethoxypyrimidin-2-yl)-3-[1-methyl-4-(2-2H-tetrazol-5-yl)pyrazol-5-yl]sulfonylurea, (B1.47) azoles, as known from EP-A-0663913, which is expressly incorporated herein by way of reference, for example 1-(3-chloro-4,5,6,7-tetrahydropyrazolo[1,5-a]pyridin-2-yl)-5-methylpropargylamino-4-pyrazolylcarbonitrile (hereinbelow "EP 913"), (B1.48) thenylchlor (PM, pp. 1182-1183), 2-chloro-N-(3-methoxy-2-thenyl)-2',6'-dimethylacetanilide, (B1.49) pentoxazone (PM, pp. 942-943), 3-(4-chloro-5-cyclopentyloxy-2-fluorophenyl)-5-isopropylidene-1,3-oxazolidine-2,4-dione, (B1.50) pyriminobac and its esters, such as the methyl ester (PM, pp. 1071-1072), methyl 2-(4,6-dimethoxy-2-pyrimidinyloxy)-6-(1-methoxyiminoethyl)benzoate, also as acid or sodium salt, (B1.51) mesosulfuron and its salts and esters (PM, pp. 630), methyl 2-[(4,6-dimethoxypyrimidin-2-ylcarbamoyl)sulfamoyl]α-(methanesulfonamido)-p-toluate, (B1.52) isoproturon (PM, pp. 732-734), 3-(4-isopropylphenyl)-1,1-dimethylurea, (B1.53) chlortuloron (PM, pp. 229-231), 3-(3-chloro-p-tolyl)-1,1-dimethylurea, (B1.54) prosulfocarb (PM, pp. 1039-1041), S-benzyl dipropylthiocarbamate, (B1.55) flucarbazone and its salts (PM13, pp. 447-448), 4,5-dihydro-3-methoxy-4-methyl-5-oxo-N-(2-trifluoromethoxyphenylsulfonyl)-1H-1,2,4-triazole-1-carboxamide sodium, (B1.56) propoxycarbazone and its salts (PM, pp. 831-832), methyl 2-[[[(4,5-dihydro-4-methyl-5-oxo-3-propoxy-1H-1,2,4-triazol-1-yl)carbonyl]amino]sulfonyl]benzoate, sodium salt, (B1.57) flupyrsulfuron and its esters, such as the methyl ester, and its salts (PM, pp. 586-588), methyl 2-(4,6-dimethoxypyrimidin-2-ylcarbamoylsulfamoyl)-6-trifluoromethylnicotinate sodium, (B1.58) sulfosulfuron and its salts (PM, pp. 1130-1131), 1-(4,6-dimethoxypyrimidin-2-yl)-3-(2-ethylsulfonylimidazo[1,2-a]pyridin-3-yl)sulfonylurea, (B1.59) trifluralin (PM13, pp. 1012-1014), α,α,α-trifluoro-2,6-dinitro-N,N-dipropyl-p-toluidine, (B1.60) ethalfluralin (PM13, pp 375-376), N-ethyl-α,α,α-trifluoro-N-(2-methylallyl)-2,6-dinitro-p-toluidine, (B1.61) norflurazon (PM13, pp. 711-712), 4-chloro-5-methylamino-2-(α,α,α-trifluoro-m-tolyl)pyridazin-3(2H)-one, (B1.62) vernolate (PM13, pp. 1099) S-propyl dipropylthiocarbamate, (B1.63) chlorotoluron (PM13, pp. 170), 3-(3-chloro-p-tolyl)-1,1-dimethylurea, (B1.64) imazethapyr and its salts and esters (PM13, pp. 558-560), (RS)-5-ethyl-2-(4-isopropyl-4-methyl-5-oxo-2-imidazolin-2-yl)nicotinic acid, (B1.65) imazamox (PM13, pp. 552-553), (RS)-2-(4-isopropyl-4-methyl-5-oxo-2-imidazolin-2-yl)-5-methoxymethylnicotinic acid, (B1.66) imazaquin and its salts and esters (PM13, pp. 557-558), (RS)-2-(4-isopropyl-4-methyl-5-oxo-2-imidazolin-2-yl)quinoline-3-carboxylic acid, (B2) Herbicides which Are Mainly Active Against Dicotyledonous Harmful Plants, for Example (B2.1) MCPA (PM, pp. 767-769), (4-chloro-2-methylphenoxy)acetic acid and its salts and esters, (B2.2) 2,4-D (PM, pp. 323-327), 2,4-dichlorophenoxyacetic acid and its salts and esters, (B2.3) bromoxynil (PM, pp. 149-151), 3,5-dibromo-4-hydroxybenzonitrile, (B2.4) bentazone (PM, pp. 1064-1066), 3-isopropyl-2,2-dioxo-1H-2,1,3-benzothiadiazin-4(3H)-one, (B2.5) fluthiacet (PM, pp. 606-608), [2-chloro-4-fluoro-5-(5,6,7,8-tetrahydro-3-oxo-1H,3H-1,3,4-thiadiazolo[3,4-a]pyridazin-1-ylideneamino)phenylthio]acetic acid and, preferably, the methyl ester, (B2.6) pyridate (PM, pp. 1064-1066), O-(6-chloro-3-phenylpyridazin-4-yl) S-(octyl)thiocarbonate, (B2.7) diflufenzopyr (BAS 654 00 H, PM pp. 81-82), 2-{1-[4-(3,5-difluorophenyl)semicarbazono]ethyl}nicotinic acid, (B2.8) carfentrazone (PM, pp. 191-193), ethyl (RS)-2-chloro-3-[2-chloro-5-(4-difluoromethyl-4,5-dihydro-3-methyl-5-oxo-1H-1,2,4-triazol-1-yl)-4-fluorophenyl]propionate, used, inter alia, as carfentrazone-ethyl (as stated) or else as acid, (B2.9) clopyralid (PM, pp. 260-263) 3,6-dichloropyridine-2-carboxylic acid, (B2.10) thifensulfuron and its esters, preferably the methyl-ester (PM, pp. 1188-1190), 3-[[[[(4-methoxy-6-methyl-1,3,5-triazin-2-yl)amino]carbonyl]amino]sulfonyl]-2-thiophenecarboxylic acid or methyl 3-[[[[(4-6-methyl-1,3,5-triazin-2-yl)amino]carbonyl]amino]sulfonyl]-2-thiophenecarboxylate and its salts, (B2.11) prosulfuron and its salts (PM, pp. 1041-1043), 1-(4-methoxy-6-methyl-1,3,5-triazin-2-yl)-3-[2-(3,3,3-trifluoropropyl)phenylsulfonyl]urea and its salts, (B2.12) tritosulfuron and its salts (PM13, p. 1022; AG Chem, New Compound Review (publ. Agranova), Vol. 17, 1999, p. 24), N-[[[4'-methoxy-6-(trifluoromethyl)-1,3,5-triazin-2-yl]amino]carbonyl]-2-trifluoromethylbenzenesulfonamide, (B2.13) triasulfuron and its salts (PM, pp. 1222-1224), 1-[2-(2-chloroethoxy)phenylsulfonyl]-3-(4-methoxy-6-methyl-1,3,5-triazin-2-yl)urea, (B2.14) 2,4-D (PM, pp. 323-327), (2,4-dichlorophenoxy) acetic acid, frequently used forms: 2,4-D-butotyl, 2,4-D-butyl, 2,4-D-dimethylammonium, 2,4-D-diolamine, 2,4-D-isooctyl, 2,4-D-isopropyl, 2,4-D-triolamine, (B2.15) MCPA (PM, pp. 770-771), (4-chloro-2-methylphenoxy)acetic acid, the forms that are mainly used are, inter alia, MCPA-butotyl, MCPA-dimethylammonium, MCPA-isoctyl, MCPA-potassium, MCPA-sodium, (B2.16) bensulfuron and its esters, preferably the methyl ester, and their salts (PM, pp. 104-105), methyl α-(4,6-dimethoxypyrimidin-2-yl-carbamoylsulfamoyl)-O-toluate, (B2.17) metsulfuron and its esters, preferably the methyl ester, and their salts (PM, pp. 842-844), methyl 2-[[[[(4-methoxy-6-methyl-1,3,5-triazin-2-yl)amino]carbonyl]amino]sulfonyl]benzoate, (B2.18) acifluorfen (PM, pp. 12-14), 5-(2-chloro-α,α,α-trifluoro-p-tolyloxy)-2-nitrobenzoic acid, also used as acifluorfen-sodium, (B2.19) bispyribac (KIH 2023), preferred is the form as sodium salt (PM, pp. 129-131), sodium 2,6-bis[4,6-dimethoxypyrimidin-2-yl)oxy]benzoate, (B2.20) ethoxysulfuron and its esters and salts (PM, pp. 488-490), 1-(4,6-dimethoxypyrimidin-2-yl)-3-(2-ethoxyphenoxysulfonyl)urea, (B2.21) cinosulfuron and its esters and salts (PM, pp. 248-250), 1-(4,6-dimethoxy-1,3,5-triazin-2-yl)-3-[2-(2-methoxyethoxy)phenylsulfonyl]urea, (B2.22) pyrazosulfuron and its esters, preferably the ethyl ester, and their salts (PM, p 1052-1054), methyl 5-(4,6-dimethoxypyrimidin-2-ylcarbamoylsulfamoyl)-1-methylpyrazole-4-carboxylate, (B2.23) imazosulfuron and its esters and salts (PM, pp. 703-704), 1-(2-chloroimidazo[1,2-a]pyridin-3-ylsulfonyl)-3-(4,6-dimethoxypyrimidin-2-yl)urea, (B2.24) cyclosulfamuron and its esters and salts (PM, pp. 288-289), N-[[[2-(cyclopropylcarbonyl)phenyl]amino]sulfonyl]-N1-(4,6-dimethoxypyrimidin-2-yl)urea, (B2.25) chlorsulfuron and its esters and salts (PM, pp. 239-240), 1-(2-chlorophenylsulfonyl)-3-(4-methoxy-6-methyl-1,3,5-triazin-2-yl)urea, (B2.26) bromobutide (PM, pp. 144-145), 2-bromo-3,3-dimethyl-N-(1-methyl-1-phenylethyl)butyramide, (B2.27) bentazone (PM, pp. 109-111), 3-isopropyl-1H-2,1,3-benzothiadiazin-4(3H)-one 2,2-dioxide, (B2.28) chlorimuron and and its esters, preferably the ethyl ester, and their salts (PM, pp. 217-218), ethyl 2-(4-chloro-6-methoxypyrimidin-2-yl-carbonylsulfamoyl)benzoate, (B2.29) diflufenican (PM, pp. 397-399), 2',4'-difluoro-2-(α,α,α-trifluoro-m-tolyloxy)nicotinanilide, (B2.30) flurtamone (PM, pp. 602-603), (RS)-5-methylamino-2-phenyl-4-(α,α,α-trifluoro-m-tolyl)furan-3(2H) one, (B2.31) tribenuron (PM, pp. 1230-1232), methyl 2-[[[[4-methoxy-6-methyl-1,3,5-triazin-2-yl)methylamino]carbonyl]amino]sulfonyl]benzoate, (B2.32) amidosulfuron and its salts (PM, pp. 37-38), 1-(4,6-dimethoxypyrimidin-2-yl)-3-mesyl(methyl)sulfamoylurea, (B2.33) mecoprop/mecoprop-P and their esters (PM, pp. 776-779), (RS)-2-(4-chloro-o-tolyloxy)propionic acid, (B2.34) dichlorprop/dichlorprop-P and their esters (PM, pp. 368-372), (RS)-2-(2,4-dichlorophenoxy)propionic acid, (B2.35) fluroxypyr (PM, pp. 597-600), 4-amino-3,5-dichloro-6-fluoro-2-pyridyloxyacetic acid, (B2.36) picloram (PM, pp. 977-979) 4-amino-3,5,6-trichloropyridine-2-carboxylic acid, (B2.37) ioxynil (PM, pp. 718-721), 4-hydroxy-3,5-diiodobenzonitrile, (B2.38) bifenox (PM, pp. 116-117), methyl 5-(2,4-dichlorophenoxy)-2-nitrobenzoate, (B2.39) pyraflufen-ethyl (PM, pp. 1048-1049), ethyl 2-chloro-5-(4-chloro-5-difluoromethoxy-1-methylpyrazol-3-yl)-4-fluorophenoxyacetate, (B2.40) fluoroglycofen-ethyl (PM, pp. 580-582), O-[5-(2-chloro-α,α,α-trifluoro-p-tolyloxy)-2-nitrobenzoyl]glycolic acid, (B2.41) cinidon-ethyl (BAS 615005) (AG Chem, New Compound Review, publ. Agranova, Vol. 17, 1999, p. 26), (B2.42) picolinafen (PM13, pp. 785-786) (AG Chem, New Compound Review (publ. Agranova), Vol. 17, 1999, p. 35), N-4-fluorophenyl-6-(3-trifluoromethylphenoxy)pyridine-2-carboxamide, (B2.43) sulfentrazone (PM13, pp. 910-911), 2',4'-dichloro-5'-(4-difluoromethyl-4,5-dihydro-3-methyl-5-oxo-1H-1,2,4-triazol-1-yl)methanesulfonanilide, (B2.44) oxyfluorfen (PM13, pp. 738-739), 2-chloro-α,α,α-trifluoro-p-tolyl 3-ethoxy-4-nitrophenyl ether, (B2.45) lactofen (PM13, pp. 596-597), ethyl O-[5-(2-chloro-α,α,α-trifluoro-p-tolyloxy)-2-nitrobenzoyl]-DL-lactate, (B2.46) fomesafen (PM13, pp. 492-493), 5-(2-chloro-α,α,α-trifluoro-p-tolyloxy)-N-methylsulfonyl-2-nitrobenzamide, (B2.47) flumiclorac (PM13, pp. 460-461), pentyl[2-chloro-5-(cyclohex-1-ene-1,2-dicarboximido)-4-fluorophenoxy]acetate, (B2.48) 2,4-DB (PM13, pp. 264-266), 4-(2,4-dichlorophenoxy)butyric acid, (B2.49) flumioxazin (PM13, pp. 461-462), N-(7-fluoro-3,4-dihydro-3-oxo-4-prop-2-ynyl-2H-1,4-benzoxazin-6-yl)cyclohex-1-ene-1,2-dicarboxamide, (B2.50) benazolin (PM13, pp. 62-64), 4-chloro-2-oxobenzothiazolin-3-ylacetic acid; 4-chloro-2,3-dihydro-2-oxobenzothiazol-3-ylacetic acid, (B3) Herbicides which Are Mainly Active Against Monocotyledonous Harmful Plants, for Example (B3.1) quizalofop/quizalofop-P and their esters, such as the ethyl or tefuryl ester (PM, pp 1087-1092), (RS)-2-[4-(6-chloroquinoxalin-2-yloxy)phenoxy]propionic acid.

(B3.2) fenoxaprop/fenoxaprop-P and their esters, such as the ethyl ester (PM, pp. 519-520), 2-[4-(6-chlorobenzoxazol-2-yloxy)phenoxy]propionate, (B3.3) fluazifop/fluazifop-P and their esters, such as the butyl ester (PM, pp. 553-557), butyl (RS)-2-[4-(5-trifluoromethyl-2-pyridyloxy)phenoxy]propionate, (B3.4) haloxyfop/haloxyfop-P and their esters, such as the methyl ester (PM, pp 659-663), (±)-2-[4-[[3-chloro-5-(trifluoromethyl)-2-pyridinyl]oxy]phenoxy]propionic acid including, inter alia, the application form as haloxyfop-etotyl, haloxyfop-methyl, haloxyfop-methyl [(R)-isomer], (B3.5) propaquizafop (PM, pp. 1021-1022), 2-isopropylideneaminooxyethyl (R)-2-[4-(6-chloroquinoxalin-2-yloxy)phenoxy]propionate, (B3.6) clodinafop and its esters, such as the propargyl ester (PM, pp. 251-253), (R)-2-[4-(5-chloro-3-fluoro-2-pyridyloxy)phenoxy]propionic acid, (B3.7) cyhalofop and its esters, such as the butyl ester (PM, pp. 297-298), butyl (R)-2-[4-(4-cyano-2-fluorophenoxy)phenoxy]propionate, (B3.8) diclofop/diclofop-P and its esters, such as the methyl ester (PM, pp. 374-377), (RS)-2-[4-(2,4-dichlorophenoxy)phenoxy]propionic acid, (B3.9) sethoxydim (PM, pp. 1101-1103), (±)-(EZ)-(1-ethoxyiminobutyl)-5-[2-(ethylthio)propyl]-3-hydroxycyclohex-2-enone, (B3.10) cycloxydim (PM, pp. 290-291), (±)-2-[1-(ethoxyimino)butyl]-3-hydroxy-5-thian-3-ylcyclohex-2-enone, (B3.11) clethodim (PM, pp. 250-251), (±)-2-[(E)-1-[(E)-3-chloroallyloxyimino]propyl]-5-[2-(ethylthio)propyl]-3-hydrocyclohex-2-enone, (B3.12) profoxydim, 2-[1-(2-(4-chlorophenoxy)propoxyimino)butyl]-3-oxo-5-thian-3-ylcyclohex-1-enol (AG Chem, New Compound Review (publ. Agranova), Vol. 17, 1999, p. 26 and PM, 13th edition pp. 808-809), (B3.13) alachlor (PM, pp. 23-24), 2-chloro-N-(2,6-diethylphenyl)-N-(methoxymethyl)acetamide, (B3.14) mefenacet (PM, pp. 779-781), 2-(1,3-benzothol-3-yloxy)-N-methylacetanilide, (B3.15) fentrazamide, N-cyclohexylethyl 4-(2-chlorophenyl)-5-oxo-4,5-dihydrotetrazole-1-carboxamide (PM13, pp. 427-428 and conference proceedings: The 1997 Brighton Crop Protection Conference, Weeds (publ. British Crop Protection Council), pp. 67-68), (B3.16) benfuresate (PM, pp. 98-99), 2,3-dihydro-3,3-dimethylbenzofuran-5yl-ethanesulfonate, (B4) Herbicides which Are Active Against Monocotyledonous and Dicotyledonous Harmful Plants, for Use in the Nonselective Field or in Specifically Tolerant Crops, Such as
(B4.1) glufosinate (PM, pp. 643-645), also including glufosinate-P, for example 4-[hydroxy(methyl)phosphinoyl]-DL-homoalanine, 4-[hydroxy(methyl)phosphinoyl]-L-homoalanine, in each case preferably as salts, for example ammonium or alkali metal salts, such as
(B4.1.1) glufosinate-ammonium,
(B4.1.2) glufosinate-P-ammonium,
(B4.1.3) glufosinate-sodium,
(B4.1.4) glufosinate-P-sodium,
(B4.2) glyphosate (PM, pp. 646-649), N-(phosphonomethyl)glycine and its salts and esters, for example
(B4.2.1) glyphosate-isopropylammonium,
(B4.2.2) glyphosate-sesquisodium,
(B4.2.3) glyphosate-trimesium,
(B4.3) paraquat and its salts, such as paraquat dichloride (PM pp. 923-925).
Imidazolinones and their salts, such as
(B4.4) imazapyr and its salts and esters (PM, pp. 697-699),
(B4.5) imazamethabenz and its salts and esters (PM, pp. 694-696),
(B4.6) imazamethabenz-methyl (PM, pp. 694-696),
(B4.7) imazapic (AC 263,222) and its salts and esters, for example the ammonium salt, (PM, pp. 5 and 6, referred to under AC 263,222).
Suitable combination partners (B) are preferably compounds which are selective in soybeans, for example (Ba) Herbicides which Act Selectively Against Monocotyledonous and Dicotyledonous Harmful Plants in Soybeans, for Example
(B1.59) trifluralin, (PM pp. 1248-1250),
(B1.10) metribuzin (PM, pp. 840-841 ),
(B1.36) clomazone (PM, pp. 256-257),
(B1.18) pendimethalin (PM, pp. 937-939),
(B1.2) metolachlor (PM, pp. 833-834),
(B1.26) flumetsulam (PM, pp. 573-574),
(B1.4) dimethenamid (PM, pp. 499-410),
(B1.22) linuron (PM, pp. 751-753),
(B1.60) ethalfluralin (PM, pp. 473-474),
(B1.1) flufenacet (BAY FOE 5043) (PM, pp. 82-83),
(B1.61) norflurazon (PM, pp. 886-888),
(B1.62) vernolate (PM, pp. 1264-1266),
(B1.63) chlortoluron, chlorotoluron (PM, pp. 229-231),
(B1.27) cloransulam and esters, such as the methyl ester (PM, p. 265),
(B1.64) imazethapyr (PM13, pp. 558-560),
(B1.65) imazamox (PM13, pp. 552-553),
(B1.66) imazaquin (PM13, pp. 557-558), (Bb) Herbicides which Act Selectively Against Dicotyledonous Harmful Plants in Soybeans, for Example
(B2.43) sulfentrazone (PM, pp. 1126-1127),
(B2.4) bentazone (PM, pp. 109-111),
(B2.10) thifensulfuron and its esters, in particular the methyl ester (PM, pp. 1188-1190),
(B2.44) oxyfluorfen (PM, pp. 919-921),
(B2.45) lactofen (PM, pp. 747-748),
(B2.46) fomesafen (PM, pp. 616-618),
(B2.47) flumiclorac (PM, pp. 575-576) and its esters, such as the pentyl ester,
(B2.18) acifluorfen and its sodium salt (PM, pp. 12-14),
(B2.48) 2,4-DB (PM, pp. 337-339) and its esters and salts,
(B2.49) flumioxazin (PM13, pp. 461-462),
(B2.50) benazolin (PM13, pp. 62-64),
(B2.2) 2,4-D (PM, pp. 323-327) and its esters and salts,
(B2.28) chlorimuron and its esters and salts, such as clorimuron-ethyl, (Bc) Herbicides which Act Selectively Against Monocotyledonous Harmful Plants in Soybeans, for Example
(B3.9) sethoxydim (PM, pp. 1101-1103),
(B3.10) cycloxydim (PM, pp 290-291),
(B3.11) clethodim (PM, pp. 250-251),
(B3.1) quizalofop-P and its esters, such as the ethyl or tefuryl ester (PM, pp. 1089-1092),
(B3.2) fenoxaprop-P and its esters, such as the ethyl ester (PM, pp. 519-520),
(B3.3) fluazifop-P and its esters, such as the butyl ester (PM, pp. 556-557),
(B3.4) haloxyfop and haloxyfop-P and their esters, such as the methyl or the etotyl ester (PM, pp. 660-663),
(B3.5) propaquizafop (PM, pp. 1021-1022),
(B3.13) alachlor (PM, pp. 23-24), (Bd) Nonselective Herbicides which can be Used in Soybeans for Specific Purposes, for Example
(B4.1) glufosinate (PM, pp. 643-645),
(B4.2) glyphosate (PM, pp. 646-649),
(B4.3) paraquat (salts), such as paraquat dichloride (PM, pp. 923-925).

Combination partners (B) which are also preferred are glufosinate, benozalin, fenoxaprop, lactofen, chlortoluron, flufenacet, metribuzin, benfuresate, fentrazamide, mefenacet, diclofop, ioxynil, bromoxynil, amidosulfuron, flurtamone, diflufenican, ethoxysulfuron, flucarbazone, propoxycarbazone, sulcotrione, mesotrione, isoproturon, iodosulfuron, mesosulfuron, foramsulfuron, anilofos, oxaziclomefone, oxadiargyl, isoxaflutole, linuron.

If, in the context of this description, the short form of the "common name" is used, this embraces all customary derivatives, such as the esters and salts, and isomers, in particular optical isomers, in particular the commercial form or forms. The stated chemical compound names refer to at least one of the compounds embraced by the "common name", frequently to a preferred compound. Also included in the case of sulfonylureas are salts which are formed by exchanging a hydrogen atom at the sulfonamide group by a cation.

Preference is given to herbicide combinations comprising one or more herbicides (A) and one or more herbicides (B), preferably from the group (B1) or (B2), (B3) or (B4). More preferred are combinations of herbicides (A) with one or more herbicides (B) according to the scheme: (A)+(B1), (A)+(B2), (A)+(B3), (A)+(B4), (A)+(B1)+(B2), (A)+(B1)+(B3), (A)+(B1)+(B4), (A)+(B2)+(B3), (A)+(B2)+(B4) (A)+(B3)+(B4) or (A)+(B1)+(B2)+(B3).

Combinations according to the invention include those combinations which additionally comprise one or more further agrochemically active compounds different from herbicides [active compounds (C)], such as safeners (for example mefenpyr-diethyl, isoxadifen-ethyl, cloquintocetmexyl, 1,8-naphthalic anhydride, dichlormid, benoxacor, fenclorim, furilazole, or n-cyclopropyl-4-[2-methoxybenzoyl)sulfamoyl]benzamide (see WO 99/16744), insecticides of fungicides, such as (A)+(B1)+(C), (A)+(B2)+(C) or (A)+(B3)+(C), (A)+(B4)+(C), (A)+(B1)+(B2)+(C), (A)+(B1)+(B3)+(C), (A)+(B1)+(B4)+(C), (A)+(B2)+(B3)+(C), (A)+(B2)+(B4)+(C), (A)+(B3)+(B4)+(C) or (A)+(B1)+(B2)+(B3)+(C).

The preferred conditions illustrated below in particular for two-component combinations according to the invention apply primarily also to combinations comprising three or more active compounds, if they comprise the two-component combinations according to the invention, and with respect to the two-component combination in question.

The applications rates of the herbicides (B) may vary considerably depending on the herbicide. The following quantities [in g of AS (active substance)/ha (hectare)] may be used as guidelines for preferred application rates for some mixing partners of group (B), where in the combinations according to the invention even amounts of less than the lowest amount may be appropriate:

herbicide of group (B1): 10-8000, preferably 50-5000, g of AS/ha, herbicide of group (B2): 5-5000, preferably 2-2500 g of AS/ha, herbicide of group (B3): 10-500, preferably 25-300, g of AS/ha, herbicide of group (B4): 20-5000, preferably 100-2000, g of AS/ha.

Ranges of suitable ratios of the compounds (A) and (B) follow, for example, from the application rates mentioned for the individual compounds. In general, in the combinations according to the invention, the application rates may be reduced. Preferred mixing ratios (A):(B) for the combinations according to the invention are listed below:

(A):(B1)=10:1 to 800 000, preferably 6:1 to 1:500 000,
(A):(B2)=200:1 to 1:500 000, preferably 5:1 to 1:250 000,
(A):(B3)=10:1 to 1:500 000, preferably 5:1 to 1:250 000,
(A):(B4)=5:1 to 1:500 000, preferably 1:10 to 1:200 000.

Of particular interest is the use of herbicidal compositions comprising the following compounds (A)+(B):

(Al-1)+(B1.1), (Al-1)+(B1.2), (Al-1)+(B1.3), (Al-1)+(B1.4), (Al-1)+(B1.5), (Al-1)+(B1.6), (Al-1)+(B1.7), (Al-1)+(B1.8), (Al-1)+(B1.9), (Al-1)+(B1.10), (Al-1)+(B1.11), (Al-1)+(B1.12), (Al-1)+(B1.13), (Al-1)+(B1.14), (Al-1)+(B1.15), (Al-1)+(B1.16), (Al-1)+(B1.17), (Al-1)+(B1.18), (Al-1)+(B1.19), (Al-1)+(B1.20), (Al-1)+(B1.21), (Al-1)+(B1.22), (Al-1)+(B1.23), (Al-1)+(B1.24), (Al-1)+(B1.25), (Al-1)+(B1.26), (Al-1)+(B1.27), (Al-1)+(B1.28), (Al-1)+(B1.29), (Al-1)+(B1.30), (Al-1)+(B1.31), (Al-1)+(B1.32), (Al-1)+(B1.33), (Al-1)+(B1.34), (Al-1)+(B1.35), (Al-1)+(B1.36), (Al-1)+(B1.37), (Al-1)+(B1.38), (Al-1)+(B1.39), (Al-1)+(B1.40), (Al-1)+(B1.41), (Al-1)+(B1.42), (Al-1)+(B1.43), (Al-1)+(B1.44), (Al-1)+(B1.45), (Al-1)+(B1.46), (Al-1)+(B1.47), (Al-1)+(B1.48), (Al-1)+(B1.49), (Al-1)+(B1.50), (Al-1)+(B1.51), (Al-1)+(B1.52), (Al-1)+(B1.53), (Al-1)+(B1.54), (Al-1)+(B1.55), (Al-1)+(B1.56), (Al-1)+(B1.57), (Al-1)+(B1.58), (Al-1)+(B1.59), (Al-1)+(B1.60), (Al-1)+(B1.61), (Al-1)+(B1.62), (Al-1)+(B1.63), (Al-1)+(B1.64), (Al-1)+(B1.65), (Al-1)+(B1.66), (Al-1)+(B2.1), (Al-1)+(B2.2), (Al-1)+(B2.3), (Al-1)+(B2.4), (Al-1)+(B2.5), (Al-1)+(B2.6), (Al-1)+(B2.7), (Al-1)+(B2.8), (Al-1)+(B2.9), (Al-1)+(B2.10), (Al-1)+(B2.11), (Al-1)+(B2.12), (Al-1)+(B2.13), (Al-1)+(B2.14), (Al-1)+(B2.15), (Al-1)+(B2.16), (Al-1)+(B2.17), (Al-1)+(B2.18), (Al-1)+(B2.19), (Al-1)+(B2.20), (Al-1)+(B2.21), (Al-1)+(B2.22), (Al-1)+(B2.23), (Al-1)+(B2.24), (Al-1)+(B2.25), (Al-1)+(B2.26), (Al-1)+(B2.27), (Al-1)+(B2.28), (Al-1)+(B2.29), (Al-1)+(B2.30), (Al-1)+(B2.31), (Al-1)+(B2.32), (Al-1)+(B2.33), (Al-1)+(B2.34), (Al-1)+(B2.35), (Al-1)+(B2.36), (Al-1)+(B2.37), (Al-1)+(B2.38), (Al-1)+(B2.39), (Al-1)+(B2.40), (Al-1)+(B2.41), (Al-1)+(B2.42), (Al-1)+(B2.43), (Al-1)+(B2.44), (Al-1)+(B2.45), (Al-1)+(B2.46), (Al-1)+(B2.47), (Al-1)+(B2.48), (Al-1)+(B2.49), (Al-1)+(B2.50), (Al-1)+(B3.1), (Al-1)+(B3.2), (A-1)+(B3.3), (Al-1)+(B3.4), (Al-1)+(B3.5), (Al-1)+(B3.6), (Al-1)+(B3.7), (Al-1)+(B3.8) (Al-1)+(B3.9), (Al-1)+(B3.10), (Al-1)+(B3.11), (Al-1)+(B3.12), (Al-1)+(B3.13), (Al-1)+(B3.14), (Al-1)+(B3.15), (Al-1)+(B3.16), (Al-1)+(B4.1), (Al-1)+(B4.2), (Al-1)+(B4.3), (Al-1)+(B4.4), (Al-1)+(B4.5), (Al-1)+(B4.6), (Al-1)+(B4.7).

(Al-2)+(B1.1), (Al-2)+(B1.2), (Al-2)+(B1.3), (Al-2)+(B1.4), (Al-2)+(B1.5), (Al-2)+(B1.6), (Al-2)+(B1.7), (Al-2)+(B1.8), (Al-2)+(B1.9), (Al-2)+(B1.10), (Al-2)+(B1.11), (Al-2)+(B1.12), (Al-2)+(B1.13), (Al-2)+(B1.14), (Al-2)+(B1.15), (Al-2)+(B1.16), (Al-2)+(B1.17), (Al-2)+(B1.18), (Al-2)+(B1.19), (Al-2)+(B1.20), (Al-2)+(B1.21), (Al-2)+(B1.22), (Al-2)+(B1.23), (Al-2)+(B1.24), (Al-2)+(B1.25), (Al-2)+(B1.26), (Al-2)+(B1.27), (Al-2)+(B1.28), (Al-2)+(B1.29), (Al-2)+(B1.30), (Al-2)+(B1.31), (Al-2)+(B1.32), (Al-2)+(B1.33), (Al-2)+(B1.34), (Al-2)+(B1.35), (Al-2)+(B1.36), (Al-2)+(B1.37), (Al-2)+(B1.38), (Al-2)+(B1.39), (Al-2)+(B1.40), (Al-2)+(B1.41), (Al-2)+(B1.42), (Al-2)+(B1.43), (Al-2)+(B1.44), (Al-2)+(B1.45), (Al-2)+(B1.46), (Al-2)+(B1.47), (Al-2)+(B1.48), (Al-2)+(B1.49), (Al-2)+(B1.50), (Al-2)+(B1.51), (Al-2)+(B1.52), (Al-2)+(B1.53), (Al-2)+(B1.54), (Al-2)+(B1.55), (Al-2)+(B1.56), (Al-2)+(B1.57), (Al-2)+(B1.58), (Al-2)+(B1.59), (Al-2)+(B1.60), (Al-2)+(B1.61), (Al-2)+(B1.62), (Al-2)+(B1.63), (Al-2)+(B1.64), (Al-2)+(B1.65), (Al-2)+(B1.66), (Al-2)+(B2.1), (Al-2)+(B2.2), (Al-2)+(B2.3), (Al-2)+(B2.4), (Al-2)+(B2.5), (Al-2)+(B2.6), (Al-2)+(B2.7), (Al-2)+(B2.8), (Al-2)+(B2.9), (Al-2)+(B2.10), (Al-2)+(B2.11), (Al-2)+(B2.12), (Al-2)+(B2.13), (Al-2)+(B2.14), (Al-2)+(B2.15), (Al-2)+(B2.16), (Al-2)+(B2.17), (Al-2)+(B2.18), (Al-2)+(B2.19), (Al-2)+(B2.20), (Al-2)+(B2.21), (Al-2)+(B2.22), (Al-2)+(B2.23), (Al-2)+(B2.24), (Al-2)+(B2.25), (Al-2)+(B2.26), (Al-2)+(B2.27), (Al-2)+(B2.28), (Al-2)+(B2.29), (Al-2)+(B2.30), (Al-2)+(B2.31), (Al-2)+(B2.32), (Al-2)+(B2.33), (Al-2)+(B2.34), (Al-2)+(B2.35), (Al-2)+(B2.36), (Al-2)+(B2.37), (Al-2)+(B2.38), (Al-2)+(B2.39), (Al-2)+(B2.40), (Al-2)+(B2.41), (Al-2)+(B2.42), (Al-2)+(B2.43), (Al-2)+(B2.44), (Al-2)+(B2.45), (Al-2)+(B2.46), (Al-2)+(B2.47), (Al-2)+(B2.48), (Al-2)+(B2.49), (Al-2)+(B2.50), (Al-2)+(B3.1), (Al-2)+(B3.2), (Al-2)+(B3.3), (Al-2)+(B3.4), (Al-2)+(B3.5), (Al-2)+(B3.6), (Al-2)+(B3.7), Al-2)+(B3.8), (Al-2)+(B3.9), (Al-2)+(B3.10), (Al-2)+(B3.11), (Al-2)+(B3.12), (Al-2)+(B3.13), (Al-2)+(B3.14), (Al-2)+(B3.15), (Al-2)+(B3.16), (Al-2)+(B4.1), (Al-2)+(B4.2), (Al-2)+(B4.3), (Al-2)+(B4.4), (A-2)+(B4.5), (Al-2)+(B4.6), (Al-2)+(B4.7).

(Al-3)+(B1.1), (Al-3)+(B1.2), (Al-3)+(B1.3), (Al-3)+(B1.4), (Al-3)+(B1.5), (Al-3)+(B1.6), (Al-3)+(B1.7), (Al-3)+(B1.8), (Al-3)+(B1.9), (Al-3)+(B1.10), (Al-3)+(B1.11), (Al-3)+(B1.12), (Al-3)+(B1.13), (Al-3)+(B1.14), (Al-3)+(B1.15), (Al-3)+(B1.16), (Al-3)+(B1.17), (Al-3)+(B1.18), (Al-3)+(B1.19), (Al-3)+(B1.20), (Al-3)+(B1.21), (Al-3)+(B1.22), (Al-3)+(B1.23), (Al-3)+(B1.24), (Al-3)+(B1.25), (Al-3)+(B1.26), (Al-3)+(B1.27), (Al-3)+(B1.28), (Al-3)+(B1.29), (Al-3)+(B1.30), (Al-3)+(B1.31), (Al-3)+(B1.32), (Al-3)+(B1.33), (Al-3)+(B1.34), (Al-3)+(B1.35), (Al-3)+(B1.36), (Al-3)+(B1.37), (Al-3)+(B1.38), (Al-3)+(B1.39), (Al-3)+(B1.40), (Al-3)+(B1.41), (Al-3)+(B1.42), (Al-3)+(B1.43), (Al-3)+(B1.44), (Al-3)+(B1.45), (Al-3)+(B1.46), (Al-3)+(B1.47), (Al-3)+(B1.48), (Al-3)+(B1.49), (Al-3)+(B1.50), (Al-3)+(B1.51), (Al-3)+(B1.52), (Al-3)+(B1.53), (Al-3)+(B1.54), (Al-3)+(B1.55), (Al-3)+(B1.56), (Al-3)+(B1.57), (Al-3)+(B1.58), (Al-3)+(B1.59), (Al-3)+(B1.60), (Al-3)+(B1.61), (Al-3)+(B1.62), (Al-3)+(B1.63), (Al-3)+(B1.64), (Al-3)+(B1.65), (Al-3)+(B1.66), (Al-3)+(B2.1), (Al-3)+(B2.2), (Al-3)+(B2.3), (Al-3)+(B2.4), (Al-3)+(B2.5), (Al-3)+(B2.6), (Al-3)+(B2.7), (Al-3)+(B2.8), (Al-3)+(B2.9), (Al-3)+(B2.10), (Al-3)+(B2.11), (Al-3)+(B2.12), (Al-3)+(B2.13), (Al-3)+(B2.14), (Al-3)+(B2.15), (Al-3)+(B2.16), (Al-3)+(B2.17), (Al-3)+(B2.18), (Al-3)+(B2.19), (Al-3)+(B2.20), (Al-3)+(B2.21), (Al-3)+(B2.22), (Al-3)+(B2.23), (Al-3)+(B2.24), (Al-3)+(B2.25), (Al-3)+(B2.26), (Al-3)+(B2.27), (Al-3)+(B2.28), (Al-3)+(B2.29), (Al-3)+(B2.30), (Al-3)+(B2.31), (Al-3)+(B2.32), (Al-3)+(B2.33), (Al-3)+

(B2.34), (Al-3)+(B2.35), (Al-3)+(B2.36), (Al-3)+(B2.37), (Al-3)+(B2.38), (Al-3)+(B2.39), (Al-3)+(B2.40), (Al-3)+(B2.41), (Al-3)+(B2.42), (Al-3)+(B2.43), (Al-3)+(B2.44), (Al-3)+(B2.45), (Al-3)+(B2.46), (Al-3)+(B2.47), (Al-3)+(B2.48), (Al-3)+(B2.49), (Al-3)+(B2.50), (Al-3)+(B3.1), (Al-3)+(B3.2.), (Al-3)+(B3.3), (Al-3)+(B3.4), (Al-3)+(B3.5), (Al-3)+(B3.6), (Al-3)+(B3.7), (Al-3)+(B3.8), (Al-3)+(B3.9), (Al-3)+(B3.10), (Al-3)+(B3.11), (Al-3)+(B3.12), (Al-3)+(B3.13), (Al-3)+(B3.14), (Al-3)+(B3.15), (Al-3)+(B3.16), (Al-3)+(B4.1), (Al-3)+(B4.2), (Al-3)+(B4.3), (Al-3)+(B4.4), (Al-3)+(B4.5), (Al-3)+(B4.6), (Al-3)+(B4.7).

(Al-4)+(B1.1), (Al-4)+(B1.2), (Al-4)+(B1.3), (Al-4)+(B1.4), (Al-4)+(B1.5), (Al-4)+(B1.6), (Al-4)+(B1.7), (Al-4)+(B1.8), (Al-4)+(B1.9), (Al-4)+(B1.10), (Al-4)+(B1.11), (Al-4)+(B1.12), (Al-4)+(B1.13), (Al-4)+(B1.14), (Al-4)+(B1.15), (Al-4)+(B1.16), (Al-4)+(B1.17), (Al-4)+(B1.18), (Al-4)+(B1.19), (Al-4)+(B1.20), (Al-4)+(B1.21), (Al-4)+(B1.22), (Al-4)+(B1.23), (Al-4)+(B1.24), (Al-4)+(B1.25), (Al-4)+(B1.26), (Al-4)+(B1.27), (Al-4)+(B1.28), (Al-4)+(B1.29), (Al-4)+(B1.30), (Al-4)+(B1.31), (Al-4)+(B1.32), (Al-4)+(B1.33), (Al-4)+(B1.34), (Al-4)+(B1.35), (Al-4)+(B1.36), (Al-4)+(B1.37), (Al-4)+(B1.38), (Al-4)+(B1.39), (Al-4)+(B1.40), (Al-4)+(B1.41), (Al-4)+(B1.42), (Al-4)+(B1.43), (Al-4)+(B1.44), (Al-4)+(B1.45), (Al-4)+(B1.46), (Al-4)+(B1.47), (Al-4)+(B1.48), (Al-4)+(B1.49), (Al-4)+(B1.50), (Al-4)+(B1.51), (Al-4)+(B1.52), (Al-4)+(B1.53), (Al-4)+(B1.54), (Al-4)+(B1.55), (Al-4)+(B1.56), (Al-4)+(B1.57), (Al-4)+(B1.58), (Al-4)+(B1.59), (Al-4)+(B1.60), (Al-4)+(B1.61), (Al-4)+(B1.62), (Al-4)+(B1.63), (Al-4)+(B1.64), (Al-4)+(B1.65), (Al-4)+(B1.66), (Al-4)+(B2.1), (Al-4)+(B2.2), (Al-4)+(B2.3), (Al-4)+(B2.4), (Al-4)+(B2.5), (Al-4)+(B2.6), (Al-4)+(B2.7), (Al-4)+(B2.8), (Al-4)+(B2.9), (Al-4)+(B2.10), (Al-4)+(B2.11), (Al-4)+(B2.12), (Al-4)+(B2.13), (Al-4)+(B2.14), (Al-4)+(B2.15), (Al-4)+(B2.16), (Al-4)+(B2.17), (Al-4)+(B2.18), (Al-4)+(B2.19), (Al-4)+(B2.20), (Al-4)+(B2.21), (Al-4)+(B2.22), (Al-4)+(B2.23), (Al-4)+(B2.24), (Al-4)+(B2.25), (Al-4)+(B2.26), (Al-4)+(B2.27), (Al-4)+(B2.28), (Al-4)+(B2.29), (Al-4)+(B2.30), (Al-4)+(B2.31), (Al-4)+(B2.32), (Al-4)+(B2.33), (Al-4)+(B2.34), (Al-4)+(B2.35), (Al-4)+(B2.36), (Al-4)+(B2.37), (Al-4)+(B2.38), (Al-4)+(B2.39), (Al-4)+(B2.40), (Al-4)+(B2.41), (Al-4)+(B2.42), (Al-4)+(B2.43), (Al-4)+(B2.44), (Al-4)+(B2.45), (Al-4)+(B2.46), (Al-4)+(B2.47), (Al-4)+(B2.48), (Al-4)+(B2.49), (Al-4)+(B2.50), (Al-4)+(B3.1), (Al-4)+(B3.2.), (Al-4)+(B3.3), (Al-4)+(B3.4), (Al-4)+(B3.5), (Al-4)+(B3.6), (Al-4)+(B3.7), (Al-4)+(B3.8), (Al-4)+(B3.9), (Al-4)+(B3.10), (Al-4)+(B3.11), (Al-4)+(B3.12), (Al-4)+(B3.13), (Al-4)+(B3.14), (Al-4)+(B3.15), (Al-4)+(B3.16), (Al-4)+(B4.1), (Al-4)+(B4.2), (Al-4)+(B4.3), (Al-4)+(B4.4), (Al-4)+(B4.5), (Al-4)+(B4.6), (Al-4)+(B4.7).

(Al-5)+(B1.1), (Al-5)+(B1.2), (Al-5)+(B1.3), (Al-5)+(B1.4), (Al-5)+(B1.5), (Al-5)+(B1.6), (Al-5)+(B1.7), (Al-5)+(B1.8), (Al-5)+(B1.9), (Al-5)+(B1.10), (Al-5)+(B1.11), (Al-5)+(B1.12), (Al-5)+(B1.13), (Al-5)+(B1.14), (Al-5)+(B1.15), (Al-5)+(B1.16), (Al-5)+(B1.17), (Al-5)+(B1.18), (Al-5)+(B1.19), (Al-5)+(B1.20), (Al-5)+(B1.21), (Al-5)+(B1.22), (Al-5)+(B1.23), (Al-5)+(B1.24), (Al-5)+(B1.25), (Al-5)+(B1.26), (Al-5)+(B1.27), (Al-5)+(B1.28), (Al-5)+(B1.29), (Al-5)+(B1.30), (Al-5)+(B1.31), (Al-5)+(B1.32), (Al-5)+(B1.33), (Al-5)+(B1.34), (Al-5)+(B1.35), (Al-5)+(B1.36), (Al-5)+(B1.37), (Al-5)+(B1.38), (Al-5)+(B1.39), (Al-5)+(B1.40), (Al-5)+(B1.41), (Al-5)+(B1.42), (Al-5)+(B1.43), (Al-5)+(B1.44), (Al-5)+(B1.45), (Al-5)+(B1.46), (Al-5)+(B1.47), (Al-5)+(B1.48), (Al-5)+(B1.49), (Al-5)+(B1.50), (Al-5)+(B1.51), (Al-5)+(B1.52), (Al-5)+(B1.53), (Al-5)+(B1.54), (Al-5)+(B1.55), (Al-5)+(B1.56), (Al-5)+(B1.57), (Al-5)+(B1.58), (Al-5)+(B1.59), (Al-5)+(B1.60), (Al-5)+(B1.61), (Al-5)+(B1.62), (Al-5)+(B1.63), (Al-5)+(B1.64), (Al-5)+(B1.65), (Al-5)+(B1.66), (Al-5)+(B2.1), (Al-5)+(B2.2), (Al-5)+(B2.3), (Al-5)+(B2.4), (Al-5)+(B2.5), (Al-5)+(B2.6), (Al-5)+(B2.7), (Al-5)+(B2.8), (Al-5)+(B2.9), (Al-5)+(B2.10), (Al-5)+(B2.11), (Al-5)+(B2.12), (Al-5)+(B2.13), (Al-5)+(B2.14), (Al-5)+(B2.15), (Al-5)+(B2.16), (Al-5)+(B2.17), (Al-5)+(B2.18), (Al-5)+(B2.19), (Al-5)+(B2.20), (Al-5)+(B2.21), (Al-5)+(B2.22), (Al-5)+(B2.23), (Al-5)+(B2.24), (Al-5)+(B2.25), (Al-5)+(B2.26), (Al-5)+(B2.27), (Al-5)+(B2.28), (Al-5)+(B2.29), (Al-5)+(B2.30), (Al-5)+(B2.31), (Al-5)+(B2.32), (Al-5)+(B2.33), (Al-5)+(B2.34), (Al-5)+(B2.35), (Al-5)+(B2.36), (Al-5)+(B2.37), (Al-5)+(B2.38), (Al-5)+(B2.39), (Al-5)+(B2.40), (Al-5)+(B2.41), (Al-5)+(B2.42), (Al-5)+(B2.43), (Al-5)+(B2.44), (Al-5)+(B2.45), (Al-5)+(B2.46), (Al-5)+(B2.47), (Al-5)+(B2.48), (Al-5)+(B2.49), (Al-5)+(B2.50), (Al-5)+(B3.1), (Al-5)+(B3.2.), (Al-5)+(B3.3), (Al-5)+(B3.4), (Al-5)+(B3.5), (Al-5)+(B3.6), (Al-5)+(B3.7), (Al-5)+(B3.8), (Al-5)+(B3.9), (Al-5)+(B3.10), (Al-5)+(B3.11), (Al-5)+(B3.12), (Al-5)+(B3.13), (Al-5)+(B3.14), (Al-5)+(B3.15), (Al-5)+(B3.16), (Al-5)+(B4.1), (Al-5)+(B4.2), (Al-5)+(B4.3), (Al-5)+(B4.4), (Al-5)+(B4.5), (Al-5)+(B4.6), (Al-5)+(B4.7).

(Al-6)+(B1.1), (Al-6)+(B1.2), (Al-6)+(B1.3), (Al-6)+(B1.4), (Al-6)+(B1.5), (Al-6)+(B1.6), (Al-6)+(B1.7), (Al-6)+(B1.8), (Al-6)+(B1.9), (Al-6)+(B1.10), (Al-6)+(B1.11), (Al-6)+(B1.12), (Al-6)+(B1.13), (Al-6)+(B1.14), (Al-6)+(B1.15), (Al-6)+(B1.16), (Al-6)+(B1.17), (Al-6)+(B1.18), (Al-6)+(B1.19), (Al-6)+(B1.20), (Al-6)+(B1.21), (Al-6)+(B1.22), (Al-6)+(B1.23), (Al-6)+(B1.24), (Al-6)+(B1.25), (Al-6)+(B1.26), (Al-6)+(B1.27), (Al-6)+(B1.28), (Al-6)+(B1.29), (Al-6)+(B1.30), (Al-6)+(B1.31), (Al-6)+(B1.32), (Al-6)+(B1.33), (Al-6)+(B1.34), (Al-6)+(B1.35), (Al-6)+(B1.36), (Al-6)+(B1.37), (Al-6)+(B1.38), (Al-6)+(B1.39), (Al-6)+(B1.40), (Al-6)+(B1.41), (Al-6)+(B1.42), (Al-6)+(B1.43), (Al-6)+(B1.44), (Al-6)+(B1.45), (Al-6)+(B1.46), (Al-6)+(B1.47), (Al-6)+(B1.48), (Al-6)+(B1.49), (Al-6)+(B1.50), (Al-6)+(B1.51), (Al-6)+(B1.52), (Al-6)+(B1.53), (Al-6)+(B1.54), (Al-6)+(B1.55), (Al-6)+(B1.56), (Al-6)+(B1.57), (Al-6)+(B1.58), (Al-6)+(B1.59), (Al-6)+(B1.60), (Al-6)+(B1.61), (Al-6)+(B1.62), (Al-6)+(B1.63), (Al-6)+(B1.64), (Al-6)+(B1.65), (Al-6)+(B1.66), (Al-6)+(B2.1), (Al-6)+(B2.2), (Al-6)+(B2.3), (Al-6)+(B2.4), (Al-6)+(B2.5), (Al-6)+(B2.6), (Al-6)+(B2.7), (Al-6)+(B2.8), (Al-6)+(B2.9), (Al-6)+(B2.10), (Al-6)+(B2.11), (Al-6)+(B2.12), (Al-6)+(B2.13), (Al-6)+(B2.14), (Al-6)+(B2.15), (Al-6)+(B2.16), (Al-6)+(B2.17), (Al-6)+(B2.18), (Al-6)+(B2.19), (Al-6)+(B2.20), (Al-6)+(B2.21), (Al-6)+(B2.22), (Al-6)+(B2.23), (Al-6)+(B2.24), (Al-6)+(B2.25), (Al-6)+(B2.26), (Al-6)+(B2.27), (Al-6)+(B2.28), (Al-6)+(B2.29), (Al-6)+(B2.30), (Al-6)+(B2.31), (Al-6)+(B2.32), (Al-6)+(B2.33), (Al-6)+(B2.34), (Al-6)+(B2.35), (Al-6)+(B2.36), (Al-6)+(B2.37), (Al-6)+(B2.38), (Al-6)+(B2.39), (Al-6)+(B2.40), (Al-6)+(B2.41), (Al-6)+(B2.42), (Al-6)+(B2.43), (Al-6)+(B2.44), (Al-6)+(B2.45), (Al-6)+(B2.46), (Al-6)+(B2.47), (Al-6)+(B2.48), (Al-6)+(B2.49), (Al-6)+(B2.50), (Al-6)+(B3.1), (Al-6)+(B3.2.), (Al-6)+(B3.3), (Al-6)+(B3.4), (Al-6)+(B3.5), (Al-6)+(B3.6), (Al-6)+(B3.7), (Al-6)+(B3.8), (Al-6)+(B3.9), (Al-6)+(B3.10), (Al-6)+(B3.11), (Al-6)+(B3.12), (Al-6)+(B3.13), (Al-6)+(B3.14), (Al-6)+(B3.15), (Al-6)+(B3.16), (Al-6)+(B4.1), (Al-6)+(B4.2), (Al-6)+(B4.3), (Al-6)+(B4.4), (Al-6)+(B4.5), (Al-6)+(B4.6), (Al-6)+(B4.7).

(Al-7)+(B1.1), (Al-7)+(B1.2), (Al-7)+(B1.3), (Al-7)+(B1.4), (Al-7)+(B1.5), (Al-7)+(B1.6), (Al-7)+(B1.7), (Al-7)+(B1.8), (Al-7)+(B1.9), (Al-7)+(B1.10), (Al-7)+(B1.11), (Al-7)+(B1.12), (Al-7)+(B1.13), (Al-7)+(B1.14), (Al-7)+(B1.15), (Al-7)+(B1.16), (Al-7)+(B1.17), (Al-7)+(B1.18), (Al-7)+(B1.19), (Al-7)+(B1.20), (Al-7)+(B1.21), (Al-7)+

(B1.22), (Al-7)+(B1.23), (Al-7)+(B1.24), (Al-7)+(B1.25), (Al-7)+(B1.26), (Al-7)+(B1.27), (Al-7)+(B1.28), (Al-7)+(B1.29), (Al-7)+(B1.30), (Al-7)+(B1.31), (Al-7)+(B1.32), (Al-7)+(B1.33), (Al-7)+(B1.34), (Al-7)+(B1.35), (Al-7)+(B1.36), (Al-7)+(B1.37), (Al-7)+(B1.38), (Al-7)+(B1.39), (Al-7)+(B1.40), (Al-7)+(B1.41), (Al-7)+(B1.42), (Al-7)+(B1.43), (Al-7)+(B1.44), (Al-7)+(B1.45), (Al-7)+(B1.46), (Al-7)+(B1.47), (Al-7)+(B1.48), (Al-7)+(B1.49), (Al-7)+(B1.50), (Al-7)+(B1.51), (Al-7)+(B1.52), (Al-7)+(B1.53), (Al-7)+(B1.54), (Al-7)+(B1.55), (Al-7)+(B1.56), (Al-7)+(B1.57), (Al-7)+(B1.58), (Al-7)+(B1.59), (Al-7)+(B1.60), (Al-7)+(B1.61), (Al-7)+(B1.62), (Al-7)+(B1.63), (Al-7)+(B1.64), (Al-7)+(B1.65), (Al-7)+(B1.66), (Al-7)+(B2.1), (Al-7)+(B2.2), (Al-7)+(B2.3), (Al-7)+(B2.4), (Al-7)+(B2.5), (Al-7)+(B2.6), (Al-7)+(B2.7), (Al-7)+(B2.8), (Al-7)+(B2.9), (Al-7)+(B2.10), (Al-7)+(B2.11), (Al-7)+(B2.12), (Al-7)+(B2.13), (Al-7)+(B2.14), (Al-7)+(B2.15), (Al-7)+(B2.16), (Al-7)+(B2.17), (Al-7)+(B2.18), (Al-7)+(B2.19), (Al-7)+(B2.20), (Al-7)+(B2.21), (Al-7)+(B2.22), (Al-7)+(B2.23), (Al-7)+(B2.24), (Al-7)+(B2.25), (Al-7)+(B2.26), (Al-7)+(B2.27), (Al-7)+(B2.28), (Al-7)+(B2.29), (Al-7)+(B2.30), (Al-7)+(B2.31), (Al-7)+(B2.32), (Al-7)+(B2.33), (Al-7)+(B2.34), (Al-7)+(B2.35), (Al-7)+(B2.36), (Al-7)+(B2.37), (Al-7)+(B2.38), (Al-7)+(B2.39), (Al-7)+(B2.40), (Al-7)+(B2.41), (Al-7)+(B2.42), (Al-7)+(B2.43), (Al-7)+(B2.44), (Al-7)+(B2.45), (Al-7)+(B2.46), (Al-7)+(B2.47), (Al-7)+(B2.48), (Al-7)+(B2.49), (Al-7)+(B2.50), (Al-7)+(B3.1), (Al-7)+(B3.2.), (Al-7)+(B3.3), (Al-7)+(B3.4), (Al-7)+(B3.5), (Al-7)+(B3.6), (Al-7)+(B3.7), (Al-7)+(B3.8), (Al-7)+(B3.9), (Al-7)+(B3.10), (Al-7)+(B3.11), (Al-7)+(B3.12), (Al-7)+(B3.13), (Al-7)+(B3.14), (Al-7)+(B3.15), (Al-7)+(B3.16), (Al-7)+(B4.1), (Al-7)+(B4.2), (Al-7)+(B4.3), (Al-7)+(B4.4), (Al-7)+(B4.5), (Al-7)+(B4.6), (Al-7)+(B4.7).

(Al-8)+(B1.1), (Al-8)+(B1.2), (Al-8)+(B1.3), (Al-8)+(B1.4), (Al-8)+(B1.5), (Al-8)+(B1.6), (Al-8)+(B1.7), (Al-8)+(B1.8), (Al-8)+(B1.9), (Al-8)+(B1.10), (Al-8)+(B1.11), (Al-8)+(B1.12), (Al-8)+(B1.13), (Al-8)+(B1.14), (Al-8)+(B1.15), (Al-8)+(B1.16), (Al-8)+(B1.17), (Al-8)+(B1.18), (Al-8)+(B1.19), (Al-8)+(B1.20), (Al-8)+(B1.21), (Al-8)+(B1.22), (Al-8)+(B1.23), (Al-8)+(B1.24), (Al-8)+(B1.25), (Al-8)+(B1.26), (Al-8)+(B1.27), (Al-8)+(B1.28), (Al-8)+(B1.29), (Al-8)+(B1.30), (Al-8)+(B1.31), (Al-8)+(B1.32), (Al-8)+(B1.33), (Al-8)+(B1.34), (Al-8)+(B1.35), (Al-8)+(B1.36), (Al-8)+(B1.37), (Al-8)+(B1.38), (Al-8)+(B1.39), (Al-8)+(B1.40), (Al-8)+(B1.41), (Al-8)+(B1.42), (Al-8)+(B1.43), (Al-8)+(B1.44), (Al-8)+(B1.45), (Al-8)+(B1.46), (Al-8)+(B1.47), (Al-8)+(B1.48), (Al-8)+(B1.49), (Al-8)+(B1.50), (Al-8)+(B1.51), (Al-8)+(B1.52), (Al-8)+(B1.53), (Al-8)+(B1.54), (Al-8)+(B1.55), (Al-8)+(B1.56), (Al-8)+(B1.57), (Al-8)+(B1.58), (Al-8)+(B1.59), (Al-8)+(B1.60), (Al-8)+(B1.61), (Al-8)+(B1.62), (Al-8)+(B1.63), (Al-8)+(B1.64), (Al-8)+(B1.65), (Al-8)+(B1.66), (Al-8)+(B2.1), (Al-8)+(B2.2), (Al-8)+(B2.3), (Al-8)+(B2.4), (Al-8)+(B2.5), (Al-8)+(B2.6), (Al-8)+(B2.7), (Al-8)+(B2.8), (Al-8)+(B2.9), (Al-8)+(B2.10), (Al-8)+(B2.11), (Al-8)+(B2.12), (Al-8)+(B2.13), (Al-8)+(B2.14), (Al-8)+(B2.15), (Al-8)+(B2.16), (Al-8)+(B2.17), (Al-8)+(B2.18), (Al-8)+(B2.19), (Al-8)+(B2.20), (Al-8)+(B2.21), (Al-8)+(B2.22), (Al-8)+(B2.23), (Al-8)+(B2.24), (Al-8)+(B2.25), (Al-8)+(B2.26), (Al-8)+(B2.27), (Al-8)+(B2.28), (Al-8)+(B2.29), (Al-8)+(B2.30), (Al-8)+(B2.31), (Al-8)+(B2.32), (Al-8)+(B2.33), (Al-8)+(B2.34), (Al-8)+(B2.35), (Al-8)+(B2.36), (Al-8)+(B2.37), (Al-8)+(B2.38), (Al-8)+(B2.39), (Al-8)+(B2.40), (Al-8)+(B2.41), (Al-8)+(B2.42), (Al-8)+(B2.43), (Al-8)+(B2.44), (Al-8)+(B2.45), (Al-8)+(B2.46), (Al-8)+(B2.47), (Al-8)+(B2.48), (Al-8)+(B2.49), (Al-8)+(B2.50), (Al-8)+(B3.1), (Al-8)+(B3.2.), (Al-8)+(B3.3), (Al-8)+(B3.4), (Al-8)+(B3.5), (Al-8)+(B3.6), (Al-8)+(B3.7), (Al-8)+(B3.8), (Al-8)+(B3.9), (Al-8)+(B3.10), (Al-8)+(B3.11), (Al-8)+(B3.12), (Al-8)+(B3.13), (Al-8)+(B3.14), (Al-8)+(B3.15), (Al-8)+(B3.16), (Al-8)+(B4.1), (Al-8)+(B4.2), (Al-8)+(B4.3), (Al-8)+(B4.4), (Al-8)+(B4.5), (Al-8)+(B4.6), (Al-8)+(B4.7).

(Al-9)+(B1.1), (Al-9)+(B1.2), (Al-9)+(B1.3), (Al-9)+(B1.4), (Al-9)+(B1.5), (Al-9)+(B1.6), (Al-9)+(B1.7), (Al-9)+(B1.8), (Al-9)+(B1.9), (Al-9)+(B1.10), (Al-9)+(B1.11), (Al-9)+(B1.12), (Al-9)+(B1.13), (Al-9)+(B1.14), (Al-9)+(B1.15), (Al-9)+(B1.16), (Al-9)+(B1.17), (Al-9)+(B1.18), (Al-9)+(B1.19), (Al-9)+(B1.20), (Al-9)+(B1.21), (Al-9)+(B1.22), (Al-9)+(B1.23), (Al-9)+(B1.24), (Al-9)+(B1.25), (Al-9)+(B1.26), (Al-9)+(B1.27), (Al-9)+(B1.28), (Al-9)+(B1.29), (Al-9)+(B1.30), (Al-9)+(B1.31), (Al-9)+(B1.32), (Al-9)+(B1.33), (Al-9)+(B1.34), (Al-9)+(B1.35), (Al-9)+(B1.36), (Al-9)+(B1.37), (Al-9)+(B1.38), (Al-9)+(B1.39), (Al-9)+(B1.40), (Al-9)+(B1.41), (Al-9)+(B1.42), (Al-9)+(B1.43), (Al-9)+(B1.44), (Al-9)+(B1.45), (Al-9)+(B1.46), (Al-9)+(B1.47), (Al-9)+(B1.48), (Al-9)+(B1.49), (Al-9)+(B1.50), (Al-9)+(B1.51), (Al-9)+(B1.52), (Al-9)+(B1.53), (Al-9)+(B1.54), (Al-9)+(B1.55), (Al-9)+(B1.56), (Al-9)+(B1.57), (Al-9)+(B1.58), (Al-9)+(B1.59), (Al-9)+(B1.60), (Al-9)+(B1.61), (Al-9)+(B1.62), (Al-9)+(B1.63), (Al-9)+(B1.64), (Al-9)+(B1.65), (Al-9)+(B1.66), (Al-9)+(B2.1), (Al-9)+(B2.2), (Al-9)+(B2.3), (Al-9)+(B2.4), (Al-9)+(B2.5), (Al-9)+(B2.6), (Al-9)+(B2.7), (Al-9)+(B2.8), (Al-9)+(B2.9), (Al-9)+(B2.10), (Al-9)+(B2.11), (Al-9)+(B2.12), (Al-9)+(B2.13), (Al-9)+(B2.14), (Al-9)+(B2.15), (Al-9)+(B2.16), (Al-9)+(B2.17), (Al-9)+(B2.18), (Al-9)+(B2.19), (Al-9)+(B2.20), (Al-9)+(B2.21), (Al-9)+(B2.22), (Al-9)+(B2.23), (Al-9)+(B2.24), (Al-9)+(B2.25), (Al-9)+(B2.26), (Al-9)+(B2.27), (Al-9)+(B2.28), (Al-9)+(B2.29), (Al-9)+(B2.30), (Al-9)+(B2.31), (Al-9)+(B2.32), (Al-9)+(B2.33), (Al-9)+(B2.34), (Al-9)+(B2.35), (Al-9)+(B2.36), (Al-9)+(B2.37), (Al-9)+(B2.38), (Al-9)+(B2.39), (Al-9)+(B2.40), (Al-9)+(B2.41), (Al-9)+(B2.42), (Al-9)+(B2.43), (Al-9)+(B2.44), (Al-9)+(B2.45), (Al-9)+(B2.46), (Al-9)+(B2.47), (Al-9)+(B2.48), (Al-9)+(B2.49), (Al-9)+(B2.50), (Al-9)+(B3.1), (Al-9)+(B3.2.), (Al-9)+(B3.3), (Al-9)+(B3.4), (Al-9)+(B3.5), (Al-9)+(B3.6), (Al-9)+(B3.7), (Al-9)+(B3.8), (Al-9)+(B3.9), (Al-9)+(B3.10), (Al-9)+(B3.11), (Al-9)+(B3.12), (Al-9)+(B3.13), (Al-9)+(B3.14), (Al-9)+(B3.15), (Al-9)+(B3.16), (Al-9)+(B4.1), (Al-9)+(B4.2), (Al-9)+(B4.3), (Al-9)+(B4.4), (Al-9)+(B4.5), (Al-9)+(B4.6), (Al-9)+(B4.7).

(Al-10)+(B1.1), (Al-10)+(B1.2), (Al-10)+(B1.3), (Al-10)+(B1.4), (Al-10)+(B1.5), (Al-10)+(B1.6), (Al-10)+(B1.7), (Al-10)+(B1.8), (Al-10)+(B1.9), (Al-10)+(B1.10), (Al-10)+(B1.11), (Al-10)+(B1.12), (Al-10)+(B1.13), (Al-10)+(B1.14), (Al-10)+(B1.15), (Al-10)+(B1.16), (Al-10)+(B1.17), (Al-10)+(B1.18), (Al-10)+(B1.19), (Al-10)+(B1.20), (Al-10)+(B1.21), (Al-10)+(B1.22), (Al-10)+(B1.23), (Al-10)+(B1.24), (Al-10)+(B1.25), (Al-10)+(B1.26), (Al-10)+(B1.27), (Al-10)+(B1.28), (Al-10)+(B1.29), (Al-10)+(B1.30), (Al-10)+(B1.31), (Al-10)+(B1.32), (Al-10)+(B1.33), (Al-10)+(B1.34), (Al-10)+(B1.35), (Al-10)+(B1.36), (Al-10)+(B1.37), (Al-10)+(B1.38), (Al-10)+(B1.39), (Al-10)+(B1.40), (Al-10)+(B1.41), (Al-10)+(B1.42), (Al-10)+(B1.43), (Al-10)+(B1.44), (Al-10)+(B1.45), (Al-10)+(B1.46), (Al-10)+(B1.47), (Al-10)+(B1.48), (Al-10)+(B1.49), (Al-10)+(B1.50), (Al-10)+(B1.51), (Al-10)+(B1.52), (Al-10)+(B1.53), (Al-10)+(B1.54), (Al-10)+(B1.55), (Al-10)+(B1.56), (Al-10)+(B1.57), (Al-10)+(B1.58), (Al-10)+(B1.59), (Al-10)+(B1.60), (Al-10)+(B1.61), (Al-10)+(B1.62), (Al-10)+(B1.63), (Al-10)+(B1.64), (Al-10)+(B1.65), (Al-10)+(B1.66), (Al-10)+(B2.1), (Al-10)+(B2.2), (Al-10)+(B2.3), (Al-10)+(B2.4), (Al-10)+(B2.5), (Al-10)+

(B2.6), (Al-10)+(B2.7), (Al-10)+(B2.8), (Al-10)+(B2.9), (Al-10)+(B2.10), (Al-10)+(B2.11), (Al-10)+(B2.12), (Al-10)+(B2.13), (Al-10)+(B2.14), (Al-10)+(B2.15), (Al-10)+(B2.16), (Al-10)+(B2.17), (Al-10)+(B2.18), (Al-10)+(B2.19), (Al-10)+(B2.20), (Al-10)+(B2.21), (Al-10)+(B2.22), (Al-10)+(B2.23), (Al-10)+(B2.24), (Al-10)+(B2.25), (Al-10)+(B2.26), (Al-10)+(B2.27), (Al-10)+(B2.28), (Al-10)+(B2.29), (Al-10)+(B2.30), (Al-10)+(B2.31), (Al-10)+(B2.32), (Al-10)+(B2.33), (Al-10)+(B2.34), (Al-10)+(B2.35), (Al-10)+(B2.36), (Al-10)+(B2.37), (Al-10)+(B2.38), (Al-10)+(B2.39), (Al-10)+(B2.40), (Al-10)+(B2.41), (Al-10)+(B2.42), (Al-10)+(B2.43), (Al-10)+(B2.44), (Al-10)+(B2.45), (Al-10)+(B2.46), (Al-10)+(B2.47), (Al-10)+(B2.48), (Al-10)+(B2.49), (Al-10)+(B2.50), (Al-10)+(B3.1), (Al-10)+(B3.2.), (Al-10)+(B3.3), (Al-10)+(B3.4), (Al-10)+(B3.5), (Al-10)+(B3.6), (Al-10)+(B3.7), (Al-10)+(B3.8), (Al-10)+(B3.9), (Al-10)+(B3.10), (Al-10)+(B3.11), (Al-10)+(B3.12), (Al-10)+(B3.13), (Al-10)+(B3.14), (Al-10)+(B3.15), (Al-10)+(B3.16), (Al-10)+(B4.1), (Al-10)+(B4.2), (Al-10)+(B4.3), (Al-10)+(B4.4), (Al-10)+(B4.5), (Al-10)+(B4.6), (Al-10)+(B4.7).

(Al-11)+(B1.1), (Al-11)+(B1.2), (Al-11)+(B1.3), (Al-11)+(B1.4), (Al-11)+(B1.5), (Al-11)+(B1.6), (Al-11)+(B1.7), (Al-11)+(B1.8), (Al-11)+(B1.9), (Al-11)+(B1.10), (Al-11)+(B1.11), (Al-11)+(B1.12), (Al-11)+(B1.13), (Al-11)+(B1.14), (Al-11)+(B1.15), (Al-11)+(B1.16), (Al-11)+(B1.17), (Al-11)+(B1.18), (Al-11)+(B1.19), (Al-11)+(B1.20), (Al-11)+(B1.21), (Al-11)+(B1.22), (Al-11)+(B1.23), (Al-11)+(B1.24), (Al-11)+(B1.25), (Al-11)+(B1.26), (Al-11)+(B1.27), (Al-11)+(B1.28), (Al-11)+(B1.29), (Al-11)+(B1.30), (Al-11)+(B1.31), (Al-11)+(B1.32), (Al-11)+(B1.33), (Al-11)+(B1.34), (Al-11)+(B1.35), (Al-11)+(B1.36), (Al-11)+(B1.37), (Al-11)+(B1.38), (Al-11)+(B1.39), (Al-11)+(B1.40), (Al-11)+(B1.41), (Al-11)+(B1.42), (Al-11)+(B1.43), (Al-11)+(B1.44), (Al-11)+(B1.45), (Al-11)+(B1.46), (Al-11)+(B1.47), (Al-11)+(B1.48), (Al-11)+(B1.49), (Al-11)+(B1.50), (Al-11)+(B1.51), (Al-11)+(B1.52), (Al-11)+(B1.53), (Al-11)+(B1.54), (Al-11)+(B1.55), (Al-11)+(B1.56), (Al-11)+(B1.57), (Al-11)+(B1.58), (Al-11)+(B1.59), (Al-11)+(B1.60), (Al-11)+(B1.61), (Al-11)+(B1.62), (Al-11)+(B1.63), (Al-11)+(B1.64), (Al-11)+(B1.65), (Al-11)+(B1.66), (Al-11)+(B2.1), (Al-11)+(B2.2), (Al-11)+(B2.3), (Al-11)+(B2.4), (Al-11)+(B2.5), (Al-11)+(B2.6), (Al-11)+(B2.7), (Al-11)+(B2.8), (Al-11)+(B2.9), (Al-11)+(B2.10), (Al-11)+(B2.11), (Al-11)+(B2.12), (Al-11)+(B2.13), (Al-11)+(B2.14), (Al-11)+(B2.15), (Al-11)+(B2.16), (Al-11)+(B2.17), (Al-11)+(B2.18), (Al-11)+(B2.19), (Al-11)+(B2.20), (Al-11)+(B2.21), (Al-11)+(B2.22), (Al-11)+(B2.23), (Al-11)+(B2.24), (Al-11)+(B2.25), (Al-11)+(B2.26), (Al-11)+(B2.27), (Al-11)+(B2.28), (Al-11)+(B2.29), (Al-11)+(B2.30), (Al-11)+(B2.31), (Al-11)+(B2.32), (Al-11)+(B2.33), (Al-11)+(B2.34), (Al-11)+(B2.35), (Al-11)+(B2.36), (Al-11)+(B2.37), (Al-11)+(B2.38), (Al-11)+(B2.39), (Al-11)+(B2.40), (Al-11)+(B2.41), (Al-11)+(B2.42), (Al-11)+(B2.43), (Al-11)+(B2.44), (Al-11)+(B2.45), (Al-11)+(B2.46), (Al-11)+(B2.47), (Al-11)+(B2.48), (Al-11)+(B2.49), (Al-11)+(B2.50), (Al-11)+(B3.1), (Al-11)+(B3.2.), (Al-11)+(B3.3), (Al-11)+(B3.4), (Al-11)+(B3.5), (Al-11)+(B3.6), (Al-11)+(B3.7), (Al-11)+(B3.8), (Al-11)+(B3.9), (Al-11)+(B3.10), (Al-11)+(B3.11), (Al-11)+(B3.12), (Al-11)+(B3.13), (Al-11)+(B3.14), (Al-11)+(B3.15), (Al-11)+(B3.16), (Al-11)+(B4.1), (Al-11)+(B4.2), (Al-11)+(B4.3), (Al-11)+(B4.4), (Al-11)+(B4.5), (Al-11)+(B4.6), (Al-11)+(B4.7).

(Al-12)+(B1.1), (Al-12)+(B1.2), (Al-12)+(B1.3), (Al-12)+(B1.4), (Al-12)+(B1.5), (Al-12)+(B1.6), (Al-12)+(B1.7), (Al-12)+(B1.8), (Al-12)+(B1.9), (Al-12)+(B1.10), (Al-12)+(B1.11), (Al-12)+(B1.12), (Al-12)+(B1.13), (Al-12)+(B1.14), (Al-12)+(B1.15), (Al-12)+(B1.16), (Al-12)+(B1.17), (Al-12)+(B1.18), (Al-12)+(B1.19), (Al-12)+(B1.20), (Al-12)+(B1.21), (Al-12)+(B1.22), (Al-12)+(B1.23), (Al-12)+(B1.24), (Al-12)+(B1.25), (Al-12)+(B1.26), (Al-12)+(B1.27), (Al-12)+(B1.28), (Al-12)+(B1.29), (Al-12)+(B1.30), (Al-12)+(B1.31), (Al-12)+(B1.32), (Al-12)+(B1.33), (Al-12)+(B1.34), (Al-12)+(B1.35), (Al-12)+(B1.36), (Al-12)+(B1.37), (Al-12)+(B1.38), (Al-12)+(B1.39), (Al-12)+(B1.40), (Al-12)+(B1.41), (Al-12)+(B1.42), (Al-12)+(B1.43), (Al-12)+(B1.44), (Al-12)+(B1.45), (Al-12)+(B1.46), (Al-12)+(B1.47), (Al-12)+(B1.48), (Al-12)+(B1.49), (Al-12)+(B1.50), (Al-12)+(B1.51), (Al-12)+(B1.52), (Al-12)+(B1.53), (Al-12)+(B1.54), (Al-12)+(B1.55), (Al-12)+(B1.56), (Al-12)+(B1.57), (Al-12)+(B1.58), (Al-12)+(B1.59), (Al-12)+(B1.60), (Al-12)+(B1.61), (Al-12)+(B1.62), (Al-12)+(B1.63), (Al-12)+(B1.64), (Al-12)+(B1.65), (Al-12)+(B1.66), (Al-12)+(B2.1), (Al-12)+(B2.2), (Al-12)+(B2.3), (Al-12)+(B2.4), (Al-12)+(B2.5), (Al-12)+(B2.6), (Al-12)+(B2.7), (Al-12)+(B2.8), (Al-12)+(B2.9), (Al-12)+(B2.10), (Al-12)+(B2.11), (Al-12)+(B2.12), (Al-12)+(B2.13), (Al-12)+(B2.14), (Al-12)+(B2.15), (Al-12)+(B2.16), (Al-12)+(B2.17), (Al-12)+(B2.18), (Al-12)+(B2.19), (Al-12)+(B2.20), (Al-12)+(B2.21), (Al-12)+(B2.22), (Al-12)+(B2.23), (Al-12)+(B2.24), (Al-12)+(B2.25), (Al-12)+(B2.26), (Al-12)+(B2.27), (Al-12)+(B2.28), (Al-12)+(B2.29), (Al-12)+(B2.30), (Al-12)+(B2.31), (Al-12)+(B2.32), (Al-12)+(B2.33), (Al-12)+(B2.34), (Al-12)+(B2.35), (Al-12)+(B2.36), (Al-12)+(B2.37), (Al-12)+(B2.38), (Al-12)+(B2.39), (Al-12)+(B2.40), (Al-12)+(B2.41), (Al-12)+(B2.42), (Al-12)+(B2.43), (Al-12)+(B2.44), (Al-12)+(B2.45), (Al-12)+(B2.46), (Al-12)+(B2.47), (Al-12)+(B2.48), (Al-12)+(B2.49), (Al-12)+(B2.50), (Al-12)+(B3.1), (Al-12)+(B3.2.), (Al-12)+(B3.3), (Al-12)+(B3.4), (Al-12)+(B3.5), (Al-12)+(B3.6), (Al-12)+(B3.7), (Al-12)+(B3.8), (Al-12)+(B3.9), (Al-12)+(B3.10), (Al-12)+(B3.11), (Al-12)+(B3.12), (Al-12)+(B3.13), (Al-12)+(B3.14), (Al-12)+(B3.15), (Al-12)+(B3.16), (Al-12)+(B4.1), (Al-12)+(B4.2), (Al-12)+(B4.3), (Al-12)+(B4.4), (Al-12)+(B4.5), (Al-12)+(B4.6), (Al-12)+(B4.7).

(Al-13)+(B1.1), (Al-13)+(B1.2), (Al-13)+(B1.3), (Al-13)+(B1.4), (Al-13)+(B1.5), (Al-13)+(B1.6), (Al-13)+(B1.7), (Al-13)+(B1.8), (Al-13)+(B1.9), (Al-13)+(B1.10), (Al-13)+(B1.11), (Al-13)+(B1.12), (Al-13)+(B1.13), (Al-13)+(B1.14), (Al-13)+(B1.15), (Al-13)+(B1.16), (Al-13)+(B1.17), (Al-13)+(B1.18), (Al-13)+(B1.19), (Al-13)+(B1.20), (Al-13)+(B1.21), (Al-13)+(B1.22), (Al-13)+(B1.23), (Al-13)+(B1.24), (Al-13)+(B1.25), (Al-13)+(B1.26), (Al-13)+(B1.27), (Al-13)+(B1.28), (Al-13)+(B1.29), (Al-13)+(B1.30), (Al-13)+(B1.31), (Al-13)+(B1.32), (Al-13)+(B1.33), (Al-13)+(B1.34), (Al-13)+(B1.35), (Al-13)+(B1.36), (Al-13)+(B1.37), (Al-13)+(B1.38), (Al-13)+(B1.39), (Al-13)+(B1.40), (Al-13)+(B1.41), (Al-13)+(B1.42), (Al-13)+(B1.43), (Al-13)+(B1.44), (Al-13)+(B1.45), (Al-13)+(B1.46), (Al-13)+(B1.47), (Al-13)+(B1.48), (Al-13)+(B1.49), (Al-13)+(B1.50), (Al-13)+(B1.51), (Al-13)+(B1.52), (Al-13)+(B1.53), (Al-13)+(B1.54), (Al-13)+(B1.55), (Al-13)+(B1.56), (Al-13)+(B1.57), (Al-13)+(B1.58), (Al-13)+(B1.59), (Al-13)+(B1.60), (Al-13)+(B1.61), (Al-13)+(B1.62), (Al-13)+(B1.63), (Al-13)+(B1.64), (Al-13)+(B1.65), (Al-13)+(B1.66), (Al-13)+(B2.1), (Al-13)+(B2.2), (Al-13)+(B2.3), (Al-13)+(B2.4), (Al-13)+(B2.5), (Al-13)+(B2.6), (Al-13)+(B2.7), (Al-13)+(B2.8), (Al-13)+(B2.9), (Al-13)+(B2.10), (Al-13)+(B2.11), (Al-13)+(B2.12), (Al-13)+(B2.13), (Al-13)+(B2.14), (Al-13)+(B2.15), (Al-13)+(B2.16), (Al-13)+(B2.17), (Al-13)+(B2.18), (Al-13)+(B2.19), (Al-13)+(B2.20), (Al-13)+(B2.21), (Al-13)+(B2.22), (Al-13)+(B2.23), (Al-13)+(B2.24), (Al-13)+(B2.25), (Al-13)+(B2.26), (Al-13)+(B2.27), (Al-13)+(B2.28), (Al-13)+(B2.29), (Al-13)+(B2.30), (Al-13)+(B2.31), (Al-13)+(B2.32), (Al-13)+(B2.33), (Al-13)+(B2.34), (Al-13)+(B2.35), (Al-13)+(B2.36), (Al-13)+(B2.37), (Al-13)+(B2.38), (Al-13)+(B2.39), (Al-13)+(B2.40), (Al-13)+(B2.41), (Al-13)+(B2.42), (Al-13)+(B2.43), (Al-13)+(B2.44), (Al-13)+(B2.45), (Al-13)+(B2.46), (Al-13)+(B2.47), (Al-13)+(B2.48), (Al-13)+(B2.49), (Al-13)+(B2.50), (Al-13)+(B3.1), (Al-13)+(B3.2.), (Al-13)+(B3.3), (Al-13)+(B3.4), (Al-13)+(B3.5), (Al-13)+(B3.6), (Al-13)+(B3.7), (Al-13)+(B3.8), (Al-13)+(B3.9), (Al-13)+(B3.10), (Al-13)+(B3.11), (Al-13)+(B3.12), (Al-13)+(B3.13), (Al-13)+(B3.14), (Al-13)+(B3.15), (Al-13)+(B3.16), (Al-13)+(B4.1), (Al-13)+(B4.2), (Al-13)+(B4.3), (Al-13)+(B4.4), (Al-13)+(B4.5), (Al-13)+(B4.6), (Al-13)+(B4.7).

(Al-14)+(B1.1), (Al-14)+(B1.2), (Al-14)+(B1.3), (Al-14)+(B1.4), (Al-14)+(B1.5), (Al-14)+(B1.6), (Al-14)+(B1.7), (Al-14)+(B1.8), (Al-14)+(B1.9), (Al-14)+(B1.10), (Al-14)+(B1.11), (Al-14)+(B1.12), (Al-14)+(B1.13), (Al-14)+(B1.14), (Al-14)+(B1.15), (Al-14)+(B1.16), (Al-14)+(B1.17), (Al-14)+(B1.18), (Al-14)+(B1.19), (Al-14)+(B1.20), (Al-14)+(B1.21), (Al-14)+(B1.22), (Al-14)+(B1.23), (Al-14)+(B1.24), (Al-14)+(B1.25), (Al-14)+(B1.26), (Al-14)+(B1.27), (Al-14)+(B1.28), (Al-14)+(B1.29), (Al-14)+(B1.30), (Al-14)+(B1.31), (Al-14)+(B1.32), (Al-14)+(B1.33), (Al-14)+(B1.34), (Al-14)+(B1.35), (Al-14)+(B1.36), (Al-14)+(B1.37), (Al-14)+(B1.38), (Al-14)+(B1.39), (Al-14)+(B1.40), (Al-14)+(B1.41), (Al-14)+(B1.42), (Al-14)+(B1.43), (Al-14)+(B1.44), (Al-14)+(B1.45), (Al-14)+(B1.46), (Al-14)+(B1.47), (Al-14)+(B1.48), (Al-14)+(B1.49), (Al-14)+(B1.50), (Al-14)+(B1.51), (Al-14)+(B1.52), (Al-14)+(B1.53), (Al-14)+(B1.54), (Al-14)+(B1.55), (Al-14)+(B1.56), (Al-14)+(B1.57), (Al-14)+(B1.58), (Al-14)+(B1.59), (Al-14)+(B1.60), (Al-14)+(B1.61), (Al-14)+(B1.62), (Al-14)+(B1.63), (Al-14)+(B1.64), (Al-14)+(B1.65), (Al-14)+(B1.66), (Al-14)+(B2.1), (Al-14)+(B2.2), (Al-14)+(B2.3), (Al-14)+(B2.4), (Al-14)+(B2.5), (Al-14)+(B2.6), (Al-14)+(B2.7), (Al-14)+(B2.8), (Al-14)+(B2.9), (Al-14)+(B2.10), (Al-14)+(B2.11), (Al-14)+(B2.12), (Al-14)+(B2.13), (Al-14)+(B2.14), (Al-14)+(B2.15), (Al-14)+(B2.16), (Al-14)+(B2.17), (Al-14)+(B2.18), (Al-14)+(B2.19), (Al-14)+(B2.20), (Al-14)+(B2.21), (Al-14)+(B2.22), (Al-14)+(B2.23), (Al-14)+(B2.24), (Al-14)+(B2.25), (Al-14)+(B2.26), (Al-14)+(B2.27), (Al-14)+(B2.28), (Al-14)+(B2.29), (Al-14)+(B2.30), (Al-14)+(B2.31), (Al-14)+(B2.32), (Al-14)+(B2.33), (Al-14)+(B2.34), (Al-14)+(B2.35), (Al-14)+(B2.36), (Al-14)+(B2.37), (Al-14)+(B2.38), (Al-14)+(B2.39), (Al-14)+(B2.40), (Al-14)+(B2.41), (Al-14)+(B2.42), (Al-14)+(B2.43), (Al-14)+(B2.44), (Al-14)+(B2.45), (Al-14)+(B2.46), (Al-14)+(B2.47), (Al-14)+(B2.48), (Al-14)+(B2.49), (Al-14)+(B2.50), (Al-14)+(B3.1), (Al-14)+(B3.2.), (Al-14)+(B3.3), (Al-14)+(B3.4), (Al-14)+(B3.5), (Al-14)+(B3.6), (Al-14)+(B3.7), (Al-14)+(B3.8), (Al-14)+(B3.9), (Al-14)+(B3.10), (Al-14)+(B3.11), (Al-14)+(B3.12), (Al-14)+(B3.13), (Al-14)+(B3.14), (Al-14)+(B3.15), (Al-14)+(B3.16), (Al-14)+(B4.1), (Al-14)+(B4.2), (Al-14)+(B4.3), (Al-14)+(B4.4), (Al-14)+(B4.5), (Al-14)+(B4.6), (Al-14)+(B4.7).

(Al-15)+(B1.1), (Al-15)+(B1.2), (Al-15)+(B1.3), (Al-15)+(B1.4), (Al-15)+(B1.5), (Al-15)+(B1.6), (Al-15)+(B1.7), (Al-15)+(B1.8), (Al-15)+(B1.9), (Al-15)+(B1.10), (Al-15)+(B1.11), (Al-15)+(B1.12), (Al-15)+(B1.13), (Al-15)+(B1.14), (Al-15)+(B1.15), (Al-15)+(B1.16), (Al-15)+(B1.17), (Al-15)+(B1.18), (Al-15)+(B1.19), (Al-15)+(B1.20), (Al-15)+(B1.21), (Al-15)+(B1.22), (Al-15)+(B1.23), (Al-15)+(B1.24), (Al-15)+(B1.25), (Al-15)+(B1.26), (Al-15)+(B1.27), (Al-15)+(B1.28), (Al-15)+(B1.29), (Al-15)+(B1.30), (Al-15)+(B1.31), (Al-15)+(B1.32), (Al-15)+(B1.33), (Al-15)+(B1.34), (Al-15)+(B1.35), (Al-15)+(B1.36), (Al-15)+(B1.37), (Al-15)+(B1.38), (Al-15)+(B1.39), (Al-15)+(B1.40), (Al-15)+(B1.41), (Al-15)+(B1.42), (Al-15)+(B1.43), (Al-15)+(B1.44), (Al-15)+(B1.45), (Al-15)+(B1.46), (Al-15)+(B1.47), (Al-15)+(B1.48), (Al-15)+(B1.49), (Al-15)+(B1.50), (Al-15)+(B1.51), (Al-15)+(B1.52), (Al-15)+(B1.53), (Al-15)+(B1.54), (Al-15)+(B1.55), (Al-15)+(B1.56), (Al-15)+(B1.57), (Al-15)+(B1.58), (Al-15)+(B1.59), (Al-15)+(B1.60), (Al-15)+(B1.61), (Al-15)+(B1.62), (Al-15)+(B1.63), (Al-15)+(B1.64), (Al-15)+(B1.65), (Al-15)+(B1.66), (Al-15)+(B2.1), (Al-15)+(B2.2), (Al-15)+(B2.3), (Al-15)+(B2.4), (Al-15)+(B2.5), (Al-15)+(B2.6), (Al-15)+(B2.7), (Al-15)+(B2.8), (Al-15)+(B2.9), (Al-15)+(B2.10), (Al-15)+(B2.11), (Al-15)+(B2.12), (Al-15)+(B2.13), (Al-15)+(B2.14), (Al-15)+(B2.15), (Al-15)+(B2.16), (Al-15)+(B2.17), (Al-15)+(B2.18), (Al-15)+(B2.19), (Al-15)+(B2.20), (Al-15)+(B2.21), (Al-15)+(B2.22), (Al-15)+(B2.23), (Al-15)+(B2.24), (Al-15)+(B2.25), (Al-15)+(B2.26), (Al-15)+(B2.27), (Al-15)+(B2.28), (Al-15)+(B2.29), (Al-15)+(B2.30), (Al-15)+(B2.31), (Al-15)+(B2.32), (Al-15)+(B2.33), (Al-15)+(B2.34), (Al-15)+(B2.35), (Al-15)+(B2.36), (Al-15)+(B2.37), (Al-15)+(B2.38), (Al-15)+(B2.39), (Al-15)+(B2.40), (Al-15)+(B2.41), (Al-15)+(B2.42), (Al-15)+(B2.43), (Al-15)+(B2.44), (Al-15)+(B2.45), (Al-15)+(B2.46), (Al-15)+(B2.47), (Al-15)+(B2.48), (Al-15)+(B2.49), (Al-15)+(B2.50), (Al-15)+(B3.1), (Al-15)+(B3.2.), (Al-15)+(B3.3), (Al-15)+(B3.4), (Al-15)+(B3.5), (Al-15)+(B3.6), (Al-15)+(B3.7), (Al-15)+(B3.8), (Al-15)+(B3.9), (Al-15)+(B3.10), (Al-15)+(B3.11), (Al-15)+(B3.12), (Al-15)+(B3.13), (Al-15)+(B3.14), (Al-15)+(B3.15), (Al-15)+(B3.16), (Al-15)+(B4.1), (Al-15)+(B4.2), (Al-15)+(B4.3), (Al-15)+(B4.4), (Al-15)+(B4.5), (Al-15)+(B4.6), (Al-15)+(B4.7).

(Al-16)+(B1.1), (Al-16)+(B1.2), (Al-16)+(B1.3), (Al-16)+(B1.4), (Al-16)+(B1.5), (Al-16)+(B1.6), (Al-16)+(B1.7), (Al-16)+(B1.8), (Al-16)+(B1.9), (Al-16)+(B1.10), (Al-16)+(B1.11), (Al-16)+(B1.12), (Al-16)+(B1.13), (Al-16)+(B1.14), (Al-16)+(B1.15), (Al-16)+(B1.16), (Al-16)+(B1.17), (Al-16)+(B1.18), (Al-16)+(B1.19), (Al-16)+(B1.20), (Al-16)+(B1.21), (Al-16)+(B1.22), (Al-16)+(B1.23), (Al-16)+(B1.24), (Al-16)+(B1.25), (Al-16)+(B1.26), (Al-16)+(B1.27), (Al-16)+(B1.28), (Al-16)+(B1.29), (Al-16)+(B1.30), (Al-16)+(B1.31), (Al-16)+(B1.32), (Al-16)+(B1.33), (Al-16)+(B1.34), (Al-16)+(B1.35), (Al-16)+(B1.36), (Al-16)+(B1.37), (Al-16)+(B1.38), (Al-16)+(B1.39), (Al-16)+(B1.40), (Al-16)+(B1.41), (Al-16)+(B1.42), (Al-16)+(B1.43), (Al-16)+(B1.44), (Al-16)+(B1.45), (Al-16)+(B1.46), (Al-16)+(B1.47), (Al-16)+(B1.48), (Al-16)+(B1.49), (Al-16)+(B1.50), (Al-16)+(B1.51), (Al-16)+(B1.52), (Al-16)+(B1.53), (Al-16)+(B1.54), (Al-16)+(B1.55), (Al-16)+(B1.56), (Al-16)+(B1.57), (Al-16)+(B1.58), (Al-16)+

(B1.59), (Al-16)+(B1.60), (Al-16)+(B1.61), (Al-16)+(B1.62), (Al-16)+(B1.63), (Al-16)+(B1.64), (Al-16)+(B1.65), (Al-16)+(B1.66), (Al-16)+(B2.1), (Al-16)+(B2.2), (Al-16)+(B2.3), (Al-16)+(B2.4), (Al-16)+(B2.5), (Al-16)+(B2.6), (Al-16)+(B2.7), (Al-16)+(B2.8), (Al-16)+(B2.9), (Al-16)+(B2.10), (Al-16)+(B2.11), (Al-16)+(B2.12), (Al-16)+(B2.13), (Al-16)+(B2.14), (Al-16)+(B2.15), (Al-16)+(B2.16), (Al-16)+(B2.17), (Al-16)+(B2.18), (Al-16)+(B2.19), (Al-16)+(B2.20), (Al-16)+(B2.21), (Al-16)+(B2.22), (Al-16)+(B2.23), (Al-16)+(B2.24), (Al-16)+(B2.25), (Al-16)+(B2.26), (Al-16)+(B2.27), (Al-16)+(B2.28), (Al-16)+(B2.29), (Al-16)+(B2.30), (Al-16)+(B2.31), (Al-16)+(B2.32), (Al-16)+(B2.33), (Al-16)+(B2.34), (Al-16)+(B2.35), (Al-16)+(B2.36), (Al-16)+(B2.37), (Al-16)+(B2.38), (Al-16)+(B2.39), (Al-16)+(B2.40), (Al-16)+(B2.41), (Al-16)+(B2.42), (Al-16)+(B2.43), (Al-16)+(B2.44), (Al-16)+(B2.45), (Al-16)+(B2.46), (Al-16)+(B2.47), (Al-16)+(B2.48), (Al-16)+(B2.49), (Al-16)+(B2.50), (Al-16)+(B3.1), (Al-16)+(B3.2.), (Al-16)+(B3.3), (Al-16)+(B3.4), (Al-16)+(B3.5), (Al-16)+(B3.6), (Al-16)+(B3.7), (Al-16)+(B3.8), (Al-16)+(B3.9), (Al-16)+(B3.10), (Al-16)+(B3.11), (Al-16)+(B3.12), (Al-16)+(B3.13), (Al-16)+(B3.14), (Al-16)+(B3.15), (Al-16)+(B3.16), (Al-16)+(B4.1), (Al-16)+(B4.2), (Al-16)+(B4.3), (Al-16)+(B4.4), (Al-16)+(B4.5), (Al-16)+(B4.6), (Al-16)+(B4.7).

(Al-17)+(B1.1), (Al-17)+(B1.2), (Al-17)+(B1.3), (Al-17)+(B1.4), (Al-17)+(B1.5), (Al-17)+(B1.6), (Al-17)+(B1.7), (Al-17)+(B1.8), (Al-17)+(B1.9), (Al-17)+(B1.10), (Al-17)+(B1.11), (Al-17)+(B1.12), (Al-17)+(B1.13), (Al-17)+(B1.14), (Al-17)+(B1.15), (Al-17)+(B1.16), (Al-17)+(B1.17), (Al-17)+(B1.18), (Al-17)+(B1.19), (Al-17)+(B1.20), (Al-17)+(B1.21), (Al-17)+(B1.22), (Al-17)+(B1.23), (Al-17)+(B1.24), (Al-17)+(B1.25), (Al-17)+(B1.26), (Al-17)+(B1.27), (Al-17)+(B1.28), (Al-17)+(B1.29), (Al-17)+(B1.30), (Al-17)+(B1.31), (Al-17)+(B1.32), (Al-17)+(B1.33), (Al-17)+(B1.34), (Al-17)+(B1.35), (Al-17)+(B1.36), (Al-17)+(B1.37), (Al-17)+(B1.38), (Al-17)+(B1.39), (Al-17)+(B1.40), (Al-17)+(B1.41), (Al-17)+(B1.42), (Al-17)+(B1.43), (Al-17)+(B1.44), (Al-17)+(B1.45), (Al-17)+(B1.46), (Al-17)+(B1.47), (Al-17)+(B1.48), (Al-17)+(B1.49), (Al-17)+(B1.50), (Al-17)+(B1.51), (Al-17)+(B1.52), (Al-17)+(B1.53), (Al-17)+(B1.54), (Al-17)+(B1.55), (Al-17)+(B1.56), (Al-17)+(B1.57), (Al-17)+(B1.58), (Al-17)+(B1.59), (Al-17)+(B1.60), (Al-17)+(B1.61), (Al-17)+(B1.62), (Al-17)+(B1.63), (Al-17)+(B1.64), (Al-17)+(B1.65), (Al-17)+(B1.66), (Al-17)+(B2.1), (Al-17)+(B2.2), (Al-17)+(B2.3), (Al-17)+(B2.4), (Al-17)+(B2.5), (Al-17)+(B2.6), (Al-17)+(B2.7), (Al-17)+(B2.8), (Al-17)+(B2.9), (Al-17)+(B2.10), (Al-17)+(B2.11), (Al-17)+(B2.12), (Al-17)+(B2.13), (Al-17)+(B2.14), (Al-17)+(B2.15), (Al-17)+(B2.16), (Al-17)+(B2.17), (Al-17)+(B2.18), (Al-17)+(B2.19), (Al-17)+(B2.20), (Al-17)+(B2.21), (Al-17)+(B2.22), (Al-17)+(B2.23), (Al-17)+(B2.24), (Al-17)+(B2.25), (Al-17)+(B2.26), (Al-17)+(B2.27), (Al-17)+(B2.28), (Al-17)+(B2.29), (Al-17)+(B2.30), (Al-17)+(B2.31), (Al-17)+(B2.32), (Al-17)+(B2.33), (Al-17)+(B2.34), (Al-17)+(B2.35), (Al-17)+(B2.36), (Al-17)+(B2.37), (Al-17)+(B2.38), (Al-17)+(B2.39), (Al-17)+(B2.40), (Al-17)+(B2.41), (Al-17)+(B2.42), (Al-17)+(B2.43), (Al-17)+(B2.44), (Al-17)+(B2.45), (Al-17)+(B2.46), (Al-17)+(B2.47), (Al-17)+(B2.48), (Al-17)+(B2.49), (Al-17)+(B2.50), (Al-17)+(B3.1), (Al-17)+(B3.2.), (Al-17)+(B3.3), (Al-17)+(B3.4), (Al-17)+(B3.5), (Al-17)+(B3.6), (Al-17)+(B3.7), (Al-17)+(B3.8), (Al-17)+(B3.9), (Al-17)+(B3.10), (Al-17)+(B3.11), (Al-17)+(B3.12), (Al-17)+(B3.13), (Al-17)+(B3.14), (Al-17)+(B3.15), (Al-17)+(B3.16), (Al-17)+(B4.1), (Al-17)+(B4.2), (Al-17)+(B4.3), (Al-17)+(B4.4), (Al-17)+(B4.5), (Al-17)+(B4.6), (Al-17)+(B4.7).

(Al-18)+(B1.1), (Al-18)+(B1.2), (Al-18)+(B1.3), (Al-18)+(B1.4), (Al-18)+(B1.5), (Al-18)+(B1.6), (Al-18)+(B1.7), (Al-18)+(B1.8), (Al-18)+(B1.9), (Al-18)+(B1.10), (Al-18)+(B1.11), (Al-18)+(B1.12), (Al-18)+(B1.13), (Al-18)+(B1.14), (Al-18)+(B1.15), (Al-18)+(B1.16), (Al-18)+(B1.17), (Al-18)+(B1.18), (Al-18)+(B1.19), (Al-18)+(B1.20), (Al-18)+(B1.21), (Al-18)+(B1.22), (Al-18)+(B1.23), (Al-18)+(B1.24), (Al-18)+(B1.25), (Al-18)+(B1.26), (Al-18)+(B1.27), (Al-18)+(B1.28), (Al-18)+(B1.29), (Al-18)+(B1.30), (Al-18)+(B1.31), (Al-18)+(B1.32), (Al-18)+(B1.33), (Al-18)+(B1.34), (Al-18)+(B1.35), (Al-18)+(B1.36), (Al-18)+(B1.37), (Al-18)+(B1.38), (Al-18)+(B1.39), (Al-18)+(B1.40), (Al-18)+(B1.41), (Al-18)+(B1.42), (Al-18)+(B1.43), (Al-18)+(B1.44), (Al-18)+(B1.45), (Al-18)+(B1.46), (Al-18)+(B1.47), (Al-18)+(B1.48), (Al-18)+(B1.49), (Al-18)+(B1.50), (Al-18)+(B1.51), (Al-18)+(B1.52), (Al-18)+(B1.53), (Al-18)+(B1.54), (Al-18)+(B1.55), (Al-18)+(B1.56), (Al-18)+(B1.57), (Al-18)+(B1.58), (Al-18)+(B1.59), (Al-18)+(B1.60), (Al-18)+(B1.61), (Al-18)+(B1.62), (Al-18)+(B1.63), (Al-18)+(B1.64), (Al-18)+(B1.65), (Al-18)+(B1.66), (Al-18)+(B2.1), (Al-18)+(B2.2), (Al-18)+(B2.3), (Al-18)+(B2.4), (Al-18)+(B2.5), (Al-18)+(B2.6), (Al-18)+(B2.7), (Al-18)+(B2.8), (Al-18)+(B2.9), (Al-18)+(B2.10), (Al-18)+(B2.11), (Al-18)+(B2.12), (Al-18)+(B2.13), (Al-18)+(B2.14), (Al-18)+(B2.15), (Al-18)+(B2.16), (Al-18)+(B2.17), (Al-18)+(B2.18), (Al-18)+(B2.19), (Al-18)+(B2.20), (Al-18)+(B2.21), (Al-18)+(B2.22), (Al-18)+(B2.23), (Al-18)+(B2.24), (Al-18)+(B2.25), (Al-18)+(B2.26), (Al-18)+(B2.27), (Al-18)+(B2.28), (Al-18)+(B2.29), (Al-18)+(B2.30), (Al-18)+(B2.31), (Al-18)+(B2.32), (Al-18)+(B2.33), (Al-18)+(B2.34), (Al-18)+(B2.35), (Al-18)+(B2.36), (Al-18)+(B2.37), (Al-18)+(B2.38), (Al-18)+(B2.39), (Al-18)+(B2.40), (Al-18)+(B2.41), (Al-18)+(B2.42), (Al-18)+(B2.43), (Al-18)+(B2.44), (Al-18)+(B2.45), (Al-18)+(B2.46), (Al-18)+(B2.47), (Al-18)+(B2.48), (Al-18)+(B2.49), (Al-18)+(B2.50), (Al-18)+(B3.1), (Al-18)+(B3.2.), (Al-18)+(B3.3), (Al-18)+(B3.4), (Al-18)+(B3.5), (Al-18)+(B3.6), (Al-18)+(B3.7), (Al-18)+(B3.8), (Al-18)+(B3.9), (Al-18)+(B3.10), (Al-18)+(B3.11), (Al-18)+(B3.12), (Al-18)+(B3.13), (Al-18)+(B3.14), (Al-18)+(B3.15), (Al-18)+(B3.16), (Al-18)+(B4.1), (Al-18)+(B4.2), (Al-18)+(B4.3), (Al-18)+(B4.4), (Al-18)+(B4.5), (Al-18)+(B4.6), (Al-18)+(B4.7).

(Al-19)+(B1.1), (Al-19)+(B1.2), (Al-19)+(B1.3), (Al-19)+(B1.4), (Al-19)+(B1.5), (Al-19)+(B1.6), (Al-19)+(B1.7), (Al-19)+(B1.8), (Al-19)+(B1.9), (Al-19)+(B1.10), (Al-19)+(B1.11), (Al-19)+(B1.12), (Al-19)+(B1.13), (Al-19)+(B1.14), (Al-19)+(B1.15), (Al-19)+(B1.16), (Al-19)+(B1.17), (Al-19)+(B1.18), (Al-19)+(B1.19), (Al-19)+(B1.20), (Al-19)+(B1.21), (Al-19)+(B1.22), (Al-19)+(B1.23), (Al-19)+(B1.24), (Al-19)+(B1.25), (Al-19)+(B1.26), (Al-19)+(B1.27), (Al-19)+(B1.28), (Al-19)+(B1.29), (Al-19)+(B1.30), (Al-19)+(B1.31), (Al-19)+(B1.32), (Al-19)+(B1.33), (Al-19)+(B1.34), (Al-19)+(B1.35), (Al-19)+(B1.36), (Al-19)+(B1.37), (Al-19)+(B1.38), (Al-19)+(B1.39), (Al-19)+(B1.40), (Al-19)+(B1.41), (Al-19)+(B1.42), (Al-19)+(B1.43), (Al-19)+(B1.44), (Al-19)+(B1.45), (Al-19)+(B1.46), (Al-19)+(B1.47), (Al-19)+(B1.48), (Al-19)+(B1.49), (Al-19)+(B1.50), (Al-19)+(B1.51), (Al-19)+(B1.52), (Al-19)+(B1.53), (Al-19)+(B1.54), (Al-19)+(B1.55), (Al-19)+

(B1.56), (Al-19)+(B1.57), (Al-19)+(B1.58), (Al-19)+(B1.59), (Al-19)+(B1.60), (Al-19)+(B1.61), (Al-19)+(B1.62), (Al-19)+(B1.63), (Al-19)+(B1.64), (Al-19)+(B1.65), (Al-19)+(B1.66), (Al-19)+(B2.1), (Al-19)+(B2.2), (Al-19)+(B2.3), (Al-19)+(B2.4), (Al-19)+(B2.5), (Al-19)+(B2.6), (Al-19)+(B2.7), (Al-19)+(B2.8), (Al-19)+(B2.9), (Al-19)+(B2.10), (Al-19)+(B2.11), (Al-19)+(B2.12), (Al-19)+(B2.13), (Al-19)+(B2.14), (Al-19)+(B2.15), (Al-19)+(B2.16), (Al-19)+(B2.17), (Al-19)+(B2.18), (Al-19)+(B2.19), (Al-19)+(B2.20), (Al-19)+(B2.21), (Al-19)+(B2.22), (Al-19)+(B2.23), (Al-19)+(B2.24), (Al-19)+(B2.25), (Al-19)+(B2.26), (Al-19)+(B2.27), (Al-19)+(B2.28), (Al-19)+(B2.29), (Al-19)+(B2.30), (Al-19)+(B2.31), (Al-19)+(B2.32), (Al-19)+(B2.33), (Al-19)+(B2.34), (Al-19)+(B2.35), (Al-19)+(B2.36), (Al-19)+(B2.37), (Al-19)+(B2.38), (Al-19)+(B2.39), (Al-19)+(B2.40), (Al-19)+(B2.41), (Al-19)+(B2.42), (Al-19)+(B2.43), (Al-19)+(B2.44), (Al-19)+(B2.45), (Al-19)+(B2.46), (Al-19)+(B2.47), (Al-19)+(B2.48), (Al-19)+(B2.49), (Al-19)+(B2.50), (Al-19)+(B3.1), (Al-19)+(B3.2.), (Al-19)+(B3.3), (Al-19)+(B3.4), (Al-19)+(B3.5), (Al-19)+(B3.6), (Al-19)+(B3.7), (Al-19)+(B3.8), (Al-19)+(B3.9), (Al-19)+(B3.10), (Al-19)+(B3.11), (Al-19)+(B3.12), (Al-19)+(B3.13), (Al-19)+(B3.14), (Al-19)+(B3.15), (Al-19)+(B3.16), (Al-19)+(B4.1), (Al-19)+(B4.2), (Al-19)+(B4.3), (Al-19)+(B4.4), (Al-19)+(B4.5), (Al-19)+(B4.6), (Al-19)+(B4.7).

(Al-20)+(B1.1), (Al-20)+(B1.2), (Al-20)+(B1.3), (Al-20)+(B1.4), (Al-20)+(B1.5), (Al-20)+(B1.6), (Al-20)+(B1.7), (Al-20)+(B1.8), (Al-20)+(B1.9), (Al-20)+(B1.10), (Al-20)+(B1.11), (Al-20)+(B1.12), (Al-20)+(B1.13), (Al-20)+(B1.14), (Al-20)+(B1.15), (Al-20)+(B1.16), (Al-20)+(B1.17), (Al-20)+(B1.18), (Al-20)+(B1.19), (Al-20)+(B1.20), (Al-20)+(B1.21), (Al-20)+(B1.22), (Al-20)+(B1.23), (Al-20)+(B1.24), (Al-20)+(B1.25), (Al-20)+(B1.26), (Al-20)+(B1.27), (Al-20)+(B1.28), (Al-20)+(B1.29), (Al-20)+(B1.30), (Al-20)+(B1.31), (Al-20)+(B1.32), (Al-20)+(B1.33), (Al-20)+(B1.34), (Al-20)+(B1.35), (Al-20)+(B1.36), (Al-20)+(B1.37), (Al-20)+(B1.38), (Al-20)+(B1.39), (Al-20)+(B1.40), (Al-20)+(B1.41), (Al-20)+(B1.42), (Al-20)+(B1.43), (Al-20)+(B1.44), (Al-20)+(B1.45), (Al-20)+(B1.46), (Al-20)+(B1.47), (Al-20)+(B1.48), (Al-20)+(B1.49), (Al-20)+(B1.50), (Al-20)+(B1.51), (Al-20)+(B1.52), (Al-20)+(B1.53), (Al-20)+(B1.54), (Al-20)+(B1.55), (Al-20)+(B1.56), (Al-20)+(B1.57), (Al-20)+(B1.58), (Al-20)+(B1.59), (Al-20)+(B1.60), (Al-20)+(B1.61), (Al-20)+(B1.62), (Al-20)+(B1.63), (Al-20)+(B1.64), (Al-20)+(B1.65), (Al-20)+(B1.66), (Al-20)+(B2.1), (Al-20)+(B2.2), (Al-20)+(B2.3), (Al-20)+(B2.4), (Al-20)+(B2.5), (Al-20)+(B2.6), (Al-20)+(B2.7), (Al-20)+(B2.8), (Al-20)+(B2.9), (Al-20)+(B2.10), (Al-20)+(B2.11), (Al-20)+(B2.12), (Al-20)+(B2.13), (Al-20)+(B2.14), (Al-20)+(B2.15), (Al-20)+(B2.16), (Al-20)+(B2.17), (Al-20)+(B2.18), (Al-20)+(B2.19), (Al-20)+(B2.20), (Al-20)+(B2.21), (Al-20)+(B2.22), (Al-20)+(B2.23), (Al-20)+(B2.24), (Al-20)+(B2.25), (Al-20)+(B2.26), (Al-20)+(B2.27), (Al-20)+(B2.28), (Al-20)+(B2.29), (Al-20)+(B2.30), (Al-20)+(B2.31), (Al-20)+(B2.32), (Al-20)+(B2.33), (Al-20)+(B2.34), (Al-20)+(B2.35), (Al-20)+(B2.36), (Al-20)+(B2.37), (Al-20)+(B2.38), (Al-20)+(B2.39), (Al-20)+(B2.40), (Al-20)+(B2.41), (Al-20)+(B2.42), (Al-20)+(B2.43), (Al-20)+(B2.44), (Al-20)+(B2.45), (Al-20)+(B2.46), (Al-20)+(B2.47), (Al-20)+(B2.48), (Al-20)+(B2.49), (Al-20)+(B2.50), (Al-20)+(B3.1), (Al-20)+(B3.2.), (Al-20)+(B3.3), (Al-20)+(B3.4), (Al-20)+(B3.5), (Al-20)+(B3.6), (Al-20)+(B3.7), (Al-20)+(B3.8), (Al-20)+(B3.9), (Al-20)+(B3.10), (Al-20)+(B3.11), (Al-20)+(B3.12), (Al-20)+(B3.13), (Al-20)+(B3.14), (Al-20)+(B3.15), (Al-20)+(B3.16), (Al-20)+(B4.1), (Al-20)+(B4.2), (Al-20)+(B4.3), (Al-20)+(B4.4), (Al-20)+(B4.5), (Al-20)+(B4.6), (Al-20)+(B4.7).

(Al-21)+(B1.1), (Al-21)+(B1.2), (Al-21)+(B1.3), (Al-21)+(B1.4), (Al-21)+(B1.5), (Al-21)+(B1.6), (Al-21)+(B1.7), (Al-21)+(B1.8), (Al-21)+(B1.9), (Al-21)+(B1.10), (Al-21)+(B1.11), (Al-21)+(B1.12), (Al-21)+(B1.13), (Al-21)+(B1.14), (Al-21)+(B1.15), (Al-21)+(B1.16), (Al-21)+(B1.17), (Al-21)+(B1.18), (Al-21)+(B1.19), (Al-21)+(B1.20), (Al-21)+(B1.21), (Al-21)+(B1.22), (Al-21)+(B1.23), (Al-21)+(B1.24), (Al-21)+(B1.25), (Al-21)+(B1.26), (Al-21)+(B1.27), (Al-21)+(B1.28), (Al-21)+(B1.29), (Al-21)+(B1.30), (Al-21)+(B1.31), (Al-21)+(B1.32), (Al-21)+(B1.33), (Al-21)+(B1.34), (Al-21)+(B1.35), (Al-21)+(B1.36), (Al-21)+(B1.37), (Al-21)+(B1.38), (Al-21)+(B1.39), (Al-21)+(B1.40), (Al-21)+(B1.41), (Al-21)+(B1.42), (Al-21)+(B1.43), (Al-21)+(B1.44), (Al-21)+(B1.45), (Al-21)+(B1.46), (Al-21)+(B1.47), (Al-21)+(B1.48), (Al-21)+(B1.49), (Al-21)+(B1.50), (Al-21)+(B1.51), (Al-21)+(B1.52), (Al-21)+(B1.53), (Al-21)+(B1.54), (Al-21)+(B1.55), (Al-21)+(B1.56), (Al-21)+(B1.57), (Al-21)+(B1.58), (Al-21)+(B1.59), (Al-21)+(B1.60), (Al-21)+(B1.61), (Al-21)+(B1.62), (Al-21)+(B1.63), (Al-21)+(B1.64), (Al-21)+(B1.65), (Al-21)+(B1.66), (Al-21)+(B2.1), (Al-21)+(B2.2), (Al-21)+(B2.3), (Al-21)+(B2.4), (Al-21)+(B2.5), (Al-21)+(B2.6), (Al-21)+(B2.7), (Al-21)+(B2.8), (Al-21)+(B2.9), (Al-21)+(B2.10), (Al-21)+(B2.11), (Al-21)+(B2.12), (Al-21)+(B2.13), (Al-21)+(B2.14), (Al-21)+(B2.15), (Al-21)+(B2.16), (Al-21)+(B2.17), (Al-21)+(B2.18), (Al-21)+(B2.19), (Al-21)+(B2.20), (Al-21)+(B2.21), (Al-21)+(B2.22), (Al-21)+(B2.23), (Al-21)+(B2.24), (Al-21)+(B2.25), (Al-21)+(B2.26), (Al-21)+(B2.27), (Al-21)+(B2.28), (Al-21)+(B2.29), (Al-21)+(B2.30), (Al-21)+(B2.31), (Al-21)+(B2.32), (Al-21)+(B2.33), (Al-21)+(B2.34), (Al-21)+(B2.35), (Al-21)+(B2.36), (Al-21)+(B2.37), (Al-21)+(B2.38), (Al-21)+(B2.39), (Al-21)+(B2.40), (Al-21)+(B2.41), (Al-21)+(B2.42), (Al-21)+(B2.43), (Al-21)+(B2.44), (Al-21)+(B2.45), (Al-21)+(B2.46), (Al-21)+(B2.47), (Al-21)+(B2.48), (Al-21)+(B2.49), (Al-21)+(B2.50), (Al-21)+(B3.1), (Al-21)+(B3.2.), (Al-21)+(B3.3), (Al-21)+(B3.4), (Al-21)+(B3.5), (Al-21)+(B3.6), (Al-21)+(B3.7), (Al-21)+(B3.8), (Al-21)+(B3.9), (Al-21)+(B3.10), (Al-21)+(B3.11), (Al-21)+(B3.12), (Al-21)+(B3.13), (Al-21)+(B3.14), (Al-21)+(B3.15), (Al-21)+(B3.16), (Al-21)+(B4.1), (Al-21)+(B4.2), (Al-21)+(B4.3), (Al-21)+(B4.4), (Al-21)+(B4.5), (Al-21)+(B4.6), (Al-21)+(B4.7).

(Al-22)+(B1.1), (Al-22)+(B1.2), (Al-22)+(B1.3), (Al-22)+(B1.4), (Al-22)+(B1.5), (Al-22)+(B1.6), (Al-22)+(B1.7), (Al-22)+(B1.8), (Al-22)+(B1.9), (Al-22)+(B1.10), (Al-22)+(B1.11), (Al-22)+(B1.12), (Al-22)+(B1.13), (Al-22)+(B1.14), (Al-22)+(B1.15), (Al-22)+(B1.16), (Al-22)+(B1.17), (Al-22)+(B1.18), (Al-22)+(B1.19), (Al-22)+(B1.20), (Al-22)+(B1.21), (Al-22)+(B1.22), (Al-22)+(B1.23), (Al-22)+(B1.24), (Al-22)+(B1.25), (Al-22)+(B1.26), (Al-22)+(B1.27), (Al-22)+(B1.28), (Al-22)+(B1.29), (Al-22)+(B1.30), (Al-22)+(B1.31), (Al-22)+(B1.32), (Al-22)+(B1.33), (Al-22)+(B1.34), (Al-22)+(B1.35), (Al-22)+(B1.36), (Al-22)+(B1.37), (Al-22)+(B1.38), (Al-22)+(B1.39), (Al-22)+(B1.40), (Al-22)+(B1.41), (Al-22)+(B1.42), (Al-22)+(B1.43), (Al-22)+(B1.44), (Al-22)+(B1.45), (Al-22)+(B1.46), (Al-22)+(B1.47), (Al-22)+(B1.48), (Al-22)+(B1.49), (Al-22)+(B1.50), (Al-22)+(B1.51), (Al-22)+(B1.52), (Al-22)+

(B1.53), (Al-22)+(B1.54), (Al-22)+(B1.55), (Al-22)+(B1.56), (Al-22)+(B1.57), (Al-22)+(B1.58), (Al-22)+(B1.59), (Al-22)+(B1.60), (Al-22)+(B1.61), (Al-22)+(B1.62), (Al-22)+(B1.63), (Al-22)+(B1.64), (Al-22)+(B1.65), (Al-22)+(B1.66), (Al-22)+(B2.1), (Al-22)+(B2.2), (Al-22)+(B2.3), (Al-22)+(B2.4), (Al-22)+(B2.5), (Al-22)+(B2.6), (Al-22)+(B2.7), (Al-22)+(B2.8), (Al-22)+(B2.9), (Al-22)+(B2.10), (Al-22)+(B2.11), (Al-22)+(B2.12), (Al-22)+(B2.13), (Al-22)+(B2.14), (Al-22)+(B2.15), (Al-22)+(B2.16), (Al-22)+(B2.17), (Al-22)+(B2.18), (Al-22)+(B2.19), (Al-22)+(B2.20), (Al-22)+(B2.21), (Al-22)+(B2.22), (Al-22)+(B2.23), (Al-22)+(B2.24), (Al-22)+(B2.25), (Al-22)+(B2.26), (Al-22)+(B2.27), (Al-22)+(B2.28), (Al-22)+(B2.29), (Al-22)+(B2.30), (Al-22)+(B2.31), (Al-22)+(B2.32), (Al-22)+(B2.33), (Al-22)+(B2.34), (Al-22)+(B2.35), (Al-22)+(B2.36), (Al-22)+(B2.37), (Al-22)+(B2.38), (Al-22)+(B2.39), (Al-22)+(B2.40), (Al-22)+(B2.41), (Al-22)+(B2.42), (Al-22)+(B2.43), (Al-22)+(B2.44), (Al-22)+(B2.45), (Al-22)+(B2.46), (Al-22)+(B2.47), (Al-22)+(B2.48), (Al-22)+(B2.49), (Al-22)+(B2.50), (Al-22)+(B3.1), (Al-22)+(B3.2.), (Al-22)+(B3.3), (Al-22)+(B3.4), (Al-22)+(B3.5), (Al-22)+(B3.6), (Al-22)+(B3.7), (Al-22)+(B3.8), (Al-22)+(B3.9), (Al-22)+(B3.10), (Al-22)+(B3.11), (Al-22)+(B3.12), (Al-22)+(B3.13), (Al-22)+(B3.14), (Al-22)+(B3.15), (Al-22)+(B3.16), (Al-22)+(B4.1), (Al-22)+(B4.2), (Al-22)+(B4.3), (Al-22)+(B4.4), (Al-22)+(B4.5), (Al-22)+(B4.6), (Al-22)+(B4.7).

(Al-23)+(B1.1), (Al-23)+(B1.2), (Al-23)+(B1.3), (Al-23)+(B1.4), (Al-23)+(B1.5), (Al-23)+(B1.6), (Al-23)+(B1.7), (Al-23)+(B1.8), (Al-23)+(B1.9), (Al-23)+(B1.10), (Al-23)+(B1.11), (Al-23)+(B1.12), (Al-23)+(B1.13), (Al-23)+(B1.14), (Al-23)+(B1.15), (Al-23)+(B1.16), (Al-23)+(B1.17), (Al-23)+(B1.18), (Al-23)+(B1.19), (Al-23)+(B1.20), (Al-23)+(B1.21), (Al-23)+(B1.22), (Al-23)+(B1.23), (Al-23)+(B1.24), (Al-23)+(B1.25), (Al-23)+(B1.26), (Al-23)+(B1.27), (Al-23)+(B1.28), (Al-23)+(B1.29), (Al-23)+(B1.30), (Al-23)+(B1.31), (Al-23)+(B1.32), (Al-23)+(B1.33), (Al-23)+(B1.34), (Al-23)+(B1.35), (Al-23)+(B1.36), (Al-23)+(B1.37), (Al-23)+(B1.38), (Al-23)+(B1.39), (Al-23)+(B1.40), (Al-23)+(B1.41), (Al-23)+(B1.42), (Al-23)+(B1.43), (Al-23)+(B1.44), (Al-23)+(B1.45), (Al-23)+(B1.46), (Al-23)+(B1.47), (Al-23)+(B1.48), (Al-23)+(B1.49), (Al-23)+(B1.50), (Al-23)+(B1.51), (Al-23)+(B1.52), (Al-23)+(B1.53), (Al-23)+(B1.54), (Al-23)+(B1.55), (Al-23)+(B1.56), (Al-23)+(B1.57), (Al-23)+(B1.58), (Al-23)+(B1.59), (Al-23)+(B1.60), (Al-23)+(B1.61), (Al-23)+(B1.62), (Al-23)+(B1.63), (Al-23)+(B1.64), (Al-23)+(B1.65), (Al-23)+(B1.66), (Al-23)+(B2.1), (Al-23)+(B2.2), (Al-23)+(B2.3), (Al-23)+(B2.4), (Al-23)+(B2.5), (Al-23)+(B2.6), (Al-23)+(B2.7), (Al-23)+(B2.8), (Al-23)+(B2.9), (Al-23)+(B2.10), (Al-23)+(B2.11), (Al-23)+(B2.12), (Al-23)+(B2.13), (Al-23)+(B2.14), (Al-23)+(B2.15), (Al-23)+(B2.16), (Al-23)+(B2.17), (Al-23)+(B2.18), (Al-23)+(B2.19), (Al-23)+(B2.20), (Al-23)+(B2.21), (Al-23)+(B2.22), (Al-23)+(B2.23), (Al-23)+(B2.24), (Al-23)+(B2.25), (Al-23)+(B2.26), (Al-23)+(B2.27), (Al-23)+(B2.28), (Al-23)+(B2.29), (Al-23)+(B2.30), (Al-23)+(B2.31), (Al-23)+(B2.32), (Al-23)+(B2.33), (Al-23)+(B2.34), (Al-23)+(B2.35), (Al-23)+(B2.36), (Al-23)+(B2.37), (Al-23)+(B2.38), (Al-23)+(B2.39), (Al-23)+(B2.40), (Al-23)+(B2.41), (Al-23)+(B2.42), (Al-23)+(B2.43), (Al-23)+(B2.44), (Al-23)+(B2.45), (Al-23)+(B2.46), (Al-23)+(B2.47), (Al-23)+(B2.48), (Al-23)+(B2.49), (Al-23)+(B2.50), (Al-23)+(B3.1), (Al-23)+(B3.2.), (Al-23)+(B3.3), (Al-23)+(B3.4), (Al-23)+(B3.5), (Al-23)+(B3.6), (Al-23)+(B3.7), (Al-23)+(B3.8), (Al-23)+(B3.9), (Al-23)+(B3.10), (Al-23)+(B3.11), (Al-23)+(B3.12), (Al-23)+(B3.13), (Al-23)+(B3.14), (Al-23)+(B3.15), (Al-23)+(B3.16), (Al-23)+(B4.1), (Al-23)+(B4.2), (Al-23)+(B4.3), (Al-23)+(B4.4), (Al-23)+(B4.5), (Al-23)+(B4.6), (Al-23)+(B4.7).

(Al-24)+(B1.1), (Al-24)+(B1.2), (Al-24)+(B1.3), (Al-24)+(B1.4), (Al-24)+(B1.5), (Al-24)+(B1.6), (Al-24)+(B1.7), (Al-24)+(B1.8), (Al-24)+(B1.9), (Al-24)+(B1.10), (Al-24)+(B1.11), (Al-24)+(B1.12), (Al-24)+(B1.13), (Al-24)+(B1.14), (Al-24)+(B1.15), (Al-24)+(B1.16), (Al-24)+(B1.17), (Al-24)+(B1.18), (Al-24)+(B1.19), (Al-24)+(B1.20), (Al-24)+(B1.21), (Al-24)+(B1.22), (Al-24)+(B1.23), (Al-24)+(B1.24), (Al-24)+(B1.25), (Al-24)+(B1.26), (Al-24)+(B1.27), (Al-24)+(B1.28), (Al-24)+(B1.29), (Al-24)+(B1.30), (Al-24)+(B1.31), (Al-24)+(B1.32), (Al-24)+(B1.33), (Al-24)+(B1.34), (Al-24)+(B1.35), (Al-24)+(B1.36), (Al-24)+(B1.37), (Al-24)+(B1.38), (Al-24)+(B1.39), (Al-24)+(B1.40), (Al-24)+(B1.41), (Al-24)+(B1.42), (Al-24)+(B1.43), (Al-24)+(B1.44), (Al-24)+(B1.45), (Al-24)+(B1.46), (Al-24)+(B1.47), (Al-24)+(B1.48), (Al-24)+(B1.49), (Al-24)+(B1.50), (Al-24)+(B1.51), (Al-24)+(B1.52), (Al-24)+(B1.53), (Al-24)+(B1.54), (Al-24)+(B1.55), (Al-24)+(B1.56), (Al-24)+(B1.57), (Al-24)+(B1.58), (Al-24)+(B1.59), (Al-24)+(B1.60), (Al-24)+(B1.61), (Al-24)+(B1.62), (Al-24)+(B1.63), (Al-24)+(B1.64), (Al-24)+(B1.65), (Al-24)+(B1.66), (Al-24)+(B2.1), (Al-24)+(B2.2), (Al-24)+(B2.3), (Al-24)+(B2.4), (Al-24)+(B2.5), (Al-24)+(B2.6), (Al-24)+(B2.7), (Al-24)+(B2.8), (Al-24)+(B2.9), (Al-24)+(B2.10), (Al-24)+(B2.11), (Al-24)+(B2.12), (Al-24)+(B2.13), (Al-24)+(B2.14), (Al-24)+(B2.15), (Al-24)+(B2.16), (Al-24)+(B2.17), (Al-24)+(B2.18), (Al-24)+(B2.19), (Al-24)+(B2.20), (Al-24)+(B2.21), (Al-24)+(B2.22), (Al-24)+(B2.23), (Al-24)+(B2.24), (Al-24)+(B2.25), (Al-24)+(B2.26), (Al-24)+(B2.27), (Al-24)+(B2.28), (Al-24)+(B2.29), (Al-24)+(B2.30), (Al-24)+(B2.31), (Al-24)+(B2.32), (Al-24)+(B2.33), (Al-24)+(B2.34), (Al-24)+(B2.35), (Al-24)+(B2.36), (Al-24)+(B2.37), (Al-24)+(B2.38), (Al-24)+(B2.39), (Al-24)+(B2.40), (Al-24)+(B2.41), (Al-24)+(B2.42), (Al-24)+(B2.43), (Al-24)+(B2.44), (Al-24)+(B2.45), (Al-24)+(B2.46), (Al-24)+(B2.47), (Al-24)+(B2.48), (Al-24)+(B2.49), (Al-24)+(B2.50), (Al-24)+(B3.1), (Al-24)+(B3.2.), (Al-24)+(B3.3), (Al-24)+(B3.4), (Al-24)+(B3.5), (Al-24)+(B3.6), (Al-24)+(B3.7), (Al-24)+(B3.8), (Al-24)+(B3.9), (Al-24)+(B3.10), (Al-24)+(B3.11), (Al-24)+(B3.12), (Al-24)+(B3.13), (Al-24)+(B3.14), (Al-24)+(B3.15), (Al-24)+(B3.16), (Al-24)+(B4.1), (Al-24)+(B4.2), (Al-24)+(B4.3), (Al-24)+(B4.4), (Al-24)+(B4.5), (Al-24)+(B4.6), (Al-24)+(B4.7).

(Al-25)+(B1.1), (Al-25)+(B1.2), (Al-25)+(B1.3), (Al-25)+(B1.4), (Al-25)+(B1.5), (Al-25)+(B1.6), (Al-25)+(B1.7), (Al-25)+(B1.8), (Al-25)+(B1.9), (Al-25)+(B1.10), (Al-25)+(B1.11), (Al-25)+(B1.12), (Al-25)+(B1.13), (Al-25)+(B1.14), (Al-25)+(B1.15), (Al-25)+(B1.16), (Al-25)+(B1.17), (Al-25)+(B1.18), (Al-25)+(B1.19), (Al-25)+(B1.20), (Al-25)+(B1.21), (Al-25)+(B1.22), (Al-25)+(B1.23), (Al-25)+(B1.24), (Al-25)+(B1.25), (Al-25)+(B1.26), (Al-25)+(B1.27), (Al-25)+(B1.28), (Al-25)+(B1.29), (Al-25)+(B1.30), (Al-25)+(B1.31), (Al-25)+(B1.32), (Al-25)+(B1.33), (Al-25)+(B1.34), (Al-25)+(B1.35), (Al-25)+(B1.36), (Al-25)+(B1.37), (Al-25)+(B1.38), (Al-25)+(B1.39), (Al-25)+(B1.40), (Al-25)+(B1.41), (Al-25)+(B1.42), (Al-25)+(B1.43), (Al-25)+(B1.44), (Al-25)+(B1.45), (Al-25)+(B1.46), (Al-25)+(B1.47), (Al-25)+(B1.48), (Al-25)+(B1.49), (Al-25)+

(B1.50), (Al-25)+(B1.51), (Al-25)+(B1.52), (Al-25)+(B1.53), (Al-25)+(B1.54), (Al-25)+(B1.55), (Al-25)+(B1.56), (Al-25)+(B1.57), (Al-25)+(B1.58), (Al-25)+(B1.59), (Al-25)+(B1.60), (Al-25)+(B1.61), (Al-25)+(B1.62), (Al-25)+(B1.63), (Al-25)+(B1.64), (Al-25)+(B1.65), (Al-25)+(B1.66), (Al-25)+(B2.1), (Al-25)+(B2.2), (Al-25)+(B2.3), (Al-25)+(B2.4), (Al-25)+(B2.5), (Al-25)+(B2.6), (Al-25)+(B2.7), (Al-25)+(B2.8), (Al-25)+(B2.9), (Al-25)+(B2.10), (Al-25)+(B2.11), (Al-25)+(B2.12), (Al-25)+(B2.13), (Al-25)+(B2.14), (Al-25)+(B2.15), (Al-25)+(B2.16), (Al-25)+(B2.17), (Al-25)+(B2.18), (Al-25)+(B2.19), (Al-25)+(B2.20), (Al-25)+(B2.21), (Al-25)+(B2.22), (Al-25)+(B2.23), (Al-25)+(B2.24), (Al-25)+(B2.25), (Al-25)+(B2.26), (Al-25)+(B2.27), (Al-25)+(B2.28), (Al-25)+(B2.29), (Al-25)+(B2.30), (Al-25)+(B2.31), (Al-25)+(B2.32), (Al-25)+(B2.33), (Al-25)+(B2.34), (Al-25)+(B2.35), (Al-25)+(B2.36), (Al-25)+(B2.37), (Al-25)+(B2.38), (Al-25)+(B2.39), (Al-25)+(B2.40), (Al-25)+(B2.41), (Al-25)+(B2.42), (Al-25)+(B2.43), (Al-25)+(B2.44), (Al-25)+(B2.45), (Al-25)+(B2.46), (Al-25)+(B2.47), (Al-25)+(B2.48), (Al-25)+(B2.49), (Al-25)+(B2.50), (Al-25)+(B3.1), (Al-25)+(B3.2.), (Al-25)+(B3.3), (Al-25)+(B3.4), (Al-25)+(B3.5), (Al-25)+(B3.6), (Al-25)+(B3.7), (Al-25)+(B3.8), (Al-25)+(B3.9), (Al-25)+(B3.10), (Al-25)+(B3.11), (Al-25)+(B3.12), (Al-25)+(B3.13), (Al-25)+(B3.14), (Al-25)+(B3.15), (Al-25)+(B3.16), (Al-25)+(B4.1), (Al-25)+(B4.2), (Al-25)+(B4.3), (Al-25)+(B4.4), (Al-25)+(B4.5), (Al-25)+(B4.6), (Al-25)+(B4.7).

(Al-26)+(B1.1), (Al-26)+(B1.2), (Al-26)+(B1.3), (Al-26)+(B1.4), (Al-26)+(B1.5), (Al-26)+(B1.6), (Al-26)+(B1.7), (Al-26)+(B1.8), (Al-26)+(B1.9), (Al-26)+(B1.10), (Al-26)+(B1.11), (Al-26)+(B1.12), (Al-26)+(B1.13), (Al-26)+(B1.14), (Al-26)+(B1.15), (Al-26)+(B1.16), (Al-26)+(B1.17), (Al-26)+(B1.18), (Al-26)+(B1.19), (Al-26)+(B1.20), (Al-26)+(B1.21), (Al-26)+(B1.22), (Al-26)+(B1.23), (Al-26)+(B1.24), (Al-26)+(B1.25), (Al-26)+(B1.26), (Al-26)+(B1.27), (Al-26)+(B1.28), (Al-26)+(B1.29), (Al-26)+(B1.30), (Al-26)+(B1.31), (Al-26)+(B1.32), (Al-26)+(B1.33), (Al-26)+(B1.34), (Al-26)+(B1.35), (Al-26)+(B1.36), (Al-26)+(B1.37), (Al-26)+(B1.38), (Al-26)+(B1.39), (Al-26)+(B1.40), (Al-26)+(B1.41), (Al-26)+(B1.42), (Al-26)+(B1.43), (Al-26)+(B1.44), (Al-26)+(B1.45), (Al-26)+(B1.46), (Al-26)+(B1.47), (Al-26)+(B1.48), (Al-26)+(B1.49), (Al-26)+(B1.50), (Al-26)+(B1.51), (Al-26)+(B1.52), (Al-26)+(B1.53), (Al-26)+(B1.54), (Al-26)+(B1.55), (Al-26)+(B1.56), (Al-26)+(B1.57), (Al-26)+(B1.58), (Al-26)+(B1.59), (Al-26)+(B1.60), (Al-26)+(B1.61), (Al-26)+(B1.62), (Al-26)+(B1.63), (Al-26)+(B1.64), (Al-26)+(B1.65), (Al-26)+(B1.66), (Al-26)+(B2.1), (Al-26)+(B2.2), (Al-26)+(B2.3), (Al-26)+(B2.4), (Al-26)+(B2.5), (Al-26)+(B2.6), (Al-26)+(B2.7), (Al-26)+(B2.8), (Al-26)+(B2.9), (Al-26)+(B2.10), (Al-26)+(B2.11), (Al-26)+(B2.12), (Al-26)+(B2.13), (Al-26)+(B2.14), (Al-26)+(B2.15), (Al-26)+(B2.16), (Al-26)+(B2.17), (Al-26)+(B2.18), (Al-26)+(B2.19), (Al-26)+(B2.20), (Al-26)+(B2.21), (Al-26)+(B2.22), (Al-26)+(B2.23), (Al-26)+(B2.24), (Al-26)+(B2.25), (Al-26)+(B2.26), (Al-26)+(B2.27), (Al-26)+(B2.28), (Al-26)+(B2.29), (Al-26)+(B2.30), (Al-26)+(B2.31), (Al-26)+(B2.32), (Al-26)+(B2.33), (Al-26)+(B2.34), (Al-26)+(B2.35), (Al-26)+(B2.36), (Al-26)+(B2.37), (Al-26)+(B2.38), (Al-26)+(B2.39), (Al-26)+(B2.40), (Al-26)+(B2.41), (Al-26)+(B2.42), (Al-26)+(B2.43), (Al-26)+(B2.44), (Al-26)+(B2.45), (Al-26)+(B2.46), (Al-26)+(B2.47), (Al-26)+(B2.48), (Al-26)+(B2.49), (Al-26)+(B2.50), (Al-26)+(B3.1), (Al-26)+(B3.2.), (Al-26)+(B3.3), (Al-26)+(B3.4), (Al-26)+(B3.5), (Al-26)+(B3.6), (Al-26)+(B3.7), (Al-26)+(B3.8), (Al-26)+(B3.9), (Al-26)+(B3.10), (Al-26)+(B3.11), (Al-26)+(B3.12), (Al-26)+(B3.13), (Al-26)+(B3.14), (Al-26)+(B3.15), (Al-26)+(B3.16), (Al-26)+(B4.1), (Al-26)+(B4.2), (Al-26)+(B4.3), (Al-26)+(B4.4), (Al-26)+(B4.5), (Al-26)+(B4.6), (Al-26)+(B4.7).

(Al-27)+(B1.1), (Al-27)+(B1.2), (Al-27)+(B1.3), (Al-27)+(B1.4), (Al-27)+(B1.5), (Al-27)+(B1.6), (Al-27)+(B1.7), (Al-27)+(B1.8), (Al-27)+(B1.9), (Al-27)+(B1.10), (Al-27)+(B1.11), (Al-27)+(B1.12), (Al-27)+(B1.13), (Al-27)+(B1.14), (Al-27)+(B1.15), (Al-27)+(B1.16), (Al-27)+(B1.17), (Al-27)+(B1.18), (Al-27)+(B1.19), (Al-27)+(B1.20), (Al-27)+(B1.21), (Al-27)+(B1.22), (Al-27)+(B1.23), (Al-27)+(B1.24), (Al-27)+(B1.25), (Al-27)+(B1.26), (Al-27)+(B1.27), (Al-27)+(B1.28), (Al-27)+(B1.29), (Al-27)+(B1.30), (Al-27)+(B1.31), (Al-27)+(B1.32), (Al-27)+(B1.33), (Al-27)+(B1.34), (Al-27)+(B1.35), (Al-27)+(B1.36), (Al-27)+(B1.37), (Al-27)+(B1.38), (Al-27)+(B1.39), (Al-27)+(B1.40), (Al-27)+(B1.41), (Al-27)+(B1.42), (Al-27)+(B1.43), (Al-27)+(B1.44), (Al-27)+(B1.45), (Al-27)+(B1.46), (Al-27)+(B1.47), (Al-27)+(B1.48), (Al-27)+(B1.49), (Al-27)+(B1.50), (Al-27)+(B1.51), (Al-27)+(B1.52), (Al-27)+(B1.53), (Al-27)+(B1.54), (Al-27)+(B1.55), (Al-27)+(B1.56), (Al-27)+(B1.57), (Al-27)+(B1.58), (Al-27)+(B1.59), (Al-27)+(B1.60), (Al-27)+(B1.61), (Al-27)+(B1.62), (Al-27)+(B1.63), (Al-27)+(B1.64), (Al-27)+(B1.65), (Al-27)+(B1.66), (Al-27)+(B2.1), (Al-27)+(B2.2), (Al-27)+(B2.3), (Al-27)+(B2.4), (Al-27)+(B2.5), (Al-27)+(B2.6), (Al-27)+(B2.7), (Al-27)+(B2.8), (Al-27)+(B2.9), (Al-27)+(B2.10), (Al-27)+(B2.11), (Al-27)+(B2.12), (Al-27)+(B2.13), (Al-27)+(B2.14), (Al-27)+(B2.15), (Al-27)+(B2.16), (Al-27)+(B2.17), (Al-27)+(B2.18), (Al-27)+(B2.19), (Al-27)+(B2.20), (Al-27)+(B2.21), (Al-27)+(B2.22), (Al-27)+(B2.23), (Al-27)+(B2.24), (Al-27)+(B2.25), (Al-27)+(B2.26), (Al-27)+(B2.27), (Al-27)+(B2.28), (Al-27)+(B2.29), (Al-27)+(B2.30), (Al-27)+(B2.31), (Al-27)+(B2.32), (Al-27)+(B2.33), (Al-27)+(B2.34), (Al-27)+(B2.35), (Al-27)+(B2.36), (Al-27)+(B2.37), (Al-27)+(B2.38), (Al-27)+(B2.39), (Al-27)+(B2.40), (Al-27)+(B2.41), (Al-27)+(B2.42), (Al-27)+(B2.43), (Al-27)+(B2.44), (Al-27)+(B2.45), (Al-27)+(B2.46), (Al-27)+(B2.47), (Al-27)+(B2.48), (Al-27)+(B2.49), (Al-27)+(B2.50), (Al-27)+(B3.1), (Al-27)+(B3.2.), (Al-27)+(B3.3), (Al-27)+(B3.4), (Al-27)+(B3.5), (Al-27)+(B3.6), (Al-27)+(B3.7), (Al-27)+(B3.8), (Al-27)+(B3.9), (Al-27)+(B3.10), (Al-27)+(B3.11), (Al-27)+(B3.12), (Al-27)+(B3.13), (Al-27)+(B3.14), (Al-27)+(B3.15), (Al-27)+(B3.16), (Al-27)+(B4.1), (Al-27)+(B4.2), (Al-27)+(B4.3), (Al-27)+(B4.4), (Al-27)+(B4.5), (Al-27)+(B4.6), (Al-27)+(B4.7).

(Al-28)+(B1.1), (Al-28)+(B1.2), (Al-28)+(B1.3), (Al-28)+(B1.4), (Al-28)+(B1.5), (Al-28)+(B1.6), (Al-28)+(B1.7), (Al-28)+(B1.8), (Al-28)+(B1.9), (Al-28)+(B1.10), (Al-28)+(B1.11), (Al-28)+(B1.12), (Al-28)+(B1.13), (Al-28)+(B1.14), (Al-28)+(B1.15), (Al-28)+(B1.16), (Al-28)+(B1.17), (Al-28)+(B1.18), (Al-28)+(B1.19), (Al-28)+(B1.20), (Al-28)+(B1.21), (Al-28)+(B1.22), (Al-28)+(B1.23), (Al-28)+(B1.24), (Al-28)+(B1.25), (Al-28)+(B1.26), (Al-28)+(B1.27), (Al-28)+(B1.28), (Al-28)+(B1.29), (Al-28)+(B1.30), (Al-28)+(B1.31), (Al-28)+(B1.32), (Al-28)+(B1.33), (Al-28)+(B1.34), (Al-28)+(B1.35), (Al-28)+(B1.36), (Al-28)+(B1.37), (Al-28)+(B1.38), (Al-28)+(B1.39), (Al-28)+(B1.40), (Al-28)+(B1.41), (Al-28)+(B1.42), (Al-28)+(B1.43), (Al-28)+(B1.44), (Al-28)+(B1.45), (Al-28)+(B1.46), (Al-28)+

(B1.47), (Al-28)+(B1.48), (Al-28)+(B1.49), (Al-28)+(B1.50), (Al-28)+(B1.51), (Al-28)+(B1.52), (Al-28)+(B1.53), (Al-28)+(B1.54), (Al-28)+(B1.55), (Al-28)+(B1.56), (Al-28)+(B1.57), (Al-28)+(B1.58), (Al-28)+(B1.59), (Al-28)+(B1.60), (Al-28)+(B1.61), (Al-28)+(B1.62), (Al-28)+(B1.63), (Al-28)+(B1.64), (Al-28)+(B1.65), (Al-28)+(B1.66), (Al-28)+(B2.1), (Al-28)+(B2.2), (Al-28)+(B2.3), (Al-28)+(B2.4), (Al-28)+(B2.5), (Al-28)+(B2.6), (Al-28)+(B2.7), (Al-28)+(B2.8), (Al-28)+(B2.9), (Al-28)+(B2.10), (Al-28)+(B2.11), (Al-28)+(B2.12), (Al-28)+(B2.13), (Al-28)+(B2.14), (Al-28)+(B2.15), (Al-28)+(B2.16), (Al-28)+(B2.17), (Al-28)+(B2.18), (Al-28)+(B2.19), (Al-28)+(B2.20), (Al-28)+(B2.21), (Al-28)+(B2.22), (Al-28)+(B2.23), (Al-28)+(B2.24), (Al-28)+(B2.25), (Al-28)+(B2.26), (Al-28)+(B2.27), (Al-28)+(B2.28), (Al-28)+(B2.29), (Al-28)+(B2.30), (Al-28)+(B2.31), (Al-28)+(B2.32), (Al-28)+(B2.33), (Al-28)+(B2.34), (Al-28)+(B2.35), (Al-28)+(B2.36), (Al-28)+(B2.37), (Al-28)+(B2.38), (Al-28)+(B2.39), (Al-28)+(B2.40), (Al-28)+(B2.41), (Al-28)+(B2.42), (Al-28)+(B2.43), (Al-28)+(B2.44), (Al-28)+(B2.45), (Al-28)+(B2.46), (Al-28)+(B2.47), (Al-28)+(B2.48), (Al-28)+(B2.49), (Al-28)+(B2.50), (Al-28)+(B3.1), (Al-28)+(B3.2.), (Al-28)+(B3.3), (Al-28)+(B3.4), (Al-28)+(B3.5), (Al-28)+(B3.6), (Al-28)+(B3.7), (Al-28)+(B3.8), (Al-28)+(B3.9), (Al-28)+(B3.10), (Al-28)+(B3.11), (Al-28)+(B3.12), (Al-28)+(B3.13), (Al-28)+(B3.14), (Al-28)+(B3.15), (Al-28)+(B3.16), (Al-28)+(B4.1), (Al-28)+(B4.2), (Al-28)+(B4.3), (Al-28)+(B4.4), (Al-28)+(B4.5), (Al-28)+(B4.6), (Al-28)+(B4.7).

(Al-29)+(B1.1), (Al-29)+(B1.2), (Al-29)+(B1.3), (Al-29)+(B1.4), (Al-29)+(B1.5), (Al-29)+(B1.6), (Al-29)+(B1.7), (Al-29)+(B1.8), (Al-29)+(B1.9), (Al-29)+(B1.10), (Al-29)+(B1.11), (Al-29)+(B1.12), (Al-29)+(B1.13), (Al-29)+(B1.14), (Al-29)+(B1.15), (Al-29)+(B1.16), (Al-29)+(B1.17), (Al-29)+(B1.18), (Al-29)+(B1.19), (Al-29)+(B1.20), (Al-29)+(B1.21), (Al-29)+(B1.22), (Al-29)+(B1.23), (Al-29)+(B1.24), (Al-29)+(B1.25), (Al-29)+(B1.26), (Al-29)+(B1.27), (Al-29)+(B1.28), (Al-29)+(B1.29), (Al-29)+(B1.30), (Al-29)+(B1.31), (Al-29)+(B1.32), (Al-29)+(B1.33), (Al-29)+(B1.34), (Al-29)+(B1.35), (Al-29)+(B1.36), (Al-29)+(B1.37), (Al-29)+(B1.38), (Al-29)+(B1.39), (Al-29)+(B1.40), (Al-29)+(B1.41), (Al-29)+(B1.42), (Al-29)+(B1.43), (Al-29)+(B1.44), (Al-29)+(B1.45), (Al-29)+(B1.46), (Al-29)+(B1.47), (Al-29)+(B1.48), (Al-29)+(B1.49), (Al-29)+(B1.50), (Al-29)+(B1.51), (Al-29)+(B1.52), (Al-29)+(B1.53), (Al-29)+(B1.54), (Al-29)+(B1.55), (Al-29)+(B1.56), (Al-29)+(B1.57), (Al-29)+(B1.58), (Al-29)+(B1.59), (Al-29)+(B1.60), (Al-29)+(B1.61), (Al-29)+(B1.62), (Al-29)+(B1.63), (Al-29)+(B1.64), (Al-29)+(B1.65), (Al-29)+(B1.66), (Al-29)+(B2.1), (Al-29)+(B2.2), (Al-29)+(B2.3), (Al-29)+(B2.4), (Al-29)+(B2.5), (Al-29)+(B2.6), (Al-29)+(B2.7), (Al-29)+(B2.8), (Al-29)+(B2.9), (Al-29)+(B2.10), (Al-29)+(B2.11), (Al-29)+(B2.12), (Al-29)+(B2.13), (Al-29)+(B2.14), (Al-29)+(B2.15), (Al-29)+(B2.16), (Al-29)+(B2.17), (Al-29)+(B2.18), (Al-29)+(B2.19), (Al-29)+(B2.20), (Al-29)+(B2.21), (Al-29)+(B2.22), (Al-29)+(B2.23), (Al-29)+(B2.24), (Al-29)+(B2.25), (Al-29)+(B2.26), (Al-29)+(B2.27), (Al-29)+(B2.28), (Al-29)+(B2.29), (Al-29)+(B2.30), (Al-29)+(B2.31), (Al-29)+(B2.32), (Al-29)+(B2.33), (Al-29)+(B2.34), (Al-29)+(B2.35), (Al-29)+(B2.36), (Al-29)+(B2.37), (Al-29)+(B2.38), (Al-29)+(B2.39), (Al-29)+(B2.40), (Al-29)+(B2.41), (Al-29)+(B2.42), (Al-29)+(B2.43), (Al-29)+(B2.44), (Al-29)+(B2.45), (Al-29)+(B2.46), (Al-29)+(B2.47), (Al-29)+(B2.48), (Al-29)+(B2.49), (Al-29)+(B2.50), (Al-29)+(B3.1), (Al-29)+(B3.2.), (Al-29)+(B3.3), (Al-29)+(B3.4), (Al-29)+(B3.5), (Al-29)+(B3.6), (Al-29)+(B3.7), (Al-29)+(B3.8), (Al-29)+(B3.9), (Al-29)+(B3.10), (Al-29)+(B3.11), (Al-29)+(B3.12), (Al-29)+(B3.13), (Al-29)+(B3.14), (Al-29)+(B3.15), (Al-29)+(B3.16), (Al-29)+(B4.1), (Al-29)+(B4.2), (Al-29)+(B4.3), (Al-29)+(B4.4), (Al-29)+(B4.5), (Al-29)+(B4.6), (Al-29)+(B4.7).

(Al-30)+(B1.1), (Al-30)+(B1.2), (Al-30)+(B1.3), (Al-30)+(B1.4), (Al-30)+(B1.5), (Al-30)+(B1.6), (Al-30)+(B1.7), (Al-30)+(B1.8), (Al-30)+(B1.9), (Al-30)+(B1.10), (Al-30)+(B1.11), (Al-30)+(B1.12), (Al-30)+(B1.13), (Al-30)+(B1.14), (Al-30)+(B1.15), (Al-30)+(B1.16), (Al-30)+(B1.17), (Al-30)+(B1.18), (Al-30)+(B1.19), (Al-30)+(B1.20), (Al-30)+(B1.21), (Al-30)+(B1.22), (Al-30)+(B1.23), (Al-30)+(B1.24), (Al-30)+(B1.25), (Al-30)+(B1.26), (Al-30)+(B1.27), (Al-30)+(B1.28), (Al-30)+(B1.29), (Al-30)+(B1.30), (Al-30)+(B1.31), (Al-30)+(B1.32), (Al-30)+(B1.33), (Al-30)+(B1.34), (Al-30)+(B1.35), (Al-30)+(B1.36), (Al-30)+(B1.37), (Al-30)+(B1.38), (Al-30)+(B1.39), (Al-30)+(B1.40), (Al-30)+(B1.41), (Al-30)+(B1.42), (Al-30)+(B1.43), (Al-30)+(B1.44), (Al-30)+(B1.45), (Al-30)+(B1.46), (Al-30)+(B1.47), (Al-30)+(B1.48), (Al-30)+(B1.49), (Al-30)+(B1.50), (Al-30)+(B1.51), (Al-30)+(B1.52), (Al-30)+(B1.53), (Al-30)+(B1.54), (Al-30)+(B1.55), (Al-30)+(B1.56), (Al-30)+(B1.57), (Al-30)+(B1.58), (Al-30)+(B1.59), (Al-30)+(B1.60), (Al-30)+(B1.61), (Al-30)+(B1.62), (Al-30)+(B1.63), (Al-30)+(B1.64), (Al-30)+(B1.65), (Al-30)+(B1.66), (Al-30)+(B2.1), (Al-30)+(B2.2), (Al-30)+(B2.3), (Al-30)+(B2.4), (Al-30)+(B2.5), (Al-30)+(B2.6), (Al-30)+(B2.7), (Al-30)+(B2.8), (Al-30)+(B2.9), (Al-30)+(B2.10), (Al-30)+(B2.11), (Al-30)+(B2.12), (Al-30)+(B2.13), (Al-30)+(B2.14), (Al-30)+(B2.15), (Al-30)+(B2.16), (Al-30)+(B2.17), (Al-30)+(B2.18), (Al-30)+(B2.19), (Al-30)+(B2.20), (Al-30)+(B2.21), (Al-30)+(B2.22), (Al-30)+(B2.23), (Al-30)+(B2.24), (Al-30)+(B2.25), (Al-30)+(B2.26), (Al-30)+(B2.27), (Al-30)+(B2.28), (Al-30)+(B2.29), (Al-30)+(B2.30), (Al-30)+(B2.31), (Al-30)+(B2.32), (Al-30)+(B2.33), (Al-30)+(B2.34), (Al-30)+(B2.35), (Al-30)+(B2.36), (Al-30)+(B2.37), (Al-30)+(B2.38), (Al-30)+(B2.39), (Al-30)+(B2.40), (Al-30)+(B2.41), (Al-30)+(B2.42), (Al-30)+(B2.43), (Al-30)+(B2.44), (Al-30)+(B2.45), (Al-30)+(B2.46), (Al-30)+(B2.47), (Al-30)+(B2.48), (Al-30)+(B2.49), (Al-30)+(B2.50), (Al-30)+(B3.1), (Al-30)+(B3.2.), (Al-30)+(B3.3), (Al-30)+(B3.4), (Al-30)+(B3.5), (Al-30)+(B3.6), (Al-30)+(B3.7), (Al-30)+(B3.8), (Al-30)+(B3.9), (Al-30)+(B3.10), (Al-30)+(B3.11), (Al-30)+(B3.12), (Al-30)+(B3.13), (Al-30)+(B3.14), (Al-30)+(B3.15), (Al-30)+(B3.16), (Al-30)+(B4.1), (Al-30)+(B4.2), (Al-30)+(B4.3), (Al-30)+(B4.4), (Al-30)+(B4.5), (Al-30)+(B4.6), (Al-30)+(B4.7).

(Al-31)+(B1.1), (Al-31)+(B1.2), (Al-31)+(B1.3), (Al-31)+(B1.4), (Al-31)+(B1.5), (Al-31)+(B1.6), (Al-31)+(B1.7), (Al-31)+(B1.8), (Al-31)+(B1.9), (Al-31)+(B1.10), (Al-31)+(B1.11), (Al-31)+(B1.12), (Al-31)+(B1.13), (Al-31)+(B1.14), (Al-31)+(B1.15), (Al-31)+(B1.16), (Al-31)+(B1.17), (Al-31)+(B1.18), (Al-31)+(B1.19), (Al-31)+(B1.20), (Al-31)+(B1.21), (Al-31)+(B1.22), (Al-31)+(B1.23), (Al-31)+(B1.24), (Al-31)+(B1.25), (Al-31)+(B1.26), (Al-31)+(B1.27), (Al-31)+(B1.28), (Al-31)+(B1.29), (Al-31)+(B1.30), (Al-31)+(B1.31), (Al-31)+(B1.32), (Al-31)+(B1.33), (Al-31)+(B1.34), (Al-31)+(B1.35), (Al-31)+(B1.36), (Al-31)+(B1.37), (Al-31)+(B1.38), (Al-31)+(B1.39), (Al-31)+(B1.40), (Al-31)+(B1.41), (Al-31)+(B1.42), (Al-31)+(B1.43), (Al-31)+

(B1.44), (Al-31)+(B1.45), (Al-31)+(B1.46), (Al-31)+(B1.47), (Al-31)+(B1.48), (Al-31)+(B1.49), (Al-31)+(B1.50), (Al-31)+(B1.51), (Al-31)+(B1.52), (Al-31)+(B1.53), (Al-31)+(B1.54), (Al-31)+(B1.55), (Al-31)+(B1.56), (Al-31)+(B1.57), (Al-31)+(B1.58), (Al-31)+(B1.59), (Al-31)+(B1.60), (Al-31)+(B1.61), (Al-31)+(B1.62), (Al-31)+(B1.63), (Al-31)+(B1.64), (Al-31)+(B1.65), (Al-31)+(B1.66), (Al-31)+(B2.1), (Al-31)+(B2.2), (Al-31)+(B2.3), (Al-31)+(B2.4), (Al-31)+(B2.5), (Al-31)+(B2.6), (Al-31)+(B2.7), (Al-31)+(B2.8), (Al-31)+(B2.9), (Al-31)+(B2.10), (Al-31)+(B2.11), (Al-31)+(B2.12), (Al-31)+(B2.13), (Al-31)+(B2.14), (Al-31)+(B2.15), (Al-31)+(B2.16), (Al-31)+(B2.17), (Al-31)+(B2.18), (Al-31)+(B2.19), (Al-31)+(B2.20), (Al-31)+(B2.21), (Al-31)+(B2.22), (Al-31)+(B2.23), (Al-31)+(B2.24), (Al-31)+(B2.25), (Al-31)+(B2.26), (Al-31)+(B2.27), (Al-31)+(B2.28), (Al-31)+(B2.29), (Al-31)+(B2.30), (Al-31)+(B2.31), (Al-31)+(B2.32), (Al-31)+(B2.33), (Al-31)+(B2.34), (Al-31)+(B2.35), (Al-31)+(B2.36), (Al-31)+(B2.37), (Al-31)+(B2.38), (Al-31)+(B2.39), (Al-31)+(B2.40), (Al-31)+(B2.41), (Al-31)+(B2.42), (Al-31)+(B2.43), (Al-31)+(B2.44), (Al-31)+(B2.45), (Al-31)+(B2.46), (Al-31)+(B2.47), (Al-31)+(B2.48), (Al-31)+(B2.49), (Al-31)+(B2.50), (Al-31)+(B3.1), (Al-31)+(B3.2.), (Al-31)+(B3.3), (Al-31)+(B3.4), (Al-31)+(B3.5), (Al-31)+(B3.6), (Al-31)+(B3.7), (Al-31)+(B3.8), (Al-31)+(B3.9), (Al-31)+(B3.10), (Al-31)+(B3.11), (Al-31)+(B3.12), (Al-31)+(B3.13), (Al-31)+(B3.14), (Al-31)+(B3.15), (Al-31)+(B3.16), (Al-31)+(B4.1), (Al-31)+(B4.2), (Al-31)+(B4.3), (Al-31)+(B4.4), (Al-31)+(B4.5), (Al-31)+(B4.6), (Al-31)+(B4.7).

(Al-32)+(B1.1), (Al-32)+(B1.2), (Al-32)+(B1.3), (Al-32)+(B1.4), (Al-32)+(B1.5), (Al-32)+(B1.6), (Al-32)+(B1.7), (Al-32)+(B1.8), (Al-32)+(B1.9), (Al-32)+(B1.10), (Al-32)+(B1.11), (Al-32)+(B1.12), (Al-32)+(B1.13), (Al-32)+(B1.14), (Al-32)+(B1.15), (Al-32)+(B1.16), (Al-32)+(B1.17), (Al-32)+(B1.18), (Al-32)+(B1.19), (Al-32)+(B1.20), (Al-32)+(B1.21), (Al-32)+(B1.22), (Al-32)+(B1.23), (Al-32)+(B1.24), (Al-32)+(B1.25), (Al-32)+(B1.26), (Al-32)+(B1.27), (Al-32)+(B1.28), (Al-32)+(B1.29), (Al-32)+(B1.30), (Al-32)+(B1.31), (Al-32)+(B1.32), (Al-32)+(B1.33), (Al-32)+(B1.34), (Al-32)+(B1.35), (Al-32)+(B1.36), (Al-32)+(B1.37), (Al-32)+(B1.38), (Al-32)+(B1.39), (Al-32)+(B1.40), (Al-32)+(B1.41), (Al-32)+(B1.42), (Al-32)+(B1.43), (Al-32)+(B1.44), (Al-32)+(B1.45), (Al-32)+(B1.46), (Al-32)+(B1.47), (Al-32)+(B1.48), (Al-32)+(B1.49), (Al-32)+(B1.50), (Al-32)+(B1.51), (Al-32)+(B1.52), (Al-32)+(B1.53), (Al-32)+(B1.54), (Al-32)+(B1.55), (Al-32)+(B1.56), (Al-32)+(B1.57), (Al-32)+(B1.58), (Al-32)+(B1.59), (Al-32)+(B1.60), (Al-32)+(B1.61), (Al-32)+(B1.62), (Al-32)+(B1.63), (Al-32)+(B1.64), (Al-32)+(B1.65), (Al-32)+(B1.66), (Al-32)+(B2.1), (Al-32)+(B2.2), (Al-32)+(B2.3), (Al-32)+(B2.4), (Al-32)+(B2.5), (Al-32)+(B2.6), (Al-32)+(B2.7), (Al-32)+(B2.8), (Al-32)+(B2.9), (Al-32)+(B2.10), (Al-32)+(B2.11), (Al-32)+(B2.12), (Al-32)+(B2.13), (Al-32)+(B2.14), (Al-32)+(B2.15), (Al-32)+(B2.16), (Al-32)+(B2.17), (Al-32)+(B2.18), (Al-32)+(B2.19), (Al-32)+(B2.20), (Al-32)+(B2.21), (Al-32)+(B2.22), (Al-32)+(B2.23), (Al-32)+(B2.24), (Al-32)+(B2.25), (Al-32)+(B2.26), (Al-32)+(B2.27), (Al-32)+(B2.28), (Al-32)+(B2.29), (Al-32)+(B2.30), (Al-32)+(B2.31), (Al-32)+(B2.32), (Al-32)+(B2.33), (Al-32)+(B2.34), (Al-32)+(B2.35), (Al-32)+(B2.36), (Al-32)+(B2.37), (Al-32)+(B2.38), (Al-32)+(B2.39), (Al-32)+(B2.40), (Al-32)+(B2.41), (Al-32)+(B2.42), (Al-32)+(B2.43), (Al-32)+(B2.44), (Al-32)+(B2.45), (Al-32)+(B2.46), (Al-32)+(B2.47), (Al-32)+(B2.48), (Al-32)+(B2.49), (Al-32)+(B2.50), (Al-32)+(B3.1), (Al-32)+(B3.2.), (Al-32)+(B3.3), (Al-32)+(B3.4), (Al-32)+(B3.5), (Al-32)+(B3.6), (Al-32)+(B3.7), (Al-32)+(B3.8), (Al-32)+(B3.9), (Al-32)+(B3.10), (Al-32)+(B3.11), (Al-32)+(B3.12), (Al-32)+(B3.13), (Al-32)+(B3.14), (Al-32)+(B3.15), (Al-32)+(B3.16), (Al-32)+(B4.1), (Al-32)+(B4.2), (Al-32)+(B4.3), (Al-32)+(B4.4), (Al-32)+(B4.5), (Al-32)+(B4.6), (Al-32)+(B4.7).

(Al-33)+(B1.1), (Al-33)+(B1.2), (Al-33)+(B1.3), (Al-33)+(B1.4), (Al-33)+(B1.5), (Al-33)+(B1.6), (Al-33)+(B1.7), (Al-33)+(B1.8), (Al-33)+(B1.9), (Al-33)+(B1.10), (Al-33)+(B1.11), (Al-33)+(B1.12), (Al-33)+(B1.13), (Al-33)+(B1.14), (Al-33)+(B1.15), (Al-33)+(B1.16), (Al-33)+(B1.17), (Al-33)+(B1.18), (Al-33)+(B1.19), (Al-33)+(B1.20), (Al-33)+(B1.21), (Al-33)+(B1.22), (Al-33)+(B1.23), (Al-33)+(B1.24), (Al-33)+(B1.25), (Al-33)+(B1.26), (Al-33)+(B1.27), (Al-33)+(B1.28), (Al-33)+(B1.29), (Al-33)+(B1.30), (Al-33)+(B1.31), (Al-33)+(B1.32), (Al-33)+(B1.33), (Al-33)+(B1.34), (Al-33)+(B1.35), (Al-33)+(B1.36), (Al-33)+(B1.37), (Al-33)+(B1.38), (Al-33)+(B1.39), (Al-33)+(B1.40), (Al-33)+(B1.41), (Al-33)+(B1.42), (Al-33)+(B1.43), (Al-33)+(B1.44), (Al-33)+(B1.45), (Al-33)+(B1.46), (Al-33)+(B1.47), (Al-33)+(B1.48), (Al-33)+(B1.49), (Al-33)+(B1.50), (Al-33)+(B1.51), (Al-33)+(B1.52), (Al-33)+(B1.53), (Al-33)+(B1.54), (Al-33)+(B1.55), (Al-33)+(B1.56), (Al-33)+(B1.57), (Al-33)+(B1.58), (Al-33)+(B1.59), (Al-33)+(B1.60), (Al-33)+(B1.61), (Al-33)+(B1.62), (Al-33)+(B1.63), (Al-33)+(B1.64), (Al-33)+(B1.65), (Al-33)+(B1.66), (Al-33)+(B2.1), (Al-33)+(B2.2), (Al-33)+(B2.3), (Al-33)+(B2.4), (Al-33)+(B2.5), (Al-33)+(B2.6), (Al-33)+(B2.7), (Al-33)+(B2.8), (Al-33)+(B2.9), (Al-33)+(B2.10), (Al-33)+(B2.11), (Al-33)+(B2.12), (Al-33)+(B2.13), (Al-33)+(B2.14), (Al-33)+(B2.15), (Al-33)+(B2.16), (Al-33)+(B2.17), (Al-33)+(B2.18), (Al-33)+(B2.19), (Al-33)+(B2.20), (Al-33)+(B2.21), (Al-33)+(B2.22), (Al-33)+(B2.23), (Al-33)+(B2.24), (Al-33)+(B2.25), (Al-33)+(B2.26), (Al-33)+(B2.27), (Al-33)+(B2.28), (Al-33)+(B2.29), (Al-33)+(B2.30), (Al-33)+(B2.31), (Al-33)+(B2.32), (Al-33)+(B2.33), (Al-33)+(B2.34), (Al-33)+(B2.35), (Al-33)+(B2.36), (Al-33)+(B2.37), (Al-33)+(B2.38), (Al-33)+(B2.39), (Al-33)+(B2.40), (Al-33)+(B2.41), (Al-33)+(B2.42), (Al-33)+(B2.43), (Al-33)+(B2.44), (Al-33)+(B2.45), (Al-33)+(B2.46), (Al-33)+(B2.47), (Al-33)+(B2.48), (Al-33)+(B2.49), (Al-33)+(B2.50), (Al-33)+(B3.1), (Al-33)+(B3.2.), (Al-33)+(B3.3), (Al-33)+(B3.4), (Al-33)+(B3.5), (Al-33)+(B3.6), (Al-33)+(B3.7), (Al-33)+(B3.8), (Al-33)+(B3.9), (Al-33)+(B3.10), (Al-33)+(B3.11), (Al-33)+(B3.12), (Al-33)+(B3.13), (Al-33)+(B3.14), (Al-33)+(B3.15), (Al-33)+(B3.16), (Al-33)+(B4.1), (Al-33)+(B4.2), (Al-33)+(B4.3), (Al-33)+(B4.4), (Al-33)+(B4.5), (Al-33)+(B4.6), (Al-33)+(B4.7).

(Al-34)+(B1.1), (Al-34)+(B1.2), (Al-34)+(B1.3), (Al-34)+(B1.4), (Al-34)+(B1.5), (Al-34)+(B1.6), (Al-34)+(B1.7), (Al-34)+(B1.8), (Al-34)+(B1.9), (Al-34)+(B1.10), (Al-34)+(B1.11), (Al-34)+(B1.12), (Al-34)+(B1.13), (Al-34)+(B1.14), (Al-34)+(B1.15), (Al-34)+(B1.16), (Al-34)+(B1.17), (Al-34)+(B1.18), (Al-34)+(B1.19), (Al-34)+(B1.20), (Al-34)+(B1.21), (Al-34)+(B1.22), (Al-34)+(B1.23), (Al-34)+(B1.24), (Al-34)+(B1.25), (Al-34)+(B1.26), (Al-34)+(B1.27), (Al-34)+(B1.28), (Al-34)+(B1.29), (Al-34)+(B1.30), (Al-34)+(B1.31), (Al-34)+(B1.32), (Al-34)+(B1.33), (Al-34)+(B1.34), (Al-34)+(B1.35), (Al-34)+(B1.36), (Al-34)+(B1.37), (Al-34)+(B1.38), (Al-34)+(B1.39), (Al-34)+(B1.40), (Al-34)+

(B1.41), (Al-34)+(B1.42), (Al-34)+(B1.43), (Al-34)+(B1.44), (Al-34)+(B1.45), (Al-34)+(B1.46), (Al-34)+(B1.47), (Al-34)+(B1.48), (Al-34)+(B1.49), (Al-34)+(B1.50), (Al-34)+(B1.51), (Al-34)+(B1.52), (Al-34)+(B1.53), (Al-34)+(B1.54), (Al-34)+(B1.55), (Al-34)+(B1.56), (Al-34)+(B1.57), (Al-34)+(B1.58), (Al-34)+(B1.59), (Al-34)+(B1.60), (Al-34)+(B1.61), (Al-34)+(B1.62), (Al-34)+(B1.63), (Al-34)+(B1.64), (Al-34)+(B1.65), (Al-34)+(B1.66), (Al-34)+(B2.1), (Al-34)+(B2.2), (Al-34)+(B2.3), (Al-34)+(B2.4), (Al-34)+(B2.5), (Al-34)+(B2.6), (Al-34)+(B2.7), (Al-34)+(B2.8), (Al-34)+(B2.9), (Al-34)+(B2.10), (Al-34)+(B2.11), (Al-34)+(B2.12), (Al-34)+(B2.13), (Al-34)+(B2.14), (Al-34)+(B2.15), (Al-34)+(B2.16), (Al-34)+(B2.17), (Al-34)+(B2.18), (Al-34)+(B2.19), (Al-34)+(B2.20), (Al-34)+(B2.21), (Al-34)+(B2.22), (Al-34)+(B2.23), (Al-34)+(B2.24), (Al-34)+(B2.25), (Al-34)+(B2.26), (Al-34)+(B2.27), (Al-34)+(B2.28), (Al-34)+(B2.29), (Al-34)+(B2.30), (Al-34)+(B2.31), (Al-34)+(B2.32), (Al-34)+(B2.33), (Al-34)+(B2.34), (Al-34)+(B2.35), (Al-34)+(B2.36), (Al-34)+(B2.37), (Al-34)+(B2.38), (Al-34)+(B2.39), (Al-34)+(B2.40), (Al-34)+(B2.41), (Al-34)+(B2.42), (Al-34)+(B2.43), (Al-34)+(B2.44), (Al-34)+(B2.45), (Al-34)+(B2.46), (Al-34)+(B2.47), (Al-34)+(B2.48), (Al-34)+(B2.49), (Al-34)+(B2.50), (Al-34)+(B3.1), (Al-34)+(B3.2.), (Al-34)+(B3.3), (Al-34)+(B3.4), (Al-34)+(B3.5), (Al-34)+(B3.6), (Al-34)+(B3.7), (Al-34)+(B3.8), (Al-34)+(B3.9), (Al-34)+(B3.10), (Al-34)+(B3.11), (Al-34)+(B3.12), (Al-34)+(B3.13), (Al-34)+(B3.14), (Al-34)+(B3.15), (Al-34)+(B3.16), (Al-34)+(B4.1), (Al-34)+(B4.2), (Al-34)+(B4.3), (Al-34)+(B4.4), (Al-34)+(B4.5), (Al-34)+(B4.6), (Al-34)+(B4.7).

(Al-35)+(B1.1), (Al-35)+(B1.2), (Al-35)+(B1.3), (Al-35)+(B1.4), (Al-35)+(B1.5), (Al-35)+(B1.6), (Al-35)+(B1.7), (Al-35)+(B1.8), (Al-35)+(B1.9), (Al-35)+(B1.10), (Al-35)+(B1.11), (Al-35)+(B1.12), (Al-35)+(B1.13), (Al-35)+(B1.14), (Al-35)+(B1.15), (Al-35)+(B1.16), (Al-35)+(B1.17), (Al-35)+(B1.18), (Al-35)+(B1.19), (Al-35)+(B1.20), (Al-35)+(B1.21), (Al-35)+(B1.22), (Al-35)+(B1.23), (Al-35)+(B1.24), (Al-35)+(B1.25), (Al-35)+(B1.26), (Al-35)+(B1.27), (Al-35)+(B1.28), (Al-35)+(B1.29), (Al-35)+(B1.30), (Al-35)+(B1.31), (Al-35)+(B1.32), (Al-35)+(B1.33), (Al-35)+(B1.34), (Al-35)+(B1.35), (Al-35)+(B1.36), (Al-35)+(B1.37), (Al-35)+(B1.38), (Al-35)+(B1.39), (Al-35)+(B1.40), (Al-35)+(B1.41), (Al-35)+(B1.42), (Al-35)+(B1.43), (Al-35)+(B1.44), (Al-35)+(B1.45), (Al-35)+(B1.46), (Al-35)+(B1.47), (Al-35)+(B1.48), (Al-35)+(B1.49), (Al-35)+(B1.50), (Al-35)+(B1.51), (Al-35)+(B1.52), (Al-35)+(B1.53), (Al-35)+(B1.54), (Al-35)+(B1.55), (Al-35)+(B1.56), (Al-35)+(B1.57), (Al-35)+(B1.58), (Al-35)+(B1.59), (Al-35)+(B1.60), (Al-35)+(B1.61), (Al-35)+(B1.62), (Al-35)+(B1.63), (Al-35)+(B1.64), (Al-35)+(B1.65), (Al-35)+(B1.66), (Al-35)+(B2.1), (Al-35)+(B2.2), (Al-35)+(B2.3), (Al-35)+(B2.4), (Al-35)+(B2.5), (Al-35)+(B2.6), (Al-35)+(B2.7), (Al-35)+(B2.8), (Al-35)+(B2.9), (Al-35)+(B2.10), (Al-35)+(B2.11), (Al-35)+(B2.12), (Al-35)+(B2.13), (Al-35)+(B2.14), (Al-35)+(B2.15), (Al-35)+(B2.16), (Al-35)+(B2.17), (Al-35)+(B2.18), (Al-35)+(B2.19), (Al-35)+(B2.20), (Al-35)+(B2.21), (Al-35)+(B2.22), (Al-35)+(B2.23), (Al-35)+(B2.24), (Al-35)+(B2.25), (Al-35)+(B2.26), (Al-35)+(B2.27), (Al-35)+(B2.28), (Al-35)+(B2.29), (Al-35)+(B2.30), (Al-35)+(B2.31), (Al-35)+(B2.32), (Al-35)+(B2.33), (Al-35)+(B2.34), (Al-35)+(B2.35), (Al-35)+(B2.36), (Al-35)+(B2.37), (Al-35)+(B2.38), (Al-35)+(B2.39), (Al-35)+(B2.40), (Al-35)+(B2.41), (Al-35)+(B2.42), (Al-35)+(B2.43), (Al-35)+(B2.44), (Al-35)+(B2.45), (Al-35)+(B2.46), (Al-35)+(B2.47), (Al-35)+(B2.48), (Al-35)+(B2.49), (Al-35)+(B2.50), (Al-35)+(B3.1), (Al-35)+(B3.2.), (Al-35)+(B3.3), (Al-35)+(B3.4), (Al-35)+(B3.5), (Al-35)+(B3.6), (Al-35)+(B3.7), (Al-35)+(B3.8), (Al-35)+(B3.9), (Al-35)+(B3.10), (Al-35)+(B3.11), (Al-35)+(B3.12), (Al-35)+(B3.13), (Al-35)+(B3.14), (Al-35)+(B3.15), (Al-35)+(B3.16), (Al-35)+(B4.1), (Al-35)+(B4.2), (Al-35)+(B4.3), (Al-35)+(B4.4), (Al-35)+(B4.5), (Al-35)+(B4.6), (Al-35)+(B4.7).

(Al-36)+(B1.1), (Al-36)+(B1.2), (Al-36)+(B1.3), (Al-36)+(B1.4), (Al-36)+(B1.5), (Al-36)+(B1.6), (Al-36)+(B1.7), (Al-36)+(B1.8), (Al-36)+(B1.9), (Al-36)+(B1.10), (Al-36)+(B1.11), (Al-36)+(B1.12), (Al-36)+(B1.13), (Al-36)+(B1.14), (Al-36)+(B1.15), (Al-36)+(B1.16), (Al-36)+(B1.17), (Al-36)+(B1.18), (Al-36)+(B1.19), (Al-36)+(B1.20), (Al-36)+(B1.21), (Al-36)+(B1.22), (Al-36)+(B1.23), (Al-36)+(B1.24), (Al-36)+(B1.25), (Al-36)+(B1.26), (Al-36)+(B1.27), (Al-36)+(B1.28), (Al-36)+(B1.29), (Al-36)+(B1.30), (Al-36)+(B1.31), (Al-36)+(B1.32), (Al-36)+(B1.33), (Al-36)+(B1.34), (Al-36)+(B1.35), (Al-36)+(B1.36), (Al-36)+(B1.37), (Al-36)+(B1.38), (Al-36)+(B1.39), (Al-36)+(B1.40), (Al-36)+(B1.41), (Al-36)+(B1.42), (Al-36)+(B1.43), (Al-36)+(B1.44), (Al-36)+(B1.45), (Al-36)+(B1.46), (Al-36)+(B1.47), (Al-36)+(B1.48), (Al-36)+(B1.49), (Al-36)+(B1.50), (Al-36)+(B1.51), (Al-36)+(B1.52), (Al-36)+(B1.53), (Al-36)+(B1.54), (Al-36)+(B1.55), (Al-36)+(B1.56), (Al-36)+(B1.57), (Al-36)+(B1.58), (Al-36)+(B1.59), (Al-36)+(B1.60), (Al-36)+(B1.61), (Al-36)+(B1.62), (Al-36)+(B1.63), (Al-36)+(B1.64), (Al-36)+(B1.65), (Al-36)+(B1.66), (Al-36)+(B2.1), (Al-36)+(B2.2), (Al-36)+(B2.3), (Al-36)+(B2.4), (Al-36)+(B2.5), (Al-36)+(B2.6), (Al-36)+(B2.7), (Al-36)+(B2.8), (Al-36)+(B2.9), (Al-36)+(B2.10), (Al-36)+(B2.11), (Al-36)+(B2.12), (Al-36)+(B2.13), (Al-36)+(B2.14), (Al-36)+(B2.15), (Al-36)+(B2.16), (Al-36)+(B2.17), (Al-36)+(B2.18), (Al-36)+(B2.19), (Al-36)+(B2.20), (Al-36)+(B2.21), (Al-36)+(B2.22), (Al-36)+(B2.23), (Al-36)+(B2.24), (Al-36)+(B2.25), (Al-36)+(B2.26), (Al-36)+(B2.27), (Al-36)+(B2.28), (Al-36)+(B2.29), (Al-36)+(B2.30), (Al-36)+(B2.31), (Al-36)+(B2.32), (Al-36)+(B2.33), (Al-36)+(B2.34), (Al-36)+(B2.35), (Al-36)+(B2.36), (Al-36)+(B2.37), (Al-36)+(B2.38), (Al-36)+(B2.39), (Al-36)+(B2.40), (Al-36)+(B2.41), (Al-36)+(B2.42), (Al-36)+(B2.43), (Al-36)+(B2.44), (Al-36)+(B2.45), (Al-36)+(B2.46), (Al-36)+(B2.47), (Al-36)+(B2.48), (Al-36)+(B2.49), (Al-36)+(B2.50), (Al-36)+(B3.1), (Al-36)+(B3.2.), (Al-36)+(B3.3), (Al-36)+(B3.4), (Al-36)+(B3.5), (Al-36)+(B3.6), (Al-36)+(B3.7), (Al-36)+(B3.8), (Al-36)+(B3.9), (Al-36)+(B3.10), (Al-36)+(B3.11), (Al-36)+(B3.12), (Al-36)+(B3.13), (Al-36)+(B3.14), (Al-36)+(B3.15), (Al-36)+(B3.16), (Al-36)+(B4.1), (Al-36)+(B4.2), (Al-36)+(B4.3), (Al-36)+(B4.4), (Al-36)+(B4.5), (Al-36)+(B4.6), (Al-36)+(B4.7).

(Al-37)+(B1.1), (Al-37)+(B1.2), (Al-37)+(B1.3), (Al-37)+(B1.4), (Al-37)+(B1.5), (Al-37)+(B1.6), (Al-37)+(B1.7), (Al-37)+(B1.8), (Al-37)+(B1.9), (Al-37)+(B1.10), (Al-37)+(B1.11), (Al-37)+(B1.12), (Al-37)+(B1.13), (Al-37)+(B1.14), (Al-37)+(B1.15), (Al-37)+(B1.16), (Al-37)+(B1.17), (Al-37)+(B1.18), (Al-37)+(B1.19), (Al-37)+(B1.20), (Al-37)+(B1.21), (Al-37)+(B1.22), (Al-37)+(B1.23), (Al-37)+(B1.24), (Al-37)+(B1.25), (Al-37)+(B1.26), (Al-37)+(B1.27), (Al-37)+(B1.28), (Al-37)+(B1.29), (Al-37)+(B1.30), (Al-37)+(B1.31), (Al-37)+(B1.32), (Al-37)+(B1.33), (Al-37)+(B1.34), (Al-37)+(B1.35), (Al-37)+(B1.36), (Al-37)+(B1.37), (Al-37)+

(B1.38), (Al-37)+(B1.39), (Al-37)+(B1.40), (Al-37)+(B1.41), (Al-37)+(B1.42), (Al-37)+(B1.43), (Al-37)+(B1.44), (Al-37)+(B1.45), (Al-37)+(B1.46), (Al-37)+(B1.47), (Al-37)+(B1.48), (Al-37)+(B1.49), (Al-37)+(B1.50), (Al-37)+(B1.51), (Al-37)+(B1.52), (Al-37)+(B1.53), (Al-37)+(B1.54), (Al-37)+(B1.55), (Al-37)+(B1.56), (Al-37)+(B1.57), (Al-37)+(B1.58), (Al-37)+(B1.59), (Al-37)+(B1.60), (Al-37)+(B1.61), (Al-37)+(B1.62), (Al-37)+(B1.63), (Al-37)+(B1.64), (Al-37)+(B1.65), (Al-37)+(B1.66), (Al-37)+(B2.1), (Al-37)+(B2.2), (Al-37)+(B2.3), (Al-37)+(B2.4), (Al-37)+(B2.5), (Al-37)+(B2.6), (Al-37)+(B2.7), (Al-37)+(B2.8), (Al-37)+(B2.9), (Al-37)+(B2.10), (Al-37)+(B2.11), (Al-37)+(B2.12), (Al-37)+(B2.13), (Al-37)+(B2.14), (Al-37)+(B2.15), (Al-37)+(B2.16), (Al-37)+(B2.17), (Al-37)+(B2.18), (Al-37)+(B2.19), (Al-37)+(B2.20), (Al-37)+(B2.21), (Al-37)+(B2.22), (Al-37)+(B2.23), (Al-37)+(B2.24), (Al-37)+(B2.25), (Al-37)+(B2.26), (Al-37)+(B2.27), (Al-37)+(B2.28), (Al-37)+(B2.29), (Al-37)+(B2.30), (Al-37)+(B2.31), (Al-37)+(B2.32), (Al-37)+(B2.33), (Al-37)+(B2.34), (Al-37)+(B2.35), (Al-37)+(B2.36), (Al-37)+(B2.37), (Al-37)+(B2.38), (Al-37)+(B2.39), (Al-37)+(B2.40), (Al-37)+(B2.41), (Al-37)+(B2.42), (Al-37)+(B2.43), (Al-37)+(B2.44), (Al-37)+(B2.45), (Al-37)+(B2.46), (Al-37)+(B2.47), (Al-37)+(B2.48), (Al-37)+(B2.49), (Al-37)+(B2.50), (Al-37)+(B3.1), (Al-37)+(B3.2.), (Al-37)+(B3.3), (Al-37)+(B3.4), (Al-37)+(B3.5), (Al-37)+(B3.6), (Al-37)+(B3.7), (Al-37)+(B3.8), (Al-37)+(B3.9), (Al-37)+(B3.10), (Al-37)+(B3.11), (Al-37)+(B3.12), (Al-37)+(B3.13), (Al-37)+(B3.14), (Al-37)+(B3.15), (Al-37)+(B3.16), (Al-37)+(B4.1), (Al-37)+(B4.2), (Al-37)+(B4.3), (Al-37)+(B4.4), (Al-37)+(B4.5), (Al-37)+(B4.6), (Al-37)+(B4.7).

(Al-38)+(B1.1), (Al-38)+(B1.2), (Al-38)+(B1.3), (Al-38)+(B1.4), (Al-38)+(B1.5), (Al-38)+(B1.6), (Al-38)+(B1.7), (Al-38)+(B1.8), (Al-38)+(B1.9), (Al-38)+(B1.10), (Al-38)+(B1.11), (Al-38)+(B1.12), (Al-38)+(B1.13), (Al-38)+(B1.14), (Al-38)+(B1.15), (Al-38)+(B1.16), (Al-38)+(B1.17), (Al-38)+(B1.18), (Al-38)+(B1.19), (Al-38)+(B1.20), (Al-38)+(B1.21), (Al-38)+(B1.22), (Al-38)+(B1.23), (Al-38)+(B1.24), (Al-38)+(B1.25), (Al-38)+(B1.26), (Al-38)+(B1.27), (Al-38)+(B1.28), (Al-38)+(B1.29), (Al-38)+(B1.30), (Al-38)+(B1.31), (Al-38)+(B1.32), (Al-38)+(B1.33), (Al-38)+(B1.34), (Al-38)+(B1.35), (Al-38)+(B1.36), (Al-38)+(B1.37), (Al-38)+(B1.38), (Al-38)+(B1.39), (Al-38)+(B1.40), (Al-38)+(B1.41), (Al-38)+(B1.42), (Al-38)+(B1.43), (Al-38)+(B1.44), (Al-38)+(B1.45), (Al-38)+(B1.46), (Al-38)+(B1.47), (Al-38)+(B1.48), (Al-38)+(B1.49), (Al-38)+(B1.50), (Al-38)+(B1.51), (Al-38)+(B1.52), (Al-38)+(B1.53), (Al-38)+(B1.54), (Al-38)+(B1.55), (Al-38)+(B1.56), (Al-38)+(B1.57), (Al-38)+(B1.58), (Al-38)+(B1.59), (Al-38)+(B1.60), (Al-38)+(B1.61), (Al-38)+(B1.62), (Al-38)+(B1.63), (Al-38)+(B1.64), (Al-38)+(B1.65), (Al-38)+(B1.66), (Al-38)+(B2.1), (Al-38)+(B2.2), (Al-38)+(B2.3), (Al-38)+(B2.4), (Al-38)+(B2.5), (Al-38)+(B2.6), (Al-38)+(B2.7), (Al-38)+(B2.8), (Al-38)+(B2.9), (Al-38)+(B2.10), (Al-38)+(B2.11), (Al-38)+(B2.12), (Al-38)+(B2.13), (Al-38)+(B2.14), (Al-38)+(B2.15), (Al-38)+(B2.16), (Al-38)+(B2.17), (Al-38)+(B2.18), (Al-38)+(B2.19), (Al-38)+(B2.20), (Al-38)+(B2.21), (Al-38)+(B2.22), (Al-38)+(B2.23), (Al-38)+(B2.24), (Al-38)+(B2.25), (Al-38)+(B2.26), (Al-38)+(B2.27), (Al-38)+(B2.28), (Al-38)+(B2.29), (Al-38)+(B2.30), (Al-38)+(B2.31), (Al-38)+(B2.32), (Al-38)+(B2.33), (Al-38)+(B2.34), (Al-38)+(B2.35), (Al-38)+(B2.36), (Al-38)+(B2.37), (Al-38)+(B2.38), (Al-38)+(B2.39), (Al-38)+(B2.40), (Al-38)+(B2.41), (Al-38)+(B2.42), (Al-38)+(B2.43), (Al-38)+(B2.44), (Al-38)+(B2.45), (Al-38)+(B2.46), (Al-38)+(B2.47), (Al-38)+(B2.48), (Al-38)+(B2.49), (Al-38)+(B2.50), (Al-38)+(B3.1), (Al-38)+(B3.2.), (Al-38)+(B3.3), (Al-38)+(B3.4), (Al-38)+(B3.5), (Al-38)+(B3.6), (Al-38)+(B3.7), (Al-38)+(B3.8), (Al-38)+(B3.9), (Al-38)+(B3.10), (Al-38)+(B3.11), (Al-38)+(B3.12), (Al-38)+(B3.13), (Al-38)+(B3.14), (Al-38)+(B3.15), (Al-38)+(B3.16), (Al-38)+(B4.1), (Al-38)+(B4.2), (Al-38)+(B4.3), (Al-38)+(B4.4), (Al-38)+(B4.5), (Al-38)+(B4.6), (Al-38)+(B4.7).

(Al-39)+(B1.1), (Al-39)+(B1.2), (Al-39)+(B1.3), (Al-39)+(B1.4), (Al-39)+(B1.5), (Al-39)+(B1.6), (Al-39)+(B1.7), (Al-39)+(B1.8), (Al-39)+(B1.9), (Al-39)+(B1.10), (Al-39)+(B1.11), (Al-39)+(B1.12), (Al-39)+(B1.13), (Al-39)+(B1.14), (Al-39)+(B1.15), (Al-39)+(B1.16), (Al-39)+(B1.17), (Al-39)+(B1.18), (Al-39)+(B1.19), (Al-39)+(B1.20), (Al-39)+(B1.21), (Al-39)+(B1.22), (Al-39)+(B1.23), (Al-39)+(B1.24), (Al-39)+(B1.25), (Al-39)+(B1.26), (Al-39)+(B1.27), (Al-39)+(B1.28), (Al-39)+(B1.29), (Al-39)+(B1.30), (Al-39)+(B1.31), (Al-39)+(B1.32), (Al-39)+(B1.33), (Al-39)+(B1.34), (Al-39)+(B1.35), (Al-39)+(B1.36), (Al-39)+(B1.37), (Al-39)+(B1.38), (Al-39)+(B1.39), (Al-39)+(B1.40), (Al-39)+(B1.41), (Al-39)+(B1.42), (Al-39)+(B1.43), (Al-39)+(B1.44), (Al-39)+(B1.45), (Al-39)+(B1.46), (Al-39)+(B1.47), (Al-39)+(B1.48), (Al-39)+(B1.49), (Al-39)+(B1.50), (Al-39)+(B1.51), (Al-39)+(B1.52), (Al-39)+(B1.53), (Al-39)+(B1.54), (Al-39)+(B1.55), (Al-39)+(B1.56), (Al-39)+(B1.57), (Al-39)+(B1.58), (Al-39)+(B1.59), (Al-39)+(B1.60), (Al-39)+(B1.61), (Al-39)+(B1.62), (Al-39)+(B1.63), (Al-39)+(B1.64), (Al-39)+(B1.65), (Al-39)+(B1.66), (Al-39)+(B2.1), (Al-39)+(B2.2), (Al-39)+(B2.3), (Al-39)+(B2.4), (Al-39)+(B2.5), (Al-39)+(B2.6), (Al-39)+(B2.7), (Al-39)+(B2.8), (Al-39)+(B2.9), (Al-39)+(B2.10), (Al-39)+(B2.11), (Al-39)+(B2.12), (Al-39)+(B2.13), (Al-39)+(B2.14), (Al-39)+(B2.15), (Al-39)+(B2.16), (Al-39)+(B2.17), (Al-39)+(B2.18), (Al-39)+(B2.19), (Al-39)+(B2.20), (Al-39)+(B2.21), (Al-39)+(B2.22), (Al-39)+(B2.23), (Al-39)+(B2.24), (Al-39)+(B2.25), (Al-39)+(B2.26), (Al-39)+(B2.27), (Al-39)+(B2.28), (Al-39)+(B2.29), (Al-39)+(B2.30), (Al-39)+(B2.31), (Al-39)+(B2.32), (Al-39)+(B2.33), (Al-39)+(B2.34), (Al-39)+(B2.35), (Al-39)+(B2.36), (Al-39)+(B2.37), (Al-39)+(B2.38), (Al-39)+(B2.39), (Al-39)+(B2.40), (Al-39)+(B2.41), (Al-39)+(B2.42), (Al-39)+(B2.43), (Al-39)+(B2.44), (Al-39)+(B2.45), (Al-39)+(B2.46), (Al-39)+(B2.47), (Al-39)+(B2.48), (Al-39)+(B2.49), (Al-39)+(B2.50), (Al-39)+(B3.1), (Al-39)+(B3.2.), (Al-39)+(B3.3), (Al-39)+(B3.4), (Al-39)+(B3.5), (Al-39)+(B3.6), (Al-39)+(B3.7), (Al-39)+(B3.8), (Al-39)+(B3.9), (Al-39)+(B3.10), (Al-39)+(B3.11), (Al-39)+(B3.12), (Al-39)+(B3.13), (Al-39)+(B3.14), (Al-39)+(B3.15), (Al-39)+(B3.16), (Al-39)+(B4.1), (Al-39)+(B4.2), (Al-39)+(B4.3), (Al-39)+(B4.4), (Al-39)+(B4.5), (Al-39)+(B4.6), (Al-39)+(B4.7).

(Al-40)+(B1.1), (Al-40)+(B1.2), (Al-40)+(B1.3), (Al-40)+(B1.4), (Al-40)+(B1.5), (Al-40)+(B1.6), (Al-40)+(B1.7), (Al-40)+(B1.8), (Al-40)+(B1.9), (Al-40)+(B1.10), (Al-40)+(B1.11), (Al-40)+(B1.12), (Al-40)+(B1.13), (Al-40)+(B1.14), (Al-40)+(B1.15), (Al-40)+(B1.16), (Al-40)+(B1.17), (Al-40)+(B1.18), (Al-40)+(B1.19), (Al-40)+(B1.20), (Al-40)+(B1.21), (Al-40)+(B1.22), (Al-40)+(B1.23), (Al-40)+(B1.24), (Al-40)+(B1.25), (Al-40)+(B1.26), (Al-40)+(B1.27), (Al-40)+(B1.28), (Al-40)+(B1.29), (Al-40)+(B1.30), (Al-40)+(B1.31), (Al-40)+(B1.32), (Al-40)+(B1.33), (Al-40)+(B1.34), (Al-40)+

(B1.35), (Al-40)+(B1.36), (Al-40)+(B1.37), (Al-40)+(B1.38), (Al-40)+(B1.39), (Al-40)+(B1.40), (Al-40)+(B1.41), (Al-40)+(B1.42), (Al-40)+(B1.43), (Al-40)+(B1.44), (Al-40)+(B1.45), (Al-40)+(B1.46), (Al-40)+(B1.47), (Al-40)+(B1.48), (Al-40)+(B1.49), (Al-40)+(B1.50), (Al-40)+(B1.51), (Al-40)+(B1.52), (Al-40)+(B1.53), (Al-40)+(B1.54), (Al-40)+(B1.55), (Al-40)+(B1.56), (Al-40)+(B1.57), (Al-40)+(B1.58), (Al-40)+(B1.59), (Al-40)+(B1.60), (Al-40)+(B1.61), (Al-40)+(B1.62), (Al-40)+(B1.63), (Al-40)+(B1.64), (Al-40)+(B1.65), (Al-40)+(B1.66), (Al-40)+(B2.1), (Al-40)+(B2.2), (Al-40)+(B2.3), (Al-40)+(B2.4), (Al-40)+(B2.5), (Al-40)+(B2.6), (Al-40)+(B2.7), (Al-40)+(B2.8), (Al-40)+(B2.9), (Al-40)+(B2.10), (Al-40)+(B2.11), (Al-40)+(B2.12), (Al-40)+(B2.13), (Al-40)+(B2.14), (Al-40)+(B2.15), (Al-40)+(B2.16), (Al-40)+(B2.17), (Al-40)+(B2.18), (Al-40)+(B2.19), (Al-40)+(B2.20), (Al-40)+(B2.21), (Al-40)+(B2.22), (Al-40)+(B2.23), (Al-40)+(B2.24), (Al-40)+(B2.25), (Al-40)+(B2.26), (Al-40)+(B2.27), (Al-40)+(B2.28), (Al-40)+(B2.29), (Al-40)+(B2.30), (Al-40)+(B2.31), (Al-40)+(B2.32), (Al-40)+(B2.33), (Al-40)+(B2.34), (Al-40)+(B2.35), (Al-40)+(B2.36), (Al-40)+(B2.37), (Al-40)+(B2.38), (Al-40)+(B2.39), (Al-40)+(B2.40), (Al-40)+(B2.41), (Al-40)+(B2.42), (Al-40)+(B2.43), (Al-40)+(B2.44), (Al-40)+(B2.45), (Al-40)+(B2.46), (Al-40)+(B2.47), (Al-40)+(B2.48), (Al-40)+(B2.49), (Al-40)+(B2.50), (Al-40)+(B3.1), (Al-40)+(B3.2.), (Al-40)+(B3.3), (Al-40)+(B3.4), (Al-40)+(B3.5), (Al-40)+(B3.6), (Al-40)+(B3.7), (Al-40)+(B3.8), (Al-40)+(B3.9), (Al-40)+(B3.10), (Al-40)+(B3.11), (Al-40)+(B3.12), (Al-40)+(B3.13), (Al-40)+(B3.14), (Al-40)+(B3.15), (Al-40)+(B3.16), (Al-40)+(B4.1), (Al-40)+(B4.2), (Al-40)+(B4.3), (Al-40)+(B4.4), (Al-40)+(B4.5), (Al-40)+(B4.6), (Al-40)+(B4.7).

(Al-41)+(B1.1), (Al-41)+(B1.2), (Al-41)+(B1.3), (Al-41)+(B1.4), (Al-41)+(B1.5), (Al-41)+(B1.6), (Al-41)+(B1.7), (Al-41)+(B1.8), (Al-41)+(B1.9), (Al-41)+(B1.10), (Al-41)+(B1.11), (Al-41)+(B1.12), (Al-41)+(B1.13), (Al-41)+(B1.14), (Al-41)+(B1.15), (Al-41)+(B1.16), (Al-41)+(B1.17), (Al-41)+(B1.18), (Al-41)+(B1.19), (Al-41)+(B1.20), (Al-41)+(B1.21), (Al-41)+(B1.22), (Al-41)+(B1.23), (Al-41)+(B1.24), (Al-41)+(B1.25), (Al-41)+(B1.26), (Al-41)+(B1.27), (Al-41)+(B1.28), (Al-41)+(B1.29), (Al-41)+(B1.30), (Al-41)+(B1.31), (Al-41)+(B1.32), (Al-41)+(B1.33), (Al-41)+(B1.34), (Al-41)+(B1.35), (Al-41)+(B1.36), (Al-41)+(B1.37), (Al-41)+(B1.38), (Al-41)+(B1.39), (Al-41)+(B1.40), (Al-41)+(B1.41), (Al-41)+(B1.42), (Al-41)+(B1.43), (Al-41)+(B1.44), (Al-41)+(B1.45), (Al-41)+(B1.46), (Al-41)+(B1.47), (Al-41)+(B1.48), (Al-41)+(B1.49), (Al-41)+(B1.50), (Al-41)+(B1.51), (Al-41)+(B1.52), (Al-41)+(B1.53), (Al-41)+(B1.54), (Al-41)+(B1.55), (Al-41)+(B1.56), (Al-41)+(B1.57), (Al-41)+(B1.58), (Al-41)+(B1.59), (Al-41)+(B1.60), (Al-41)+(B1.61), (Al-41)+(B1.62), (Al-41)+(B1.63), (Al-41)+(B1.64), (Al-41)+(B1.65), (Al-41)+(B1.66), (Al-41)+(B2.1), (Al-41)+(B2.2), (Al-41)+(B2.3), (Al-41)+(B2.4), (Al-41)+(B2.5), (Al-41)+(B2.6), (Al-41)+(B2.7), (Al-41)+(B2.8), (Al-41)+(B2.9), (Al-41)+(B2.10), (Al-41)+(B2.11), (Al-41)+(B2.12), (Al-41)+(B2.13), (Al-41)+(B2.14), (Al-41)+(B2.15), (Al-41)+(B2.16), (Al-41)+(B2.17), (Al-41)+(B2.18), (Al-41)+(B2.19), (Al-41)+(B2.20), (Al-41)+(B2.21), (Al-41)+(B2.22), (Al-41)+(B2.23), (Al-41)+(B2.24), (Al-41)+(B2.25), (Al-41)+(B2.26), (Al-41)+(B2.27), (Al-41)+(B2.28), (Al-41)+(B2.29), (Al-41)+(B2.30), (Al-41)+(B2.31), (Al-41)+(B2.32), (Al-41)+(B2.33), (Al-41)+(B2.34), (Al-41)+(B2.35), (Al-41)+(B2.36), (Al-41)+(B2.37), (Al-41)+(B2.38), (Al-41)+(B2.39), (Al-41)+(B2.40), (Al-41)+(B2.41), (Al-41)+(B2.42), (Al-41)+(B2.43), (Al-41)+(B2.44), (Al-41)+(B2.45), (Al-41)+(B2.46), (Al-41)+(B2.47), (Al-41)+(B2.48), (Al-41)+(B2.49), (Al-41)+(B2.50), (Al-41)+(B3.1), (Al-41)+(B3.2.), (Al-41)+(B3.3), (Al-41)+(B3.4), (Al-41)+(B3.5), (Al-41)+(B3.6), (Al-41)+(B3.7), (Al-41)+(B3.8), (Al-41)+(B3.9), (Al-41)+(B3.10), (Al-41)+(B3.11), (Al-41)+(B3.12), (Al-41)+(B3.13), (Al-41)+(B3.14), (Al-41)+(B3.15), (Al-41)+(B3.16), (Al-41)+(B4.1), (Al-41)+(B4.2), (Al-41)+(B4.3), (Al-41)+(B4.4), (Al-41)+(B4.5), (Al-41)+(B4.6), (Al-41)+(B4.7).

(Al-42)+(B1.1), (Al-42)+(B1.2), (Al-42)+(B1.3), (Al-42)+(B1.4), (Al-42)+(B1.5), (Al-42)+(B1.6), (Al-42)+(B1.7), (Al-42)+(B1.8), (Al-42)+(B1.9), (Al-42)+(B1.10), (Al-42)+(B1.11), (Al-42)+(B1.12), (Al-42)+(B1.13), (Al-42)+(B1.14), (Al-42)+(B1.15), (Al-42)+(B1.16), (Al-42)+(B1.17), (Al-42)+(B1.18), (Al-42)+(B1.19), (Al-42)+(B1.20), (Al-42)+(B1.21), (Al-42)+(B1.22), (Al-42)+(B1.23), (Al-42)+(B1.24), (Al-42)+(B1.25), (Al-42)+(B1.26), (Al-42)+(B1.27), (Al-42)+(B1.28), (Al-42)+(B1.29), (Al-42)+(B1.30), (Al-42)+(B1.31), (Al-42)+(B1.32), (Al-42)+(B1.33), (Al-42)+(B1.34), (Al-42)+(B1.35), (Al-42)+(B1.36), (Al-42)+(B1.37), (Al-42)+(B1.38), (Al-42)+(B1.39), (Al-42)+(B1.40), (Al-42)+(B1.41), (Al-42)+(B1.42), (Al-42)+(B1.43), (Al-42)+(B1.44), (Al-42)+(B1.45), (Al-42)+(B1.46), (Al-42)+(B1.47), (Al-42)+(B1.48), (Al-42)+(B1.49), (Al-42)+(B1.50), (Al-42)+(B1.51), (Al-42)+(B1.52), (Al-42)+(B1.53), (Al-42)+(B1.54), (Al-42)+(B1.55), (Al-42)+(B1.56), (Al-42)+(B1.57), (Al-42)+(B1.58), (Al-42)+(B1.59), (Al-42)+(B1.60), (Al-42)+(B1.61), (Al-42)+(B1.62), (Al-42)+(B1.63), (Al-42)+(B1.64), (Al-42)+(B1.65), (Al-42)+(B1.66), (Al-42)+(B2.1), (Al-42)+(B2.2), (Al-42)+(B2.3), (Al-42)+(B2.4), (Al-42)+(B2.5), (Al-42)+(B2.6), (Al-42)+(B2.7), (Al-42)+(B2.8), (Al-42)+(B2.9), (Al-42)+(B2.10), (Al-42)+(B2.11), (Al-42)+(B2.12), (Al-42)+(B2.13), (Al-42)+(B2.14), (Al-42)+(B2.15), (Al-42)+(B2.16), (Al-42)+(B2.17), (Al-42)+(B2.18), (Al-42)+(B2.19), (Al-42)+(B2.20), (Al-42)+(B2.21), (Al-42)+(B2.22), (Al-42)+(B2.23), (Al-42)+(B2.24), (Al-42)+(B2.25), (Al-42)+(B2.26), (Al-42)+(B2.27), (Al-42)+(B2.28), (Al-42)+(B2.29), (Al-42)+(B2.30), (Al-42)+(B2.31), (Al-42)+(B2.32), (Al-42)+(B2.33), (Al-42)+(B2.34), (Al-42)+(B2.35), (Al-42)+(B2.36), (Al-42)+(B2.37), (Al-42)+(B2.38), (Al-42)+(B2.39), (Al-42)+(B2.40), (Al-42)+(B2.41), (Al-42)+(B2.42), (Al-42)+(B2.43), (Al-42)+(B2.44), (Al-42)+(B2.45), (Al-42)+(B2.46), (Al-42)+(B2.47), (Al-42)+(B2.48), (Al-42)+(B2.49), (Al-42)+(B2.50), (Al-42)+(B3.1), (Al-42)+(B3.2.), (Al-42)+(B3.3), (Al-42)+(B3.4), (Al-42)+(B3.5), (Al-42)+(B3.6), (Al-42)+(B3.7), (Al-42)+(B3.8), (Al-42)+(B3.9), (Al-42)+(B3.10), (Al-42)+(B3.11), (Al-42)+(B3.12), (Al-42)+(B3.13), (Al-42)+(B3.14), (Al-42)+(B3.15), (Al-42)+(B3.16), (Al-42)+(B4.1), (Al-42)+(B4.2), (Al-42)+(B4.3), (Al-42)+(B4.4), (Al-42)+(B4.5), (Al-42)+(B4.6), (Al-42)+(B4.7).

(Al-43)+(B1.1), (Al-43)+(B1.2), (Al-43)+(B1.3), (Al-43)+(B1.4), (Al-43)+(B1.5), (Al-43)+(B1.6), (Al-43)+(B1.7), (Al-43)+(B1.8), (Al-43)+(B1.9), (Al-43)+(B1.10), (Al-43)+(B1.11), (Al-43)+(B1.12), (Al-43)+(B1.13), (Al-43)+(B1.14), (Al-43)+(B1.15), (Al-43)+(B1.16), (Al-43)+(B1.17), (Al-43)+(B1.18), (Al-43)+(B1.19), (Al-43)+(B1.20), (Al-43)+(B1.21), (Al-43)+(B1.22), (Al-43)+(B1.23), (Al-43)+(B1.24), (Al-43)+(B1.25), (Al-43)+(B1.26), (Al-43)+(B1.27), (Al-43)+(B1.28), (Al-43)+(B1.29), (Al-43)+(B1.30), (Al-43)+(B1.31), (Al-43)+

(B1.32), (Al-43)+(B1.33), (Al-43)+(B1.34), (Al-43)+(B1.35), (Al-43)+(B1.36), (Al-43)+(B1.37), (Al-43)+(B1.38), (Al-43)+(B1.39), (Al-43)+(B1.40), (Al-43)+(B1.41), (Al-43)+(B1.42), (Al-43)+(B1.43), (Al-43)+(B1.44), (Al-43)+(B1.45), (Al-43)+(B1.46), (Al-43)+(B1.47), (Al-43)+(B1.48), (Al-43)+(B1.49), (Al-43)+(B1.50), (Al-43)+(B1.51), (Al-43)+(B1.52), (Al-43)+(B1.53), (Al-43)+(B1.54), (Al-43)+(B1.55), (Al-43)+(B1.56), (Al-43)+(B1.57), (Al-43)+(B1.58), (Al-43)+(B1.59), (Al-43)+(B1.60), (Al-43)+(B1.61), (Al-43)+(B1.62), (Al-43)+(B1.63), (Al-43)+(B1.64), (Al-43)+(B1.65), (Al-43)+(B1.66), (Al-43)+(B2.1), (Al-43)+(B2.2), (Al-43)+(B2.3), (Al-43)+(B2.4), (Al-43)+(B2.5), (Al-43)+(B2.6), (Al-43)+(B2.7), (Al-43)+(B2.8), (Al-43)+(B2.9), (Al-43)+(B2.10), (Al-43)+(B2.11), (Al-43)+(B2.12), (Al-43)+(B2.13), (Al-43)+(B2.14), (Al-43)+(B2.15), (Al-43)+(B2.16), (Al-43)+(B2.17), (Al-43)+(B2.18), (Al-43)+(B2.19), (Al-43)+(B2.20), (Al-43)+(B2.21), (Al-43)+(B2.22), (Al-43)+(B2.23), (Al-43)+(B2.24), (Al-43)+(B2.25), (Al-43)+(B2.26), (Al-43)+(B2.27), (Al-43)+(B2.28), (Al-43)+(B2.29), (Al-43)+(B2.30), (Al-43)+(B2.31), (Al-43)+(B2.32), (Al-43)+(B2.33), (Al-43)+(B2.34), (Al-43)+(B2.35), (Al-43)+(B2.36), (Al-43)+(B2.37), (Al-43)+(B2.38), (Al-43)+(B2.39), (Al-43)+(B2.40), (Al-43)+(B2.41), (Al-43)+(B2.42), (Al-43)+(B2.43), (Al-43)+(B2.44), (Al-43)+(B2.45), (Al-43)+(B2.46), (Al-43)+(B2.47), (Al-43)+(B2.48), (Al-43)+(B2.49), (Al-43)+(B2.50), (Al-43)+(B3.1), (Al-43)+(B3.2.), (Al-43)+(B3.3), (Al-43)+(B3.4), (Al-43)+(B3.5), (Al-43)+(B3.6), (Al-43)+(B3.7), (Al-43)+(B3.8), (Al-43)+(B3.9), (Al-43)+(B3.10), (Al-43)+(B3.11), (Al-43)+(B3.12), (Al-43)+(B3.13), (Al-43)+(B3.14), (Al-43)+(B3.15), (Al-43)+(B3.16), (Al-43)+(B4.1), (Al-43)+(B4.2), (Al-43)+(B4.3), (Al-43)+(B4.4), (Al-43)+(B4.5), (Al-43)+(B4.6), (Al-43)+(B4.7).

(Al-44)+(B1.1), (Al-44)+(B1.2), (Al-44)+(B1.3), (Al-44)+(B1.4), (Al-44)+(B1.5), (Al-44)+(B1.6), (Al-44)+(B1.7), (Al-44)+(B1.8), (Al-44)+(B1.9), (Al-44)+(B1.10), (Al-44)+(B1.11), (Al-44)+(B1.12), (Al-44)+(B1.13), (Al-44)+(B1.14), (Al-44)+(B1.15), (Al-44)+(B1.16), (Al-44)+(B1.17), (Al-44)+(B1.18), (Al-44)+(B1.19), (Al-44)+(B1.20), (Al-44)+(B1.21), (Al-44)+(B1.22), (Al-44)+(B1.23), (Al-44)+(B1.24), (Al-44)+(B1.25), (Al-44)+(B1.26), (Al-44)+(B1.27), (Al-44)+(B1.28), (Al-44)+(B1.29), (Al-44)+(B1.30), (Al-44)+(B1.31), (Al-44)+(B1.32), (Al-44)+(B1.33), (Al-44)+(B1.34), (Al-44)+(B1.35), (Al-44)+(B1.36), (Al-44)+(B1.37), (Al-44)+(B1.38), (Al-44)+(B1.39), (Al-44)+(B1.40), (Al-44)+(B1.41), (Al-44)+(B1.42), (Al-44)+(B1.43), (Al-44)+(B1.44), (Al-44)+(B1.45), (Al-44)+(B1.46), (Al-44)+(B1.47), (Al-44)+(B1.48), (Al-44)+(B1.49), (Al-44)+(B1.50), (Al-44)+(B1.51), (Al-44)+(B1.52), (Al-44)+(B1.53), (Al-44)+(B1.54), (Al-44)+(B1.55), (Al-44)+(B1.56), (Al-44)+(B1.57), (Al-44)+(B1.58), (Al-44)+(B1.59), (Al-44)+(B1.60), (Al-44)+(B1.61), (Al-44)+(B1.62), (Al-44)+(B1.63), (Al-44)+(B1.64), (Al-44)+(B1.65), (Al-44)+(B1.66), (Al-44)+(B2.1), (Al-44)+(B2.2), (Al-44)+(B2.3), (Al-44)+(B2.4), (Al-44)+(B2.5), (Al-44)+(B2.6), (Al-44)+(B2.7), (Al-44)+(B2.8), (Al-44)+(B2.9), (Al-44)+(B2.10), (Al-44)+(B2.11), (Al-44)+(B2.12), (Al-44)+(B2.13), (Al-44)+(B2.14), (Al-44)+(B2.15), (Al-44)+(B2.16), (Al-44)+(B2.17), (Al-44)+(B2.18), (Al-44)+(B2.19), (Al-44)+(B2.20), (Al-44)+(B2.21), (Al-44)+(B2.22), (Al-44)+(B2.23), (Al-44)+(B2.24), (Al-44)+(B2.25), (Al-44)+(B2.26), (Al-44)+(B2.27), (Al-44)+(B2.28), (Al-44)+(B2.29), (Al-44)+(B2.30), (Al-44)+(B2.31), (Al-44)+(B2.32), (Al-44)+(B2.33), (Al-44)+(B2.34), (Al-44)+(B2.35), (Al-44)+(B2.36), (Al-44)+(B2.37), (Al-44)+(B2.38), (Al-44)+(B2.39), (Al-44)+(B2.40), (Al-44)+(B2.41), (Al-44)+(B2.42), (Al-44)+(B2.43), (Al-44)+(B2.44), (Al-44)+(B2.45), (Al-44)+(B2.46), (Al-44)+(B2.47), (Al-44)+(B2.48), (Al-44)+(B2.49), (Al-44)+(B2.50), (Al-44)+(B3.1), (Al-44)+(B3.2.), (Al-44)+(B3.3), (Al-44)+(B3.4), (Al-44)+(B3.5), (Al-44)+(B3.6), (Al-44)+(B3.7), (Al-44)+(B3.8), (Al-44)+(B3.9), (Al-44)+(B3.10), (Al-44)+(B3.11), (Al-44)+(B3.12), (Al-44)+(B3.13), (Al-44)+(B3.14), (Al-44)+(B3.15), (Al-44)+(B3.16), (Al-44)+(B4.1), (Al-44)+(B4.2), (Al-44)+(B4.3), (Al-44)+(B4.4), (Al-44)+(B4.5), (Al-44)+(B4.6), (Al-44)+(B4.7).

(Al-45)+(B1.1), (Al-45)+(B1.2), (Al-45)+(B1.3), (Al-45)+(B1.4), (Al-45)+(B1.5), (Al-45)+(B1.6), (Al-45)+(B1.7), (Al-45)+(B1.8), (Al-45)+(B1.9), (Al-45)+(B1.10), (Al-45)+(B1.11), (Al-45)+(B1.12), (Al-45)+(B1.13), (Al-45)+(B1.14), (Al-45)+(B1.15), (Al-45)+(B1.16), (Al-45)+(B1.17), (Al-45)+(B1.18), (Al-45)+(B1.19), (Al-45)+(B1.20), (Al-45)+(B1.21), (Al-45)+(B1.22), (Al-45)+(B1.23), (Al-45)+(B1.24), (Al-45)+(B1.25), (Al-45)+(B1.26), (Al-45)+(B1.27), (Al-45)+(B1.28), (Al-45)+(B1.29), (Al-45)+(B1.30), (Al-45)+(B1.31), (Al-45)+(B1.32), (Al-45)+(B1.33), (Al-45)+(B1.34), (Al-45)+(B1.35), (Al-45)+(B1.36), (Al-45)+(B1.37), (Al-45)+(B1.38), (Al-45)+(B1.39), (Al-45)+(B1.40), (Al-45)+(B1.41), (Al-45)+(B1.42), (Al-45)+(B1.43), (Al-45)+(B1.44), (Al-45)+(B1.45), (Al-45)+(B1.46), (Al-45)+(B1.47), (Al-45)+(B1.48), (Al-45)+(B1.49), (Al-45)+(B1.50), (Al-45)+(B1.51), (Al-45)+(B1.52), (Al-45)+(B1.53), (Al-45)+(B1.54), (Al-45)+(B1.55), (Al-45)+(B1.56), (Al-45)+(B1.57), (Al-45)+(B1.58), (Al-45)+(B1.59), (Al-45)+(B1.60), (Al-45)+(B1.61), (Al-45)+(B1.62), (Al-45)+(B1.63), (Al-45)+(B1.64), (Al-45)+(B1.65), (Al-45)+(B1.66), (Al-45)+(B2.1), (Al-45)+(B2.2), (Al-45)+(B2.3), (Al-45)+(B2.4), (Al-45)+(B2.5), (Al-45)+(B2.6), (Al-45)+(B2.7), (Al-45)+(B2.8), (Al-45)+(B2.9), (Al-45)+(B2.10), (Al-45)+(B2.11), (Al-45)+(B2.12), (Al-45)+(B2.13), (Al-45)+(B2.14), (Al-45)+(B2.15), (Al-45)+(B2.16), (Al-45)+(B2.17), (Al-45)+(B2.18), (Al-45)+(B2.19), (Al-45)+(B2.20), (Al-45)+(B2.21), (Al-45)+(B2.22), (Al-45)+(B2.23), (Al-45)+(B2.24), (Al-45)+(B2.25), (Al-45)+(B2.26), (Al-45)+(B2.27), (Al-45)+(B2.28), (Al-45)+(B2.29), (Al-45)+(B2.30), (Al-45)+(B2.31), (Al-45)+(B2.32), (Al-45)+(B2.33), (Al-45)+(B2.34), (Al-45)+(B2.35), (Al-45)+(B2.36), (Al-45)+(B2.37), (Al-45)+(B2.38), (Al-45)+(B2.39), (Al-45)+(B2.40), (Al-45)+(B2.41), (Al-45)+(B2.42), (Al-45)+(B2.43), (Al-45)+(B2.44), (Al-45)+(B2.45), (Al-45)+(B2.46), (Al-45)+(B2.47), (Al-45)+(B2.48), (Al-45)+(B2.49), (Al-45)+(B2.50), (Al-45)+(B3.1), (Al-45)+(B3.2.), (Al-45)+(B3.3), (Al-45)+(B3.4), (Al-45)+(B3.5), (Al-45)+(B3.6), (Al-45)+(B3.7), (Al-45)+(B3.8), (Al-45)+(B3.9), (Al-45)+(B3.10), (Al-45)+(B3.11), (Al-45)+(B3.12), (Al-45)+(B3.13), (Al-45)+(B3.14), (Al-45)+(B3.15), (Al-45)+(B3.16), (Al-45)+(B4.1), (Al-45)+(B4.2), (Al-45)+(B4.3), (Al-45)+(B4.4), (Al-45)+(B4.5), (Al-45)+(B4.6), (Al-45)+(B4.7).

(Al-46)+(B1.1), (Al-46)+(B1.2), (Al-46)+(B1.3), (Al-46)+(B1.4), (Al-46)+(B1.5), (Al-46)+(B1.6), (Al-46)+(B1.7), (Al-46)+(B1.8), (Al-46)+(B1.9), (Al-46)+(B1.10), (Al-46)+(B1.11), (Al-46)+(B1.12), (Al-46)+(B1.13), (Al-46)+(B1.14), (Al-46)+(B1.15), (Al-46)+(B1.16), (Al-46)+(B1.17), (Al-46)+(B1.18), (Al-46)+(B1.19), (Al-46)+(B1.20), (Al-46)+(B1.21), (Al-46)+(B1.22), (Al-46)+(B1.23), (Al-46)+(B1.24), (Al-46)+(B1.25), (Al-46)+(B1.26), (Al-46)+(B1.27), (Al-46)+(B1.28), (Al-46)+

(B1.29), (Al-46)+(B1.30), (Al-46)+(B1.31), (Al-46)+(B1.32), (Al-46)+(B1.33), (Al-46)+(B1.34), (Al-46)+(B1.35), (Al-46)+(B1.36), (Al-46)+(B1.37), (Al-46)+(B1.38), (Al-46)+(B1.39), (Al-46)+(B1.40), (Al-46)+(B1.41), (Al-46)+(B1.42), (Al-46)+(B1.43), (Al-46)+(B1.44), (Al-46)+(B1.45), (Al-46)+(B1.46), (Al-46)+(B1.47), (Al-46)+(B1.48), (Al-46)+(B1.49), (Al-46)+(B1.50), (Al-46)+(B1.51), (Al-46)+(B1.52), (Al-46)+(B1.53), (Al-46)+(B1.54), (Al-46)+(B1.55), (Al-46)+(B1.56), (Al-46)+(B1.57), (Al-46)+(B1.58), (Al-46)+(B1.59), (Al-46)+(B1.60), (Al-46)+(B1.61), (Al-46)+(B1.62), (Al-46)+(B1.63), (Al-46)+(B1.64), (Al-46)+(B1.65), (Al-46)+(B1.66), (Al-46)+(B2.1), (Al-46)+(B2.2), (Al-46)+(B2.3), (Al-46)+(B2.4), (Al-46)+(B2.5), (Al-46)+(B2.6), (Al-46)+(B2.7), (Al-46)+(B2.8), (Al-46)+(B2.9), (Al-46)+(B2.10), (Al-46)+(B2.11), (Al-46)+(B2.12), (Al-46)+(B2.13), (Al-46)+(B2.14), (Al-46)+(B2.15), (Al-46)+(B2.16), (Al-46)+(B2.17), (Al-46)+(B2.18), (Al-46)+(B2.19), (Al-46)+(B2.20), (Al-46)+(B2.21), (Al-46)+(B2.22), (Al-46)+(B2.23), (Al-46)+(B2.24), (Al-46)+(B2.25), (Al-46)+(B2.26), (Al-46)+(B2.27), (Al-46)+(B2.28), (Al-46)+(B2.29), (Al-46)+(B2.30), (Al-46)+(B2.31), (Al-46)+(B2.32), (Al-46)+(B2.33), (Al-46)+(B2.34), (Al-46)+(B2.35), (Al-46)+(B2.36), (Al-46)+(B2.37), (Al-46)+(B2.38), (Al-46)+(B2.39), (Al-46)+(B2.40), (Al-46)+(B2.41), (Al-46)+(B2.42), (Al-46)+(B2.43), (Al-46)+(B2.44), (Al-46)+(B2.45), (Al-46)+(B2.46), (Al-46)+(B2.47), (Al-46)+(B2.48), (Al-46)+(B2.49), (Al-46)+(B2.50), (Al-46)+(B3.1), (Al-46)+(B3.2.), (Al-46)+(B3.3), (Al-46)+(B3.4), (Al-46)+(B3.5), (Al-46)+(B3.6), (Al-46)+(B3.7), (Al-46)+(B3.8), (Al-46)+(B3.9), (Al-46)+(B3.10), (Al-46)+(B3.11), (Al-46)+(B3.12), (Al-46)+(B3.13), (Al-46)+(B3.14), (Al-46)+(B3.15), (Al-46)+(B3.16), (Al-46)+(B4.1), (Al-46)+(B4.2), (Al-46)+(B4.3), (Al-46)+(B4.4), (Al-46)+(B4.5), (Al-46)+(B4.6), (Al-46)+(B4.7).

(Al-47)+(B1.1), (Al-47)+(B1.2), (Al-47)+(B1.3), (Al-47)+(B1.4), (Al-47)+(B1.5), (Al-47)+(B1.6), (Al-47)+(B1.7), (Al-47)+(B1.8), (Al-47)+(B1.9), (Al-47)+(B1.10), (Al-47)+(B1.11), (Al-47)+(B1.12), (Al-47)+(B1.13), (Al-47)+(B1.14), (Al-47)+(B1.15), (Al-47)+(B1.16), (Al-47)+(B1.17), (Al-47)+(B1.18), (Al-47)+(B1.19), (Al-47)+(B1.20), (Al-47)+(B1.21), (Al-47)+(B1.22), (Al-47)+(B1.23), (Al-47)+(B1.24), (Al-47)+(B1.25), (Al-47)+(B1.26), (Al-47)+(B1.27), (Al-47)+(B1.28), (Al-47)+(B1.29), (Al-47)+(B1.30), (Al-47)+(B1.31), (Al-47)+(B1.32), (Al-47)+(B1.33), (Al-47)+(B1.34), (Al-47)+(B1.35), (Al-47)+(B1.36), (Al-47)+(B1.37), (Al-47)+(B1.38), (Al-47)+(B1.39), (Al-47)+(B1.40), (Al-47)+(B1.41), (Al-47)+(B1.42), (Al-47)+(B1.43), (Al-47)+(B1.44), (Al-47)+(B1.45), (Al-47)+(B1.46), (Al-47)+(B1.47), (Al-47)+(B1.48), (Al-47)+(B1.49), (Al-47)+(B1.50), (Al-47)+(B1.51), (Al-47)+(B1.52), (Al-47)+(B1.53), (Al-47)+(B1.54), (Al-47)+(B1.55), (Al-47)+(B1.56), (Al-47)+(B1.57), (Al-47)+(B1.58), (Al-47)+(B1.59), (Al-47)+(B1.60), (Al-47)+(B1.61), (Al-47)+(B1.62), (Al-47)+(B1.63), (Al-47)+(B1.64), (Al-47)+(B1.65), (Al-47)+(B1.66), (Al-47)+(B2.1), (Al-47)+(B2.2), (Al-47)+(B2.3), (Al-47)+(B2.4), (Al-47)+(B2.5), (Al-47)+(B2.6), (Al-47)+(B2.7), (Al-47)+(B2.8), (Al-47)+(B2.9), (Al-47)+(B2.10), (Al-47)+(B2.11), (Al-47)+(B2.12), (Al-47)+(B2.13), (Al-47)+(B2.14), (Al-47)+(B2.15), (Al-47)+(B2.16), (Al-47)+(B2.17), (Al-47)+(B2.18), (Al-47)+(B2.19), (Al-47)+(B2.20), (Al-47)+(B2.21), (Al-47)+(B2.22), (Al-47)+(B2.23), (Al-47)+(B2.24), (Al-47)+(B2.25), (Al-47)+(B2.26), (Al-47)+(B2.27), (Al-47)+(B2.28), (Al-47)+(B2.29), (Al-47)+(B2.30), (Al-47)+(B2.31), (Al-47)+(B2.32), (Al-47)+(B2.33), (Al-47)+(B2.34), (Al-47)+(B2.35), (Al-47)+(B2.36), (Al-47)+(B2.37), (Al-47)+(B2.38), (Al-47)+(B2.39), (Al-47)+(B2.40), (Al-47)+(B2.41), (Al-47)+(B2.42), (Al-47)+(B2.43), (Al-47)+(B2.44), (Al-47)+(B2.45), (Al-47)+(B2.46), (Al-47)+(B2.47), (Al-47)+(B2.48), (Al-47)+(B2.49), (Al-47)+(B2.50), (Al-47)+(B3.1), (Al-47)+(B3.2.), (Al-47)+(B3.3), (Al-47)+(B3.4), (Al-47)+(B3.5), (Al-47)+(B3.6), (Al-47)+(B3.7), (Al-47)+(B3.8), (Al-47)+(B3.9), (Al-47)+(B3.10), (Al-47)+(B3.11), (Al-47)+(B3.12), (Al-47)+(B3.13), (Al-47)+(B3.14), (Al-47)+(B3.15), (Al-47)+(B3.16), (Al-47)+(B4.1), (Al-47)+(B4.2), (Al-47)+(B4.3), (Al-47)+(B4.4), (Al-47)+(B4.5), (Al-47)+(B4.6), (Al-47)+(B4.7).

(Al-48)+(B1.1), (Al-48)+(B1.2), (Al-48)+(B1.3), (Al-48)+(B1.4), (Al-48)+(B1.5), (Al-48)+(B1.6), (Al-48)+(B1.7), (Al-48)+(B1.8), (Al-48)+(B1.9), (Al-48)+(B1.10), (Al-48)+(B1.11), (Al-48)+(B1.12), (Al-48)+(B1.13), (Al-48)+(B1.14), (Al-48)+(B1.15), (Al-48)+(B1.16), (Al-48)+(B1.17), (Al-48)+(B1.18), (Al-48)+(B1.19), (Al-48)+(B1.20), (Al-48)+(B1.21), (Al-48)+(B1.22), (Al-48)+(B1.23), (Al-48)+(B1.24), (Al-48)+(B1.25), (Al-48)+(B1.26), (Al-48)+(B1.27), (Al-48)+(B1.28), (Al-48)+(B1.29), (Al-48)+(B1.30), (Al-48)+(B1.31), (Al-48)+(B1.32), (Al-48)+(B1.33), (Al-48)+(B1.34), (Al-48)+(B1.35), (Al-48)+(B1.36), (Al-48)+(B1.37), (Al-48)+(B1.38), (Al-48)+(B1.39), (Al-48)+(B1.40), (Al-48)+(B1.41), (Al-48)+(B1.42), (Al-48)+(B1.43), (Al-48)+(B1.44), (Al-48)+(B1.45), (Al-48)+(B1.46), (Al-48)+(B1.47), (Al-48)+(B1.48), (Al-48)+(B1.49), (Al-48)+(B1.50), (Al-48)+(B1.51), (Al-48)+(B1.52), (Al-48)+(B1.53), (Al-48)+(B1.54), (Al-48)+(B1.55), (Al-48)+(B1.56), (Al-48)+(B1.57), (Al-48)+(B1.58), (Al-48)+(B1.59), (Al-48)+(B1.60), (Al-48)+(B1.61), (Al-48)+(B1.62), (Al-48)+(B1.63), (Al-48)+(B1.64), (Al-48)+(B1.65), (Al-48)+(B1.66), (Al-48)+(B2.1), (Al-48)+(B2.2), (Al-48)+(B2.3), (Al-48)+(B2.4), (Al-48)+(B2.5), (Al-48)+(B2.6), (Al-48)+(B2.7), (Al-48)+(B2.8), (Al-48)+(B2.9), (Al-48)+(B2.10), (Al-48)+(B2.11), (Al-48)+(B2.12), (Al-48)+(B2.13), (Al-48)+(B2.14), (Al-48)+(B2.15), (Al-48)+(B2.16), (Al-48)+(B2.17), (Al-48)+(B2.18), (Al-48)+(B2.19), (Al-48)+(B2.20), (Al-48)+(B2.21), (Al-48)+(B2.22), (Al-48)+(B2.23), (Al-48)+(B2.24), (Al-48)+(B2.25), (Al-48)+(B2.26), (Al-48)+(B2.27), (Al-48)+(B2.28), (Al-48)+(B2.29), (Al-48)+(B2.30), (Al-48)+(B2.31), (Al-48)+(B2.32), (Al-48)+(B2.33), (Al-48)+(B2.34), (Al-48)+(B2.35), (Al-48)+(B2.36), (Al-48)+(B2.37), (Al-48)+(B2.38), (Al-48)+(B2.39), (Al-48)+(B2.40), (Al-48)+(B2.41), (Al-48)+(B2.42), (Al-48)+(B2.43), (Al-48)+(B2.44), (Al-48)+(B2.45), (Al-48)+(B2.46), (Al-48)+(B2.47), (Al-48)+(B2.48), (Al-48)+(B2.49), (Al-48)+(B2.50), (Al-48)+(B3.1), (Al-48)+(B3.2.), (Al-48)+(B3.3), (Al-48)+(B3.4), (Al-48)+(B3.5), (Al-48)+(B3.6), (Al-48)+(B3.7), (Al-48)+(B3.8), (Al-48)+(B3.9), (Al-48)+(B3.10), (Al-48)+(B3.11), (Al-48)+(B3.12), (Al-48)+(B3.13), (Al-48)+(B3.14), (Al-48)+(B3.15), (Al-48)+(B3.16), (Al-48)+(B4.1), (Al-48)+(B4.2), (Al-48)+(B4.3), (Al-48)+(B4.4), (Al-48)+(B4.5), (Al-48)+(B4.6), (Al-48)+(B4.7).

(Al-49)+(B1.1), (Al-49)+(B1.2), (Al-49)+(B1.3), (Al-49)+(B1.4), (Al-49)+(B1.5), (Al-49)+(B1.6), (Al-49)+(B1.7), (Al-49)+(B1.8), (Al-49)+(B1.9), (Al-49)+(B1.10), (Al-49)+(B1.11), (Al-49)+(B1.12), (Al-49)+(B1.13), (Al-49)+(B1.14), (Al-49)+(B1.15), (Al-49)+(B1.16), (Al-49)+(B1.17), (Al-49)+(B1.18), (Al-49)+(B1.19), (Al-49)+(B1.20), (Al-49)+(B1.21), (Al-49)+(B1.22), (Al-49)+(B1.23), (Al-49)+(B1.24), (Al-49)+(B1.25), (Al-49)+

(B1.26), (Al-49)+(B1.27), (Al-49)+(B1.28), (Al-49)+(B1.29), (Al-49)+(B1.30), (Al-49)+(B1.31), (Al-49)+(B1.32), (Al-49)+(B1.33), (Al-49)+(B1.34), (Al-49)+(B1.35), (Al-49)+(B1.36), (Al-49)+(B1.37), (Al-49)+(B1.38), (Al-49)+(B1.39), (Al-49)+(B1.40), (Al-49)+(B1.41), (Al-49)+(B1.42), (Al-49)+(B1.43), (Al-49)+(B1.44), (Al-49)+(B1.45), (Al-49)+(B1.46), (Al-49)+(B1.47), (Al-49)+(B1.48), (Al-49)+(B1.49), (Al-49)+(B1.50), (Al-49)+(B1.51), (Al-49)+(B1.52), (Al-49)+(B1.53), (Al-49)+(B1.54), (Al-49)+(B1.55), (Al-49)+(B1.56), (Al-49)+(B1.57), (Al-49)+(B1.58), (Al-49)+(B1.59), (Al-49)+(B1.60), (Al-49)+(B1.61), (Al-49)+(B1.62), (Al-49)+(B1.63), (Al-49)+(B1.64), (Al-49)+(B1.65), (Al-49)+(B1.66), (Al-49)+(B2.1), (Al-49)+(B2.2), (Al-49)+(B2.3), (Al-49)+(B2.4), (Al-49)+(B2.5), (Al-49)+(B2.6), (Al-49)+(B2.7), (Al-49)+(B2.8), (Al-49)+(B2.9), (Al-49)+(B2.10), (Al-49)+(B2.11), (Al-49)+(B2.12), (Al-49)+(B2.13), (Al-49)+(B2.14), (Al-49)+(B2.15), (Al-49)+(B2.16), (Al-49)+(B2.17), (Al-49)+(B2.18), (Al-49)+(B2.19), (Al-49)+(B2.20), (Al-49)+(B2.21), (Al-49)+(B2.22), (Al-49)+(B2.23), (Al-49)+(B2.24), (Al-49)+(B2.25), (Al-49)+(B2.26), (Al-49)+(B2.27), (Al-49)+(B2.28), (Al-49)+(B2.29), (Al-49)+(B2.30), (Al-49)+(B2.31), (Al-49)+(B2.32), (Al-49)+(B2.33), (Al-49)+(B2.34), (Al-49)+(B2.35), (Al-49)+(B2.36), (Al-49)+(B2.37), (Al-49)+(B2.38), (Al-49)+(B2.39), (Al-49)+(B2.40), (Al-49)+(B2.41), (Al-49)+(B2.42), (Al-49)+(B2.43), (Al-49)+(B2.44), (Al-49)+(B2.45), (Al-49)+(B2.46), (Al-49)+(B2.47), (Al-49)+(B2.48), (Al-49)+(B2.49), (Al-49)+(B2.50), (Al-49)+(B3.1), (Al-49)+(B3.2.), (Al-49)+(B3.3), (Al-49)+(B3.4), (Al-49)+(B3.5), (Al-49)+(B3.6), (Al-49)+(B3.7), (Al-49)+(B3.8), (Al-49)+(B3.9), (Al-49)+(B3.10), (Al-49)+(B3.11), (Al-49)+(B3.12), (Al-49)+(B3.13), (Al-49)+(B3.14), (Al-49)+(B3.15), (Al-49)+(B3.16), (Al-49)+(B4.1), (Al-49)+(B4.2), (Al-49)+(B4.3), (Al-49)+(B4.4), (Al-49)+(B4.5), (Al-49)+(B4.6), (Al-49)+(B4.7).

(Al-50)+(B1.1), (Al-50)+(B1.2), (Al-50)+(B1.3), (Al-50)+(B1.4), (Al-50)+(B1.5), (Al-50)+(B1.6), (Al-50)+(B1.7), (Al-50)+(B1.8), (Al-50)+(B1.9), (Al-50)+(B1.10), (Al-50)+(B1.11), (Al-50)+(B1.12), (Al-50)+(B1.13), (Al-50)+(B1.14), (Al-50)+(B1.15), (Al-50)+(B1.16), (Al-50)+(B1.17), (Al-50)+(B1.18), (Al-50)+(B1.19), (Al-50)+(B1.20), (Al-50)+(B1.21), (Al-50)+(B1.22), (Al-50)+(B1.23), (Al-50)+(B1.24), (Al-50)+(B1.25), (Al-50)+(B1.26), (Al-50)+(B1.27), (Al-50)+(B1.28), (Al-50)+(B1.29), (Al-50)+(B1.30), (Al-50)+(B1.31), (Al-50)+(B1.32), (Al-50)+(B1.33), (Al-50)+(B1.34), (Al-50)+(B1.35), (Al-50)+(B1.36), (Al-50)+(B1.37), (Al-50)+(B1.38), (Al-50)+(B1.39), (Al-50)+(B1.40), (Al-50)+(B1.41), (Al-50)+(B1.42), (Al-50)+(B1.43), (Al-50)+(B1.44), (Al-50)+(B1.45), (Al-50)+(B1.46), (Al-50)+(B1.47), (Al-50)+(B1.48), (Al-50)+(B1.49), (Al-50)+(B1.50), (Al-50)+(B1.51), (Al-50)+(B1.52), (Al-50)+(B1.53), (Al-50)+(B1.54), (Al-50)+(B1.55), (Al-50)+(B1.56), (Al-50)+(B1.57), (Al-50)+(B1.58), (Al-50)+(B1.59), (Al-50)+(B1.60), (Al-50)+(B1.61), (Al-50)+(B1.62), (Al-50)+(B1.63), (Al-50)+(B1.64), (Al-50)+(B1.65), (Al-50)+(B1.66), (Al-50)+(B2.1), (Al-50)+(B2.2), (Al-50)+(B2.3), (Al-50)+(B2.4), (Al-50)+(B2.5), (Al-50)+(B2.6), (Al-50)+(B2.7), (Al-50)+(B2.8), (Al-50)+(B2.9), (Al-50)+(B2.10), (Al-50)+(B2.11), (Al-50)+(B2.12), (Al-50)+(B2.13), (Al-50)+(B2.14), (Al-50)+(B2.15), (Al-50)+(B2.16), (Al-50)+(B2.17), (Al-50)+(B2.18), (Al-50)+(B2.19), (Al-50)+(B2.20), (Al-50)+(B2.21), (Al-50)+(B2.22), (Al-50)+(B2.23), (Al-50)+(B2.24), (Al-50)+(B2.25), (Al-50)+(B2.26), (Al-50)+(B2.27), (Al-50)+(B2.28), (Al-50)+(B2.29), (Al-50)+(B2.30), (Al-50)+(B2.31), (Al-50)+(B2.32), (Al-50)+(B2.33), (Al-50)+(B2.34), (Al-50)+(B2.35), (Al-50)+(B2.36), (Al-50)+(B2.37), (Al-50)+(B2.38), (Al-50)+(B2.39), (Al-50)+(B2.40), (Al-50)+(B2.41), (Al-50)+(B2.42), (Al-50)+(B2.43), (Al-50)+(B2.44), (Al-50)+(B2.45), (Al-50)+(B2.46), (Al-50)+(B2.47), (Al-50)+(B2.48), (Al-50)+(B2.49), (Al-50)+(B2.50), (Al-50)+(B3.1), (Al-50)+(B3.2.), (Al-50)+(B3.3), (Al-50)+(B3.4), (Al-50)+(B3.5), (Al-50)+(B3.6), (Al-50)+(B3.7), (Al-50)+(B3.8), (Al-50)+(B3.9), (Al-50)+(B3.10), (Al-50)+(B3.11), (Al-50)+(B3.12), (Al-50)+(B3.13), (Al-50)+(B3.14), (Al-50)+(B3.15), (Al-50)+(B3.16), (Al-50)+(B4.1), (Al-50)+(B4.2), (Al-50)+(B4.3), (Al-50)+(B4.4), (Al-50)+(B4.5), (Al-50)+(B4.6), (Al-50)+(B4.7).

(Al-51)+(B1.1), (Al-51)+(B1.2), (Al-51)+(B1.3), (Al-51)+(B1.4), (Al-51)+(B1.5), (Al-51)+(B1.6), (Al-51)+(B1.7), (Al-51)+(B1.8), (Al-51)+(B1.9), (Al-51)+(B1.10), (Al-51)+(B1.11), (Al-51)+(B1.12), (Al-51)+(B1.13), (Al-51)+(B1.14), (Al-51)+(B1.15), (Al-51)+(B1.16), (Al-51)+(B1.17), (Al-51)+(B1.18), (Al-51)+(B1.19), (Al-51)+(B1.20), (Al-51)+(B1.21), (Al-51)+(B1.22), (Al-51)+(B1.23), (Al-51)+(B1.24), (Al-51)+(B1.25), (Al-51)+(B1.26), (Al-51)+(B1.27), (Al-51)+(B1.28), (Al-51)+(B1.29), (Al-51)+(B1.30), (Al-51)+(B1.31), (Al-51)+(B1.32), (Al-51)+(B1.33), (Al-51)+(B1.34), (Al-51)+(B1.35), (Al-51)+(B1.36), (Al-51)+(B1.37), (Al-51)+(B1.38), (Al-51)+(B1.39), (Al-51)+(B1.40), (Al-51)+(B1.41), (Al-51)+(B1.42), (Al-51)+(B1.43), (Al-51)+(B1.44), (Al-51)+(B1.45), (Al-51)+(B1.46), (Al-51)+(B1.47), (Al-51)+(B1.48), (Al-51)+(B1.49), (Al-51)+(B1.50), (Al-51)+(B1.51), (Al-51)+(B1.52), (Al-51)+(B1.53), (Al-51)+(B1.54), (Al-51)+(B1.55), (Al-51)+(B1.56), (Al-51)+(B1.57), (Al-51)+(B1.58), (Al-51)+(B1.59), (Al-51)+(B1.60), (Al-51)+(B1.61), (Al-51)+(B1.62), (Al-51)+(B1.63), (Al-51)+(B1.64), (Al-51)+(B1.65), (Al-51)+(B1.66), (Al-51)+(B2.1), (Al-51)+(B2.2), (Al-51)+(B2.3), (Al-51)+(B2.4), (Al-51)+(B2.5), (Al-51)+(B2.6), (Al-51)+(B2.7), (Al-51)+(B2.8), (Al-51)+(B2.9), (Al-51)+(B2.10), (Al-51)+(B2.11), (Al-51)+(B2.12), (Al-51)+(B2.13), (Al-51)+(B2.14), (Al-51)+(B2.15), (Al-51)+(B2.16), (Al-51)+(B2.17), (Al-51)+(B2.18), (Al-51)+(B2.19), (Al-51)+(B2.20), (Al-51)+(B2.21), (Al-51)+(B2.22), (Al-51)+(B2.23), (Al-51)+(B2.24), (Al-51)+(B2.25), (Al-51)+(B2.26), (Al-51)+(B2.27), (Al-51)+(B2.28), (Al-51)+(B2.29), (Al-51)+(B2.30), (Al-51)+(B2.31), (Al-51)+(B2.32), (Al-51)+(B2.33), (Al-51)+(B2.34), (Al-51)+(B2.35), (Al-51)+(B2.36), (Al-51)+(B2.37), (Al-51)+(B2.38), (Al-51)+(B2.39), (Al-51)+(B2.40), (Al-51)+(B2.41), (Al-51)+(B2.42), (Al-51)+(B2.43), (Al-51)+(B2.44), (Al-51)+(B2.45), (Al-51)+(B2.46), (Al-51)+(B2.47), (Al-51)+(B2.48), (Al-51)+(B2.49), (Al-51)+(B2.50), (Al-51)+(B3.1), (Al-51)+(B3.2.), (Al-51)+(B3.3), (Al-51)+(B3.4), (Al-51)+(B3.5), (Al-51)+(B3.6), (Al-51)+(B3.7), (Al-51)+(B3.8), (Al-51)+(B3.9), (Al-51)+(B3.10), (Al-51)+(B3.11), (Al-51)+(B3.12), (Al-51)+(B3.13), (Al-51)+(B3.14), (Al-51)+(B3.15), (Al-51)+(B3.16), (Al-51)+(B4.1), (Al-51)+(B4.2), (Al-51)+(B4.3), (Al-51)+(B4.4), (Al-51)+(B4.5), (Al-51)+(B4.6), (Al-51)+(B4.7).

(Al-52)+(B1.1), (Al-52)+(B1.2), (Al-52)+(B1.3), (Al-52)+(B1.4), (Al-52)+(B1.5), (Al-52)+(B1.6), (Al-52)+(B1.7), (Al-52)+(B1.8), (Al-52)+(B1.9), (Al-52)+(B1.10), (Al-52)+(B1.11), (Al-52)+(B1.12), (Al-52)+(B1.13), (Al-52)+(B1.14), (Al-52)+(B1.15), (Al-52)+(B1.16), (Al-52)+(B1.17), (Al-52)+(B1.18), (Al-52)+(B1.19), (Al-52)+(B1.20), (Al-52)+(B1.21), (Al-52)+(B1.22), (Al-52)+

(B1.23), (Al-52)+(B1.24), (Al-52)+(B1.25), (Al-52)+(B1.26), (Al-52)+(B1.27), (Al-52)+(B1.28), (Al-52)+(B1.29), (Al-52)+(B1.30), (Al-52)+(B1.31), (Al-52)+(B1.32), (Al-52)+(B1.33), (Al-52)+(B1.34), (Al-52)+(B1.35), (Al-52)+(B1.36), (Al-52)+(B1.37), (Al-52)+(B1.38), (Al-52)+(B1.39), (Al-52)+(B1.40), (Al-52)+(B1.41), (Al-52)+(B1.42), (Al-52)+(B1.43), (Al-52)+(B1.44), (Al-52)+(B1.45), (Al-52)+(B1.46), (Al-52)+(B1.47), (Al-52)+(B1.48), (Al-52)+(B1.49), (Al-52)+(B1.50), (Al-52)+(B1.51), (Al-52)+(B1.52), (Al-52)+(B1.53), (Al-52)+(B1.54), (Al-52)+(B1.55), (Al-52)+(B1.56), (Al-52)+(B1.57), (Al-52)+(B1.58), (Al-52)+(B1.59), (Al-52)+(B1.60), (Al-52)+(B1.61), (Al-52)+(B1.62), (Al-52)+(B1.63), (Al-52)+(B1.64), (Al-52)+(B1.65), (Al-52)+(B1.66), (Al-52)+(B2.1), (Al-52)+(B2.2), (Al-52)+(B2.3), (Al-52)+(B2.4), (Al-52)+(B2.5), (Al-52)+(B2.6), (Al-52)+(B2.7), (Al-52)+(B2.8), (Al-52)+(B2.9), (Al-52)+(B2.10), (Al-52)+(B2.11), (Al-52)+(B2.12), (Al-52)+(B2.13), (Al-52)+(B2.14), (Al-52)+(B2.15), (Al-52)+(B2.16), (Al-52)+(B2.17), (Al-52)+(B2.18), (Al-52)+(B2.19), (Al-52)+(B2.20), (Al-52)+(B2.21), (Al-52)+(B2.22), (Al-52)+(B2.23), (Al-52)+(B2.24), (Al-52)+(B2.25), (Al-52)+(B2.26), (Al-52)+(B2.27), (Al-52)+(B2.28), (Al-52)+(B2.29), (Al-52)+(B2.30), (Al-52)+(B2.31), (Al-52)+(B2.32), (Al-52)+(B2.33), (Al-52)+(B2.34), (Al-52)+(B2.35), (Al-52)+(B2.36), (Al-52)+(B2.37), (Al-52)+(B2.38), (Al-52)+(B2.39), (Al-52)+(B2.40), (Al-52)+(B2.41), (Al-52)+(B2.42), (Al-52)+(B2.43), (Al-52)+(B2.44), (Al-52)+(B2.45), (Al-52)+(B2.46), (Al-52)+(B2.47), (Al-52)+(B2.48), (Al-52)+(B2.49), (Al-52)+(B2.50), (Al-52)+(B3.1), (Al-52)+(B3.2.), (Al-52)+(B3.3), (Al-52)+(B3.4), (Al-52)+(B3.5), (Al-52)+(B3.6), (Al-52)+(B3.7), (Al-52)+(B3.8), (Al-52)+(B3.9), (Al-52)+(B3.10), (Al-52)+(B3.11), (Al-52)+(B3.12), (Al-52)+(B3.13), (Al-52)+(B3.14), (Al-52)+(B3.15), (Al-52)+(B3.16), (Al-52)+(B4.1), (Al-52)+(B4.2), (Al-52)+(B4.3), (Al-52)+(B4.4), (Al-52)+(B4.5), (Al-52)+(B4.6), (Al-52)+(B4.7).

(Al-53)+(B1.1), (Al-53)+(B1.2), (Al-53)+(B1.3), (Al-53)+(B1.4), (Al-53)+(B1.5), (Al-53)+(B1.6), (Al-53)+(B1.7), (Al-53)+(B1.8), (Al-53)+(B1.9), (Al-53)+(B1.10), (Al-53)+(B1.11), (Al-53)+(B1.12), (Al-53)+(B1.13), (Al-53)+(B1.14), (Al-53)+(B1.15), (Al-53)+(B1.16), (Al-53)+(B1.17), (Al-53)+(B1.18), (Al-53)+(B1.19), (Al-53)+(B1.20), (Al-53)+(B1.21), (Al-53)+(B1.22), (Al-53)+(B1.23), (Al-53)+(B1.24), (Al-53)+(B1.25), (Al-53)+(B1.26), (Al-53)+(B1.27), (Al-53)+(B1.28), (Al-53)+(B1.29), (Al-53)+(B1.30), (Al-53)+(B1.31), (Al-53)+(B1.32), (Al-53)+(B1.33), (Al-53)+(B1.34), (Al-53)+(B1.35), (Al-53)+(B1.36), (Al-53)+(B1.37), (Al-53)+(B1.38), (Al-53)+(B1.39), (Al-53)+(B1.40), (Al-53)+(B1.41), (Al-53)+(B1.42), (Al-53)+(B1.43), (Al-53)+(B1.44), (Al-53)+(B1.45), (Al-53)+(B1.46), (Al-53)+(B1.47), (Al-53)+(B1.48), (Al-53)+(B1.49), (Al-53)+(B1.50), (Al-53)+(B1.51), (Al-53)+(B1.52), (Al-53)+(B1.53), (Al-53)+(B1.54), (Al-53)+(B1.55), (Al-53)+(B1.56), (Al-53)+(B1.57), (Al-53)+(B1.58), (Al-53)+(B1.59), (Al-53)+(B1.60), (Al-53)+(B1.61), (Al-53)+(B1.62), (Al-53)+(B1.63), (Al-53)+(B1.64), (Al-53)+(B1.65), (Al-53)+(B1.66), (Al-53)+(B2.1), (Al-53)+(B2.2), (Al-53)+(B2.3), (Al-53)+(B2.4), (Al-53)+(B2.5), (Al-53)+(B2.6), (Al-53)+(B2.7), (Al-53)+(B2.8), (Al-53)+(B2.9), (Al-53)+(B2.10), (Al-53)+(B2.11), (Al-53)+(B2.12), (Al-53)+(B2.13), (Al-53)+(B2.14), (Al-53)+(B2.15), (Al-53)+(B2.16), (Al-53)+(B2.17), (Al-53)+(B2.18), (Al-53)+(B2.19), (Al-53)+(B2.20), (Al-53)+(B2.21), (Al-53)+(B2.22), (Al-53)+(B2.23), (Al-53)+(B2.24), (Al-53)+(B2.25), (Al-53)+(B2.26), (Al-53)+(B2.27), (Al-53)+(B2.28), (Al-53)+(B2.29), (Al-53)+(B2.30), (Al-53)+(B2.31), (Al-53)+(B2.32), (Al-53)+(B2.33), (Al-53)+(B2.34), (Al-53)+(B2.35), (Al-53)+(B2.36), (Al-53)+(B2.37), (Al-53)+(B2.38), (Al-53)+(B2.39), (Al-53)+(B2.40), (Al-53)+(B2.41), (Al-53)+(B2.42), (Al-53)+(B2.43), (Al-53)+(B2.44), (Al-53)+(B2.45), (Al-53)+(B2.46), (Al-53)+(B2.47), (Al-53)+(B2.48), (Al-53)+(B2.49), (Al-53)+(B2.50), (Al-53)+(B3.1), (Al-53)+(B3.2.), (Al-53)+(B3.3), (Al-53)+(B3.4), (Al-53)+(B3.5), (Al-53)+(B3.6), (Al-53)+(B3.7), (Al-53)+(B3.8), (Al-53)+(B3.9), (Al-53)+(B3.10), (Al-53)+(B3.11), (Al-53)+(B3.12), (Al-53)+(B3.13), (Al-53)+(B3.14), (Al-53)+(B3.15), (Al-53)+(B3.16), (Al-53)+(B4.1), (Al-53)+(B4.2), (Al-53)+(B4.3), (Al-53)+(B4.4), (Al-53)+(B4.5), (Al-53)+(B4.6), (Al-53)+(B4.7).

(Al-54)+(B1.1), (Al-54)+(B1.2), (Al-54)+(B1.3), (Al-54)+(B1.4), (Al-54)+(B1.5), (Al-54)+(B1.6), (Al-54)+(B1.7), (Al-54)+(B1.8), (Al-54)+(B1.9), (Al-54)+(B1.10), (Al-54)+(B1.11), (Al-54)+(B1.12), (Al-54)+(B1.13), (Al-54)+(B1.14), (Al-54)+(B1.15), (Al-54)+(B1.16), (Al-54)+(B1.17), (Al-54)+(B1.18), (Al-54)+(B1.19), (Al-54)+(B1.20), (Al-54)+(B1.21), (Al-54)+(B1.22), (Al-54)+(B1.23), (Al-54)+(B1.24), (Al-54)+(B1.25), (Al-54)+(B1.26), (Al-54)+(B1.27), (Al-54)+(B1.28), (Al-54)+(B1.29), (Al-54)+(B1.30), (Al-54)+(B1.31), (Al-54)+(B1.32), (Al-54)+(B1.33), (Al-54)+(B1.34), (Al-54)+(B1.35), (Al-54)+(B1.36), (Al-54)+(B1.37), (Al-54)+(B1.38), (Al-54)+(B1.39), (Al-54)+(B1.40), (Al-54)+(B1.41), (Al-54)+(B1.42), (Al-54)+(B1.43), (Al-54)+(B1.44), (Al-54)+(B1.45), (Al-54)+(B1.46), (Al-54)+(B1.47), (Al-54)+(B1.48), (Al-54)+(B1.49), (Al-54)+(B1.50), (Al-54)+(B1.51), (Al-54)+(B1.52), (Al-54)+(B1.53), (Al-54)+(B1.54), (Al-54)+(B1.55), (Al-54)+(B1.56), (Al-54)+(B1.57), (Al-54)+(B1.58), (Al-54)+(B1.59), (Al-54)+(B1.60), (Al-54)+(B1.61), (Al-54)+(B1.62), (Al-54)+(B1.63), (Al-54)+(B1.64), (Al-54)+(B1.65), (Al-54)+(B1.66), (Al-54)+(B2.1), (Al-54)+(B2.2), (Al-54)+(B2.3), (Al-54)+(B2.4), (Al-54)+(B2.5), (Al-54)+(B2.6), (Al-54)+(B2.7), (Al-54)+(B2.8), (Al-54)+(B2.9), (Al-54)+(B2.10), (Al-54)+(B2.11), (Al-54)+(B2.12), (Al-54)+(B2.13), (Al-54)+(B2.14), (Al-54)+(B2.15), (Al-54)+(B2.16), (Al-54)+(B2.17), (Al-54)+(B2.18), (Al-54)+(B2.19), (Al-54)+(B2.20), (Al-54)+(B2.21), (Al-54)+(B2.22), (Al-54)+(B2.23), (Al-54)+(B2.24), (Al-54)+(B2.25), (Al-54)+(B2.26), (Al-54)+(B2.27), (Al-54)+(B2.28), (Al-54)+(B2.29), (Al-54)+(B2.30), (Al-54)+(B2.31), (Al-54)+(B2.32), (Al-54)+(B2.33), (Al-54)+(B2.34), (Al-54)+(B2.35), (Al-54)+(B2.36), (Al-54)+(B2.37), (Al-54)+(B2.38), (Al-54)+(B2.39), (Al-54)+(B2.40), (Al-54)+(B2.41), (Al-54)+(B2.42), (Al-54)+(B2.43), (Al-54)+(B2.44), (Al-54)+(B2.45), (Al-54)+(B2.46), (Al-54)+(B2.47), (Al-54)+(B2.48), (Al-54)+(B2.49), (Al-54)+(B2.50), (Al-54)+(B3.1), (Al-54)+(B3.2.), (Al-54)+(B3.3), (Al-54)+(B3.4), (Al-54)+(B3.5), (Al-54)+(B3.6), (Al-54)+(B3.7), (Al-54)+(B3.8), (Al-54)+(B3.9), (Al-54)+(B3.10), (Al-54)+(B3.11), (Al-54)+(B3.12), (Al-54)+(B3.13), (Al-54)+(B3.14), (Al-54)+(B3.15), (Al-54)+(B3.16), (Al-54)+(B4.1), (Al-54)+(B4.2), (Al-54)+(B4.3), (Al-54)+(B4.4), (Al-54)+(B4.5), (Al-54)+(B4.6), (Al-54)+(B4.7).

(Al-55)+(B1.1), (Al-55)+(B1.2), (Al-55)+(B1.3), (Al-55)+(B1.4), (Al-55)+(B1.5), (Al-55)+(B1.6), (Al-55)+(B1.7), (Al-55)+(B1.8), (Al-55)+(B1.9), (Al-55)+(B1.10), (Al-55)+(B1.11), (Al-55)+(B1.12), (Al-55)+(B1.13), (Al-55)+(B1.14), (Al-55)+(B1.15), (Al-55)+(B1.16), (Al-55)+(B1.17), (Al-55)+(B1.18), (Al-55)+(B1.19), (Al-55)+

(B1.20), (Al-55)+(B1.21), (Al-55)+(B1.22), (Al-55)+(B1.23), (Al-55)+(B1.24), (Al-55)+(B1.25), (Al-55)+(B1.26), (Al-55)+(B1.27), (Al-55)+(B1.28), (Al-55)+(B1.29), (Al-55)+(B1.30), (Al-55)+(B1.31), (Al-55)+(B1.32), (Al-55)+(B1.33), (Al-55)+(B1.34), (Al-55)+(B1.35), (Al-55)+(B1.36), (Al-55)+(B1.37), (Al-55)+(B1.38), (Al-55)+(B1.39), (Al-55)+(B1.40), (Al-55)+(B1.41), (Al-55)+(B1.42), (Al-55)+(B1.43), (Al-55)+(B1.44), (Al-55)+(B1.45), (Al-55)+(B1.46), (Al-55)+(B1.47), (Al-55)+(B1.48), (Al-55)+(B1.49), (Al-55)+(B1.50), (Al-55)+(B1.51), (Al-55)+(B1.52), (Al-55)+(B1.53), (Al-55)+(B1.54), (Al-55)+(B1.55), (Al-55)+(B1.56), (Al-55)+(B1.57), (Al-55)+(B1.58), (Al-55)+(B1.59), (Al-55)+(B1.60), (Al-55)+(B1.61), (Al-55)+(B1.62), (Al-55)+(B1.63), (Al-55)+(B1.64), (Al-55)+(B1.65), (Al-55)+(B1.66), (Al-55)+(B2.1), (Al-55)+(B2.2), (Al-55)+(B2.3), (Al-55)+(B2.4), (Al-55)+(B2.5), (Al-55)+(B2.6), (Al-55)+(B2.7), (Al-55)+(B2.8), (Al-55)+(B2.9), (Al-55)+(B2.10), (Al-55)+(B2.11), (Al-55)+(B2.12), (Al-55)+(B2.13), (Al-55)+(B2.14), (Al-55)+(B2.15), (Al-55)+(B2.16), (Al-55)+(B2.17), (Al-55)+(B2.18), (Al-55)+(B2.19), (Al-55)+(B2.20), (Al-55)+(B2.21), (Al-55)+(B2.22), (Al-55)+(B2.23), (Al-55)+(B2.24), (Al-55)+(B2.25), (Al-55)+(B2.26), (Al-55)+(B2.27), (Al-55)+(B2.28), (Al-55)+(B2.29), (Al-55)+(B2.30), (Al-55)+(B2.31), (Al-55)+(B2.32), (Al-55)+(B2.33), (Al-55)+(B2.34), (Al-55)+(B2.35), (Al-55)+(B2.36), (Al-55)+(B2.37), (Al-55)+(B2.38), (Al-55)+(B2.39), (Al-55)+(B2.40), (Al-55)+(B2.41), (Al-55)+(B2.42), (Al-55)+(B2.43), (Al-55)+(B2.44), (Al-55)+(B2.45), (Al-55)+(B2.46), (Al-55)+(B2.47), (Al-55)+(B2.48), (Al-55)+(B2.49), (Al-55)+(B2.50), (Al-55)+(B3.1), (Al-55)+(B3.2.), (Al-55)+(B3.3), (Al-55)+(B3.4), (Al-55)+(B3.5), (Al-55)+(B3.6), (Al-55)+(B3.7), (Al-55)+(B3.8), (Al-55)+(B3.9), (Al-55)+(B3.10), (Al-55)+(B3.11), (Al-55)+(B3.12), (Al-55)+(B3.13), (Al-55)+(B3.14), (Al-55)+(B3.15), (Al-55)+(B3.16), (Al-55)+(B4.1), (Al-55)+(B4.2), (Al-55)+(B4.3), (Al-55)+(B4.4), (Al-55)+(B4.5), (Al-55)+(B4.6), (Al-55)+(B4.7).

(Al-56)+(B1.1), (Al-56)+(B1.2), (Al-56)+(B1.3), (Al-56)+(B1.4), (Al-56)+(B1.5), (Al-56)+(B1.6), (Al-56)+(B1.7), (Al-56)+(B1.8), (Al-56)+(B1.9), (Al-56)+(B1.10), (Al-56)+(B1.11), (Al-56)+(B1.12), (Al-56)+(B1.13), (Al-56)+(B1.14), (Al-56)+(B1.15), (Al-56)+(B1.16), (Al-56)+(B1.17), (Al-56)+(B1.18), (Al-56)+(B1.19), (Al-56)+(B1.20), (Al-56)+(B1.21), (Al-56)+(B1.22), (Al-56)+(B1.23), (Al-56)+(B1.24), (Al-56)+(B1.25), (Al-56)+(B1.26), (Al-56)+(B1.27), (Al-56)+(B1.28), (Al-56)+(B1.29), (Al-56)+(B1.30), (Al-56)+(B1.31), (Al-56)+(B1.32), (Al-56)+(B1.33), (Al-56)+(B1.34), (Al-56)+(B1.35), (Al-56)+(B1.36), (Al-56)+(B1.37), (Al-56)+(B1.38), (Al-56)+(B1.39), (Al-56)+(B1.40), (Al-56)+(B1.41), (Al-56)+(B1.42), (Al-56)+(B1.43), (Al-56)+(B1.44), (Al-56)+(B1.45), (Al-56)+(B1.46), (Al-56)+(B1.47), (Al-56)+(B1.48), (Al-56)+(B1.49), (Al-56)+(B1.50), (Al-56)+(B1.51), (Al-56)+(B1.52), (Al-56)+(B1.53), (Al-56)+(B1.54), (Al-56)+(B1.55), (Al-56)+(B1.56), (Al-56)+(B1.57), (Al-56)+(B1.58), (Al-56)+(B1.59), (Al-56)+(B1.60), (Al-56)+(B1.61), (Al-56)+(B1.62), (Al-56)+(B1.63), (Al-56)+(B1.64), (Al-56)+(B1.65), (Al-56)+(B1.66), (Al-56)+(B2.1), (Al-56)+(B2.2), (Al-56)+(B2.3), (Al-56)+(B2.4), (Al-56)+(B2.5), (Al-56)+(B2.6), (Al-56)+(B2.7), (Al-56)+(B2.8), (Al-56)+(B2.9), (Al-56)+(B2.10), (Al-56)+(B2.11), (Al-56)+(B2.12), (Al-56)+(B2.13), (Al-56)+(B2.14), (Al-56)+(B2.15), (Al-56)+(B2.16), (Al-56)+(B2.17), (Al-56)+(B2.18), (Al-56)+(B2.19), (Al-56)+(B2.20), (Al-56)+(B2.21), (Al-56)+(B2.22), (Al-56)+(B2.23), (Al-56)+(B2.24), (Al-56)+(B2.25), (Al-56)+(B2.26), (Al-56)+(B2.27), (Al-56)+(B2.28), (Al-56)+(B2.29), (Al-56)+(B2.30), (Al-56)+(B2.31), (Al-56)+(B2.32), (Al-56)+(B2.33), (Al-56)+(B2.34), (Al-56)+(B2.35), (Al-56)+(B2.36), (Al-56)+(B2.37), (Al-56)+(B2.38), (Al-56)+(B2.39), (Al-56)+(B2.40), (Al-56)+(B2.41), (Al-56)+(B2.42), (Al-56)+(B2.43), (Al-56)+(B2.44), (Al-56)+(B2.45), (Al-56)+(B2.46), (Al-56)+(B2.47), (Al-56)+(B2.48), (Al-56)+(B2.49), (Al-56)+(B2.50), (Al-56)+(B3.1), (Al-56)+(B3.2.), (Al-56)+(B3.3), (Al-56)+(B3.4), (Al-56)+(B3.5), (Al-56)+(B3.6), (Al-56)+(B3.7), (Al-56)+(B3.8), (Al-56)+(B3.9), (Al-56)+(B3.10), (Al-56)+(B3.11), (Al-56)+(B3.12), (Al-56)+(B3.13), (Al-56)+(B3.14), (Al-56)+(B3.15), (Al-56)+(B3.16), (Al-56)+(B4.1), (Al-56)+(B4.2), (Al-56)+(B4.3), (Al-56)+(B4.4), (Al-56)+(B4.5), (Al-56)+(B4.6), (Al-56)+(B4.7).

(Al-57)+(B1.1), (Al-57)+(B1.2), (Al-57)+(B1.3), (Al-57)+(B1.4), (Al-57)+(B1.5), (Al-57)+(B1.6), (Al-57)+(B1.7), (Al-57)+(B1.8), (Al-57)+(B1.9), (Al-57)+(B1.10), (Al-57)+(B1.11), (Al-57)+(B1.12), (Al-57)+(B1.13), (Al-57)+(B1.14), (Al-57)+(B1.15), (Al-57)+(B1.16), (Al-57)+(B1.17), (Al-57)+(B1.18), (Al-57)+(B1.19), (Al-57)+(B1.20), (Al-57)+(B1.21), (Al-57)+(B1.22), (Al-57)+(B1.23), (Al-57)+(B1.24), (Al-57)+(B1.25), (Al-57)+(B1.26), (Al-57)+(B1.27), (Al-57)+(B1.28), (Al-57)+(B1.29), (Al-57)+(B1.30), (Al-57)+(B1.31), (Al-57)+(B1.32), (Al-57)+(B1.33), (Al-57)+(B1.34), (Al-57)+(B1.35), (Al-57)+(B1.36), (Al-57)+(B1.37), (Al-57)+(B1.38), (Al-57)+(B1.39), (Al-57)+(B1.40), (Al-57)+(B1.41), (Al-57)+(B1.42), (Al-57)+(B1.43), (Al-57)+(B1.44), (Al-57)+(B1.45), (Al-57)+(B1.46), (Al-57)+(B1.47), (Al-57)+(B1.48), (Al-57)+(B1.49), (Al-57)+(B1.50), (Al-57)+(B1.51), (Al-57)+(B1.52), (Al-57)+(B1.53), (Al-57)+(B1.54), (Al-57)+(B1.55), (Al-57)+(B1.56), (Al-57)+(B1.57), (Al-57)+(B1.58), (Al-57)+(B1.59), (Al-57)+(B1.60), (Al-57)+(B1.61), (Al-57)+(B1.62), (Al-57)+(B1.63), (Al-57)+(B1.64), (Al-57)+(B1.65), (Al-57)+(B1.66), (Al-57)+(B2.1), (Al-57)+(B2.2), (Al-57)+(B2.3), (Al-57)+(B2.4), (Al-57)+(B2.5), (Al-57)+(B2.6), (Al-57)+(B2.7), (Al-57)+(B2.8), (Al-57)+(B2.9), (Al-57)+(B2.10), (Al-57)+(B2.11), (Al-57)+(B2.12), (Al-57)+(B2.13), (Al-57)+(B2.14), (Al-57)+(B2.15), (Al-57)+(B2.16), (Al-57)+(B2.17), (Al-57)+(B2.18), (Al-57)+(B2.19), (Al-57)+(B2.20), (Al-57)+(B2.21), (Al-57)+(B2.22), (Al-57)+(B2.23), (Al-57)+(B2.24), (Al-57)+(B2.25), (Al-57)+(B2.26), (Al-57)+(B2.27), (Al-57)+(B2.28), (Al-57)+(B2.29), (Al-57)+(B2.30), (Al-57)+(B2.31), (Al-57)+(B2.32), (Al-57)+(B2.33), (Al-57)+(B2.34), (Al-57)+(B2.35), (Al-57)+(B2.36), (Al-57)+(B2.37), (Al-57)+(B2.38), (Al-57)+(B2.39), (Al-57)+(B2.40), (Al-57)+(B2.41), (Al-57)+(B2.42), (Al-57)+(B2.43), (Al-57)+(B2.44), (Al-57)+(B2.45), (Al-57)+(B2.46), (Al-57)+(B2.47), (Al-57)+(B2.48), (Al-57)+(B2.49), (Al-57)+(B2.50), (Al-57)+(B3.1), (Al-57)+(B3.2.), (Al-57)+(B3.3), (Al-57)+(B3.4), (Al-57)+(B3.5), (Al-57)+(B3.6), (Al-57)+(B3.7), (Al-57)+(B3.8), (Al-57)+(B3.9), (Al-57)+(B3.10), (Al-57)+(B3.11), (Al-57)+(B3.12), (Al-57)+(B3.13), (Al-57)+(B3.14), (Al-57)+(B3.15), (Al-57)+(B3.16), (Al-57)+(B4.1), (Al-57)+(B4.2), (Al-57)+(B4.3), (Al-57)+(B4.4), (Al-57)+(B4.5), (Al-57)+(B4.6), (Al-57)+(B4.7).

(Al-58)+(B1.1), (Al-58)+(B1.2), (Al-58)+(B1.3), (Al-58)+(B1.4), (Al-58)+(B1.5), (Al-58)+(B1.6), (Al-58)+(B1.7), (Al-58)+(B1.8), (Al-58)+(B1.9), (Al-58)+(B1.10), (Al-58)+(B1.11), (Al-58)+(B1.12), (Al-58)+(B1.13), (Al-58)+(B1.14), (Al-58)+(B1.15), (Al-58)+(B1.16), (Al-58)+

(B1.17), (Al-58)+(B1.18), (Al-58)+(B1.19), (Al-58)+(B1.20), (Al-58)+(B1.21), (Al-58)+(B1.22), (Al-58)+(B1.23), (Al-58)+(B1.24), (Al-58)+(B1.25), (Al-58)+(B1.26), (Al-58)+(B1.27), (Al-58)+(B1.28), (Al-58)+(B1.29), (Al-58)+(B1.30), (Al-58)+(B1.31), (Al-58)+(B1.32), (Al-58)+(B1.33), (Al-58)+(B1.34), (Al-58)+(B1.35), (Al-58)+(B1.36), (Al-58)+(B1.37), (Al-58)+(B1.38), (Al-58)+(B1.39), (Al-58)+(B1.40), (Al-58)+(B1.41), (Al-58)+(B1.42), (Al-58)+(B1.43), (Al-58)+(B1.44), (Al-58)+(B1.45), (Al-58)+(B1.46), (Al-58)+(B1.47), (Al-58)+(B1.48), (Al-58)+(B1.49), (Al-58)+(B1.50), (Al-58)+(B1.51), (Al-58)+(B1.52), (Al-58)+(B1.53), (Al-58)+(B1.54), (Al-58)+(B1.55), (Al-58)+(B1.56), (Al-58)+(B1.57), (Al-58)+(B1.58), (Al-58)+(B1.59), (Al-58)+(B1.60), (Al-58)+(B1.61), (Al-58)+(B1.62), (Al-58)+(B1.63), (Al-58)+(B1.64), (Al-58)+(B1.65), (Al-58)+(B1.66), (Al-58)+(B2.1), (Al-58)+(B2.2), (Al-58)+(B2.3), (Al-58)+(B2.4), (Al-58)+(B2.5), (Al-58)+(B2.6), (Al-58)+(B2.7), (Al-58)+(B2.8), (Al-58)+(B2.9), (Al-58)+(B2.10), (Al-58)+(B2.11), (Al-58)+(B2.12), (Al-58)+(B2.13), (Al-58)+(B2.14), (Al-58)+(B2.15), (Al-58)+(B2.16), (Al-58)+(B2.17), (Al-58)+(B2.18), (Al-58)+(B2.19), (Al-58)+(B2.20), (Al-58)+(B2.21), (Al-58)+(B2.22), (Al-58)+(B2.23), (Al-58)+(B2.24), (Al-58)+(B2.25), (Al-58)+(B2.26), (Al-58)+(B2.27), (Al-58)+(B2.28), (Al-58)+(B2.29), (Al-58)+(B2.30), (Al-58)+(B2.31), (Al-58)+(B2.32), (Al-58)+(B2.33), (Al-58)+(B2.34), (Al-58)+(B2.35), (Al-58)+(B2.36), (Al-58)+(B2.37), (Al-58)+(B2.38), (Al-58)+(B2.39), (Al-58)+(B2.40), (Al-58)+(B2.41), (Al-58)+(B2.42), (Al-58)+(B2.43), (Al-58)+(B2.44), (Al-58)+(B2.45), (Al-58)+(B2.46), (Al-58)+(B2.47), (Al-58)+(B2.48), (Al-58)+(B2.49), (Al-58)+(B2.50), (Al-58)+(B3.1), (Al-58)+(B3.2.), (Al-58)+(B3.3), (Al-58)+(B3.4), (Al-58)+(B3.5), (Al-58)+(B3.6), (Al-58)+(B3.7), (Al-58)+(B3.8), (Al-58)+(B3.9), (Al-58)+(B3.10), (Al-58)+(B3.11), (Al-58)+(B3.12), (Al-58)+(B3.13), (Al-58)+(B3.14), (Al-58)+(B3.15), (Al-58)+(B3.16), (Al-58)+(B4.1), (Al-58)+(B4.2), (Al-58)+(B4.3), (Al-58)+(B4.4), (Al-58)+(B4.5), (Al-58)+(B4.6), (Al-58)+(B4.7).

(Al-59)+(B1.1), (Al-59)+(B1.2), (Al-59)+(B1.3), (Al-59)+(B1.4), (Al-59)+(B1.5), (Al-59)+(B1.6), (Al-59)+(B1.7), (Al-59)+(B1.8), (Al-59)+(B1.9), (Al-59)+(B1.10), (Al-59)+(B1.11), (Al-59)+(B1.12), (Al-59)+(B1.13), (Al-59)+(B1.14), (Al-59)+(B1.15), (Al-59)+(B1.16), (Al-59)+(B1.17), (Al-59)+(B1.18), (Al-59)+(B1.19), (Al-59)+(B1.20), (Al-59)+(B1.21), (Al-59)+(B1.22), (Al-59)+(B1.23), (Al-59)+(B1.24), (Al-59)+(B1.25), (Al-59)+(B1.26), (Al-59)+(B1.27), (Al-59)+(B1.28), (Al-59)+(B1.29), (Al-59)+(B1.30), (Al-59)+(B1.31), (Al-59)+(B1.32), (Al-59)+(B1.33), (Al-59)+(B1.34), (Al-59)+(B1.35), (Al-59)+(B1.36), (Al-59)+(B1.37), (Al-59)+(B1.38), (Al-59)+(B1.39), (Al-59)+(B1.40), (Al-59)+(B1.41), (Al-59)+(B1.42), (Al-59)+(B1.43), (Al-59)+(B1.44), (Al-59)+(B1.45), (Al-59)+(B1.46), (Al-59)+(B1.47), (Al-59)+(B1.48), (Al-59)+(B1.49), (Al-59)+(B1.50), (Al-59)+(B1.51), (Al-59)+(B1.52), (Al-59)+(B1.53), (Al-59)+(B1.54), (Al-59)+(B1.55), (Al-59)+(B1.56), (Al-59)+(B1.57), (Al-59)+(B1.58), (Al-59)+(B1.59), (Al-59)+(B1.60), (Al-59)+(B1.61), (Al-59)+(B1.62), (Al-59)+(B1.63), (Al-59)+(B1.64), (Al-59)+(B1.65), (Al-59)+(B1.66), (Al-59)+(B2.1), (Al-59)+(B2.2), (Al-59)+(B2.3), (Al-59)+(B2.4), (Al-59)+(B2.5), (Al-59)+(B2.6), (Al-59)+(B2.7), (Al-59)+(B2.8), (Al-59)+(B2.9), (Al-59)+(B2.10), (Al-59)+(B2.11), (Al-59)+(B2.12), (Al-59)+(B2.13), (Al-59)+(B2.14), (Al-59)+(B2.15), (Al-59)+(B2.16), (Al-59)+(B2.17), (Al-59)+(B2.18), (Al-59)+(B2.19), (Al-59)+(B2.20), (Al-59)+(B2.21), (Al-59)+(B2.22), (Al-59)+(B2.23), (Al-59)+(B2.24), (Al-59)+(B2.25), (Al-59)+(B2.26), (Al-59)+(B2.27), (Al-59)+(B2.28), (Al-59)+(B2.29), (Al-59)+(B2.30), (Al-59)+(B2.31), (Al-59)+(B2.32), (Al-59)+(B2.33), (Al-59)+(B2.34), (Al-59)+(B2.35), (Al-59)+(B2.36), (Al-59)+(B2.37), (Al-59)+(B2.38), (Al-59)+(B2.39), (Al-59)+(B2.40), (Al-59)+(B2.41), (Al-59)+(B2.42), (Al-59)+(B2.43), (Al-59)+(B2.44), (Al-59)+(B2.45), (Al-59)+(B2.46), (Al-59)+(B2.47), (Al-59)+(B2.48), (Al-59)+(B2.49), (Al-59)+(B2.50), (Al-59)+(B3.1), (Al-59)+(B3.2.), (Al-59)+(B3.3), (Al-59)+(B3.4), (Al-59)+(B3.5), (Al-59)+(B3.6), (Al-59)+(B3.7), (Al-59)+(B3.8), (Al-59)+(B3.9), (Al-59)+(B3.10), (Al-59)+(B3.11), (Al-59)+(B3.12), (Al-59)+(B3.13), (Al-59)+(B3.14), (Al-59)+(B3.15), (Al-59)+(B3.16), (Al-59)+(B4.1), (Al-59)+(B4.2), (Al-59)+(B4.3), (Al-59)+(B4.4), (Al-59)+(B4.5), (Al-59)+(B4.6), (Al-59)+(B4.7).

(Al-60)+(B1.1), (Al-60)+(B1.2), (Al-60)+(B1.3), (Al-60)+(B1.4), (Al-60)+(B1.5), (Al-60)+(B1.6), (Al-60)+(B1.7), (Al-60)+(B1.8), (Al-60)+(B1.9), (Al-60)+(B1.10), (Al-60)+(B1.11), (Al-60)+(B1.12), (Al-60)+(B1.13), (Al-60)+(B1.14), (Al-60)+(B1.15), (Al-60)+(B1.16), (Al-60)+(B1.17), (Al-60)+(B1.18), (Al-60)+(B1.19), (Al-60)+(B1.20), (Al-60)+(B1.21), (Al-60)+(B1.22), (Al-60)+(B1.23), (Al-60)+(B1.24), (Al-60)+(B1.25), (Al-60)+(B1.26), (Al-60)+(B1.27), (Al-60)+(B1.28), (Al-60)+(B1.29), (Al-60)+(B1.30), (Al-60)+(B1.31), (Al-60)+(B1.32), (Al-60)+(B1.33), (Al-60)+(B1.34), (Al-60)+(B1.35), (Al-60)+(B1.36), (Al-60)+(B1.37), (Al-60)+(B1.38), (Al-60)+(B1.39), (Al-60)+(B1.40), (Al-60)+(B1.41), (Al-60)+(B1.42), (Al-60)+(B1.43), (Al-60)+(B1.44), (Al-60)+(B1.45), (Al-60)+(B1.46), (Al-60)+(B1.47), (Al-60)+(B1.48), (Al-60)+(B1.49), (Al-60)+(B1.50), (Al-60)+(B1.51), (Al-60)+(B1.52), (Al-60)+(B1.53), (Al-60)+(B1.54), (Al-60)+(B1.55), (Al-60)+(B1.56), (Al-60)+(B1.57), (Al-60)+(B1.58), (Al-60)+(B1.59), (Al-60)+(B1.60), (Al-60)+(B1.61), (Al-60)+(B1.62), (Al-60)+(B1.63), (Al-60)+(B1.64), (Al-60)+(B1.65), (Al-60)+(B1.66), (Al-60)+(B2.1), (Al-60)+(B2.2), (Al-60)+(B2.3), (Al-60)+(B2.4), (Al-60)+(B2.5), (Al-60)+(B2.6), (Al-60)+(B2.7), (Al-60)+(B2.8), (Al-60)+(B2.9), (Al-60)+(B2.10), (Al-60)+(B2.11), (Al-60)+(B2.12), (Al-60)+(B2.13), (Al-60)+(B2.14), (Al-60)+(B2.15), (Al-60)+(B2.16), (Al-60)+(B2.17), (Al-60)+(B2.18), (Al-60)+(B2.19), (Al-60)+(B2.20), (Al-60)+(B2.21), (Al-60)+(B2.22), (Al-60)+(B2.23), (Al-60)+(B2.24), (Al-60)+(B2.25), (Al-60)+(B2.26), (Al-60)+(B2.27), (Al-60)+(B2.28), (Al-60)+(B2.29), (Al-60)+(B2.30), (Al-60)+(B2.31), (Al-60)+(B2.32), (Al-60)+(B2.33), (Al-60)+(B2.34), (Al-60)+(B2.35), (Al-60)+(B2.36), (Al-60)+(B2.37), (Al-60)+(B2.38), (Al-60)+(B2.39), (Al-60)+(B2.40), (Al-60)+(B2.41), (Al-60)+(B2.42), (Al-60)+(B2.43), (Al-60)+(B2.44), (Al-60)+(B2.45), (Al-60)+(B2.46), (Al-60)+(B2.47), (Al-60)+(B2.48), (Al-60)+(B2.49), (Al-60)+(B2.50), (Al-60)+(B3.1), (Al-60)+(B3.2.), (Al-60)+(B3.3), (Al-60)+(B3.4), (Al-60)+(B3.5), (Al-60)+(B3.6), (Al-60)+(B3.7), (Al-60)+(B3.8), (Al-60)+(B3.9), (Al-60)+(B3.10), (Al-60)+(B3.11), (Al-60)+(B3.12), (Al-60)+(B3.13), (Al-60)+(B3.14), (Al-60)+(B3.15), (Al-60)+(B3.16), (Al-60)+(B4.1), (Al-60)+(B4.2), (Al-60)+(B4.3), (Al-60)+(B4.4), (Al-60)+(B4.5), (Al-60)+(B4.6), (Al-60)+(B4.7).

(Al-61)+(B1.1), (Al-61)+(B1.2), (Al-61)+(B1.3), (Al-61)+(B1.4), (Al-61)+(B1.5), (Al-61)+(B1.6), (Al-61)+(B1.7), (Al-61)+(B1.8), (Al-61)+(B1.9), (Al-61)+(B1.10), (Al-61)+(B1.11), (Al-61)+(B1.12), (Al-61)+(B1.13), (Al-

61)+(B1.14), (Al-61)+(B1.15), (Al-61)+(B1.16), (Al-61)+(B1.17), (Al-61)+(B1.18), (Al-61)+(B1.19), (Al-61)+(B1.20), (Al-61)+(B1.21), (Al-61)+(B1.22), (Al-61)+(B1.23), (Al-61)+(B1.24), (Al-61)+(B1.25), (Al-61)+(B1.26), (Al-61)+(B1.27), (Al-61)+(B1.28), (Al-61)+(B1.29), (Al-61)+(B1.30), (Al-61)+(B1.31), (Al-61)+(B1.32), (Al-61)+(B1.33), (Al-61)+(B1.34), (Al-61)+(B1.35), (Al-61)+(B1.36), (Al-61)+(B1.37), (Al-61)+(B1.38), (Al-61)+(B1.39), (Al-61)+(B1.40), (Al-61)+(B1.41), (Al-61)+(B1.42), (Al-61)+(B1.43), (Al-61)+(B1.44), (Al-61)+(B1.45), (Al-61)+(B1.46), (Al-61)+(B1.47), (Al-61)+(B1.48), (Al-61)+(B1.49), (Al-61)+(B1.50), (Al-61)+(B1.51), (Al-61)+(B1.52), (Al-61)+(B1.53), (Al-61)+(B1.54), (Al-61)+(B1.55), (Al-61)+(B1.56), (Al-61)+(B1.57), (Al-61)+(B1.58), (Al-61)+(B1.59), (Al-61)+(B1.60), (Al-61)+(B1.61), (Al-61)+(B1.62), (Al-61)+(B1.63), (Al-61)+(B1.64), (Al-61)+(B1.65), (Al-61)+(B1.66), (Al-61)+(B2.1), (Al-61)+(B2.2), (Al-61)+(B2.3), (Al-61)+(B2.4), (Al-61)+(B2.5), (Al-61)+(B2.6), (Al-61)+(B2.7), (Al-61)+(B2.8), (Al-61)+(B2.9), (Al-61)+(B2.10), (Al-61)+(B2.11), (Al-61)+(B2.12), (Al-61)+(B2.13), (Al-61)+(B2.14), (Al-61)+(B2.15), (Al-61)+(B2.16), (Al-61)+(B2.17), (Al-61)+(B2.18), (Al-61)+(B2.19), (Al-61)+(B2.20), (Al-61)+(B2.21), (Al-61)+(B2.22), (Al-61)+(B2.23), (Al-61)+(B2.24), (Al-61)+(B2.25), (Al-61)+(B2.26), (Al-61)+(B2.27), (Al-61)+(B2.28), (Al-61)+(B2.29), (Al-61)+(B2.30), (Al-61)+(B2.31), (Al-61)+(B2.32), (Al-61)+(B2.33), (Al-61)+(B2.34), (Al-61)+(B2.35), (Al-61)+(B2.36), (Al-61)+(B2.37), (Al-61)+(B2.38), (Al-61)+(B2.39), (Al-61)+(B2.40), (Al-61)+(B2.41), (Al-61)+(B2.42), (Al-61)+(B2.43), (Al-61)+(B2.44), (Al-61)+(B2.45), (Al-61)+(B2.46), (Al-61)+(B2.47), (Al-61)+(B2.48), (Al-61)+(B2.49), (Al-61)+(B2.50), (Al-61)+(B3.1), (Al-61)+(B3.2.), (Al-61)+(B3.3), (Al-61)+(B3.4), (Al-61)+(B3.5), (Al-61)+(B3.6), (Al-61)+(B3.7), (Al-61)+(B3.8), (Al-61)+(B3.9), (Al-61)+(B3.10), (Al-61)+(B3.11), (Al-61)+(B3.12), (Al-61)+(B3.13), (Al-61)+(B3.14), (Al-61)+(B3.15), (Al-61)+(B3.16), (Al-61)+(B4.1), (Al-61)+(B4.2), (Al-61)+(B4.3), (Al-61)+(B4.4), (Al-61)+(B4.5), (Al-61)+(B4.6), (Al-61)+(B4.7).

(Al-62)+(B1.1), (Al-62)+(B1.2), (Al-62)+(B1.3), (Al-62)+(B1.4), (Al-62)+(B1.5), (Al-62)+(B1.6), (Al-62)+(B1.7), (Al-62)+(B1.8), (Al-62)+(B1.9), (Al-62)+(B1.10), (Al-62)+(B1.11), (Al-62)+(B1.12), (Al-62)+(B1.13), (Al-62)+(B1.14), (Al-62)+(B1.15), (Al-62)+(B1.16), (Al-62)+(B1.17), (Al-62)+(B1.18), (Al-62)+(B1.19), (Al-62)+(B1.20), (Al-62)+(B1.21), (Al-62)+(B1.22), (Al-62)+(B1.23), (Al-62)+(B1.24), (Al-62)+(B1.25), (Al-62)+(B1.26), (Al-62)+(B1.27), (Al-62)+(B1.28), (Al-62)+(B1.29), (Al-62)+(B1.30), (Al-62)+(B1.31), (Al-62)+(B1.32), (Al-62)+(B1.33), (Al-62)+(B1.34), (Al-62)+(B1.35), (Al-62)+(B1.36), (Al-62)+(B1.37), (Al-62)+(B1.38), (Al-62)+(B1.39), (Al-62)+(B1.40), (Al-62)+(B1.41), (Al-62)+(B1.42), (Al-62)+(B1.43), (Al-62)+(B1.44), (Al-62)+(B1.45), (Al-62)+(B1.46), (Al-62)+(B1.47), (Al-62)+(B1.48), (Al-62)+(B1.49), (Al-62)+(B1.50), (Al-62)+(B1.51), (Al-62)+(B1.52), (Al-62)+(B1.53), (Al-62)+(B1.54), (Al-62)+(B1.55), (Al-62)+(B1.56), (Al-62)+(B1.57), (Al-62)+(B1.58), (Al-62)+(B1.59), (Al-62)+(B1.60), (Al-62)+(B1.61), (Al-62)+(B1.62), (Al-62)+(B1.63), (Al-62)+(B1.64), (Al-62)+(B1.65), (Al-62)+(B1.66), (Al-62)+(B2.1), (Al-62)+(B2.2), (Al-62)+(B2.3), (Al-62)+(B2.4), (Al-62)+(B2.5), (Al-62)+(B2.6), (Al-62)+(B2.7), (Al-62)+(B2.8), (Al-62)+(B2.9), (Al-62)+(B2.10), (Al-62)+(B2.11), (Al-62)+(B2.12), (Al-62)+(B2.13), (Al-62)+(B2.14), (Al-62)+(B2.15), (Al-62)+(B2.16), (Al-62)+(B2.17), (Al-62)+(B2.18), (Al-62)+(B2.19), (Al-62)+(B2.20), (Al-62)+(B2.21), (Al-62)+(B2.22), (Al-62)+(B2.23), (Al-62)+(B2.24), (Al-62)+(B2.25), (Al-62)+(B2.26), (Al-62)+(B2.27), (Al-62)+(B2.28), (Al-62)+(B2.29), (Al-62)+(B2.30), (Al-62)+(B2.31), (Al-62)+(B2.32), (Al-62)+(B2.33), (Al-62)+(B2.34), (Al-62)+(B2.35), (Al-62)+(B2.36), (Al-62)+(B2.37), (Al-62)+(B2.38), (Al-62)+(B2.39), (Al-62)+(B2.40), (Al-62)+(B2.41), (Al-62)+(B2.42), (Al-62)+(B2.43), (Al-62)+(B2.44), (Al-62)+(B2.45), (Al-62)+(B2.46), (Al-62)+(B2.47), (Al-62)+(B2.48), (Al-62)+(B2.49), (Al-62)+(B2.50), (Al-62)+(B3.1), (Al-62)+(B3.2.), (Al-62)+(B3.3), (Al-62)+(B3.4), (Al-62)+(B3.5), (Al-62)+(B3.6), (Al-62)+(B3.7), (Al-62)+(B3.8), (Al-62)+(B3.9), (Al-62)+(B3.10), (Al-62)+(B3.11), (Al-62)+(B3.12), (Al-62)+(B3.13), (Al-62)+(B3.14), (Al-62)+(B3.15), (Al-62)+(B3.16), (Al-62)+(B4.1), (Al-62)+(B4.2), (Al-62)+(B4.3), (Al-62)+(B4.4), (Al-62)+(B4.5), (Al-62)+(B4.6), (Al-62)+(B4.7).

(Al-63)+(B1.1), (Al-63)+(B1.2), (Al-63)+(B1.3), (Al-63)+(B1.4), (Al-63)+(B1.5), (Al-63)+(B1.6), (Al-63)+(B1.7), (Al-63)+(B1.8), (Al-63)+(B1.9), (Al-63)+(B1.10), (Al-63)+(B1.11), (Al-63)+(B1.12), (Al-63)+(B1.13), (Al-63)+(B1.14), (Al-63)+(B1.15), (Al-63)+(B1.16), (Al-63)+(B1.17), (Al-63)+(B1.18), (Al-63)+(B1.19), (Al-63)+(B1.20), (Al-63)+(B1.21), (Al-63)+(B1.22), (Al-63)+(B1.23), (Al-63)+(B1.24), (Al-63)+(B1.25), (Al-63)+(B1.26), (Al-63)+(B1.27), (Al-63)+(B1.28), (Al-63)+(B1.29), (Al-63)+(B1.30), (Al-63)+(B1.31), (Al-63)+(B1.32), (Al-63)+(B1.33), (Al-63)+(B1.34), (Al-63)+(B1.35), (Al-63)+(B1.36), (Al-63)+(B1.37), (Al-63)+(B1.38), (Al-63)+(B1.39), (Al-63)+(B1.40), (Al-63)+(B1.41), (Al-63)+(B1.42), (Al-63)+(B1.43), (Al-63)+(B1.44), (Al-63)+(B1.45), (Al-63)+(B1.46), (Al-63)+(B1.47), (Al-63)+(B1.48), (Al-63)+(B1.49), (Al-63)+(B1.50), (Al-63)+(B1.51), (Al-63)+(B1.52), (Al-63)+(B1.53), (Al-63)+(B1.54), (Al-63)+(B1.55), (Al-63)+(B1.56), (Al-63)+(B1.57), (Al-63)+(B1.58), (Al-63)+(B1.59), (Al-63)+(B1.60), (Al-63)+(B1.61), (Al-63)+(B1.62), (Al-63)+(B1.63), (Al-63)+(B1.64), (Al-63)+(B1.65), (Al-63)+(B1.66), (Al-63)+(B2.1), (Al-63)+(B2.2), (Al-63)+(B2.3), (Al-63)+(B2.4), (Al-63)+(B2.5), (Al-63)+(B2.6), (Al-63)+(B2.7), (Al-63)+(B2.8), (Al-63)+(B2.9), (Al-63)+(B2.10), (Al-63)+(B2.11), (Al-63)+(B2.12), (Al-63)+(B2.13), (Al-63)+(B2.14), (Al-63)+(B2.15), (Al-63)+(B2.16), (Al-63)+(B2.17), (Al-63)+(B2.18), (Al-63)+(B2.19), (Al-63)+(B2.20), (Al-63)+(B2.21), (Al-63)+(B2.22), (Al-63)+(B2.23), (Al-63)+(B2.24), (Al-63)+(B2.25), (Al-63)+(B2.26), (Al-63)+(B2.27), (Al-63)+(B2.28), (Al-63)+(B2.29), (Al-63)+(B2.30), (Al-63)+(B2.31), (Al-63)+(B2.32), (Al-63)+(B2.33), (Al-63)+(B2.34), (Al-63)+(B2.35), (Al-63)+(B2.36), (Al-63)+(B2.37), (Al-63)+(B2.38), (Al-63)+(B2.39), (Al-63)+(B2.40), (Al-63)+(B2.41), (Al-63)+(B2.42), (Al-63)+(B2.43), (Al-63)+(B2.44), (Al-63)+(B2.45), (Al-63)+(B2.46), (Al-63)+(B2.47), (Al-63)+(B2.48), (Al-63)+(B2.49), (Al-63)+(B2.50), (Al-63)+(B3.1), (Al-63)+(B3.2.), (Al-63)+(B3.3), (Al-63)+(B3.4), (Al-63)+(B3.5), (Al-63)+(B3.6), (Al-63)+(B3.7), (Al-63)+(B3.8), (Al-63)+(B3.9), (Al-63)+(B3.10), (Al-63)+(B3.11), (Al-63)+(B3.12), (Al-63)+(B3.13), (Al-63)+(B3.14), (Al-63)+(B3.15), (Al-63)+(B3.16), (Al-63)+(B4.1), (Al-63)+(B4.2), (Al-63)+(B4.3), (Al-63)+(B4.4), (Al-63)+(B4.5), (Al-63)+(B4.6), (Al-63)+(B4.7).

(Al-64)+(B1.1), (Al-64)+(B1.2), (Al-64)+(B1.3), (Al-64)+(B1.4), (Al-64)+(B1.5), (Al-64)+(B1.6), (Al-64)+(B1.7), (Al-64)+(B1.8), (Al-64)+(B1.9), (Al-64)+(B1.10), (Al-64)+(B1.11), (Al-64)+(B1.12), (Al-64)+(B1.13), (Al-64)+(B1.14), (Al-64)+(B1.15), (Al-64)+(B1.16), (Al-64)+(B1.17), (Al-64)+(B1.18), (Al-64)+(B1.19), (Al-64)+(B1.20), (Al-64)+(B1.21), (Al-64)+(B1.22), (Al-64)+(B1.23), (Al-64)+(B1.24), (Al-64)+(B1.25), (Al-64)+(B1.26), (Al-64)+(B1.27), (Al-64)+(B1.28), (Al-64)+(B1.29), (Al-64)+(B1.30), (Al-64)+(B1.31), (Al-64)+(B1.32), (Al-64)+(B1.33), (Al-64)+(B1.34), (Al-64)+(B1.35), (Al-64)+(B1.36), (Al-64)+(B1.37), (Al-64)+(B1.38), (Al-64)+(B1.39), (Al-64)+(B1.40), (Al-64)+(B1.41), (Al-64)+(B1.42), (Al-64)+(B1.43), (Al-64)+(B1.44), (Al-64)+(B1.45), (Al-64)+(B1.46), (Al-64)+(B1.47), (Al-64)+(B1.48), (Al-64)+(B1.49), (Al-64)+(B1.50), (Al-64)+(B1.51), (Al-64)+(B1.52), (Al-64)+(B1.53), (Al-64)+(B1.54), (Al-64)+(B1.55), (Al-64)+(B1.56), (Al-64)+(B1.57), (Al-64)+(B1.58), (Al-64)+(B1.59), (Al-64)+(B1.60), (Al-64)+(B1.61), (Al-64)+(B1.62), (Al-64)+(B1.63), (Al-64)+(B1.64), (Al-64)+(B1.65), (Al-64)+(B1.66), (Al-64)+(B2.1), (Al-64)+(B2.2), (Al-64)+(B2.3), (Al-64)+(B2.4), (Al-64)+(B2.5), (Al-64)+(B2.6), (Al-64)+(B2.7), (Al-64)+(B2.8), (Al-64)+(B2.9), (Al-64)+(B2.10), (Al-64)+(B2.11), (Al-64)+(B2.12), (Al-64)+(B2.13), (Al-64)+(B2.14), (Al-64)+(B2.15), (Al-64)+(B2.16), (Al-64)+(B2.17), (Al-64)+(B2.18), (Al-64)+(B2.19), (Al-64)+(B2.20), (Al-64)+(B2.21), (Al-64)+(B2.22), (Al-64)+(B2.23), (Al-64)+(B2.24), (Al-64)+(B2.25), (Al-64)+(B2.26), (Al-64)+(B2.27), (Al-64)+(B2.28), (Al-64)+(B2.29), (Al-64)+(B2.30), (Al-64)+(B2.31), (Al-64)+(B2.32), (Al-64)+(B2.33), (Al-64)+(B2.34), (Al-64)+(B2.35), (Al-64)+(B2.36), (Al-64)+(B2.37), (Al-64)+(B2.38), (Al-64)+(B2.39), (Al-64)+(B2.40), (Al-64)+(B2.41), (Al-64)+(B2.42), (Al-64)+(B2.43), (Al-64)+(B2.44), (Al-64)+(B2.45), (Al-64)+(B2.46), (Al-64)+(B2.47), (Al-64)+(B2.48), (Al-64)+(B2.49), (Al-64)+(B2.50), (Al-64)+(B3.1), (Al-64)+(B3.2.), (Al-64)+(B3.3), (Al-64)+(B3.4), (Al-64)+(B3.5), (Al-64)+(B3.6), (Al-64)+(B3.7), (Al-64)+(B3.8), (Al-64)+(B3.9), (Al-64)+(B3.10), (Al-64)+(B3.11), (Al-64)+(B3.12), (Al-64)+(B3.13), (Al-64)+(B3.14), (Al-64)+(B3.15), (Al-64)+(B3.16), (Al-64)+(B4.1), (Al-64)+(B4.2), (Al-64)+(B4.3), (Al-64)+(B4.4), (Al-64)+(B4.5), (Al-64)+(B4.6), (Al-64)+(B4.7).

(Al-65)+(B1.1), (Al-65)+(B1.2), (Al-65)+(B1.3), (Al-65)+(B1.4), (Al-65)+(B1.5), (Al-65)+(B1.6), (Al-65)+(B1.7), (Al-65)+(B1.8), (Al-65)+(B1.9), (Al-65)+(B1.10), (Al-65)+(B1.11), (Al-65)+(B1.12), (Al-65)+(B1.13), (Al-65)+(B1.14), (Al-65)+(B1.15), (Al-65)+(B1.16), (Al-65)+(B1.17), (Al-65)+(B1.18), (Al-65)+(B1.19), (Al-65)+(B1.20), (Al-65)+(B1.21), (Al-65)+(B1.22), (Al-65)+(B1.23), (Al-65)+(B1.24), (Al-65)+(B1.25), (Al-65)+(B1.26), (Al-65)+(B1.27), (Al-65)+(B1.28), (Al-65)+(B1.29), (Al-65)+(B1.30), (Al-65)+(B1.31), (Al-65)+(B1.32), (Al-65)+(B1.33), (Al-65)+(B1.34), (Al-65)+(B1.35), (Al-65)+(B1.36), (Al-65)+(B1.37), (Al-65)+(B1.38), (Al-65)+(B1.39), (Al-65)+(B1.40), (Al-65)+(B1.41), (Al-65)+(B1.42), (Al-65)+(B1.43), (Al-65)+(B1.44), (Al-65)+(B1.45), (Al-65)+(B1.46), (Al-65)+(B1.47), (Al-65)+(B1.48), (Al-65)+(B1.49), (Al-65)+(B1.50), (Al-65)+(B1.51), (Al-65)+(B1.52), (Al-65)+(B1.53), (Al-65)+(B1.54), (Al-65)+(B1.55), (Al-65)+(B1.56), (Al-65)+(B1.57), (Al-65)+(B1.58), (Al-65)+(B1.59), (Al-65)+(B1.60), (Al-65)+(B1.61), (Al-65)+(B1.62), (Al-65)+(B1.63), (Al-65)+(B1.64), (Al-65)+(B1.65), (Al-65)+(B1.66), (Al-65)+(B2.1), (Al-65)+(B2.2), (Al-65)+(B2.3), (Al-65)+(B2.4), (Al-65)+(B2.5), (Al-65)+(B2.6), (Al-65)+(B2.7), (Al-65)+(B2.8), (Al-65)+(B2.9), (Al-65)+(B2.10), (Al-65)+(B2.11), (Al-65)+(B2.12), (Al-65)+(B2.13), (Al-65)+(B2.14), (Al-65)+(B2.15), (Al-65)+(B2.16), (Al-65)+(B2.17), (Al-65)+(B2.18), (Al-65)+(B2.19), (Al-65)+(B2.20), (Al-65)+(B2.21), (Al-65)+(B2.22), (Al-65)+(B2.23), (Al-65)+(B2.24), (Al-65)+(B2.25), (Al-65)+(B2.26), (Al-65)+(B2.27), (Al-65)+(B2.28), (Al-65)+(B2.29), (Al-65)+(B2.30), (Al-65)+(B2.31), (Al-65)+(B2.32), (Al-65)+(B2.33), (Al-65)+(B2.34), (Al-65)+(B2.35), (Al-65)+(B2.36), (Al-65)+(B2.37), (Al-65)+(B2.38), (Al-65)+(B2.39), (Al-65)+(B2.40), (Al-65)+(B2.41), (Al-65)+(B2.42), (Al-65)+(B2.43), (Al-65)+(B2.44), (Al-65)+(B2.45), (Al-65)+(B2.46), (Al-65)+(B2.47), (Al-65)+(B2.48), (Al-65)+(B2.49), (Al-65)+(B2.50), (Al-65)+(B3.1), (Al-65)+(B3.2.), (Al-65)+(B3.3), (Al-65)+(B3.4), (Al-65)+(B3.5), (Al-65)+(B3.6), (Al-65)+(B3.7), (Al-65)+(B3.8), (Al-65)+(B3.9), (Al-65)+(B3.10), (Al-65)+(B3.11), (Al-65)+(B3.12), (Al-65)+(B3.13), (Al-65)+(B3.14), (Al-65)+(B3.15), (Al-65)+(B3.16), (Al-65)+(B4.1), (Al-65)+(B4.2), (Al-65)+(B4.3), (Al-65)+(B4.4), (Al-65)+(B4.5), (Al-65)+(B4.6), (Al-65)+(B4.7).

(Al-66)+(B1.1), (Al-66)+(B1.2), (Al-66)+(B1.3), (Al-66)+(B1.4), (Al-66)+(B1.5), (Al-66)+(B1.6), (Al-66)+(B1.7), (Al-66)+(B1.8), (Al-66)+(B1.9), (Al-66)+(B1.10), (Al-66)+(B1.11), (Al-66)+(B1.12), (Al-66)+(B1.13), (Al-66)+(B1.14), (Al-66)+(B1.15), (Al-66)+(B1.16), (Al-66)+(B1.17), (Al-66)+(B1.18), (Al-66)+(B1.19), (Al-66)+(B1.20), (Al-66)+(B1.21), (Al-66)+(B1.22), (Al-66)+(B1.23), (Al-66)+(B1.24), (Al-66)+(B1.25), (Al-66)+(B1.26), (Al-66)+(B1.27), (Al-66)+(B1.28), (Al-66)+(B1.29), (Al-66)+(B1.30), (Al-66)+(B1.31), (Al-66)+(B1.32), (Al-66)+(B1.33), (Al-66)+(B1.34), (Al-66)+(B1.35), (Al-66)+(B1.36), (Al-66)+(B1.37), (Al-66)+(B1.38), (Al-66)+(B1.39), (Al-66)+(B1.40), (Al-66)+(B1.41), (Al-66)+(B1.42), (Al-66)+(B1.43), (Al-66)+(B1.44), (Al-66)+(B1.45), (Al-66)+(B1.46), (Al-66)+(B1.47), (Al-66)+(B1.48), (Al-66)+(B1.49), (Al-66)+(B1.50), (Al-66)+(B1.51), (Al-66)+(B1.52), (Al-66)+(B1.53), (Al-66)+(B1.54), (Al-66)+(B1.55), (Al-66)+(B1.56), (Al-66)+(B1.57), (Al-66)+(B1.58), (Al-66)+(B1.59), (Al-66)+(B1.60), (Al-66)+(B1.61), (Al-66)+(B1.62), (Al-66)+(B1.63), (Al-66)+(B1.64), (Al-66)+(B1.65), (Al-66)+(B1.66), (Al-66)+(B2.1), (Al-66)+(B2.2), (Al-66)+(B2.3), (Al-66)+(B2.4), (Al-66)+(B2.5), (Al-66)+(B2.6), (Al-66)+(B2.7), (Al-66)+(B2.8), (Al-66)+(B2.9), (Al-66)+(B2.10), (Al-66)+(B2.11), (Al-66)+(B2.12), (Al-66)+(B2.13), (Al-66)+(B2.14), (Al-66)+(B2.15), (Al-66)+(B2.16), (Al-66)+(B2.17), (Al-66)+(B2.18), (Al-66)+(B2.19), (Al-66)+(B2.20), (Al-66)+(B2.21), (Al-66)+(B2.22), (Al-66)+(B2.23), (Al-66)+(B2.24), (Al-66)+(B2.25), (Al-66)+(B2.26), (Al-66)+(B2.27), (Al-66)+(B2.28), (Al-66)+(B2.29), (Al-66)+(B2.30), (Al-66)+(B2.31), (Al-66)+(B2.32), (Al-66)+(B2.33), (Al-66)+(B2.34), (Al-66)+(B2.35), (Al-66)+(B2.36), (Al-66)+(B2.37), (Al-66)+(B2.38), (Al-66)+(B2.39), (Al-66)+(B2.40), (Al-66)+(B2.41), (Al-66)+(B2.42), (Al-66)+(B2.43), (Al-66)+(B2.44), (Al-66)+(B2.45), (Al-66)+(B2.46), (Al-66)+(B2.47), (Al-66)+(B2.48), (Al-66)+(B2.49), (Al-66)+(B2.50), (Al-66)+(B3.1), (Al-66)+(B3.2.), (Al-66)+(B3.3), (Al-66)+(B3.4), (Al-66)+(B3.5), (Al-66)+(B3.6), (Al-66)+(B3.7), (Al-66)+(B3.8), (Al-66)+(B3.9), (Al-66)+(B3.10), (Al-66)+(B3.11), (Al-66)+(B3.12), (Al-66)+(B3.13), (Al-66)+(B3.14), (Al-66)+(B3.15), (Al-66)+(B3.16), (Al-66)+(B4.1), (Al-66)+(B4.2), (Al-66)+(B4.3), (Al-66)+(B4.4), (Al-66)+(B4.5), (Al-66)+(B4.6), (Al-66)+(B4.7).

(Al-67)+(B1.1), (Al-67)+(B1.2), (Al-67)+(B1.3), (Al-67)+(B1.4), (Al-67)+(B1.5), (Al-67)+(B1.6), (Al-67)+

(B1.7), (Al-67)+(B1.8), (Al-67)+(B1.9), (Al-67)+(B1.10), (Al-67)+(B1.11), (Al-67)+(B1.12), (Al-67)+(B1.13), (Al-67)+(B1.14), (Al-67)+(B1.15), (Al-67)+(B1.16), (Al-67)+(B1.17), (Al-67)+(B1.18), (Al-67)+(B1.19), (Al-67)+(B1.20), (Al-67)+(B1.21), (Al-67)+(B1.22), (Al-67)+(B1.23), (Al-67)+(B1.24), (Al-67)+(B1.25), (Al-67)+(B1.26), (Al-67)+(B1.27), (Al-67)+(B1.28), (Al-67)+(B1.29), (Al-67)+(B1.30), (Al-67)+(B1.31), (Al-67)+(B1.32), (Al-67)+(B1.33), (Al-67)+(B1.34), (Al-67)+(B1.35), (Al-67)+(B1.36), (Al-67)+(B1.37), (Al-67)+(B1.38), (Al-67)+(B1.39), (Al-67)+(B1.40), (Al-67)+(B1.41), (Al-67)+(B1.42), (Al-67)+(B1.43), (Al-67)+(B1.44), (Al-67)+(B1.45), (Al-67)+(B1.46), (Al-67)+(B1.47), (Al-67)+(B1.48), (Al-67)+(B1.49), (Al-67)+(B1.50), (Al-67)+(B1.51), (Al-67)+(B1.52), (Al-67)+(B1.53), (Al-67)+(B1.54), (Al-67)+(B1.55), (Al-67)+(B1.56), (Al-67)+(B1.57), (Al-67)+(B1.58), (Al-67)+(B1.59), (Al-67)+(B1.60), (Al-67)+(B1.61), (Al-67)+(B1.62), (Al-67)+(B1.63), (Al-67)+(B1.64), (Al-67)+(B1.65), (Al-67)+(B1.66), (Al-67)+(B2.1), (Al-67)+(B2.2), (Al-67)+(B2.3), (Al-67)+(B2.4), (Al-67)+(B2.5), (Al-67)+(B2.6), (Al-67)+(B2.7), (Al-67)+(B2.8), (Al-67)+(B2.9), (Al-67)+(B2.10), (Al-67)+(B2.11), (Al-67)+(B2.12), (Al-67)+(B2.13), (Al-67)+(B2.14), (Al-67)+(B2.15), (Al-67)+(B2.16), (Al-67)+(B2.17), (Al-67)+(B2.18), (Al-67)+(B2.19), (Al-67)+(B2.20), (Al-67)+(B2.21), (Al-67)+(B2.22), (Al-67)+(B2.23), (Al-67)+(B2.24), (Al-67)+(B2.25), (Al-67)+(B2.26), (Al-67)+(B2.27), (Al-67)+(B2.28), (Al-67)+(B2.29), (Al-67)+(B2.30), (Al-67)+(B2.31), (Al-67)+(B2.32), (Al-67)+(B2.33), (Al-67)+(B2.34), (Al-67)+(B2.35), (Al-67)+(B2.36), (Al-67)+(B2.37), (Al-67)+(B2.38), (Al-67)+(B2.39), (Al-67)+(B2.40), (Al-67)+(B2.41), (Al-67)+(B2.42), (Al-67)+(B2.43), (Al-67)+(B2.44), (Al-67)+(B2.45), (Al-67)+(B2.46), (Al-67)+(B2.47), (Al-67)+(B2.48), (Al-67)+(B2.49), (Al-67)+(B2.50), (Al-67)+(B3.1), (Al-67)+(B3.2.), (Al-67)+(B3.3), (Al-67)+(B3.4), (Al-67)+(B3.5), (Al-67)+(B3.6), (Al-67)+(B3.7), (Al-67)+(B3.8), (Al-67)+(B3.9), (Al-67)+(B3.10), (Al-67)+(B3.11), (Al-67)+(B3.12), (Al-67)+(B3.13), (Al-67)+(B3.14), (Al-67)+(B3.15), (Al-67)+(B3.16), (Al-67)+(B4.1), (Al-67)+(B4.2), (Al-67)+(B4.3), (Al-67)+(B4.4), (Al-67)+(B4.5), (Al-67)+(B4.6), (Al-67)+(B4.7).

(Al-68)+(B1.1), (Al-68)+(B1.2), (Al-68)+(B1.3), (Al-68)+(B1.4), (Al-68)+(B1.5), (Al-68)+(B1.6), (Al-68)+(B1.7), (Al-68)+(B1.8), (Al-68)+(B1.9), (Al-68)+(B1.10), (Al-68)+(B1.11), (Al-68)+(B1.12), (Al-68)+(B1.13), (Al-68)+(B1.14), (Al-68)+(B1.15), (Al-68)+(B1.16), (Al-68)+(B1.17), (Al-68)+(B1.18), (Al-68)+(B1.19), (Al-68)+(B1.20), (Al-68)+(B1.21), (Al-68)+(B1.22), (Al-68)+(B1.23), (Al-68)+(B1.24), (Al-68)+(B1.25), (Al-68)+(B1.26), (Al-68)+(B1.27), (Al-68)+(B1.28), (Al-68)+(B1.29), (Al-68)+(B1.30), (Al-68)+(B1.31), (Al-68)+(B1.32), (Al-68)+(B1.33), (Al-68)+(B1.34), (Al-68)+(B1.35), (Al-68)+(B1.36), (Al-68)+(B1.37), (Al-68)+(B1.38), (Al-68)+(B1.39), (Al-68)+(B1.40), (Al-68)+(B1.41), (Al-68)+(B1.42), (Al-68)+(B1.43), (Al-68)+(B1.44), (Al-68)+(B1.45), (Al-68)+(B1.46), (Al-68)+(B1.47), (Al-68)+(B1.48), (Al-68)+(B1.49), (Al-68)+(B1.50), (Al-68)+(B1.51), (Al-68)+(B1.52), (Al-68)+(B1.53), (Al-68)+(B1.54), (Al-68)+(B1.55), (Al-68)+(B1.56), (Al-68)+(B1.57), (Al-68)+(B1.58), (Al-68)+(B1.59), (Al-68)+(B1.60), (Al-68)+(B1.61), (Al-68)+(B1.62), (Al-68)+(B1.63), (Al-68)+(B1.64), (Al-68)+(B1.65), (Al-68)+(B1.66), (Al-68)+(B2.1), (Al-68)+(B2.2), (Al-68)+(B2.3), (Al-68)+(B2.4), (Al-68)+(B2.5), (Al-68)+(B2.6), (Al-68)+(B2.7), (Al-68)+(B2.8), (Al-68)+(B2.9), (Al-68)+(B2.10), (Al-68)+(B2.11), (Al-68)+(B2.12), (Al-68)+(B2.13), (Al-68)+(B2.14), (Al-68)+(B2.15), (Al-68)+(B2.16), (Al-68)+(B2.17), (Al-68)+(B2.18), (Al-68)+(B2.19), (Al-68)+(B2.20), (Al-68)+(B2.21), (Al-68)+(B2.22), (Al-68)+(B2.23), (Al-68)+(B2.24), (Al-68)+(B2.25), (Al-68)+(B2.26), (Al-68)+(B2.27), (Al-68)+(B2.28), (Al-68)+(B2.29), (Al-68)+(B2.30), (Al-68)+(B2.31), (Al-68)+(B2.32), (Al-68)+(B2.33), (Al-68)+(B2.34), (Al-68)+(B2.35), (Al-68)+(B2.36), (Al-68)+(B2.37), (Al-68)+(B2.38), (Al-68)+(B2.39), (Al-68)+(B2.40), (Al-68)+(B2.41), (Al-68)+(B2.42), (Al-68)+(B2.43), (Al-68)+(B2.44), (Al-68)+(B2.45), (Al-68)+(B2.46), (Al-68)+(B2.47), (Al-68)+(B2.48), (Al-68)+(B2.49), (Al-68)+(B2.50), (Al-68)+(B3.1), (Al-68)+(B3.2.), (Al-68)+(B3.3), (Al-68)+(B3.4), (Al-68)+(B3.5), (Al-68)+(B3.6), (Al-68)+(B3.7), (Al-68)+(B3.8), (Al-68)+(B3.9), (Al-68)+(B3.10), (Al-68)+(B3.11), (Al-68)+(B3.12), (Al-68)+(B3.13), (Al-68)+(B3.14), (Al-68)+(B3.15), (Al-68)+(B3.16), (Al-68)+(B4.1), (Al-68)+(B4.2), (Al-68)+(B4.3), (Al-68)+(B4.4), (Al-68)+(B4.5), (Al-68)+(B4.6), (Al-68)+(B4.7).

(Al-69)+(B1.1), (Al-69)+(B1.2), (Al-69)+(B1.3), (Al-69)+(B1.4), (Al-69)+(B1.5), (Al-69)+(B1.6), (Al-69)+(B1.7), (Al-69)+(B1.8), (Al-69)+(B1.9), (Al-69)+(B1.10), (Al-69)+(B1.11), (Al-69)+(B1.12), (Al-69)+(B1.13), (Al-69)+(B1.14), (Al-69)+(B1.15), (Al-69)+(B1.16), (Al-69)+(B1.17), (Al-69)+(B1.18), (Al-69)+(B1.19), (Al-69)+(B1.20), (Al-69)+(B1.21), (Al-69)+(B1.22), (Al-69)+(B1.23), (Al-69)+(B1.24), (Al-69)+(B1.25), (Al-69)+(B1.26), (Al-69)+(B1.27), (Al-69)+(B1.28), (Al-69)+(B1.29), (Al-69)+(B1.30), (Al-69)+(B1.31), (Al-69)+(B1.32), (Al-69)+(B1.33), (Al-69)+(B1.34), (Al-69)+(B1.35), (Al-69)+(B1.36), (Al-69)+(B1.37), (Al-69)+(B1.38), (Al-69)+(B1.39), (Al-69)+(B1.40), (Al-69)+(B1.41), (Al-69)+(B1.42), (Al-69)+(B1.43), (Al-69)+(B1.44), (Al-69)+(B1.45), (Al-69)+(B1.46), (Al-69)+(B1.47), (Al-69)+(B1.48), (Al-69)+(B1.49), (Al-69)+(B1.50), (Al-69)+(B1.51), (Al-69)+(B1.52), (Al-69)+(B1.53), (Al-69)+(B1.54), (Al-69)+(B1.55), (Al-69)+(B1.56), (Al-69)+(B1.57), (Al-69)+(B1.58), (Al-69)+(B1.59), (Al-69)+(B1.60), (Al-69)+(B1.61), (Al-69)+(B1.62), (Al-69)+(B1.63), (Al-69)+(B1.64), (Al-69)+(B1.65), (Al-69)+(B1.66), (Al-69)+(B2.1), (Al-69)+(B2.2), (Al-69)+(B2.3), (Al-69)+(B2.4), (Al-69)+(B2.5), (Al-69)+(B2.6), (Al-69)+(B2.7), (Al-69)+(B2.8), (Al-69)+(B2.9), (Al-69)+(B2.10), (Al-69)+(B2.11), (Al-69)+(B2.12), (Al-69)+(B2.13), (Al-69)+(B2.14), (Al-69)+(B2.15), (Al-69)+(B2.16), (Al-69)+(B2.17), (Al-69)+(B2.18), (Al-69)+(B2.19), (Al-69)+(B2.20), (Al-69)+(B2.21), (Al-69)+(B2.22), (Al-69)+(B2.23), (Al-69)+(B2.24), (Al-69)+(B2.25), (Al-69)+(B2.26), (Al-69)+(B2.27), (Al-69)+(B2.28), (Al-69)+(B2.29), (Al-69)+(B2.30), (Al-69)+(B2.31), (Al-69)+(B2.32), (Al-69)+(B2.33), (Al-69)+(B2.34), (Al-69)+(B2.35), (Al-69)+(B2.36), (Al-69)+(B2.37), (Al-69)+(B2.38), (Al-69)+(B2.39), (Al-69)+(B2.40), (Al-69)+(B2.41), (Al-69)+(B2.42), (Al-69)+(B2.43), (Al-69)+(B2.44), (Al-69)+(B2.45), (Al-69)+(B2.46), (Al-69)+(B2.47), (Al-69)+(B2.48), (Al-69)+(B2.49), (Al-69)+(B2.50), (Al-69)+(B3.1), (Al-69)+(B3.2.), (Al-69)+(B3.3), (Al-69)+(B3.4), (Al-69)+(B3.5), (Al-69)+(B3.6), (Al-69)+(B3.7), (Al-69)+(B3.8), (Al-69)+(B3.9), (Al-69)+(B3.10), (Al-69)+(B3.11), (Al-69)+(B3.12), (Al-69)+(B3.13), (Al-69)+(B3.14), (Al-69)+(B3.15), (Al-69)+(B3.16), (Al-69)+(B4.1), (Al-69)+(B4.2), (Al-69)+(B4.3), (Al-69)+(B4.4), (Al-69)+(B4.5), (Al-69)+(B4.6), (Al-69)+(B4.7).

(Al-70)+(B1.1), (Al-70)+(B1.2), (Al-70)+(B1.3), (Al-70)+(B1.4), (Al-70)+(B1.5), (Al-70)+(B1.6), (Al-70)+(B1.7), (Al-70)+(B1.8), (Al-70)+(B1.9), (Al-70)+(B1.10), (Al-70)+(B1.11), (Al-70)+(B1.12), (Al-70)+(B1.13), (Al-70)+(B1.14), (Al-70)+(B1.15), (Al-70)+(B1.16), (Al-70)+(B1.17), (Al-70)+(B1.18), (Al-70)+(B1.19), (Al-70)+(B1.20), (Al-70)+(B1.21), (Al-70)+(B1.22), (Al-70)+(B1.23), (Al-70)+(B1.24), (Al-70)+(B1.25), (Al-70)+(B1.26), (Al-70)+(B1.27), (Al-70)+(B1.28), (Al-70)+(B1.29), (Al-70)+(B1.30), (Al-70)+(B1.31), (Al-70)+(B1.32), (Al-70)+(B1.33), (Al-70)+(B1.34), (Al-70)+(B1.35), (Al-70)+(B1.36), (Al-70)+(B1.37), (Al-70)+(B1.38), (Al-70)+(B1.39), (Al-70)+(B1.40), (Al-70)+(B1.41), (Al-70)+(B1.42), (Al-70)+(B1.43), (Al-70)+(B1.44), (Al-70)+(B1.45), (Al-70)+(B1.46), (Al-70)+(B1.47), (Al-70)+(B1.48), (Al-70)+(B1.49), (Al-70)+(B1.50), (Al-70)+(B1.51), (Al-70)+(B1.52), (Al-70)+(B1.53), (Al-70)+(B1.54), (Al-70)+(B1.55), (Al-70)+(B1.56), (Al-70)+(B1.57), (Al-70)+(B1.58), (Al-70)+(B1.59), (Al-70)+(B1.60), (Al-70)+(B1.61), (Al-70)+(B1.62), (Al-70)+(B1.63), (Al-70)+(B1.64), (Al-70)+(B1.65), (Al-70)+(B1.66), (Al-70)+(B2.1), (Al-70)+(B2.2), (Al-70)+(B2.3), (Al-70)+(B2.4), (Al-70)+(B2.5), (Al-70)+(B2.6), (Al-70)+(B2.7), (Al-70)+(B2.8), (Al-70)+(B2.9), (Al-70)+(B2.10), (Al-70)+(B2.11), (Al-70)+(B2.12), (Al-70)+(B2.13), (Al-70)+(B2.14), (Al-70)+(B2.15), (Al-70)+(B2.16), (Al-70)+(B2.17), (Al-70)+(B2.18), (Al-70)+(B2.19), (Al-70)+(B2.20), (Al-70)+(B2.21), (Al-70)+(B2.22), (Al-70)+(B2.23), (Al-70)+(B2.24), (Al-70)+(B2.25), (Al-70)+(B2.26), (Al-70)+(B2.27), (Al-70)+(B2.28), (Al-70)+(B2.29), (Al-70)+(B2.30), (Al-70)+(B2.31), (Al-70)+(B2.32), (Al-70)+(B2.33), (Al-70)+(B2.34), (Al-70)+(B2.35), (Al-70)+(B2.36), (Al-70)+(B2.37), (Al-70)+(B2.38), (Al-70)+(B2.39), (Al-70)+(B2.40), (Al-70)+(B2.41), (Al-70)+(B2.42), (Al-70)+(B2.43), (Al-70)+(B2.44), (Al-70)+(B2.45), (Al-70)+(B2.46), (Al-70)+(B2.47), (Al-70)+(B2.48), (Al-70)+(B2.49), (Al-70)+(B2.50), (Al-70)+(B3.1), (Al-70)+(B3.2.), (Al-70)+(B3.3), (Al-70)+(B3.4), (Al-70)+(B3.5), (Al-70)+(B3.6), (Al-70)+(B3.7), (Al-70)+(B3.8), (Al-70)+(B3.9), (Al-70)+(B3.10), (Al-70)+(B3.11), (Al-70)+(B3.12), (Al-70)+(B3.13), (Al-70)+(B3.14), (Al-70)+(B3.15), (Al-70)+(B3.16), (Al-70)+(B4.1), (Al-70)+(B4.2), (Al-70)+(B4.3), (Al-70)+(B4.4), (Al-70)+(B4.5), (Al-70)+(B4.6), (Al-70)+(B4.7).

(Al-71)+(B1.1), (Al-71)+(B1.2), (Al-71)+(B1.3), (Al-71)+(B1.4), (Al-71)+(B1.5), (Al-71)+(B1.6), (Al-71)+(B1.7), (Al-71)+(B1.8), (Al-71)+(B1.9), (Al-71)+(B1.10), (Al-71)+(B1.11), (Al-71)+(B1.12), (Al-71)+(B1.13), (Al-71)+(B1.14), (Al-71)+(B1.15), (Al-71)+(B1.16), (Al-71)+(B1.17), (Al-71)+(B1.18), (Al-71)+(B1.19), (Al-71)+(B1.20), (Al-71)+(B1.21), (Al-71)+(B1.22), (Al-71)+(B1.23), (Al-71)+(B1.24), (Al-71)+(B1.25), (Al-71)+(B1.26), (Al-71)+(B1.27), (Al-71)+(B1.28), (Al-71)+(B1.29), (Al-71)+(B1.30), (Al-71)+(B1.31), (Al-71)+(B1.32), (Al-71)+(B1.33), (Al-71)+(B1.34), (Al-71)+(B1.35), (Al-71)+(B1.36), (Al-71)+(B1.37), (Al-71)+(B1.38), (Al-71)+(B1.39), (Al-71)+(B1.40), (Al-71)+(B1.41), (Al-71)+(B1.42), (Al-71)+(B1.43), (Al-71)+(B1.44), (Al-71)+(B1.45), (Al-71)+(B1.46), (Al-71)+(B1.47), (Al-71)+(B1.48), (Al-71)+(B1.49), (Al-71)+(B1.50), (Al-71)+(B1.51), (Al-71)+(B1.52), (Al-71)+(B1.53), (Al-71)+(B1.54), (Al-71)+(B1.55), (Al-71)+(B1.56), (Al-71)+(B1.57), (Al-71)+(B1.58), (Al-71)+(B1.59), (Al-71)+(B1.60), (Al-71)+(B1.61), (Al-71)+(B1.62), (Al-71)+(B1.63), (Al-71)+(B1.64), (Al-71)+(B1.65), (Al-71)+(B1.66), (Al-71)+(B2.1), (Al-71)+(B2.2), (Al-71)+(B2.3), (Al-71)+(B2.4), (Al-71)+(B2.5), (Al-71)+(B2.6), (Al-71)+(B2.7), (Al-71)+(B2.8), (Al-71)+(B2.9), (Al-71)+(B2.10), (Al-71)+(B2.11), (Al-71)+(B2.12), (Al-71)+(B2.13), (Al-71)+(B2.14), (Al-71)+(B2.15), (Al-71)+(B2.16), (Al-71)+(B2.17), (Al-71)+(B2.18), (Al-71)+(B2.19), (Al-71)+(B2.20), (Al-71)+(B2.21), (Al-71)+(B2.22), (Al-71)+(B2.23), (Al-71)+(B2.24), (Al-71)+(B2.25), (Al-71)+(B2.26), (Al-71)+(B2.27), (Al-71)+(B2.28), (Al-71)+(B2.29), (Al-71)+(B2.30), (Al-71)+(B2.31), (Al-71)+(B2.32), (Al-71)+(B2.33), (Al-71)+(B2.34), (Al-71)+(B2.35), (Al-71)+(B2.36), (Al-71)+(B2.37), (Al-71)+(B2.38), (Al-71)+(B2.39), (Al-71)+(B2.40), (Al-71)+(B2.41), (Al-71)+(B2.42), (Al-71)+(B2.43), (Al-71)+(B2.44), (Al-71)+(B2.45), (Al-71)+(B2.46), (Al-71)+(B2.47), (Al-71)+(B2.48), (Al-71)+(B2.49), (Al-71)+(B2.50), (Al-71)+(B3.1), (Al-71)+(B3.2.), (Al-71)+(B3.3), (Al-71)+(B3.4), (Al-71)+(B3.5), (Al-71)+(B3.6), (Al-71)+(B3.7), (Al-71)+(B3.8), (Al-71)+(B3.9), (Al-71)+(B3.10), (Al-71)+(B3.11), (Al-71)+(B3.12), (Al-71)+(B3.13), (Al-71)+(B3.14), (Al-71)+(B3.15), (Al-71)+(B3.16), (Al-71)+(B4.1), (Al-71)+(B4.2), (Al-71)+(B4.3), (Al-71)+(B4.4), (Al-71)+(B4.5), (Al-71)+(B4.6), (Al-71)+(B4.7).

(Al-72)+(B1.1), (Al-72)+(B1.2), (Al-72)+(B1.3), (Al-72)+(B1.4), (Al-72)+(B1.5), (Al-72)+(B1.6), (Al-72)+(B1.7), (Al-72)+(B1.8), (Al-72)+(B1.9), (Al-72)+(B1.10), (Al-72)+(B1.11), (Al-72)+(B1.12), (Al-72)+(B1.13), (Al-72)+(B1.14), (Al-72)+(B1.15), (Al-72)+(B1.16), (Al-72)+(B1.17), (Al-72)+(B1.18), (Al-72)+(B1.19), (Al-72)+(B1.20), (Al-72)+(B1.21), (Al-72)+(B1.22), (Al-72)+(B1.23), (Al-72)+(B1.24), (Al-72)+(B1.25), (Al-72)+(B1.26), (Al-72)+(B1.27), (Al-72)+(B1.28), (Al-72)+(B1.29), (Al-72)+(B1.30), (Al-72)+(B1.31), (Al-72)+(B1.32), (Al-72)+(B1.33), (Al-72)+(B1.34), (Al-72)+(B1.35), (Al-72)+(B1.36), (Al-72)+(B1.37), (Al-72)+(B1.38), (Al-72)+(B1.39), (Al-72)+(B1.40), (Al-72)+(B1.41), (Al-72)+(B1.42), (Al-72)+(B1.43), (Al-72)+(B1.44), (Al-72)+(B1.45), (Al-72)+(B1.46), (Al-72)+(B1.47), (Al-72)+(B1.48), (Al-72)+(B1.49), (Al-72)+(B1.50), (Al-72)+(B1.51), (Al-72)+(B1.52), (Al-72)+(B1.53), (Al-72)+(B1.54), (Al-72)+(B1.55), (Al-72)+(B1.56), (Al-72)+(B1.57), (Al-72)+(B1.58), (Al-72)+(B1.59), (Al-72)+(B1.60), (Al-72)+(B1.61), (Al-72)+(B1.62), (Al-72)+(B1.63), (Al-72)+(B1.64), (Al-72)+(B1.65), (Al-72)+(B1.66), (Al-72)+(B2.1), (Al-72)+(B2.2), (Al-72)+(B2.3), (Al-72)+(B2.4), (Al-72)+(B2.5), (Al-72)+(B2.6), (Al-72)+(B2.7), (Al-72)+(B2.8), (Al-72)+(B2.9), (Al-72)+(B2.10), (Al-72)+(B2.11), (Al-72)+(B2.12), (Al-72)+(B2.13), (Al-72)+(B2.14), (Al-72)+(B2.15), (Al-72)+(B2.16), (Al-72)+(B2.17), (Al-72)+(B2.18), (Al-72)+(B2.19), (Al-72)+(B2.20), (Al-72)+(B2.21), (Al-72)+(B2.22), (Al-72)+(B2.23), (Al-72)+(B2.24), (Al-72)+(B2.25), (Al-72)+(B2.26), (Al-72)+(B2.27), (Al-72)+(B2.28), (Al-72)+(B2.29), (Al-72)+(B2.30), (Al-72)+(B2.31), (Al-72)+(B2.32), (Al-72)+(B2.33), (Al-72)+(B2.34), (Al-72)+(B2.35), (Al-72)+(B2.36), (Al-72)+(B2.37), (Al-72)+(B2.38), (Al-72)+(B2.39), (Al-72)+(B2.40), (Al-72)+(B2.41), (Al-72)+(B2.42), (Al-72)+(B2.43), (Al-72)+(B2.44), (Al-72)+(B2.45), (Al-72)+(B2.46), (Al-72)+(B2.47), (Al-72)+(B2.48), (Al-72)+(B2.49), (Al-72)+(B2.50), (Al-72)+(B3.1), (Al-72)+(B3.2.), (Al-72)+(B3.3), (Al-72)+(B3.4), (Al-72)+(B3.5), (Al-72)+(B3.6), (Al-72)+(B3.7), (Al-72)+(B3.8), (Al-72)+(B3.9), (Al-72)+(B3.10), (Al-72)+(B3.11), (Al-72)+(B3.12), (Al-72)+(B3.13), (Al-72)+(B3.14), (Al-72)+(B3.15), (Al-72)+

(B3.16), (Al-72)+(B4.1), (Al-72)+(B4.2), (Al-72)+(B4.3), (Al-72)+(B4.4), (Al-72)+(B4.5), (Al-72)+(B4.6), (Al-72)+(B4.7).

(Al-73)+(B1.1), (Al-73)+(B1.2), (Al-73)+(B1.3), (Al-73)+(B1.4), (Al-73)+(B1.5), (Al-73)+(B1.6), (Al-73)+(B1.7), (Al-73)+(B1.8), (Al-73)+(B1.9), (Al-73)+(B1.10), (Al-73)+(B1.11), (Al-73)+(B1.12), (Al-73)+(B1.13), (Al-73)+(B1.14), (Al-73)+(B1.15), (Al-73)+(B1.16), (Al-73)+(B1.17), (Al-73)+(B1.18), (Al-73)+(B1.19), (Al-73)+(B1.20), (Al-73)+(B1.21), (Al-73)+(B1.22), (Al-73)+(B1.23), (Al-73)+(B1.24), (Al-73)+(B1.25), (Al-73)+(B1.26), (Al-73)+(B1.27), (Al-73)+(B1.28), (Al-73)+(B1.29), (Al-73)+(B1.30), (Al-73)+(B1.31), (Al-73)+(B1.32), (Al-73)+(B1.33), (Al-73)+(B1.34), (Al-73)+(B1.35), (Al-73)+(B1.36), (Al-73)+(B1.37), (Al-73)+(B1.38), (Al-73)+(B1.39), (Al-73)+(B1.40), (Al-73)+(B1.41), (Al-73)+(B1.42), (Al-73)+(B1.43), (Al-73)+(B1.44), (Al-73)+(B1.45), (Al-73)+(B1.46), (Al-73)+(B1.47), (Al-73)+(B1.48), (Al-73)+(B1.49), (Al-73)+(B1.50), (Al-73)+(B1.51), (Al-73)+(B1.52), (Al-73)+(B1.53), (Al-73)+(B1.54), (Al-73)+(B1.55), (Al-73)+(B1.56), (Al-73)+(B1.57), (Al-73)+(B1.58), (Al-73)+(B1.59), (Al-73)+(B1.60), (Al-73)+(B1.61), (Al-73)+(B1.62), (Al-73)+(B1.63), (Al-73)+(B1.64), (Al-73)+(B1.65), (Al-73)+(B1.66), (Al-73)+(B2.1), (Al-73)+(B2.2), (Al-73)+(B2.3), (Al-73)+(B2.4), (Al-73)+(B2.5), (Al-73)+(B2.6), (Al-73)+(B2.7), (Al-73)+(B2.8), (Al-73)+(B2.9), (Al-73)+(B2.10), (Al-73)+(B2.11), (Al-73)+(B2.12), (Al-73)+(B2.13), (Al-73)+(B2.14), (Al-73)+(B2.15), (Al-73)+(B2.16), (Al-73)+(B2.17), (Al-73)+(B2.18), (Al-73)+(B2.19), (Al-73)+(B2.20), (Al-73)+(B2.21), (Al-73)+(B2.22), (Al-73)+(B2.23), (Al-73)+(B2.24), (Al-73)+(B2.25), (Al-73)+(B2.26), (Al-73)+(B2.27), (Al-73)+(B2.28), (Al-73)+(B2.29), (Al-73)+(B2.30), (Al-73)+(B2.31), (Al-73)+(B2.32), (Al-73)+(B2.33), (Al-73)+(B2.34), (Al-73)+(B2.35), (Al-73)+(B2.36), (Al-73)+(B2.37), (Al-73)+(B2.38), (Al-73)+(B2.39), (Al-73)+(B2.40), (Al-73)+(B2.41), (Al-73)+(B2.42), (Al-73)+(B2.43), (Al-73)+(B2.44), (Al-73)+(B2.45), (Al-73)+(B2.46), (Al-73)+(B2.47), (Al-73)+(B2.48), (Al-73)+(B2.49), (Al-73)+(B2.50), (Al-73)+(B3.1), (Al-73)+(B3.2.), (Al-73)+(B3.3), (Al-73)+(B3.4), (Al-73)+(B3.5), (Al-73)+(B3.6), (Al-73)+(B3.7), (Al-73)+(B3.8), (Al-73)+(B3.9), (Al-73)+(B3.10), (Al-73)+(B3.11), (Al-73)+(B3.12), (Al-73)+(B3.13), (Al-73)+(B3.14), (Al-73)+(B3.15), (Al-73)+(B3.16), (Al-73)+(B4.1), (Al-73)+(B4.2), (Al-73)+(B4.3), (Al-73)+(B4.4), (Al-73)+(B4.5), (Al-73)+(B4.6), (Al-73)+(B4.7).

(Al-74)+(B1.1), (Al-74)+(B1.2), (Al-74)+(B1.3), (Al-74)+(B1.4), (Al-74)+(B1.5), (Al-74)+(B1.6), (Al-74)+(B1.7), (Al-74)+(B1.8), (Al-74)+(B1.9), (Al-74)+(B1.10), (Al-74)+(B1.11), (Al-74)+(B1.12), (Al-74)+(B1.13), (Al-74)+(B1.14), (Al-74)+(B1.15), (Al-74)+(B1.16), (Al-74)+(B1.17), (Al-74)+(B1.18), (Al-74)+(B1.19), (Al-74)+(B1.20), (Al-74)+(B1.21), (Al-74)+(B1.22), (Al-74)+(B1.23), (Al-74)+(B1.24), (Al-74)+(B1.25), (Al-74)+(B1.26), (Al-74)+(B1.27), (Al-74)+(B1.28), (Al-74)+(B1.29), (Al-74)+(B1.30), (Al-74)+(B1.31), (Al-74)+(B1.32), (Al-74)+(B1.33), (Al-74)+(B1.34), (Al-74)+(B1.35), (Al-74)+(B1.36), (Al-74)+(B1.37), (Al-74)+(B1.38), (Al-74)+(B1.39), (Al-74)+(B1.40), (Al-74)+(B1.41), (Al-74)+(B1.42), (Al-74)+(B1.43), (Al-74)+(B1.44), (Al-74)+(B1.45), (Al-74)+(B1.46), (Al-74)+(B1.47), (Al-74)+(B1.48), (Al-74)+(B1.49), (Al-74)+(B1.50), (Al-74)+(B1.51), (Al-74)+(B1.52), (Al-74)+(B1.53), (Al-74)+(B1.54), (Al-74)+(B1.55), (Al-74)+(B1.56), (Al-74)+(B1.57), (Al-74)+(B1.58), (Al-74)+(B1.59), (Al-74)+(B1.60), (Al-74)+(B1.61), (Al-74)+(B1.62), (Al-74)+(B1.63), (Al-74)+(B1.64), (Al-74)+(B1.65), (Al-74)+(B1.66), (Al-74)+(B2.1), (Al-74)+(B2.2), (Al-74)+(B2.3), (Al-74)+(B2.4), (Al-74)+(B2.5), (Al-74)+(B2.6), (Al-74)+(B2.7), (Al-74)+(B2.8), (Al-74)+(B2.9), (Al-74)+(B2.10), (Al-74)+(B2.11), (Al-74)+(B2.12), (Al-74)+(B2.13), (Al-74)+(B2.14), (Al-74)+(B2.15), (Al-74)+(B2.16), (Al-74)+(B2.17), (Al-74)+(B2.18), (Al-74)+(B2.19), (Al-74)+(B2.20), (Al-74)+(B2.21), (Al-74)+(B2.22), (Al-74)+(B2.23), (Al-74)+(B2.24), (Al-74)+(B2.25), (Al-74)+(B2.26), (Al-74)+(B2.27), (Al-74)+(B2.28), (Al-74)+(B2.29), (Al-74)+(B2.30), (Al-74)+(B2.31), (Al-74)+(B2.32), (Al-74)+(B2.33), (Al-74)+(B2.34), (Al-74)+(B2.35), (Al-74)+(B2.36), (Al-74)+(B2.37), (Al-74)+(B2.38), (Al-74)+(B2.39), (Al-74)+(B2.40), (Al-74)+(B2.41), (Al-74)+(B2.42), (Al-74)+(B2.43), (Al-74)+(B2.44), (Al-74)+(B2.45), (Al-74)+(B2.46), (Al-74)+(B2.47), (Al-74)+(B2.48), (Al-74)+(B2.49), (Al-74)+(B2.50), (Al-74)+(B3.1), (Al-74)+(B3.2.), (Al-74)+(B3.3), (Al-74)+(B3.4), (Al-74)+(B3.5), (Al-74)+(B3.6), (Al-74)+(B3.7), (Al-74)+(B3.8), (Al-74)+(B3.9), (Al-74)+(B3.10), (Al-74)+(B3.11), (Al-74)+(B3.12), (Al-74)+(B3.13), (Al-74)+(B3.14), (Al-74)+(B3.15), (Al-74)+(B3.16), (Al-74)+(B4.1), (Al-74)+(B4.2), (Al-74)+(B4.3), (Al-74)+(B4.4), (Al-74)+(B4.5), (Al-74)+(B4.6), (Al-74)+(B4.7).

(Al-75)+(B1.1), (Al-75)+(B1.2), (Al-75)+(B1.3), (Al-75)+(B1.4), (Al-75)+(B1.5), (Al-75)+(B1.6), (Al-75)+(B1.7), (Al-75)+(B1.8), (Al-75)+(B1.9), (Al-75)+(B1.10), (Al-75)+(B1.11), (Al-75)+(B1.12), (Al-75)+(B1.13), (Al-75)+(B1.14), (Al-75)+(B1.15), (Al-75)+(B1.16), (Al-75)+(B1.17), (Al-75)+(B1.18), (Al-75)+(B1.19), (Al-75)+(B1.20), (Al-75)+(B1.21), (Al-75)+(B1.22), (Al-75)+(B1.23), (Al-75)+(B1.24), (Al-75)+(B1.25), (Al-75)+(B1.26), (Al-75)+(B1.27), (Al-75)+(B1.28), (Al-75)+(B1.29), (Al-75)+(B1.30), (Al-75)+(B1.31), (Al-75)+(B1.32), (Al-75)+(B1.33), (Al-75)+(B1.34), (Al-75)+(B1.35), (Al-75)+(B1.36), (Al-75)+(B1.37), (Al-75)+(B1.38), (Al-75)+(B1.39), (Al-75)+(B1.40), (Al-75)+(B1.41), (Al-75)+(B1.42), (Al-75)+(B1.43), (Al-75)+(B1.44), (Al-75)+(B1.45), (Al-75)+(B1.46), (Al-75)+(B1.47), (Al-75)+(B1.48), (Al-75)+(B1.49), (Al-75)+(B1.50), (Al-75)+(B1.51), (Al-75)+(B1.52), (Al-75)+(B1.53), (Al-75)+(B1.54), (Al-75)+(B1.55), (Al-75)+(B1.56), (Al-75)+(B1.57), (Al-75)+(B1.58), (Al-75)+(B1.59), (Al-75)+(B1.60), (Al-75)+(B1.61), (Al-75)+(B1.62), (Al-75)+(B1.63), (Al-75)+(B1.64), (Al-75)+(B1.65), (Al-75)+(B1.66), (Al-75)+(B2.1), (Al-75)+(B2.2), (Al-75)+(B2.3), (Al-75)+(B2.4), (Al-75)+(B2.5), (Al-75)+(B2.6), (Al-75)+(B2.7), (Al-75)+(B2.8), (Al-75)+(B2.9), (Al-75)+(B2.10), (Al-75)+(B2.11), (Al-75)+(B2.12), (Al-75)+(B2.13), (Al-75)+(B2.14), (Al-75)+(B2.15), (Al-75)+(B2.16), (Al-75)+(B2.17), (Al-75)+(B2.18), (Al-75)+(B2.19), (Al-75)+(B2.20), (Al-75)+(B2.21), (Al-75)+(B2.22), (Al-75)+(B2.23), (Al-75)+(B2.24), (Al-75)+(B2.25), (Al-75)+(B2.26), (Al-75)+(B2.27), (Al-75)+(B2.28), (Al-75)+(B2.29), (Al-75)+(B2.30), (Al-75)+(B2.31), (Al-75)+(B2.32), (Al-75)+(B2.33), (Al-75)+(B2.34), (Al-75)+(B2.35), (Al-75)+(B2.36), (Al-75)+(B2.37), (Al-75)+(B2.38), (Al-75)+(B2.39), (Al-75)+(B2.40), (Al-75)+(B2.41), (Al-75)+(B2.42), (Al-75)+(B2.43), (Al-75)+(B2.44), (Al-75)+(B2.45), (Al-75)+(B2.46), (Al-75)+(B2.47), (Al-75)+(B2.48), (Al-75)+(B2.49), (Al-75)+(B2.50), (Al-75)+(B3.1), (Al-75)+(B3.2.), (Al-75)+(B3.3), (Al-75)+(B3.4), (Al-75)+(B3.5), (Al-75)+(B3.6), (Al-75)+(B3.7), (Al-75)+(B3.8), (Al-75)+(B3.9), (Al-75)+(B3.10), (Al-75)+(B3.11), (Al-75)+(B3.12), (Al-

75)+(B3.13), (Al-75)+(B3.14), (Al-75)+(B3.15), (Al-75)+(B3.16), (Al-75)+(B4.1), (Al-75)+(B4.2), (Al-75)+(B4.3), (Al-75)+(B4.4), (Al-75)+(B4.5), (Al-75)+(B4.6), (Al-75)+(B4.7).

(Al-76)+(B1.1), (Al-76)+(B1.2), (Al-76)+(B1.3), (Al-76)+(B1.4), (Al-76)+(B1.5), (Al-76)+(B1.6), (Al-76)+(B1.7), (Al-76)+(B1.8), (Al-76)+(B1.9), (Al-76)+(B1.10), (Al-76)+(B1.11), (Al-76)+(B1.12), (Al-76)+(B1.13), (Al-76)+(B1.14), (Al-76)+(B1.15), (Al-76)+(B1.16), (Al-76)+(B1.17), (Al-76)+(B1.18), (Al-76)+(B1.19), (Al-76)+(B1.20), (Al-76)+(B1.21), (Al-76)+(B1.22), (Al-76)+(B1.23), (Al-76)+(B1.24), (Al-76)+(B1.25), (Al-76)+(B1.26), (Al-76)+(B1.27), (Al-76)+(B1.28), (Al-76)+(B1.29), (Al-76)+(B1.30), (Al-76)+(B1.31), (Al-76)+(B1.32), (Al-76)+(B1.33), (Al-76)+(B1.34), (Al-76)+(B1.35), (Al-76)+(B1.36), (Al-76)+(B1.37), (Al-76)+(B1.38), (Al-76)+(B1.39), (Al-76)+(B1.40), (Al-76)+(B1.41), (Al-76)+(B1.42), (Al-76)+(B1.43), (Al-76)+(B1.44), (Al-76)+(B1.45), (Al-76)+(B1.46), (Al-76)+(B1.47), (Al-76)+(B1.48), (Al-76)+(B1.49), (Al-76)+(B1.50), (Al-76)+(B1.51), (Al-76)+(B1.52), (Al-76)+(B1.53), (Al-76)+(B1.54), (Al-76)+(B1.55), (Al-76)+(B1.56), (Al-76)+(B1.57), (Al-76)+(B1.58), (Al-76)+(B1.59), (Al-76)+(B1.60), (Al-76)+(B1.61), (Al-76)+(B1.62), (Al-76)+(B1.63), (Al-76)+(B1.64), (Al-76)+(B1.65), (Al-76)+(B1.66), (Al-76)+(B2.1), (Al-76)+(B2.2), (Al-76)+(B2.3), (Al-76)+(B2.4), (Al-76)+(B2.5), (Al-76)+(B2.6), (Al-76)+(B2.7), (Al-76)+(B2.8), (Al-76)+(B2.9), (Al-76)+(B2.10), (Al-76)+(B2.11), (Al-76)+(B2.12), (Al-76)+(B2.13), (Al-76)+(B2.14), (Al-76)+(B2.15), (Al-76)+(B2.16), (Al-76)+(B2.17), (Al-76)+(B2.18), (Al-76)+(B2.19), (Al-76)+(B2.20), (Al-76)+(B2.21), (Al-76)+(B2.22), (Al-76)+(B2.23), (Al-76)+(B2.24), (Al-76)+(B2.25), (Al-76)+(B2.26), (Al-76)+(B2.27), (Al-76)+(B2.28), (Al-76)+(B2.29), (Al-76)+(B2.30), (Al-76)+(B2.31), (Al-76)+(B2.32), (Al-76)+(B2.33), (Al-76)+(B2.34), (Al-76)+(B2.35), (Al-76)+(B2.36), (Al-76)+(B2.37), (Al-76)+(B2.38), (Al-76)+(B2.39), (Al-76)+(B2.40), (Al-76)+(B2.41), (Al-76)+(B2.42), (Al-76)+(B2.43), (Al-76)+(B2.44), (Al-76)+(B2.45), (Al-76)+(B2.46), (Al-76)+(B2.47), (Al-76)+(B2.48), (Al-76)+(B2.49), (Al-76)+(B2.50), (Al-76)+(B3.1), (Al-76)+(B3.2.), (Al-76)+(B3.3), (Al-76)+(B3.4), (Al-76)+(B3.5), (Al-76)+(B3.6), (Al-76)+(B3.7), (Al-76)+(B3.8), (Al-76)+(B3.9), (Al-76)+(B3.10), (Al-76)+(B3.11), (Al-76)+(B3.12), (Al-76)+(B3.13), (Al-76)+(B3.14), (Al-76)+(B3.15), (Al-76)+(B3.16), (Al-76)+(B4.1), (Al-76)+(B4.2), (Al-76)+(B4.3), (Al-76)+(B4.4), (Al-76)+(B4.5), (Al-76)+(B4.6), (Al-76)+(B4.7).

(Al-77)+(B1.1), (Al-77)+(B1.2), (Al-77)+(B1.3), (Al-77)+(B1.4), (Al-77)+(B1.5), (Al-77)+(B1.6), (Al-77)+(B1.7), (Al-77)+(B1.8), (Al-77)+(B1.9), (Al-77)+(B1.10), (Al-77)+(B1.11), (Al-77)+(B1.12), (Al-77)+(B1.13), (Al-77)+(B1.14), (Al-77)+(B1.15), (Al-77)+(B1.16), (Al-77)+(B1.17), (Al-77)+(B1.18), (Al-77)+(B1.19), (Al-77)+(B1.20), (Al-77)+(B1.21), (Al-77)+(B1.22), (Al-77)+(B1.23), (Al-77)+(B1.24), (Al-77)+(B1.25), (Al-77)+(B1.26), (Al-77)+(B1.27), (Al-77)+(B1.28), (Al-77)+(B1.29), (Al-77)+(B1.30), (Al-77)+(B1.31), (Al-77)+(B1.32), (Al-77)+(B1.33), (Al-77)+(B1.34), (Al-77)+(B1.35), (Al-77)+(B1.36), (Al-77)+(B1.37), (Al-77)+(B1.38), (Al-77)+(B1.39), (Al-77)+(B1.40), (Al-77)+(B1.41), (Al-77)+(B1.42), (Al-77)+(B1.43), (Al-77)+(B1.44), (Al-77)+(B1.45), (Al-77)+(B1.46), (Al-77)+(B1.47), (Al-77)+(B1.48), (Al-77)+(B1.49), (Al-77)+(B1.50), (Al-77)+(B1.51), (Al-77)+(B1.52), (Al-77)+(B1.53), (Al-77)+(B1.54), (Al-77)+(B1.55), (Al-77)+(B1.56), (Al-77)+(B1.57), (Al-77)+(B1.58), (Al-77)+(B1.59), (Al-77)+(B1.60), (Al-77)+(B1.61), (Al-77)+(B1.62), (Al-77)+(B1.63), (Al-77)+(B1.64), (Al-77)+(B1.65), (Al-77)+(B1.66), (Al-77)+(B2.1), (Al-77)+(B2.2), (Al-77)+(B2.3), (Al-77)+(B2.4), (Al-77)+(B2.5), (Al-77)+(B2.6), (Al-77)+(B2.7), (Al-77)+(B2.8), (Al-77)+(B2.9), (Al-77)+(B2.10), (Al-77)+(B2.11), (Al-77)+(B2.12), (Al-77)+(B2.13), (Al-77)+(B2.14), (Al-77)+(B2.15), (Al-77)+(B2.16), (Al-77)+(B2.17), (Al-77)+(B2.18), (Al-77)+(B2.19), (Al-77)+(B2.20), (Al-77)+(B2.21), (Al-77)+(B2.22), (Al-77)+(B2.23), (Al-77)+(B2.24), (Al-77)+(B2.25), (Al-77)+(B2.26), (Al-77)+(B2.27), (Al-77)+(B2.28), (Al-77)+(B2.29), (Al-77)+(B2.30), (Al-77)+(B2.31), (Al-77)+(B2.32), (Al-77)+(B2.33), (Al-77)+(B2.34), (Al-77)+(B2.35), (Al-77)+(B2.36), (Al-77)+(B2.37), (Al-77)+(B2.38), (Al-77)+(B2.39), (Al-77)+(B2.40), (Al-77)+(B2.41), (Al-77)+(B2.42), (Al-77)+(B2.43), (Al-77)+(B2.44), (Al-77)+(B2.45), (Al-77)+(B2.46), (Al-77)+(B2.47), (Al-77)+(B2.48), (Al-77)+(B2.49), (Al-77)+(B2.50), (Al-77)+(B3.1), (Al-77)+(B3.2.), (Al-77)+(B3.3), (Al-77)+(B3.4), (Al-77)+(B3.5), (Al-77)+(B3.6), (Al-77)+(B3.7), (Al-77)+(B3.8), (Al-77)+(B3.9), (Al-77)+(B3.10), (Al-77)+(B3.11), (Al-77)+(B3.12), (Al-77)+(B3.13), (Al-77)+(B3.14), (Al-77)+(B3.15), (Al-77)+(B3.16), (Al-77)+(B4.1), (Al-77)+(B4.2), (Al-77)+(B4.3), (Al-77)+(B4.4), (Al-77)+(B4.5), (Al-77)+(B4.6), (Al-77)+(B4.7).

(Al-78)+(B1.1), (Al-78)+(B1.2), (Al-78)+(B1.3), (Al-78)+(B1.4), (Al-78)+(B1.5), (Al-78)+(B1.6), (Al-78)+(B1.7), (Al-78)+(B1.8), (Al-78)+(B1.9), (Al-78)+(B1.10), (Al-78)+(B1.11), (Al-78)+(B1.12), (Al-78)+(B1.13), (Al-78)+(B1.14), (Al-78)+(B1.15), (Al-78)+(B1.16), (Al-78)+(B1.17), (Al-78)+(B1.18), (Al-78)+(B1.19), (Al-78)+(B1.20), (Al-78)+(B1.21), (Al-78)+(B1.22), (Al-78)+(B1.23), (Al-78)+(B1.24), (Al-78)+(B1.25), (Al-78)+(B1.26), (Al-78)+(B1.27), (Al-78)+(B1.28), (Al-78)+(B1.29), (Al-78)+(B1.30), (Al-78)+(B1.31), (Al-78)+(B1.32), (Al-78)+(B1.33), (Al-78)+(B1.34), (Al-78)+(B1.35), (Al-78)+(B1.36), (Al-78)+(B1.37), (Al-78)+(B1.38), (Al-78)+(B1.39), (Al-78)+(B1.40), (Al-78)+(B1.41), (Al-78)+(B1.42), (Al-78)+(B1.43), (Al-78)+(B1.44), (Al-78)+(B1.45), (Al-78)+(B1.46), (Al-78)+(B1.47), (Al-78)+(B1.48), (Al-78)+(B1.49), (Al-78)+(B1.50), (Al-78)+(B1.51), (Al-78)+(B1.52), (Al-78)+(B1.53), (Al-78)+(B1.54), (Al-78)+(B1.55), (Al-78)+(B1.56), (Al-78)+(B1.57), (Al-78)+(B1.58), (Al-78)+(B1.59), (Al-78)+(B1.60), (Al-78)+(B1.61), (Al-78)+(B1.62), (Al-78)+(B1.63), (Al-78)+(B1.64), (Al-78)+(B1.65), (Al-78)+(B1.66), (Al-78)+(B2.1), (Al-78)+(B2.2), (Al-78)+(B2.3), (Al-78)+(B2.4), (Al-78)+(B2.5), (Al-78)+(B2.6), (Al-78)+(B2.7), (Al-78)+(B2.8), (Al-78)+(B2.9), (Al-78)+(B2.10), (Al-78)+(B2.11), (Al-78)+(B2.12), (Al-78)+(B2.13), (Al-78)+(B2.14), (Al-78)+(B2.15), (Al-78)+(B2.16), (Al-78)+(B2.17), (Al-78)+(B2.18), (Al-78)+(B2.19), (Al-78)+(B2.20), (Al-78)+(B2.21), (Al-78)+(B2.22), (Al-78)+(B2.23), (Al-78)+(B2.24), (Al-78)+(B2.25), (Al-78)+(B2.26), (Al-78)+(B2.27), (Al-78)+(B2.28), (Al-78)+(B2.29), (Al-78)+(B2.30), (Al-78)+(B2.31), (Al-78)+(B2.32), (Al-78)+(B2.33), (Al-78)+(B2.34), (Al-78)+(B2.35), (Al-78)+(B2.36), (Al-78)+(B2.37), (Al-78)+(B2.38), (Al-78)+(B2.39), (Al-78)+(B2.40), (Al-78)+(B2.41), (Al-78)+(B2.42), (Al-78)+(B2.43), (Al-78)+(B2.44), (Al-78)+(B2.45), (Al-78)+(B2.46), (Al-78)+(B2.47), (Al-78)+(B2.48), (Al-78)+(B2.49), (Al-78)+(B2.50), (Al-78)+(B3.1), (Al-78)+(B3.2.), (Al-78)+(B3.3), (Al-78)+(B3.4), (Al-78)+(B3.5), (Al-78)+(B3.6), (Al-78)+(B3.7), (Al-78)+(B3.8), (Al-78)+(B3.9), (Al-78)+(B3.10), (Al-78)+(B3.11), (Al-78)+(B3.12), (Al-78)+(B3.13), (Al-78)+(B3.14), (Al-78)+(B3.15), (Al-78)+(B3.16), (Al-78)+(B4.1), (Al-78)+(B4.2), (Al-78)+(B4.3), (Al-78)+(B4.4), (Al-78)+(B4.5), (Al-78)+(B4.6), (Al-78)+(B4.7).

(Al-79)+(B1.1), (Al-79)+(B1.2), (Al-79)+(B1.3), (Al-79)+(B1.4), (Al-79)+(B1.5), (Al-79)+(B1.6), (Al-79)+(B1.7), (Al-79)+(B1.8), (Al-79)+(B1.9), (Al-79)+(B1.10), (Al-79)+(B1.11), (Al-79)+(B1.12), (Al-79)+(B1.13), (Al-79)+(B1.14), (Al-79)+(B1.15), (Al-79)+(B1.16), (Al-79)+(B1.17), (Al-79)+(B1.18), (Al-79)+(B1.19), (Al-79)+(B1.20), (Al-79)+(B1.21), (Al-79)+(B1.22), (Al-79)+(B1.23), (Al-79)+(B1.24), (Al-79)+(B1.25), (Al-79)+(B1.26), (Al-79)+(B1.27), (Al-79)+(B1.28), (Al-79)+(B1.29), (Al-79)+(B1.30), (Al-79)+(B1.31), (Al-79)+(B1.32), (Al-79)+(B1.33), (Al-79)+(B1.34), (Al-79)+(B1.35), (Al-79)+(B1.36), (Al-79)+(B1.37), (Al-79)+(B1.38), (Al-79)+(B1.39), (Al-79)+(B1.40), (Al-79)+(B1.41), (Al-79)+(B1.42), (Al-79)+(B1.43), (Al-79)+(B1.44), (Al-79)+(B1.45), (Al-79)+(B1.46), (Al-79)+(B1.47), (Al-79)+(B1.48), (Al-79)+(B1.49), (Al-79)+(B1.50), (Al-79)+(B1.51), (Al-79)+(B1.52), (Al-79)+(B1.53), (Al-79)+(B1.54), (Al-79)+(B1.55), (Al-79)+(B1.56), (Al-79)+(B1.57), (Al-79)+(B1.58), (Al-79)+(B1.59), (Al-79)+(B1.60), (Al-79)+(B1.61), (Al-79)+(B1.62), (Al-79)+(B1.63), (Al-79)+(B1.64), (Al-79)+(B1.65), (Al-79)+(B1.66), (Al-79)+(B2.1), (Al-79)+(B2.2), (Al-79)+(B2.3), (Al-79)+(B2.4), (Al-79)+(B2.5), (Al-79)+(B2.6), (Al-79)+(B2.7), (Al-79)+(B2.8), (Al-79)+(B2.9), (Al-79)+(B2.10), (Al-79)+(B2.11), (Al-79)+(B2.12), (Al-79)+(B2.13), (Al-79)+(B2.14), (Al-79)+(B2.15), (Al-79)+(B2.16), (Al-79)+(B2.17), (Al-79)+(B2.18), (Al-79)+(B2.19), (Al-79)+(B2.20), (Al-79)+(B2.21), (Al-79)+(B2.22), (Al-79)+(B2.23), (Al-79)+(B2.24), (Al-79)+(B2.25), (Al-79)+(B2.26), (Al-79)+(B2.27), (Al-79)+(B2.28), (Al-79)+(B2.29), (Al-79)+(B2.30), (Al-79)+(B2.31), (Al-79)+(B2.32), (Al-79)+(B2.33), (Al-79)+(B2.34), (Al-79)+(B2.35), (Al-79)+(B2.36), (Al-79)+(B2.37), (Al-79)+(B2.38), (Al-79)+(B2.39), (Al-79)+(B2.40), (Al-79)+(B2.41), (Al-79)+(B2.42), (Al-79)+(B2.43), (Al-79)+(B2.44), (Al-79)+(B2.45), (Al-79)+(B2.46), (Al-79)+(B2.47), (Al-79)+(B2.48), (Al-79)+(B2.49), (Al-79)+(B2.50), (Al-79)+(B3.1), (Al-79)+(B3.2.), (Al-79)+(B3.3), (Al-79)+(B3.4), (Al-79)+(B3.5), (Al-79)+(B3.6), (Al-79)+(B3.7), (Al-79)+(B3.8), (Al-79)+(B3.9), (Al-79)+(B3.10), (Al-79)+(B3.11), (Al-79)+(B3.12), (Al-79)+(B3.13), (Al-79)+(B3.14), (Al-79)+(B3.15), (Al-79)+(B3.16), (Al-79)+(B4.1), (Al-79)+(B4.2), (Al-79)+(B4.3), (Al-79)+(B4.4), (Al-79)+(B4.5), (Al-79)+(B4.6), (Al-79)+(B4.7).

(Al-80)+(B1.1), (Al-80)+(B1.2), (Al-80)+(B1.3), (Al-80)+(B1.4), (Al-80)+(B1.5), (Al-80)+(B1.6), (Al-80)+(B1.7), (Al-80)+(B1.8), (Al-80)+(B1.9), (Al-80)+(B1.10), (Al-80)+(B1.11), (Al-80)+(B1.12), (Al-80)+(B1.13), (Al-80)+(B1.14), (Al-80)+(B1.15), (Al-80)+(B1.16), (Al-80)+(B1.17), (Al-80)+(B1.18), (Al-80)+(B1.19), (Al-80)+(B1.20), (Al-80)+(B1.21), (Al-80)+(B1.22), (Al-80)+(B1.23), (Al-80)+(B1.24), (Al-80)+(B1.25), (Al-80)+(B1.26), (Al-80)+(B1.27), (Al-80)+(B1.28), (Al-80)+(B1.29), (Al-80)+(B1.30), (Al-80)+(B1.31), (Al-80)+(B1.32), (Al-80)+(B1.33), (Al-80)+(B1.34), (Al-80)+(B1.35), (Al-80)+(B1.36), (Al-80)+(B1.37), (Al-80)+(B1.38), (Al-80)+(B1.39), (Al-80)+(B1.40), (Al-80)+(B1.41), (Al-80)+(B1.42), (Al-80)+(B1.43), (Al-80)+(B1.44), (Al-80)+(B1.45), (Al-80)+(B1.46), (Al-80)+(B1.47), (Al-80)+(B1.48), (Al-80)+(B1.49), (Al-80)+(B1.50), (Al-80)+(B1.51), (Al-80)+(B1.52), (Al-80)+(B1.53), (Al-80)+(B1.54), (Al-80)+(B1.55), (Al-80)+(B1.56), (Al-80)+(B1.57), (Al-80)+(B1.58), (Al-80)+(B1.59), (Al-80)+(B1.60), (Al-80)+(B1.61), (Al-80)+(B1.62), (Al-80)+(B1.63), (Al-80)+(B1.64), (Al-80)+(B1.65), (Al-80)+(B1.66), (Al-80)+(B2.1), (Al-80)+(B2.2), (Al-80)+(B2.3), (Al-80)+(B2.4), (Al-80)+(B2.5), (Al-80)+(B2.6), (Al-80)+(B2.7), (Al-80)+(B2.8), (Al-80)+(B2.9), (Al-80)+(B2.10), (Al-80)+(B2.11), (Al-80)+(B2.12), (Al-80)+(B2.13), (Al-80)+(B2.14), (Al-80)+(B2.15), (Al-80)+(B2.16), (Al-80)+(B2.17), (Al-80)+(B2.18), (Al-80)+(B2.19), (Al-80)+(B2.20), (Al-80)+(B2.21), (Al-80)+(B2.22), (Al-80)+(B2.23), (Al-80)+(B2.24), (Al-80)+(B2.25), (Al-80)+(B2.26), (Al-80)+(B2.27), (Al-80)+(B2.28), (Al-80)+(B2.29), (Al-80)+(B2.30), (Al-80)+(B2.31), (Al-80)+(B2.32), (Al-80)+(B2.33), (Al-80)+(B2.34), (Al-80)+(B2.35), (Al-80)+(B2.36), (Al-80)+(B2.37), (Al-80)+(B2.38), (Al-80)+(B2.39), (Al-80)+(B2.40), (Al-80)+(B2.41), (Al-80)+(B2.42), (Al-80)+(B2.43), (Al-80)+(B2.44), (Al-80)+(B2.45), (Al-80)+(B2.46), (Al-80)+(B2.47), (Al-80)+(B2.48), (Al-80)+(B2.49), (Al-80)+(B2.50), (Al-80)+(B3.1), (Al-80)+(B3.2.), (Al-80)+(B3.3), (Al-80)+(B3.4), (Al-80)+(B3.5), (Al-80)+(B3.6), (Al-80)+(B3.7), (Al-80)+(B3.8), (Al-80)+(B3.9), (Al-80)+(B3.10), (Al-80)+(B3.11), (Al-80)+(B3.12), (Al-80)+(B3.13), (Al-80)+(B3.14), (Al-80)+(B3.15), (Al-80)+(B3.16), (Al-80)+(B4.1), (Al-80)+(B4.2), (Al-80)+(B4.3), (Al-80)+(B4.4), (Al-80)+(B4.5), (Al-80)+(B4.6), (Al-80)+(B4.7).

(Al-81)+(B1.1), (Al-81)+(B1.2), (Al-81)+(B1.3), (Al-81)+(B1.4), (Al-81)+(B1.5), (Al-81)+(B1.6), (Al-81)+(B1.7), (Al-81)+(B1.8), (Al-81)+(B1.9), (Al-81)+(B1.10), (Al-81)+(B1.11), (Al-81)+(B1.12), (Al-81)+(B1.13), (Al-81)+(B1.14), (Al-81)+(B1.15), (Al-81)+(B1.16), (Al-81)+(B1.17), (Al-81)+(B1.18), (Al-81)+(B1.19), (Al-81)+(B1.20), (Al-81)+(B1.21), (Al-81)+(B1.22), (Al-81)+(B1.23), (Al-81)+(B1.24), (Al-81)+(B1.25), (Al-81)+(B1.26), (Al-81)+(B1.27), (Al-81)+(B1.28), (Al-81)+(B1.29), (Al-81)+(B1.30), (Al-81)+(B1.31), (Al-81)+(B1.32), (Al-81)+(B1.33), (Al-81)+(B1.34), (Al-81)+(B1.35), (Al-81)+(B1.36), (Al-81)+(B1.37), (Al-81)+(B1.38), (Al-81)+(B1.39), (Al-81)+(B1.40), (Al-81)+(B1.41), (Al-81)+(B1.42), (Al-81)+(B1.43), (Al-81)+(B1.44), (Al-81)+(B1.45), (Al-81)+(B1.46), (Al-81)+(B1.47), (Al-81)+(B1.48), (Al-81)+(B1.49), (Al-81)+(B1.50), (Al-81)+(B1.51), (Al-81)+(B1.52), (Al-81)+(B1.53), (Al-81)+(B1.54), (Al-81)+(B1.55), (Al-81)+(B1.56), (Al-81)+(B1.57), (Al-81)+(B1.58), (Al-81)+(B1.59), (Al-81)+(B1.60), (Al-81)+(B1.61), (Al-81)+(B1.62), (Al-81)+(B1.63), (Al-81)+(B1.64), (Al-81)+(B1.65), (Al-81)+(B1.66), (Al-81)+(B2.1), (Al-81)+(B2.2), (Al-81)+(B2.3), (Al-81)+(B2.4), (Al-81)+(B2.5), (Al-81)+(B2.6), (Al-81)+(B2.7), (Al-81)+(B2.8), (Al-81)+(B2.9), (Al-81)+(B2.10), (Al-81)+(B2.11), (Al-81)+(B2.12), (Al-81)+(B2.13), (Al-81)+(B2.14), (Al-81)+(B2.15), (Al-81)+(B2.16), (Al-81)+(B2.17), (Al-81)+(B2.18), (Al-81)+(B2.19), (Al-81)+(B2.20), (Al-81)+(B2.21), (Al-81)+(B2.22), (Al-81)+(B2.23), (Al-81)+(B2.24), (Al-81)+(B2.25), (Al-81)+(B2.26), (Al-81)+(B2.27), (Al-81)+(B2.28), (Al-81)+(B2.29), (Al-81)+(B2.30), (Al-81)+(B2.31), (Al-81)+(B2.32), (Al-81)+(B2.33), (Al-81)+(B2.34), (Al-81)+(B2.35), (Al-81)+(B2.36), (Al-81)+(B2.37), (Al-81)+(B2.38), (Al-81)+(B2.39), (Al-81)+(B2.40), (Al-81)+(B2.41), (Al-81)+(B2.42), (Al-81)+(B2.43), (Al-81)+(B2.44), (Al-81)+(B2.45), (Al-81)+(B2.46), (Al-81)+(B2.47), (Al-81)+(B2.48), (Al-81)+(B2.49), (Al-81)+(B2.50), (Al-81)+(B3.1), (Al-81)+(B3.2.), (Al-81)+(B3.3), (Al-81)+(B3.4), (Al-81)+(B3.5), (Al-81)+

(B3.6), (Al-81)+(B3.7), (Al-81)+(B3.8), (Al-81)+(B3.9), (Al-81)+(B3.10), (Al-81)+(B3.11), (Al-81)+(B3.12), (Al-81)+(B3.13), (Al-81)+(B3.14), (Al-81)+(B3.15), (Al-81)+(B3.16), (Al-81)+(B4.1), (Al-81)+(B4.2), (Al-81)+(B4.3), (Al-81)+(B4.4), (Al-81)+(B4.5), (Al-81)+(B4.6), (Al-81)+(B4.7).

(Al-82)+(B1.1), (Al-82)+(B1.2), (Al-82)+(B1.3), (Al-82)+(B1.4), (Al-82)+(B1.5), (Al-82)+(B1.6), (Al-82)+(B1.7), (Al-82)+(B1.8), (Al-82)+(B1.9), (Al-82)+(B1.10), (Al-82)+(B1.11), (Al-82)+(B1.12), (Al-82)+(B1.13), (Al-82)+(B1.14), (Al-82)+(B1.15), (Al-82)+(B1.16), (Al-82)+(B1.17), (Al-82)+(B1.18), (Al-82)+(B1.19), (Al-82)+(B1.20), (Al-82)+(B1.21), (Al-82)+(B1.22), (Al-82)+(B1.23), (Al-82)+(B1.24), (Al-82)+(B1.25), (Al-82)+(B1.26), (Al-82)+(B1.27), (Al-82)+(B1.28), (Al-82)+(B1.29), (Al-82)+(B1.30), (Al-82)+(B1.31), (Al-82)+(B1.32), (Al-82)+(B1.33), (Al-82)+(B1.34), (Al-82)+(B1.35), (Al-82)+(B1.36), (Al-82)+(B1.37), (Al-82)+(B1.38), (Al-82)+(B1.39), (Al-82)+(B1.40), (Al-82)+(B1.41), (Al-82)+(B1.42), (Al-82)+(B1.43), (Al-82)+(B1.44), (Al-82)+(B1.45), (Al-82)+(B1.46), (Al-82)+(B1.47), (Al-82)+(B1.48), (Al-82)+(B1.49), (Al-82)+(B1.50), (Al-82)+(B1.51), (Al-82)+(B1.52), (Al-82)+(B1.53), (Al-82)+(B1.54), (Al-82)+(B1.55), (Al-82)+(B1.56), (Al-82)+(B1.57), (Al-82)+(B1.58), (Al-82)+(B1.59), (Al-82)+(B1.60), (Al-82)+(B1.61), (Al-82)+(B1.62), (Al-82)+(B1.63), (Al-82)+(B1.64), (Al-82)+(B1.65), (Al-82)+(B1.66), (Al-82)+(B2.1), (Al-82)+(B2.2), (Al-82)+(B2.3), (Al-82)+(B2.4), (Al-82)+(B2.5), (Al-82)+(B2.6), (Al-82)+(B2.7), (Al-82)+(B2.8), (Al-82)+(B2.9), (Al-82)+(B2.10), (Al-82)+(B2.11), (Al-82)+(B2.12), (Al-82)+(B2.13), (Al-82)+(B2.14), (Al-82)+(B2.15), (Al-82)+(B2.16), (Al-82)+(B2.17), (Al-82)+(B2.18), (Al-82)+(B2.19), (Al-82)+(B2.20), (Al-82)+(B2.21), (Al-82)+(B2.22), (Al-82)+(B2.23), (Al-82)+(B2.24), (Al-82)+(B2.25), (Al-82)+(B2.26), (Al-82)+(B2.27), (Al-82)+(B2.28), (Al-82)+(B2.29), (Al-82)+(B2.30), (Al-82)+(B2.31), (Al-82)+(B2.32), (Al-82)+(B2.33), (Al-82)+(B2.34), (Al-82)+(B2.35), (Al-82)+(B2.36), (Al-82)+(B2.37), (Al-82)+(B2.38), (Al-82)+(B2.39), (Al-82)+(B2.40), (Al-82)+(B2.41), (Al-82)+(B2.42), (Al-82)+(B2.43), (Al-82)+(B2.44), (Al-82)+(B2.45), (Al-82)+(B2.46), (Al-82)+(B2.47), (Al-82)+(B2.48), (Al-82)+(B2.49), (Al-82)+(B2.50), (Al-82)+(B3.1), (Al-82)+(B3.2.), (Al-82)+(B3.3), (Al-82)+(B3.4), (Al-82)+(B3.5), (Al-82)+(B3.6), (Al-82)+(B3.7), (Al-82)+(B3.8), (Al-82)+(B3.9), (Al-82)+(B3.10), (Al-82)+(B3.11), (Al-82)+(B3.12), (Al-82)+(B3.13), (Al-82)+(B3.14), (Al-82)+(B3.15), (Al-82)+(B3.16), (Al-82)+(B4.1), (Al-82)+(B4.2), (Al-82)+(B4.3), (Al-82)+(B4.4), (Al-82)+(B4.5), (Al-82)+(B4.6), (Al-82)+(B4.7).

(Al-83)+(B1.1), (Al-83)+(B1.2), (Al-83)+(B1.3), (Al-83)+(B1.4), (Al-83)+(B1.5), (Al-83)+(B1.6), (Al-83)+(B1.7), (Al-83)+(B1.8), (Al-83)+(B1.9), (Al-83)+(B1.10), (Al-83)+(B1.11), (Al-83)+(B1.12), (Al-83)+(B1.13), (Al-83)+(B1.14), (Al-83)+(B1.15), (Al-83)+(B1.16), (Al-83)+(B1.17), (Al-83)+(B1.18), (Al-83)+(B1.19), (Al-83)+(B1.20), (Al-83)+(B1.21), (Al-83)+(B1.22), (Al-83)+(B1.23), (Al-83)+(B1.24), (Al-83)+(B1.25), (Al-83)+(B1.26), (Al-83)+(B1.27), (Al-83)+(B1.28), (Al-83)+(B1.29), (Al-83)+(B1.30), (Al-83)+(B1.31), (Al-83)+(B1.32), (Al-83)+(B1.33), (Al-83)+(B1.34), (Al-83)+(B1.35), (Al-83)+(B1.36), (Al-83)+(B1.37), (Al-83)+(B1.38), (Al-83)+(B1.39), (Al-83)+(B1.40), (Al-83)+(B1.41), (Al-83)+(B1.42), (Al-83)+(B1.43), (Al-83)+(B1.44), (Al-83)+(B1.45), (Al-83)+(B1.46), (Al-83)+(B1.47), (Al-83)+(B1.48), (Al-83)+(B1.49), (Al-83)+(B1.50), (Al-83)+(B1.51), (Al-83)+(B1.52), (Al-83)+(B1.53), (Al-83)+(B1.54), (Al-83)+(B1.55), (Al-83)+(B1.56), (Al-83)+(B1.57), (Al-83)+(B1.58), (Al-83)+(B1.59), (Al-83)+(B1.60), (Al-83)+(B1.61), (Al-83)+(B1.62), (Al-83)+(B1.63), (Al-83)+(B1.64), (Al-83)+(B1.65), (Al-83)+(B1.66), (Al-83)+(B2.1), (Al-83)+(B2.2), (Al-83)+(B2.3), (Al-83)+(B2.4), (Al-83)+(B2.5), (Al-83)+(B2.6), (Al-83)+(B2.7), (Al-83)+(B2.8), (Al-83)+(B2.9), (Al-83)+(B2.10), (Al-83)+(B2.11), (Al-83)+(B2.12), (Al-83)+(B2.13), (Al-83)+(B2.14), (Al-83)+(B2.15), (Al-83)+(B2.16), (Al-83)+(B2.17), (Al-83)+(B2.18), (Al-83)+(B2.19), (Al-83)+(B2.20), (Al-83)+(B2.21), (Al-83)+(B2.22), (Al-83)+(B2.23), (Al-83)+(B2.24), (Al-83)+(B2.25), (Al-83)+(B2.26), (Al-83)+(B2.27), (Al-83)+(B2.28), (Al-83)+(B2.29), (Al-83)+(B2.30), (Al-83)+(B2.31), (Al-83)+(B2.32), (Al-83)+(B2.33), (Al-83)+(B2.34), (Al-83)+(B2.35), (Al-83)+(B2.36), (Al-83)+(B2.37), (Al-83)+(B2.38), (Al-83)+(B2.39), (Al-83)+(B2.40), (Al-83)+(B2.41), (Al-83)+(B2.42), (Al-83)+(B2.43), (Al-83)+(B2.44), (Al-83)+(B2.45), (Al-83)+(B2.46), (Al-83)+(B2.47), (Al-83)+(B2.48), (Al-83)+(B2.49), (Al-83)+(B2.50), (Al-83)+(B3.1), (Al-83)+(B3.2.), (Al-83)+(B3.3), (Al-83)+(B3.4), (Al-83)+(B3.5), (Al-83)+(B3.6), (Al-83)+(B3.7), (Al-83)+(B3.8), (Al-83)+(B3.9), (Al-83)+(B3.10), (Al-83)+(B3.11), (Al-83)+(B3.12), (Al-83)+(B3.13), (Al-83)+(B3.14), (Al-83)+(B3.15), (Al-83)+(B3.16), (Al-83)+(B4.1), (Al-83)+(B4.2), (Al-83)+(B4.3), (Al-83)+(B4.4), (Al-83)+(B4.5), (Al-83)+(B4.6), (Al-83)+(B4.7).

(Al-84)+(B1.1), (Al-84)+(B1.2), (Al-84)+(B1.3), (Al-84)+(B1.4), (Al-84)+(B1.5), (Al-84)+(B1.6), (Al-84)+(B1.7), (Al-84)+(B1.8), (Al-84)+(B1.9), (Al-84)+(B1.10), (Al-84)+(B1.11), (Al-84)+(B1.12), (Al-84)+(B1.13), (Al-84)+(B1.14), (Al-84)+(B1.15), (Al-84)+(B1.16), (Al-84)+(B1.17), (Al-84)+(B1.18), (Al-84)+(B1.19), (Al-84)+(B1.20), (Al-84)+(B1.21), (Al-84)+(B1.22), (Al-84)+(B1.23), (Al-84)+(B1.24), (Al-84)+(B1.25), (Al-84)+(B1.26), (Al-84)+(B1.27), (Al-84)+(B1.28), (Al-84)+(B1.29), (Al-84)+(B1.30), (Al-84)+(B1.31), (Al-84)+(B1.32), (Al-84)+(B1.33), (Al-84)+(B1.34), (Al-84)+(B1.35), (Al-84)+(B1.36), (Al-84)+(B1.37), (Al-84)+(B1.38), (Al-84)+(B1.39), (Al-84)+(B1.40), (Al-84)+(B1.41), (Al-84)+(B1.42), (Al-84)+(B1.43), (Al-84)+(B1.44), (Al-84)+(B1.45), (Al-84)+(B1.46), (Al-84)+(B1.47), (Al-84)+(B1.48), (Al-84)+(B1.49), (Al-84)+(B1.50), (Al-84)+(B1.51), (Al-84)+(B1.52), (Al-84)+(B1.53), (Al-84)+(B1.54), (Al-84)+(B1.55), (Al-84)+(B1.56), (Al-84)+(B1.57), (Al-84)+(B1.58), (Al-84)+(B1.59), (Al-84)+(B1.60), (Al-84)+(B1.61), (Al-84)+(B1.62), (Al-84)+(B1.63), (Al-84)+(B1.64), (Al-84)+(B1.65), (Al-84)+(B1.66), (Al-84)+(B2.1), (Al-84)+(B2.2), (Al-84)+(B2.3), (Al-84)+(B2.4), (Al-84)+(B2.5), (Al-84)+(B2.6), (Al-84)+(B2.7), (Al-84)+(B2.8), (Al-84)+(B2.9), (Al-84)+(B2.10), (Al-84)+(B2.11), (Al-84)+(B2.12), (Al-84)+(B2.13), (Al-84)+(B2.14), (Al-84)+(B2.15), (Al-84)+(B2.16), (Al-84)+(B2.17), (Al-84)+(B2.18), (Al-84)+(B2.19), (Al-84)+(B2.20), (Al-84)+(B2.21), (Al-84)+(B2.22), (Al-84)+(B2.23), (Al-84)+(B2.24), (Al-84)+(B2.25), (Al-84)+(B2.26), (Al-84)+(B2.27), (Al-84)+(B2.28), (Al-84)+(B2.29), (Al-84)+(B2.30), (Al-84)+(B2.31), (Al-84)+(B2.32), (Al-84)+(B2.33), (Al-84)+(B2.34), (Al-84)+(B2.35), (Al-84)+(B2.36), (Al-84)+(B2.37), (Al-84)+(B2.38), (Al-84)+(B2.39), (Al-84)+(B2.40), (Al-84)+(B2.41), (Al-84)+(B2.42), (Al-84)+(B2.43), (Al-84)+(B2.44), (Al-84)+(B2.45), (Al-84)+(B2.46), (Al-84)+(B2.47), (Al-84)+(B2.48), (Al-84)+(B2.49), (Al-84)+(B2.50), (Al-84)+(B3.1), (Al-84)+(B3.2.), (Al-84)+(B3.3), (Al-84)+(B3.4), (Al-84)+(B3.5), (Al-84)+(B3.6), (Al-84)+(B3.7), (Al-84)+(B3.8), (Al-84)+(B3.9), (Al-84)+(B3.10), (Al-84)+(B3.11), (Al-84)+(B3.12), (Al-84)+(B3.13), (Al-84)+(B3.14), (Al-84)+(B3.15), (Al-84)+(B3.16), (Al-84)+(B4.1), (Al-84)+(B4.2), (Al-84)+(B4.3), (Al-84)+(B4.4), (Al-84)+(B4.5), (Al-84)+(B4.6), (Al-84)+(B4.7).

(Al-85)+(B1.1), (Al-85)+(B1.2), (Al-85)+(B1.3), (Al-85)+(B1.4), (Al-85)+(B1.5), (Al-85)+(B1.6), (Al-85)+(B1.7), (Al-85)+(B1.8), (Al-85)+(B1.9), (Al-85)+(B1.10), (Al-85)+(B1.11), (Al-85)+(B1.12), (Al-85)+(B1.13), (Al-85)+(B1.14), (Al-85)+(B1.15), (Al-85)+(B1.16), (Al-85)+(B1.17), (Al-85)+(B1.18), (Al-85)+(B1.19), (Al-85)+(B1.20), (Al-85)+(B1.21), (Al-85)+(B1.22), (Al-85)+(B1.23), (Al-85)+(B1.24), (Al-85)+(B1.25), (Al-85)+(B1.26), (Al-85)+(B1.27), (Al-85)+(B1.28), (Al-85)+(B1.29), (Al-85)+(B1.30), (Al-85)+(B1.31), (Al-85)+(B1.32), (Al-85)+(B1.33), (Al-85)+(B1.34), (Al-85)+(B1.35), (Al-85)+(B1.36), (Al-85)+(B1.37), (Al-85)+(B1.38), (Al-85)+(B1.39), (Al-85)+(B1.40), (Al-85)+(B1.41), (Al-85)+(B1.42), (Al-85)+(B1.43), (Al-85)+(B1.44), (Al-85)+(B1.45), (Al-85)+(B1.46), (Al-85)+(B1.47), (Al-85)+(B1.48), (Al-85)+(B1.49), (Al-85)+(B1.50), (Al-85)+(B1.51), (Al-85)+(B1.52), (Al-85)+(B1.53), (Al-85)+(B1.54), (Al-85)+(B1.55), (Al-85)+(B1.56), (Al-85)+(B1.57), (Al-85)+(B1.58), (Al-85)+(B1.59), (Al-85)+(B1.60), (Al-85)+(B1.61), (Al-85)+(B1.62), (Al-85)+(B1.63), (Al-85)+(B1.64), (Al-85)+(B1.65), (Al-85)+(B1.66), (Al-85)+(B2.1), (Al-85)+(B2.2), (Al-85)+(B2.3), (Al-85)+(B2.4), (Al-85)+(B2.5), (Al-85)+(B2.6), (Al-85)+(B2.7), (Al-85)+(B2.8), (Al-85)+(B2.9), (Al-85)+(B2.10), (Al-85)+(B2.11), (Al-85)+(B2.12), (Al-85)+(B2.13), (Al-85)+(B2.14), (Al-85)+(B2.15), (Al-85)+(B2.16), (Al-85)+(B2.17), (Al-85)+(B2.18), (Al-85)+(B2.19), (Al-85)+(B2.20), (Al-85)+(B2.21), (Al-85)+(B2.22), (Al-85)+(B2.23), (Al-85)+(B2.24), (Al-85)+(B2.25), (Al-85)+(B2.26), (Al-85)+(B2.27), (Al-85)+(B2.28), (Al-85)+(B2.29), (Al-85)+(B2.30), (Al-85)+(B2.31), (Al-85)+(B2.32), (Al-85)+(B2.33), (Al-85)+(B2.34), (Al-85)+(B2.35), (Al-85)+(B2.36), (Al-85)+(B2.37), (Al-85)+(B2.38), (Al-85)+(B2.39), (Al-85)+(B2.40), (Al-85)+(B2.41), (Al-85)+(B2.42), (Al-85)+(B2.43), (Al-85)+(B2.44), (Al-85)+(B2.45), (Al-85)+(B2.46), (Al-85)+(B2.47), (Al-85)+(B2.48), (Al-85)+(B2.49), (Al-85)+(B2.50), (Al-85)+(B3.1), (Al-85)+(B3.2.), (Al-85)+(B3.3), (Al-85)+(B3.4), (Al-85)+(B3.5), (Al-85)+(B3.6), (Al-85)+(B3.7), (Al-85)+(B3.8), (Al-85)+(B3.9), (Al-85)+(B3.10), (Al-85)+(B3.11), (Al-85)+(B3.12), (Al-85)+(B3.13), (Al-85)+(B3.14), (Al-85)+(B3.15), (Al-85)+(B3.16), (Al-85)+(B4.1), (Al-85)+(B4.2), (Al-85)+(B4.3), (Al-85)+(B4.4), (Al-85)+(B4.5), (Al-85)+(B4.6), (Al-85)+(B4.7).

(Al-86)+(B1.1), (Al-86)+(B1.2), (Al-86)+(B1.3), (Al-86)+(B1.4), (Al-86)+(B1.5), (Al-86)+(B1.6), (Al-86)+(B1.7), (Al-86)+(B1.8), (Al-86)+(B1.9), (Al-86)+(B1.10), (Al-86)+(B1.11), (Al-86)+(B1.12), (Al-86)+(B1.13), (Al-86)+(B1.14), (Al-86)+(B1.15), (Al-86)+(B1.16), (Al-86)+(B1.17), (Al-86)+(B1.18), (Al-86)+(B1.19), (Al-86)+(B1.20), (Al-86)+(B1.21), (Al-86)+(B1.22), (Al-86)+(B1.23), (Al-86)+(B1.24), (Al-86)+(B1.25), (Al-86)+(B1.26), (Al-86)+(B1.27), (Al-86)+(B1.28), (Al-86)+(B1.29), (Al-86)+(B1.30), (Al-86)+(B1.31), (Al-86)+(B1.32), (Al-86)+(B1.33), (Al-86)+(B1.34), (Al-86)+(B1.35), (Al-86)+(B1.36), (Al-86)+(B1.37), (Al-86)+(B1.38), (Al-86)+(B1.39), (Al-86)+(B1.40), (Al-86)+(B1.41), (Al-86)+(B1.42), (Al-86)+(B1.43), (Al-86)+(B1.44), (Al-86)+(B1.45), (Al-86)+(B1.46), (Al-86)+(B1.47), (Al-86)+(B1.48), (Al-86)+(B1.49), (Al-86)+(B1.50), (Al-86)+(B1.51), (Al-86)+(B1.52), (Al-86)+(B1.53), (Al-86)+(B1.54), (Al-86)+(B1.55), (Al-86)+(B1.56), (Al-86)+(B1.57), (Al-86)+(B1.58), (Al-86)+(B1.59), (Al-86)+(B1.60), (Al-86)+(B1.61), (Al-86)+(B1.62), (Al-86)+(B1.63), (Al-86)+(B1.64), (Al-86)+(B1.65), (Al-86)+(B1.66), (Al-86)+(B2.1), (Al-86)+(B2.2), (Al-86)+(B2.3), (Al-86)+(B2.4), (Al-86)+(B2.5), (Al-86)+(B2.6), (Al-86)+(B2.7), (Al-86)+(B2.8), (Al-86)+(B2.9), (Al-86)+(B2.10), (Al-86)+(B2.11), (Al-86)+(B2.12), (Al-86)+(B2.13), (Al-86)+(B2.14), (Al-86)+(B2.15), (Al-86)+(B2.16), (Al-86)+(B2.17), (Al-86)+(B2.18), (Al-86)+(B2.19), (Al-86)+(B2.20), (Al-86)+(B2.21), (Al-86)+(B2.22), (Al-86)+(B2.23), (Al-86)+(B2.24), (Al-86)+(B2.25), (Al-86)+(B2.26), (Al-86)+(B2.27), (Al-86)+(B2.28), (Al-86)+(B2.29), (Al-86)+(B2.30), (Al-86)+(B2.31), (Al-86)+(B2.32), (Al-86)+(B2.33), (Al-86)+(B2.34), (Al-86)+(B2.35), (Al-86)+(B2.36), (Al-86)+(B2.37), (Al-86)+(B2.38), (Al-86)+(B2.39), (Al-86)+(B2.40), (Al-86)+(B2.41), (Al-86)+(B2.42), (Al-86)+(B2.43), (Al-86)+(B2.44), (Al-86)+(B2.45), (Al-86)+(B2.46), (Al-86)+(B2.47), (Al-86)+(B2.48), (Al-86)+(B2.49), (Al-86)+(B2.50), (Al-86)+(B3.1), (Al-86)+(B3.2.), (Al-86)+(B3.3), (Al-86)+(B3.4), (Al-86)+(B3.5), (Al-86)+(B3.6), (Al-86)+(B3.7), (Al-86)+(B3.8), (Al-86)+(B3.9), (Al-86)+(B3.10), (Al-86)+(B3.11), (Al-86)+(B3.12), (Al-86)+(B3.13), (Al-86)+(B3.14), (Al-86)+(B3.15), (Al-86)+(B3.16), (Al-86)+(B4.1), (Al-86)+(B4.2), (Al-86)+(B4.3), (Al-86)+(B4.4), (Al-86)+(B4.5), (Al-86)+(B4.6), (Al-86)+(B4.7).

(Al-87)+(B1.1), (Al-87)+(B1.2), (Al-87)+(B1.3), (Al-87)+(B1.4), (Al-87)+(B1.5), (Al-87)+(B1.6), (Al-87)+(B1.7), (Al-87)+(B1.8), (Al-87)+(B1.9), (Al-87)+(B1.10), (Al-87)+(B1.11), (Al-87)+(B1.12), (Al-87)+(B1.13), (Al-87)+(B1.14), (Al-87)+(B1.15), (Al-87)+(B1.16), (Al-87)+(B1.17), (Al-87)+(B1.18), (Al-87)+(B1.19), (Al-87)+(B1.20), (Al-87)+(B1.21), (Al-87)+(B1.22), (Al-87)+(B1.23), (Al-87)+(B1.24), (Al-87)+(B1.25), (Al-87)+(B1.26), (Al-87)+(B1.27), (Al-87)+(B1.28), (Al-87)+(B1.29), (Al-87)+(B1.30), (Al-87)+(B1.31), (Al-87)+(B1.32), (Al-87)+(B1.33), (Al-87)+(B1.34), (Al-87)+(B1.35), (Al-87)+(B1.36), (Al-87)+(B1.37), (Al-87)+(B1.38), (Al-87)+(B1.39), (Al-87)+(B1.40), (Al-87)+(B1.41), (Al-87)+(B1.42), (Al-87)+(B1.43), (Al-87)+(B1.44), (Al-87)+(B1.45), (Al-87)+(B1.46), (Al-87)+(B1.47), (Al-87)+(B1.48), (Al-87)+(B1.49), (Al-87)+(B1.50), (Al-87)+(B1.51), (Al-87)+(B1.52), (Al-87)+(B1.53), (Al-87)+(B1.54), (Al-87)+(B1.55), (Al-87)+(B1.56), (Al-87)+(B1.57), (Al-87)+(B1.58), (Al-87)+(B1.59), (Al-87)+(B1.60), (Al-87)+(B1.61), (Al-87)+(B1.62), (Al-87)+(B1.63), (Al-87)+(B1.64), (Al-87)+(B1.65), (Al-87)+(B1.66), (Al-87)+(B2.1), (Al-87)+(B2.2), (Al-87)+(B2.3), (Al-87)+(B2.4), (Al-87)+(B2.5), (Al-87)+(B2.6), (Al-87)+(B2.7), (Al-87)+(B2.8), (Al-87)+(B2.9), (Al-87)+(B2.10), (Al-87)+(B2.11), (Al-87)+(B2.12), (Al-87)+(B2.13), (Al-87)+(B2.14), (Al-87)+(B2.15), (Al-87)+(B2.16), (Al-87)+(B2.17), (Al-87)+(B2.18), (Al-87)+(B2.19), (Al-87)+(B2.20), (Al-87)+(B2.21), (Al-87)+(B2.22), (Al-87)+(B2.23), (Al-87)+(B2.24), (Al-87)+(B2.25), (Al-87)+(B2.26), (Al-87)+(B2.27), (Al-87)+(B2.28), (Al-87)+(B2.29), (Al-87)+(B2.30), (Al-87)+(B2.31), (Al-87)+(B2.32), (Al-87)+(B2.33), (Al-87)+(B2.34), (Al-87)+(B2.35), (Al-87)+(B2.36), (Al-87)+(B2.37), (Al-87)+(B2.38), (Al-87)+(B2.39), (Al-87)+(B2.40), (Al-87)+(B2.41), (Al-87)+(B2.42), (Al-87)+(B2.43), (Al-87)+(B2.44), (Al-87)+(B2.45), (Al-87)+(B2.46), (Al-87)+(B2.47), (Al-87)+(B2.48), (Al-87)+

(B2.49), (Al-87)+(B2.50), (Al-87)+(B3.1), (Al-87)+(B3.2.), (Al-87)+(B3.3), (Al-87)+(B3.4), (Al-87)+(B3.5), (Al-87)+(B3.6), (Al-87)+(B3.7), (Al-87)+(B3.8), (Al-87)+(B3.9), (Al-87)+(B3.10), (Al-87)+(B3.11), (Al-87)+(B3.12), (Al-87)+(B3.13), (Al-87)+(B3.14), (Al-87)+(B3.15), (Al-87)+(B3.16), (Al-87)+(B4.1), (Al-87)+(B4.2), (Al-87)+(B4.3), (Al-87)+(B4.4), (Al-87)+(B4.5), (Al-87)+(B4.6), (Al-87)+(B4.7).

(Al-88)+(B1.1), (Al-88)+(B1.2), (Al-88)+(B1.3), (Al-88)+(B1.4), (Al-88)+(B1.5), (Al-88)+(B1.6), (Al-88)+(B1.7), (Al-88)+(B1.8), (Al-88)+(B1.9), (Al-88)+(B1.10), (Al-88)+(B1.11), (Al-88)+(B1.12), (Al-88)+(B1.13), (Al-88)+(B1.14), (Al-88)+(B1.15), (Al-88)+(B1.16), (Al-88)+(B1.17), (Al-88)+(B1.18), (Al-88)+(B1.19), (Al-88)+(B1.20), (Al-88)+(B1.21), (Al-88)+(B1.22), (Al-88)+(B1.23), (Al-88)+(B1.24), (Al-88)+(B1.25), (Al-88)+(B1.26), (Al-88)+(B1.27), (Al-88)+(B1.28), (Al-88)+(B1.29), (Al-88)+(B1.30), (Al-88)+(B1.31), (Al-88)+(B1.32), (Al-88)+(B1.33), (Al-88)+(B1.34), (Al-88)+(B1.35), (Al-88)+(B1.36), (Al-88)+(B1.37), (Al-88)+(B1.38), (Al-88)+(B1.39), (Al-88)+(B1.40), (Al-88)+(B1.41), (Al-88)+(B1.42), (Al-88)+(B1.43), (Al-88)+(B1.44), (Al-88)+(B1.45), (Al-88)+(B1.46), (Al-88)+(B1.47), (Al-88)+(B1.48), (Al-88)+(B1.49), (Al-88)+(B1.50), (Al-88)+(B1.51), (Al-88)+(B1.52), (Al-88)+(B1.53), (Al-88)+(B1.54), (Al-88)+(B1.55), (Al-88)+(B1.56), (Al-88)+(B1.57), (Al-88)+(B1.58), (Al-88)+(B1.59), (Al-88)+(B1.60), (Al-88)+(B1.61), (Al-88)+(B1.62), (Al-88)+(B1.63), (Al-88)+(B1.64), (Al-88)+(B1.65), (Al-88)+(B1.66), (Al-88)+(B2.1), (Al-88)+(B2.2), (Al-88)+(B2.3), (Al-88)+(B2.4), (Al-88)+(B2.5), (Al-88)+(B2.6), (Al-88)+(B2.7), (Al-88)+(B2.8), (Al-88)+(B2.9), (Al-88)+(B2.10), (Al-88)+(B2.11), (Al-88)+(B2.12), (Al-88)+(B2.13), (Al-88)+(B2.14), (Al-88)+(B2.15), (Al-88)+(B2.16), (Al-88)+(B2.17), (Al-88)+(B2.18), (Al-88)+(B2.19), (Al-88)+(B2.20), (Al-88)+(B2.21), (Al-88)+(B2.22), (Al-88)+(B2.23), (Al-88)+(B2.24), (Al-88)+(B2.25), (Al-88)+(B2.26), (Al-88)+(B2.27), (Al-88)+(B2.28), (Al-88)+(B2.29), (Al-88)+(B2.30), (Al-88)+(B2.31), (Al-88)+(B2.32), (Al-88)+(B2.33), (Al-88)+(B2.34), (Al-88)+(B2.35), (Al-88)+(B2.36), (Al-88)+(B2.37), (Al-88)+(B2.38), (Al-88)+(B2.39), (Al-88)+(B2.40), (Al-88)+(B2.41), (Al-88)+(B2.42), (Al-88)+(B2.43), (Al-88)+(B2.44), (Al-88)+(B2.45), (Al-88)+(B2.46), (Al-88)+(B2.47), (Al-88)+(B2.48), (Al-88)+(B2.49), (Al-88)+(B2.50), (Al-88)+(B3.1), (Al-88)+(B3.2.), (Al-88)+(B3.3), (Al-88)+(B3.4), (Al-88)+(B3.5), (Al-88)+(B3.6), (Al-88)+(B3.7), (Al-88)+(B3.8), (Al-88)+(B3.9), (Al-88)+(B3.10), (Al-88)+(B3.11), (Al-88)+(B3.12), (Al-88)+(B3.13), (Al-88)+(B3.14), (Al-88)+(B3.15), (Al-88)+(B3.16), (Al-88)+(B4.1), (Al-88)+(B4.2), (Al-88)+(B4.3), (Al-88)+(B4.4), (Al-88)+(B4.5), (Al-88)+(B4.6), (Al-88)+(B4.7).

(Al-89)+(B1.1), (Al-89)+(B1.2), (Al-89)+(B1.3), (Al-89)+(B1.4), (Al-89)+(B1.5), (Al-89)+(B1.6), (Al-89)+(B1.7), (Al-89)+(B1.8), (Al-89)+(B1.9), (Al-89)+(B1.10), (Al-89)+(B1.11), (Al-89)+(B1.12), (Al-89)+(B1.13), (Al-89)+(B1.14), (Al-89)+(B1.15), (Al-89)+(B1.16), (Al-89)+(B1.17), (Al-89)+(B1.18), (Al-89)+(B1.19), (Al-89)+(B1.20), (Al-89)+(B1.21), (Al-89)+(B1.22), (Al-89)+(B1.23), (Al-89)+(B1.24), (Al-89)+(B1.25), (Al-89)+(B1.26), (Al-89)+(B1.27), (Al-89)+(B1.28), (Al-89)+(B1.29), (Al-89)+(B1.30), (Al-89)+(B1.31), (Al-89)+(B1.32), (Al-89)+(B1.33), (Al-89)+(B1.34), (Al-89)+(B1.35), (Al-89)+(B1.36), (Al-89)+(B1.37), (Al-89)+(B1.38), (Al-89)+(B1.39), (Al-89)+(B1.40), (Al-89)+(B1.41), (Al-89)+(B1.42), (Al-89)+(B1.43), (Al-89)+(B1.44), (Al-89)+(B1.45), (Al-89)+(B1.46), (Al-89)+(B1.47), (Al-89)+(B1.48), (Al-89)+(B1.49), (Al-89)+(B1.50), (Al-89)+(B1.51), (Al-89)+(B1.52), (Al-89)+(B1.53), (Al-89)+(B1.54), (Al-89)+(B1.55), (Al-89)+(B1.56), (Al-89)+(B1.57), (Al-89)+(B1.58), (Al-89)+(B1.59), (Al-89)+(B1.60), (Al-89)+(B1.61), (Al-89)+(B1.62), (Al-89)+(B1.63), (Al-89)+(B1.64), (Al-89)+(B1.65), (Al-89)+(B1.66), (Al-89)+(B2.1), (Al-89)+(B2.2), (Al-89)+(B2.3), (Al-89)+(B2.4), (Al-89)+(B2.5), (Al-89)+(B2.6), (Al-89)+(B2.7), (Al-89)+(B2.8), (Al-89)+(B2.9), (Al-89)+(B2.10), (Al-89)+(B2.11), (Al-89)+(B2.12), (Al-89)+(B2.13), (Al-89)+(B2.14), (Al-89)+(B2.15), (Al-89)+(B2.16), (Al-89)+(B2.17), (Al-89)+(B2.18), (Al-89)+(B2.19), (Al-89)+(B2.20), (Al-89)+(B2.21), (Al-89)+(B2.22), (Al-89)+(B2.23), (Al-89)+(B2.24), (Al-89)+(B2.25), (Al-89)+(B2.26), (Al-89)+(B2.27), (Al-89)+(B2.28), (Al-89)+(B2.29), (Al-89)+(B2.30), (Al-89)+(B2.31), (Al-89)+(B2.32), (Al-89)+(B2.33), (Al-89)+(B2.34), (Al-89)+(B2.35), (Al-89)+(B2.36), (Al-89)+(B2.37), (Al-89)+(B2.38), (Al-89)+(B2.39), (Al-89)+(B2.40), (Al-89)+(B2.41), (Al-89)+(B2.42), (Al-89)+(B2.43), (Al-89)+(B2.44), (Al-89)+(B2.45), (Al-89)+(B2.46), (Al-89)+(B2.47), (Al-89)+(B2.48), (Al-89)+(B2.49), (Al-89)+(B2.50), (Al-89)+(B3.1), (Al-89)+(B3.2.), (Al-89)+(B3.3), (Al-89)+(B3.4), (Al-89)+(B3.5), (Al-89)+(B3.6), (Al-89)+(B3.7), (Al-89)+(B3.8), (Al-89)+(B3.9), (Al-89)+(B3.10), (Al-89)+(B3.11), (Al-89)+(B3.12), (Al-89)+(B3.13), (Al-89)+(B3.14), (Al-89)+(B3.15), (Al-89)+(B3.16), (Al-89)+(B4.1), (Al-89)+(B4.2), (Al-89)+(B4.3), (Al-89)+(B4.4), (Al-89)+(B4.5), (Al-89)+(B4.6), (Al-89)+(B4.7).

(Al-90)+(B1.1), (Al-90)+(B1.2), (Al-90)+(B1.3), (Al-90)+(B1.4), (Al-90)+(B1.5), (Al-90)+(B1.6), (Al-90)+(B1.7), (Al-90)+(B1.8), (Al-90)+(B1.9), (Al-90)+(B1.10), (Al-90)+(B1.11), (Al-90)+(B1.12), (Al-90)+(B1.13), (Al-90)+(B1.14), (Al-90)+(B1.15), (Al-90)+(B1.16), (Al-90)+(B1.17), (Al-90)+(B1.18), (Al-90)+(B1.19), (Al-90)+(B1.20), (Al-90)+(B1.21), (Al-90)+(B1.22), (Al-90)+(B1.23), (Al-90)+(B1.24), (Al-90)+(B1.25), (Al-90)+(B1.26), (Al-90)+(B1.27), (Al-90)+(B1.28), (Al-90)+(B1.29), (Al-90)+(B1.30), (Al-90)+(B1.31), (Al-90)+(B1.32), (Al-90)+(B1.33), (Al-90)+(B1.34), (Al-90)+(B1.35), (Al-90)+(B1.36), (Al-90)+(B1.37), (Al-90)+(B1.38), (Al-90)+(B1.39), (Al-90)+(B1.40), (Al-90)+(B1.41), (Al-90)+(B1.42), (Al-90)+(B1.43), (Al-90)+(B1.44), (Al-90)+(B1.45), (Al-90)+(B1.46), (Al-90)+(B1.47), (Al-90)+(B1.48), (Al-90)+(B1.49), (Al-90)+(B1.50), (Al-90)+(B1.51), (Al-90)+(B1.52), (Al-90)+(B1.53), (Al-90)+(B1.54), (Al-90)+(B1.55), (Al-90)+(B1.56), (Al-90)+(B1.57), (Al-90)+(B1.58), (Al-90)+(B1.59), (Al-90)+(B1.60), (Al-90)+(B1.61), (Al-90)+(B1.62), (Al-90)+(B1.63), (Al-90)+(B1.64), (Al-90)+(B1.65), (Al-90)+(B1.66), (Al-90)+(B2.1), (Al-90)+(B2.2), (Al-90)+(B2.3), (Al-90)+(B2.4), (Al-90)+(B2.5), (Al-90)+(B2.6), (Al-90)+(B2.7), (Al-90)+(B2.8), (Al-90)+(B2.9), (Al-90)+(B2.10), (Al-90)+(B2.11), (Al-90)+(B2.12), (Al-90)+(B2.13), (Al-90)+(B2.14), (Al-90)+(B2.15), (Al-90)+(B2.16), (Al-90)+(B2.17), (Al-90)+(B2.18), (Al-90)+(B2.19), (Al-90)+(B2.20), (Al-90)+(B2.21), (Al-90)+(B2.22), (Al-90)+(B2.23), (Al-90)+(B2.24), (Al-90)+(B2.25), (Al-90)+(B2.26), (Al-90)+(B2.27), (Al-90)+(B2.28), (Al-90)+(B2.29), (Al-90)+(B2.30), (Al-90)+(B2.31), (Al-90)+(B2.32), (Al-90)+(B2.33), (Al-90)+(B2.34), (Al-90)+(B2.35), (Al-90)+(B2.36), (Al-90)+(B2.37), (Al-90)+(B2.38), (Al-90)+(B2.39), (Al-90)+(B2.40), (Al-90)+(B2.41), (Al-90)+(B2.42), (Al-90)+(B2.43), (Al-90)+(B2.44), (Al-90)+(B2.45), (Al-90)+

(B2.46), (Al-90)+(B2.47), (Al-90)+(B2.48), (Al-90)+(B2.49), (Al-90)+(B2.50), (Al-90)+(B3.1), (Al-90)+(B3.2.), (Al-90)+(B3.3), (Al-90)+(B3.4), (Al-90)+(B3.5), (Al-90)+(B3.6), (Al-90)+(B3.7), (Al-90)+(B3.8), (Al-90)+(B3.9), (Al-90)+(B3.10), (Al-90)+(B3.11), (Al-90)+(B3.12), (Al-90)+(B3.13), (Al-90)+(B3.14), (Al-90)+(B3.15), (Al-90)+(B3.16), (Al-90)+(B4.1), (Al-90)+(B4.2), (Al-90)+(B4.3), (Al-90)+(B4.4), (Al-90)+(B4.5), (Al-90)+(B4.6), (Al-90)+(B4.7).

(Al-91)+(B1.1), (Al-91)+(B1.2), (Al-91)+(B1.3), (Al-91)+(B1.4), (Al-91)+(B1.5), (Al-91)+(B1.6), (Al-91)+(B1.7), (Al-91)+(B1.8), (Al-91)+(B1.9), (Al-91)+(B1.10), (Al-91)+(B1.11), (Al-91)+(B1.12), (Al-91)+(B1.13), (Al-91)+(B1.14), (Al-91)+(B1.15), (Al-91)+(B1.16), (Al-91)+(B1.17), (Al-91)+(B1.18), (Al-91)+(B1.19), (Al-91)+(B1.20), (Al-91)+(B1.21), (Al-91)+(B1.22), (Al-91)+(B1.23), (Al-91)+(B1.24), (Al-91)+(B1.25), (Al-91)+(B1.26), (Al-91)+(B1.27), (Al-91)+(B1.28), (Al-91)+(B1.29), (Al-91)+(B1.30), (Al-91)+(B1.31), (Al-91)+(B1.32), (Al-91)+(B1.33), (Al-91)+(B1.34), (Al-91)+(B1.35), (Al-91)+(B1.36), (Al-91)+(B1.37), (Al-91)+(B1.38), (Al-91)+(B1.39), (Al-91)+(B1.40), (Al-91)+(B1.41), (Al-91)+(B1.42), (Al-91)+(B1.43), (Al-91)+(B1.44), (Al-91)+(B1.45), (Al-91)+(B1.46), (Al-91)+(B1.47), (Al-91)+(B1.48), (Al-91)+(B1.49), (Al-91)+(B1.50), (Al-91)+(B1.51), (Al-91)+(B1.52), (Al-91)+(B1.53), (Al-91)+(B1.54), (Al-91)+(B1.55), (Al-91)+(B1.56), (Al-91)+(B1.57), (Al-91)+(B1.58), (Al-91)+(B1.59), (Al-91)+(B1.60), (Al-91)+(B1.61), (Al-91)+(B1.62), (Al-91)+(B1.63), (Al-91)+(B1.64), (Al-91)+(B1.65), (Al-91)+(B1.66), (Al-91)+(B2.1), (Al-91)+(B2.2), (Al-91)+(B2.3), (Al-91)+(B2.4), (Al-91)+(B2.5), (Al-91)+(B2.6), (Al-91)+(B2.7), (Al-91)+(B2.8), (Al-91)+(B2.9), (Al-91)+(B2.10), (Al-91)+(B2.11), (Al-91)+(B2.12), (Al-91)+(B2.13), (Al-91)+(B2.14), (Al-91)+(B2.15), (Al-91)+(B2.16), (Al-91)+(B2.17), (Al-91)+(B2.18), (Al-91)+(B2.19), (Al-91)+(B2.20), (Al-91)+(B2.21), (Al-91)+(B2.22), (Al-91)+(B2.23), (Al-91)+(B2.24), (Al-91)+(B2.25), (Al-91)+(B2.26), (Al-91)+(B2.27), (Al-91)+(B2.28), (Al-91)+(B2.29), (Al-91)+(B2.30), (Al-91)+(B2.31), (Al-91)+(B2.32), (Al-91)+(B2.33), (Al-91)+(B2.34), (Al-91)+(B2.35), (Al-91)+(B2.36), (Al-91)+(B2.37), (Al-91)+(B2.38), (Al-91)+(B2.39), (Al-91)+(B2.40), (Al-91)+(B2.41), (Al-91)+(B2.42), (Al-91)+(B2.43), (Al-91)+(B2.44), (Al-91)+(B2.45), (Al-91)+(B2.46), (Al-91)+(B2.47), (Al-91)+(B2.48), (Al-91)+(B2.49), (Al-91)+(B2.50), (Al-91)+(B3.1), (Al-91)+(B3.2.), (Al-91)+(B3.3), (Al-91)+(B3.4), (Al-91)+(B3.5), (Al-91)+(B3.6), (Al-91)+(B3.7), (Al-91)+(B3.8), (Al-91)+(B3.9), (Al-91)+(B3.10), (Al-91)+(B3.11), (Al-91)+(B3.12), (Al-91)+(B3.13), (Al-91)+(B3.14), (Al-91)+(B3.15), (Al-91)+(B3.16), (Al-91)+(B4.1), (Al-91)+(B4.2), (Al-91)+(B4.3), (Al-91)+(B4.4), (Al-91)+(B4.5), (Al-91)+(B4.6), (Al-91)+(B4.7).

(Al-92)+(B1.1), (Al-92)+(B1.2), (Al-92)+(B1.3), (Al-92)+(B1.4), (Al-92)+(B1.5), (Al-92)+(B1.6), (Al-92)+(B1.7), (Al-92)+(B1.8), (Al-92)+(B1.9), (Al-92)+(B1.10), (Al-92)+(B1.11), (Al-92)+(B1.12), (Al-92)+(B1.13), (Al-92)+(B1.14), (Al-92)+(B1.15), (Al-92)+(B1.16), (Al-92)+(B1.17), (Al-92)+(B1.18), (Al-92)+(B1.19), (Al-92)+(B1.20), (Al-92)+(B1.21), (Al-92)+(B1.22), (Al-92)+(B1.23), (Al-92)+(B1.24), (Al-92)+(B1.25), (Al-92)+(B1.26), (Al-92)+(B1.27), (Al-92)+(B1.28), (Al-92)+(B1.29), (Al-92)+(B1.30), (Al-92)+(B1.31), (Al-92)+(B1.32), (Al-92)+(B1.33), (Al-92)+(B1.34), (Al-92)+(B1.35), (Al-92)+(B1.36), (Al-92)+(B1.37), (Al-92)+(B1.38), (Al-92)+(B1.39), (Al-92)+(B1.40), (Al-92)+(B1.41), (Al-92)+(B1.42), (Al-92)+(B1.43), (Al-92)+(B1.44), (Al-92)+(B1.45), (Al-92)+(B1.46), (Al-92)+(B1.47), (Al-92)+(B1.48), (Al-92)+(B1.49), (Al-92)+(B1.50), (Al-92)+(B1.51), (Al-92)+(B1.52), (Al-92)+(B1.53), (Al-92)+(B1.54), (Al-92)+(B1.55), (Al-92)+(B1.56), (Al-92)+(B1.57), (Al-92)+(B1.58), (Al-92)+(B1.59), (Al-92)+(B1.60), (Al-92)+(B1.61), (Al-92)+(B1.62), (Al-92)+(B1.63), (Al-92)+(B1.64), (Al-92)+(B1.65), (Al-92)+(B1.66), (Al-92)+(B2.1), (Al-92)+(B2.2), (Al-92)+(B2.3), (Al-92)+(B2.4), (Al-92)+(B2.5), (Al-92)+(B2.6), (Al-92)+(B2.7), (Al-92)+(B2.8), (Al-92)+(B2.9), (Al-92)+(B2.10), (Al-92)+(B2.11), (Al-92)+(B2.12), (Al-92)+(B2.13), (Al-92)+(B2.14), (Al-92)+(B2.15), (Al-92)+(B2.16), (Al-92)+(B2.17), (Al-92)+(B2.18), (Al-92)+(B2.19), (Al-92)+(B2.20), (Al-92)+(B2.21), (Al-92)+(B2.22), (Al-92)+(B2.23), (Al-92)+(B2.24), (Al-92)+(B2.25), (Al-92)+(B2.26), (Al-92)+(B2.27), (Al-92)+(B2.28), (Al-92)+(B2.29), (Al-92)+(B2.30), (Al-92)+(B2.31), (Al-92)+(B2.32), (Al-92)+(B2.33), (Al-92)+(B2.34), (Al-92)+(B2.35), (Al-92)+(B2.36), (Al-92)+(B2.37), (Al-92)+(B2.38), (Al-92)+(B2.39), (Al-92)+(B2.40), (Al-92)+(B2.41), (Al-92)+(B2.42), (Al-92)+(B2.43), (Al-92)+(B2.44), (Al-92)+(B2.45), (Al-92)+(B2.46), (Al-92)+(B2.47), (Al-92)+(B2.48), (Al-92)+(B2.49), (Al-92)+(B2.50), (Al-92)+(B3.1), (Al-92)+(B3.2.), (Al-92)+(B3.3), (Al-92)+(B3.4), (Al-92)+(B3.5), (Al-92)+(B3.6), (Al-92)+(B3.7), (Al-92)+(B3.8), (Al-92)+(B3.9), (Al-92)+(B3.10), (Al-92)+(B3.11), (Al-92)+(B3.12), (Al-92)+(B3.13), (Al-92)+(B3.14), (Al-92)+(B3.15), (Al-92)+(B3.16), (Al-92)+(B4.1), (Al-92)+(B4.2), (Al-92)+(B4.3), (Al-92)+(B4.4), (Al-92)+(B4.5), (Al-92)+(B4.6), (Al-92)+(B4.7).

(Al-93)+(B1.1), (Al-93)+(B1.2), (Al-93)+(B1.3), (Al-93)+(B1.4), (Al-93)+(B1.5), (Al-93)+(B1.6), (Al-93)+(B1.7), (Al-93)+(B1.8), (Al-93)+(B1.9), (Al-93)+(B1.10), (Al-93)+(B1.11), (Al-93)+(B1.12), (Al-93)+(B1.13), (Al-93)+(B1.14), (Al-93)+(B1.15), (Al-93)+(B1.16), (Al-93)+(B1.17), (Al-93)+(B1.18), (Al-93)+(B1.19), (Al-93)+(B1.20), (Al-93)+(B1.21), (Al-93)+(B1.22), (Al-93)+(B1.23), (Al-93)+(B1.24), (Al-93)+(B1.25), (Al-93)+(B1.26), (Al-93)+(B1.27), (Al-93)+(B1.28), (Al-93)+(B1.29), (Al-93)+(B1.30), (Al-93)+(B1.31), (Al-93)+(B1.32), (Al-93)+(B1.33), (Al-93)+(B1.34), (Al-93)+(B1.35), (Al-93)+(B1.36), (Al-93)+(B1.37), (Al-93)+(B1.38), (Al-93)+(B1.39), (Al-93)+(B1.40), (Al-93)+(B1.41), (Al-93)+(B1.42), (Al-93)+(B1.43), (Al-93)+(B1.44), (Al-93)+(B1.45), (Al-93)+(B1.46), (Al-93)+(B1.47), (Al-93)+(B1.48), (Al-93)+(B1.49), (Al-93)+(B1.50), (Al-93)+(B1.51), (Al-93)+(B1.52), (Al-93)+(B1.53), (Al-93)+(B1.54), (Al-93)+(B1.55), (Al-93)+(B1.56), (Al-93)+(B1.57), (Al-93)+(B1.58), (Al-93)+(B1.59), (Al-93)+(B1.60), (Al-93)+(B1.61), (Al-93)+(B1.62), (Al-93)+(B1.63), (Al-93)+(B1.64), (Al-93)+(B1.65), (Al-93)+(B1.66), (Al-93)+(B2.1), (Al-93)+(B2.2), (Al-93)+(B2.3), (Al-93)+(B2.4), (Al-93)+(B2.5), (Al-93)+(B2.6), (Al-93)+(B2.7), (Al-93)+(B2.8), (Al-93)+(B2.9), (Al-93)+(B2.10), (Al-93)+(B2.11), (Al-93)+(B2.12), (Al-93)+(B2.13), (Al-93)+(B2.14), (Al-93)+(B2.15), (Al-93)+(B2.16), (Al-93)+(B2.17), (Al-93)+(B2.18), (Al-93)+(B2.19), (Al-93)+(B2.20), (Al-93)+(B2.21), (Al-93)+(B2.22), (Al-93)+(B2.23), (Al-93)+(B2.24), (Al-93)+(B2.25), (Al-93)+(B2.26), (Al-93)+(B2.27), (Al-93)+(B2.28), (Al-93)+(B2.29), (Al-93)+(B2.30), (Al-93)+(B2.31), (Al-93)+(B2.32), (Al-93)+(B2.33), (Al-93)+(B2.34), (Al-93)+(B2.35), (Al-93)+(B2.36), (Al-93)+(B2.37), (Al-93)+(B2.38), (Al-93)+(B2.39), (Al-93)+(B2.40), (Al-93)+(B2.41), (Al-93)+(B2.42), (Al-93)+

(B2.43), (Al-93)+(B2.44), (Al-93)+(B2.45), (Al-93)+(B2.46), (Al-93)+(B2.47), (Al-93)+(B2.48), (Al-93)+(B2.49), (Al-93)+(B2.50), (Al-93)+(B3.1), (Al-93)+(B3.2.), (Al-93)+(B3.3), (Al-93)+(B3.4), (Al-93)+(B3.5), (Al-93)+(B3.6), (Al-93)+(B3.7), (Al-93)+(B3.8), (Al-93)+(B3.9), (Al-93)+(B3.10), (Al-93)+(B3.11), (Al-93)+(B3.12), (Al-93)+(B3.13), (Al-93)+(B3.14), (Al-93)+(B3.15), (Al-93)+(B3.16), (Al-93)+(B4.1), (Al-93)+(B4.2), (Al-93)+(B4.3), (Al-93)+(B4.4), (Al-93)+(B4.5), (Al-93)+(B4.6), (Al-93)+(B4.7).

(Al-94)+(B1.1), (Al-94)+(B1.2), (Al-94)+(B1.3), (Al-94)+(B1.4), (Al-94)+(B1.5), (Al-94)+(B1.6), (Al-94)+(B1.7), (Al-94)+(B1.8), (Al-94)+(B1.9), (Al-94)+(B1.10), (Al-94)+(B1.11), (Al-94)+(B1.12), (Al-94)+(B1.13), (Al-94)+(B1.14), (Al-94)+(B1.15), (Al-94)+(B1.16), (Al-94)+(B1.17), (Al-94)+(B1.18), (Al-94)+(B1.19), (Al-94)+(B1.20), (Al-94)+(B1.21), (Al-94)+(B1.22), (Al-94)+(B1.23), (Al-94)+(B1.24), (Al-94)+(B1.25), (Al-94)+(B1.26), (Al-94)+(B1.27), (Al-94)+(B1.28), (Al-94)+(B1.29), (Al-94)+(B1.30), (Al-94)+(B1.31), (Al-94)+(B1.32), (Al-94)+(B1.33), (Al-94)+(B1.34), (Al-94)+(B1.35), (Al-94)+(B1.36), (Al-94)+(B1.37), (Al-94)+(B1.38), (Al-94)+(B1.39), (Al-94)+(B1.40), (Al-94)+(B1.41), (Al-94)+(B1.42), (Al-94)+(B1.43), (Al-94)+(B1.44), (Al-94)+(B1.45), (Al-94)+(B1.46), (Al-94)+(B1.47), (Al-94)+(B1.48), (Al-94)+(B1.49), (Al-94)+(B1.50), (Al-94)+(B1.51), (Al-94)+(B1.52), (Al-94)+(B1.53), (Al-94)+(B1.54), (Al-94)+(B1.55), (Al-94)+(B1.56), (Al-94)+(B1.57), (Al-94)+(B1.58), (Al-94)+(B1.59), (Al-94)+(B1.60), (Al-94)+(B1.61), (Al-94)+(B1.62), (Al-94)+(B1.63), (Al-94)+(B1.64), (Al-94)+(B1.65), (Al-94)+(B1.66), (Al-94)+(B2.1), (Al-94)+(B2.2), (Al-94)+(B2.3), (Al-94)+(B2.4), (Al-94)+(B2.5), (Al-94)+(B2.6), (Al-94)+(B2.7), (Al-94)+(B2.8), (Al-94)+(B2.9), (Al-94)+(B2.10), (Al-94)+(B2.11), (Al-94)+(B2.12), (Al-94)+(B2.13), (Al-94)+(B2.14), (Al-94)+(B2.15), (Al-94)+(B2.16), (Al-94)+(B2.17), (Al-94)+(B2.18), (Al-94)+(B2.19), (Al-94)+(B2.20), (Al-94)+(B2.21), (Al-94)+(B2.22), (Al-94)+(B2.23), (Al-94)+(B2.24), (Al-94)+(B2.25), (Al-94)+(B2.26), (Al-94)+(B2.27), (Al-94)+(B2.28), (Al-94)+(B2.29), (Al-94)+(B2.30), (Al-94)+(B2.31), (Al-94)+(B2.32), (Al-94)+(B2.33), (Al-94)+(B2.34), (Al-94)+(B2.35), (Al-94)+(B2.36), (Al-94)+(B2.37), (Al-94)+(B2.38), (Al-94)+(B2.39), (Al-94)+(B2.40), (Al-94)+(B2.41), (Al-94)+(B2.42), (Al-94)+(B2.43), (Al-94)+(B2.44), (Al-94)+(B2.45), (Al-94)+(B2.46), (Al-94)+(B2.47), (Al-94)+(B2.48), (Al-94)+(B2.49), (Al-94)+(B2.50), (Al-94)+(B3.1), (Al-94)+(B3.2.), (Al-94)+(B3.3), (Al-94)+(B3.4), (Al-94)+(B3.5), (Al-94)+(B3.6), (Al-94)+(B3.7), (Al-94)+(B3.8), (Al-94)+(B3.9), (Al-94)+(B3.10), (Al-94)+(B3.11), (Al-94)+(B3.12), (Al-94)+(B3.13), (Al-94)+(B3.14), (Al-94)+(B3.15), (Al-94)+(B3.16), (Al-94)+(B4.1), (Al-94)+(B4.2), (Al-94)+(B4.3), (Al-94)+(B4.4), (Al-94)+(B4.5), (Al-94)+(B4.6), (Al-94)+(B4.7).

(Al-95)+(B1.1), (Al-95)+(B1.2), (Al-95)+(B1.3), (Al-95)+(B1.4), (Al-95)+(B1.5), (Al-95)+(B1.6), (Al-95)+(B1.7), (Al-95)+(B1.8), (Al-95)+(B1.9), (Al-95)+(B1.10), (Al-95)+(B1.11), (Al-95)+(B1.12), (Al-95)+(B1.13), (Al-95)+(B1.14), (Al-95)+(B1.15), (Al-95)+(B1.16), (Al-95)+(B1.17), (Al-95)+(B1.18), (Al-95)+(B1.19), (Al-95)+(B1.20), (Al-95)+(B1.21), (Al-95)+(B1.22), (Al-95)+(B1.23), (Al-95)+(B1.24), (Al-95)+(B1.25), (Al-95)+(B1.26), (Al-95)+(B1.27), (Al-95)+(B1.28), (Al-95)+(B1.29), (Al-95)+(B1.30), (Al-95)+(B1.31), (Al-95)+(B1.32), (Al-95)+(B1.33), (Al-95)+(B1.34), (Al-95)+(B1.35), (Al-95)+(B1.36), (Al-95)+(B1.37), (Al-95)+(B1.38), (Al-95)+(B1.39), (Al-95)+(B1.40), (Al-95)+(B1.41), (Al-95)+(B1.42), (Al-95)+(B1.43), (Al-95)+(B1.44), (Al-95)+(B1.45), (Al-95)+(B1.46), (Al-95)+(B1.47), (Al-95)+(B1.48), (Al-95)+(B1.49), (Al-95)+(B1.50), (Al-95)+(B1.51), (Al-95)+(B1.52), (Al-95)+(B1.53), (Al-95)+(B1.54), (Al-95)+(B1.55), (Al-95)+(B1.56), (Al-95)+(B1.57), (Al-95)+(B1.58), (Al-95)+(B1.59), (Al-95)+(B1.60), (Al-95)+(B1.61), (Al-95)+(B1.62), (Al-95)+(B1.63), (Al-95)+(B1.64), (Al-95)+(B1.65), (Al-95)+(B1.66), (Al-95)+(B2.1), (Al-95)+(B2.2), (Al-95)+(B2.3), (Al-95)+(B2.4), (Al-95)+(B2.5), (Al-95)+(B2.6), (Al-95)+(B2.7), (Al-95)+(B2.8), (Al-95)+(B2.9), (Al-95)+(B2.10), (Al-95)+(B2.11), (Al-95)+(B2.12), (Al-95)+(B2.13), (Al-95)+(B2.14), (Al-95)+(B2.15), (Al-95)+(B2.16), (Al-95)+(B2.17), (Al-95)+(B2.18), (Al-95)+(B2.19), (Al-95)+(B2.20), (Al-95)+(B2.21), (Al-95)+(B2.22), (Al-95)+(B2.23), (Al-95)+(B2.24), (Al-95)+(B2.25), (Al-95)+(B2.26), (Al-95)+(B2.27), (Al-95)+(B2.28), (Al-95)+(B2.29), (Al-95)+(B2.30), (Al-95)+(B2.31), (Al-95)+(B2.32), (Al-95)+(B2.33), (Al-95)+(B2.34), (Al-95)+(B2.35), (Al-95)+(B2.36), (Al-95)+(B2.37), (Al-95)+(B2.38), (Al-95)+(B2.39), (Al-95)+(B2.40), (Al-95)+(B2.41), (Al-95)+(B2.42), (Al-95)+(B2.43), (Al-95)+(B2.44), (Al-95)+(B2.45), (Al-95)+(B2.46), (Al-95)+(B2.47), (Al-95)+(B2.48), (Al-95)+(B2.49), (Al-95)+(B2.50), (Al-95)+(B3.1), (Al-95)+(B3.2.), (Al-95)+(B3.3), (Al-95)+(B3.4), (Al-95)+(B3.5), (Al-95)+(B3.6), (Al-95)+(B3.7), (Al-95)+(B3.8), (Al-95)+(B3.9), (Al-95)+(B3.10), (Al-95)+(B3.11), (Al-95)+(B3.12), (Al-95)+(B3.13), (Al-95)+(B3.14), (Al-95)+(B3.15), (Al-95)+(B3.16), (Al-95)+(B4.1), (Al-95)+(B4.2), (Al-95)+(B4.3), (Al-95)+(B4.4), (Al-95)+(B4.5), (Al-95)+(B4.6), (Al-95)+(B4.7).

(Al-96)+(B1.1), (Al-96)+(B1.2), (Al-96)+(B1.3), (Al-96)+(B1.4), (Al-96)+(B1.5), (Al-96)+(B1.6), (Al-96)+(B1.7), (Al-96)+(B1.8), (Al-96)+(B1.9), (Al-96)+(B1.10), (Al-96)+(B1.11), (Al-96)+(B1.12), (Al-96)+(B1.13), (Al-96)+(B1.14), (Al-96)+(B1.15), (Al-96)+(B1.16), (Al-96)+(B1.17), (Al-96)+(B1.18), (Al-96)+(B1.19), (Al-96)+(B1.20), (Al-96)+(B1.21), (Al-96)+(B1.22), (Al-96)+(B1.23), (Al-96)+(B1.24), (Al-96)+(B1.25), (Al-96)+(B1.26), (Al-96)+(B1.27), (Al-96)+(B1.28), (Al-96)+(B1.29), (Al-96)+(B1.30), (Al-96)+(B1.31), (Al-96)+(B1.32), (Al-96)+(B1.33), (Al-96)+(B1.34), (Al-96)+(B1.35), (Al-96)+(B1.36), (Al-96)+(B1.37), (Al-96)+(B1.38), (Al-96)+(B1.39), (Al-96)+(B1.40), (Al-96)+(B1.41), (Al-96)+(B1.42), (Al-96)+(B1.43), (Al-96)+(B1.44), (Al-96)+(B1.45), (Al-96)+(B1.46), (Al-96)+(B1.47), (Al-96)+(B1.48), (Al-96)+(B1.49), (Al-96)+(B1.50), (Al-96)+(B1.51), (Al-96)+(B1.52), (Al-96)+(B1.53), (Al-96)+(B1.54), (Al-96)+(B1.55), (Al-96)+(B1.56), (Al-96)+(B1.57), (Al-96)+(B1.58), (Al-96)+(B1.59), (Al-96)+(B1.60), (Al-96)+(B1.61), (Al-96)+(B1.62), (Al-96)+(B1.63), (Al-96)+(B1.64), (Al-96)+(B1.65), (Al-96)+(B1.66), (Al-96)+(B2.1), (Al-96)+(B2.2), (Al-96)+(B2.3), (Al-96)+(B2.4), (Al-96)+(B2.5), (Al-96)+(B2.6), (Al-96)+(B2.7), (Al-96)+(B2.8), (Al-96)+(B2.9), (Al-96)+(B2.10), (Al-96)+(B2.11), (Al-96)+(B2.12), (Al-96)+(B2.13), (Al-96)+(B2.14), (Al-96)+(B2.15), (Al-96)+(B2.16), (Al-96)+(B2.17), (Al-96)+(B2.18), (Al-96)+(B2.19), (Al-96)+(B2.20), (Al-96)+(B2.21), (Al-96)+(B2.22), (Al-96)+(B2.23), (Al-96)+(B2.24), (Al-96)+(B2.25), (Al-96)+(B2.26), (Al-96)+(B2.27), (Al-96)+(B2.28), (Al-96)+(B2.29), (Al-96)+(B2.30), (Al-96)+(B2.31), (Al-96)+(B2.32), (Al-96)+(B2.33), (Al-96)+(B2.34), (Al-96)+(B2.35), (Al-96)+(B2.36), (Al-96)+(B2.37), (Al-96)+(B2.38), (Al-96)+(B2.39), (Al-96)+

(B2.40), (Al-96)+(B2.41), (Al-96)+(B2.42), (Al-96)+(B2.43), (Al-96)+(B2.44), (Al-96)+(B2.45), (Al-96)+(B2.46), (Al-96)+(B2.47), (Al-96)+(B2.48), (Al-96)+(B2.49), (Al-96)+(B2.50), (Al-96)+(B3.1), (Al-96)+(B3.2.), (Al-96)+(B3.3), (Al-96)+(B3.4), (Al-96)+(B3.5), (Al-96)+(B3.6), (Al-96)+(B3.7), (Al-96)+(B3.8), (Al-96)+(B3.9), (Al-96)+(B3.10), (Al-96)+(B3.11), (Al-96)+(B3.12), (Al-96)+(B3.13), (Al-96)+(B3.14), (Al-96)+(B3.15), (Al-96)+(B3.16), (Al-96)+(B4.1), (Al-96)+(B4.2), (Al-96)+(B4.3), (Al-96)+(B4.4), (Al-96)+(B4.5), (Al-96)+(B4.6), (Al-96)+(B4.7).

(Al-97)+(B1.1), (Al-97)+(B1.2), (Al-97)+(B1.3), (Al-97)+(B1.4), (Al-97)+(B1.5), (Al-97)+(B1.6), (Al-97)+(B1.7), (Al-97)+(B1.8), (Al-97)+(B1.9), (Al-97)+(B1.10), (Al-97)+(B1.11), (Al-97)+(B1.12), (Al-97)+(B1.13), (Al-97)+(B1.14), (Al-97)+(B1.15), (Al-97)+(B1.16), (Al-97)+(B1.17), (Al-97)+(B1.18), (Al-97)+(B1.19), (Al-97)+(B1.20), (Al-97)+(B1.21), (Al-97)+(B1.22), (Al-97)+(B1.23), (Al-97)+(B1.24), (Al-97)+(B1.25), (Al-97)+(B1.26), (Al-97)+(B1.27), (Al-97)+(B1.28), (Al-97)+(B1.29), (Al-97)+(B1.30), (Al-97)+(B1.31), (Al-97)+(B1.32), (Al-97)+(B1.33), (Al-97)+(B1.34), (Al-97)+(B1.35), (Al-97)+(B1.36), (Al-97)+(B1.37), (Al-97)+(B1.38), (Al-97)+(B1.39), (Al-97)+(B1.40), (Al-97)+(B1.41), (Al-97)+(B1.42), (Al-97)+(B1.43), (Al-97)+(B1.44), (Al-97)+(B1.45), (Al-97)+(B1.46), (Al-97)+(B1.47), (Al-97)+(B1.48), (Al-97)+(B1.49), (Al-97)+(B1.50), (Al-97)+(B1.51), (Al-97)+(B1.52), (Al-97)+(B1.53), (Al-97)+(B1.54), (Al-97)+(B1.55), (Al-97)+(B1.56), (Al-97)+(B1.57), (Al-97)+(B1.58), (Al-97)+(B1.59), (Al-97)+(B1.60), (Al-97)+(B1.61), (Al-97)+(B1.62), (Al-97)+(B1.63), (Al-97)+(B1.64), (Al-97)+(B1.65), (Al-97)+(B1.66), (Al-97)+(B2.1), (Al-97)+(B2.2), (Al-97)+(B2.3), (Al-97)+(B2.4), (Al-97)+(B2.5), (Al-97)+(B2.6), (Al-97)+(B2.7), (Al-97)+(B2.8), (Al-97)+(B2.9), (Al-97)+(B2.10), (Al-97)+(B2.11), (Al-97)+(B2.12), (Al-97)+(B2.13), (Al-97)+(B2.14), (Al-97)+(B2.15), (Al-97)+(B2.16), (Al-97)+(B2.17), (Al-97)+(B2.18), (Al-97)+(B2.19), (Al-97)+(B2.20), (Al-97)+(B2.21), (Al-97)+(B2.22), (Al-97)+(B2.23), (Al-97)+(B2.24), (Al-97)+(B2.25), (Al-97)+(B2.26), (Al-97)+(B2.27), (Al-97)+(B2.28), (Al-97)+(B2.29), (Al-97)+(B2.30), (Al-97)+(B2.31), (Al-97)+(B2.32), (Al-97)+(B2.33), (Al-97)+(B2.34), (Al-97)+(B2.35), (Al-97)+(B2.36), (Al-97)+(B2.37), (Al-97)+(B2.38), (Al-97)+(B2.39), (Al-97)+(B2.40), (Al-97)+(B2.41), (Al-97)+(B2.42), (Al-97)+(B2.43), (Al-97)+(B2.44), (Al-97)+(B2.45), (Al-97)+(B2.46), (Al-97)+(B2.47), (Al-97)+(B2.48), (Al-97)+(B2.49), (Al-97)+(B2.50), (Al-97)+(B3.1), (Al-97)+(B3.2.), (Al-97)+(B3.3), (Al-97)+(B3.4), (Al-97)+(B3.5), (Al-97)+(B3.6), (Al-97)+(B3.7), (Al-97)+(B3.8), (Al-97)+(B3.9), (Al-97)+(B3.10), (Al-97)+(B3.11), (Al-97)+(B3.12), (Al-97)+(B3.13), (Al-97)+(B3.14), (Al-97)+(B3.15), (Al-97)+(B3.16), (Al-97)+(B4.1), (Al-97)+(B4.2), (Al-97)+(B4.3), (Al-97)+(B4.4), (Al-97)+(B4.5), (Al-97)+(B4.6), (Al-97)+(B4.7).

(Al-98)+(B1.1), (Al-98)+(B1.2), (Al-98)+(B1.3), (Al-98)+(B1.4), (Al-98)+(B1.5), (Al-98)+(B1.6), (Al-98)+(B1.7), (Al-98)+(B1.8), (Al-98)+(B1.9), (Al-98)+(B1.10), (Al-98)+(B1.11), (Al-98)+(B1.12), (Al-98)+(B1.13), (Al-98)+(B1.14), (Al-98)+(B1.15), (Al-98)+(B1.16), (Al-98)+(B1.17), (Al-98)+(B1.18), (Al-98)+(B1.19), (Al-98)+(B1.20), (Al-98)+(B1.21), (Al-98)+(B1.22), (Al-98)+(B1.23), (Al-98)+(B1.24), (Al-98)+(B1.25), (Al-98)+(B1.26), (Al-98)+(B1.27), (Al-98)+(B1.28), (Al-98)+(B1.29), (Al-98)+(B1.30), (Al-98)+(B1.31), (Al-98)+(B1.32), (Al-98)+(B1.33), (Al-98)+(B1.34), (Al-98)+(B1.35), (Al-98)+(B1.36), (Al-98)+(B1.37), (Al-98)+(B1.38), (Al-98)+(B1.39), (Al-98)+(B1.40), (Al-98)+(B1.41), (Al-98)+(B1.42), (Al-98)+(B1.43), (Al-98)+(B1.44), (Al-98)+(B1.45), (Al-98)+(B1.46), (Al-98)+(B1.47), (Al-98)+(B1.48), (Al-98)+(B1.49), (Al-98)+(B1.50), (Al-98)+(B1.51), (Al-98)+(B1.52), (Al-98)+(B1.53), (Al-98)+(B1.54), (Al-98)+(B1.55), (Al-98)+(B1.56), (Al-98)+(B1.57), (Al-98)+(B1.58), (Al-98)+(B1.59), (Al-98)+(B1.60), (Al-98)+(B1.61), (Al-98)+(B1.62), (Al-98)+(B1.63), (Al-98)+(B1.64), (Al-98)+(B1.65), (Al-98)+(B1.66), (Al-98)+(B2.1), (Al-98)+(B2.2), (Al-98)+(B2.3), (Al-98)+(B2.4), (Al-98)+(B2.5), (Al-98)+(B2.6), (Al-98)+(B2.7), (Al-98)+(B2.8), (Al-98)+(B2.9), (Al-98)+(B2.10), (Al-98)+(B2.11), (Al-98)+(B2.12), (Al-98)+(B2.13), (Al-98)+(B2.14), (Al-98)+(B2.15), (Al-98)+(B2.16), (Al-98)+(B2.17), (Al-98)+(B2.18), (Al-98)+(B2.19), (Al-98)+(B2.20), (Al-98)+(B2.21), (Al-98)+(B2.22), (Al-98)+(B2.23), (Al-98)+(B2.24), (Al-98)+(B2.25), (Al-98)+(B2.26), (Al-98)+(B2.27), (Al-98)+(B2.28), (Al-98)+(B2.29), (Al-98)+(B2.30), (Al-98)+(B2.31), (Al-98)+(B2.32), (Al-98)+(B2.33), (Al-98)+(B2.34), (Al-98)+(B2.35), (Al-98)+(B2.36), (Al-98)+(B2.37), (Al-98)+(B2.38), (Al-98)+(B2.39), (Al-98)+(B2.40), (Al-98)+(B2.41), (Al-98)+(B2.42), (Al-98)+(B2.43), (Al-98)+(B2.44), (Al-98)+(B2.45), (Al-98)+(B2.46), (Al-98)+(B2.47), (Al-98)+(B2.48), (Al-98)+(B2.49), (Al-98)+(B2.50), (Al-98)+(B3.1), (Al-98)+(B3.2.), (Al-98)+(B3.3), (Al-98)+(B3.4), (Al-98)+(B3.5), (Al-98)+(B3.6), (Al-98)+(B3.7), (Al-98)+(B3.8), (Al-98)+(B3.9), (Al-98)+(B3.10), (Al-98)+(B3.11), (Al-98)+(B3.12), (Al-98)+(B3.13), (Al-98)+(B3.14), (Al-98)+(B3.15), (Al-98)+(B3.16), (Al-98)+(B4.1), (Al-98)+(B4.2), (Al-98)+(B4.3), (Al-98)+(B4.4), (Al-98)+(B4.5), (Al-98)+(B4.6), (Al-98)+(B4.7).

(Al-99)+(B1.1), (Al-99)+(B1.2), (Al-99)+(B1.3), (Al-99)+(B1.4), (Al-99)+(B1.5), (Al-99)+(B1.6), (Al-99)+(B1.7), (Al-99)+(B1.8), (Al-99)+(B1.9), (Al-99)+(B1.10), (Al-99)+(B1.11), (Al-99)+(B1.12), (Al-99)+(B1.13), (Al-99)+(B1.14), (Al-99)+(B1.15), (Al-99)+(B1.16), (Al-99)+(B1.17), (Al-99)+(B1.18), (Al-99)+(B1.19), (Al-99)+(B1.20), (Al-99)+(B1.21), (Al-99)+(B1.22), (Al-99)+(B1.23), (Al-99)+(B1.24), (Al-99)+(B1.25), (Al-99)+(B1.26), (Al-99)+(B1.27), (Al-99)+(B1.28), (Al-99)+(B1.29), (Al-99)+(B1.30), (Al-99)+(B1.31), (Al-99)+(B1.32), (Al-99)+(B1.33), (Al-99)+(B1.34), (Al-99)+(B1.35), (Al-99)+(B1.36), (Al-99)+(B1.37), (Al-99)+(B1.38), (Al-99)+(B1.39), (Al-99)+(B1.40), (Al-99)+(B1.41), (Al-99)+(B1.42), (Al-99)+(B1.43), (Al-99)+(B1.44), (Al-99)+(B1.45), (Al-99)+(B1.46), (Al-99)+(B1.47), (Al-99)+(B1.48), (Al-99)+(B1.49), (Al-99)+(B1.50), (Al-99)+(B1.51), (Al-99)+(B1.52), (Al-99)+(B1.53), (Al-99)+(B1.54), (Al-99)+(B1.55), (Al-99)+(B1.56), (Al-99)+(B1.57), (Al-99)+(B1.58), (Al-99)+(B1.59), (Al-99)+(B1.60), (Al-99)+(B1.61), (Al-99)+(B1.62), (Al-99)+(B1.63), (Al-99)+(B1.64), (Al-99)+(B1.65), (Al-99)+(B1.66), (Al-99)+(B2.1), (Al-99)+(B2.2), (Al-99)+(B2.3), (Al-99)+(B2.4), (Al-99)+(B2.5), (Al-99)+(B2.6), (Al-99)+(B2.7), (Al-99)+(B2.8), (Al-99)+(B2.9), (Al-99)+(B2.10), (Al-99)+(B2.11), (Al-99)+(B2.12), (Al-99)+(B2.13), (Al-99)+(B2.14), (Al-99)+(B2.15), (Al-99)+(B2.16), (Al-99)+(B2.17), (Al-99)+(B2.18), (Al-99)+(B2.19), (Al-99)+(B2.20), (Al-99)+(B2.21), (Al-99)+(B2.22), (Al-99)+(B2.23), (Al-99)+(B2.24), (Al-99)+(B2.25), (Al-99)+(B2.26), (Al-99)+(B2.27), (Al-99)+(B2.28), (Al-99)+(B2.29), (Al-99)+(B2.30), (Al-99)+(B2.31), (Al-99)+(B2.32), (Al-99)+(B2.33), (Al-99)+(B2.34), (Al-99)+(B2.35), (Al-99)+(B2.36), (Al-99)+

(B2.37), (Al-99)+(B2.38), (Al-99)+(B2.39), (Al-99)+(B2.40), (Al-99)+(B2.41), (Al-99)+(B2.42), (Al-99)+(B2.43), (Al-99)+(B2.44), (Al-99)+(B2.45), (Al-99)+(B2.46), (Al-99)+(B2.47), (Al-99)+(B2.48), (Al-99)+(B2.49), (Al-99)+(B2.50), (Al-99)+(B3.1), (Al-99)+(B3.2.), (Al-99)+(B3.3), (Al-99)+(B3.4), (Al-99)+(B3.5), (Al-99)+(B3.6), (Al-99)+(B3.7), (Al-99)+(B3.8), (Al-99)+(B3.9), (Al-99)+(B3.10), (Al-99)+(B3.11), (Al-99)+(B3.12), (Al-99)+(B3.13), (Al-99)+(B3.14), (Al-99)+(B3.15), (Al-99)+(B3.16), (Al-99)+(B4.1), (Al-99)+(B4.2), (Al-99)+(B4.3), (Al-99)+(B4.4), (Al-99)+(B4.5), (Al-99)+(B4.6), (Al-99)+(B4.7).

(Al-100)+(B1.1), (Al-100)+(B1.2), (Al-100)+(B1.3), (Al-100)+(B1.4), (Al-100)+(B1.5), (Al-100)+(B1.6), (Al-100)+(B1.7), (Al-100)+(B1.8), (Al-100)+(B1.9), (Al-100)+(B1.10), (Al-100)+(B1.11), (Al-100)+(B1.12), (Al-100)+(B1.13), (Al-100)+(B1.14), (Al-100)+(B1.15), (Al-100)+(B1.16), (Al-100)+(B1.17), (Al-100)+(B1.18), (Al-100)+(B1.19), (Al-100)+(B1.20), (Al-100)+(B1.21), (Al-100)+(B1.22), (Al-100)+(B1.23), (Al-100)+(B1.24), (Al-100)+(B1.25), (Al-100)+(B1.26), (Al-100)+(B1.27), (Al-100)+(B1.28), (Al-100)+(B1.29), (Al-100)+(B1.30), (Al-100)+(B1.31), (Al-100)+(B1.32), (Al-100)+(B1.33), (Al-100)+(B1.34), (Al-100)+(B1.35), (Al-100)+(B1.36), (Al-100)+(B1.37), (Al-100)+(B1.38), (Al-100)+(B1.39), (Al-100)+(B1.40), (Al-100)+(B1.41), (Al-100)+(B1.42), (Al-100)+(B1.43), (Al-100)+(B1.44), (Al-100)+(B1.45), (Al-100)+(B1.46), (Al-100)+(B1.47), (Al-100)+(B1.48), (Al-100)+(B1.49), (Al-100)+(B1.50), (Al-100)+(B1.51), (Al-100)+(B1.52), (Al-100)+(B1.53), (Al-100)+(B1.54), (Al-100)+(B1.55), (Al-100)+(B1.56), (Al-100)+(B1.57), (Al-100)+(B1.58), (Al-100)+(B1.59), (Al-100)+(B1.60), (Al-100)+(B1.61), (Al-100)+(B1.62), (Al-100)+(B1.63), (Al-100)+(B1.64), (Al-100)+(B1.65), (Al-100)+(B1.66), (Al-100)+(B2.1), (Al-100)+(B2.2), (Al-100)+(B2.3), (Al-100)+(B2.4), (Al-100)+(B2.5), (Al-100)+(B2.6), (Al-100)+(B2.7), (Al-100)+(B2.8), (Al-100)+(B2.9), (Al-100)+(B2.10), (Al-100)+(B2.11), (Al-100)+(B2.12), (Al-100)+(B2.13), (Al-100)+(B2.14), (Al-100)+(B2.15), (Al-100)+(B2.16), (Al-100)+(B2.17), (Al-100)+(B2.18), (Al-100)+(B2.19), (Al-100)+(B2.20), (Al-100)+(B2.21), (Al-100)+(B2.22), (Al-100)+(B2.23), (Al-100)+(B2.24), (Al-100)+(B2.25), (Al-100)+(B2.26), (Al-100)+(B2.27), (Al-100)+(B2.28), (Al-100)+(B2.29), (Al-100)+(B2.30), (Al-100)+(B2.31), (Al-100)+(B2.32), (Al-100)+(B2.33), (Al-100)+(B2.34), (Al-100)+(B2.35), (Al-100)+(B2.36), (Al-100)+(B2.37), (Al-100)+(B2.38), (Al-100)+(B2.39), (Al-100)+(B2.40), (Al-100)+(B2.41), (Al-100)+(B2.42), (Al-100)+(B2.43), (Al-100)+(B2.44), (Al-100)+(B2.45), (Al-100)+(B2.46), (Al-100)+(B2.47), (Al-100)+(B2.48), (Al-100)+(B2.49), (Al-100)+(B2.50), (Al-100)+(B3.1), (Al-100)+(B3.2.), (Al-100)+(B3.3), (Al-100)+(B3.4), (Al-100)+(B3.5), (Al-100)+(B3.6), (Al-100)+(B3.7), (Al-100)+(B3.8), (Al-100)+(B3.9), (Al-100)+(B3.10), (Al-100)+(B3.11), (Al-100)+(B3.12), (Al-100)+(B3.13), (Al-100)+(B3.14), (Al-100)+(B3.15), (Al-100)+(B3.16), (Al-100)+(B4.1), (Al-100)+(B4.2), (Al-100)+(B4.3), (Al-100)+(B4.4), (Al-100)+(B4.5), (Al-100)+(B4.6), (Al-100)+(B4.7).

(Al-101)+(B1.1), (Al-101)+(B1.2), (Al-101)+(B1.3), (Al-101)+(B1.4), (Al-101)+(B1.5), (Al-101)+(B1.6), (Al-101)+(B1.7), (Al-101)+(B1.8), (Al-101)+(B1.9), (Al-101)+(B1.10), (Al-101)+(B1.11), (Al-101)+(B1.12), (Al-101)+(B1.13), (Al-101)+(B1.14), (Al-101)+(B1.15), (Al-101)+(B1.16), (Al-101)+(B1.17), (Al-101)+(B1.18), (Al-101)+(B1.19), (Al-101)+(B1.20), (Al-101)+(B1.21), (Al-101)+(B1.22), (Al-101)+(B1.23), (Al-101)+(B1.24), (Al-101)+(B1.25), (Al-101)+(B1.26), (Al-101)+(B1.27), (Al-101)+(B1.28), (Al-101)+(B1.29), (Al-101)+(B1.30), (Al-101)+(B1.31), (Al-101)+(B1.32), (Al-101)+(B1.33), (Al-101)+(B1.34), (Al-101)+(B1.35), (Al-101)+(B1.36), (Al-101)+(B1.37), (Al-101)+(B1.38), (Al-101)+(B1.39), (Al-101)+(B1.40), (Al-101)+(B1.41), (Al-101)+(B1.42), (Al-101)+(B1.43), (Al-101)+(B1.44), (Al-101)+(B1.45), (Al-101)+(B1.46), (Al-101)+(B1.47), (Al-101)+(B1.48), (Al-101)+(B1.49), (Al-101)+(B1.50), (Al-101)+(B1.51), (Al-101)+(B1.52), (Al-101)+(B1.53), (Al-101)+(B1.54), (Al-101)+(B1.55), (Al-101)+(B1.56), (Al-101)+(B1.57), (Al-101)+(B1.58), (Al-101)+(B1.59), (Al-101)+(B1.60), (Al-101)+(B1.61), (Al-101)+(B1.62), (Al-101)+(B1.63), (Al-101)+(B1.64), (Al-101)+(B1.65), (Al-101)+(B1.66), (Al-101)+(B2.1), (Al-101)+(B2.2), (Al-101)+(B2.3), (Al-101)+(B2.4), (Al-101)+(B2.5), (Al-101)+(B2.6), (Al-101)+(B2.7), (Al-101)+(B2.8), (Al-101)+(B2.9), (Al-101)+(B2.10), (Al-101)+(B2.11), (Al-101)+(B2.12), (Al-101)+(B2.13), (Al-101)+(B2.14), (Al-101)+(B2.15), (Al-101)+(B2.16), (Al-101)+(B2.17), (Al-101)+(B2.18), (Al-101)+(B2.19), (Al-101)+(B2.20), (Al-101)+(B2.21), (Al-101)+(B2.22), (Al-101)+(B2.23), (Al-101)+(B2.24), (Al-101)+(B2.25), (Al-101)+(B2.26), (Al-101)+(B2.27), (Al-101)+(B2.28), (Al-101)+(B2.29), (Al-101)+(B2.30), (Al-101)+(B2.31), (Al-101)+(B2.32), (Al-101)+(B2.33), (Al-101)+(B2.34), (Al-101)+(B2.35), (Al-101)+(B2.36), (Al-101)+(B2.37), (Al-101)+(B2.38), (Al-101)+(B2.39), (Al-101)+(B2.40), (Al-101)+(B2.41), (Al-101)+(B2.42), (Al-101)+(B2.43), (Al-101)+(B2.44), (Al-101)+(B2.45), (Al-101)+(B2.46), (Al-101)+(B2.47), (Al-101)+(B2.48), (Al-101)+(B2.49), (Al-101)+(B2.50), (Al-101)+(B3.1), (Al-101)+(B3.2.), (Al-101)+(B3.3), (Al-101)+(B3.4), (Al-101)+(B3.5), (Al-101)+(B3.6), (Al-101)+(B3.7), (Al-101)+(B3.8), (Al-101)+(B3.9), (Al-101)+(B3.10), (Al-101)+(B3.11), (Al-101)+(B3.12), (Al-101)+(B3.13), (Al-101)+(B3.14), (Al-101)+(B3.15), (Al-101)+(B3.16), (Al-101)+(B4.1), (Al-101)+(B4.2), (Al-101)+(B4.3), (Al-101)+(B4.4), (Al-101)+(B4.5), (Al-101)+(B4.6), (Al-101)+(B4.7).

(Al-102)+(B1.1), (Al-102)+(B1.2), (Al-102)+(B1.3), (Al-102)+(B1.4), (Al-102)+(B1.5), (Al-102)+(B1.6), (Al-102)+(B1.7), (Al-102)+(B1.8), (Al-102)+(B1.9), (Al-102)+(B1.10), (Al-102)+(B1.11), (Al-102)+(B1.12), (Al-102)+(B1.13), (Al-102)+(B1.14), (Al-102)+(B1.15), (Al-102)+(B1.16), (Al-102)+(B1.17), (Al-102)+(B1.18), (Al-102)+(B1.19), (Al-102)+(B1.20), (Al-102)+(B1.21), (Al-102)+(B1.22), (Al-102)+(B1.23), (Al-102)+(B1.24), (Al-102)+(B1.25), (Al-102)+(B1.26), (Al-102)+(B1.27), (Al-102)+(B1.28), (Al-102)+(B1.29), (Al-102)+(B1.30), (Al-102)+(B1.31), (Al-102)+(B1.32), (Al-102)+(B1.33), (Al-102)+(B1.34), (Al-102)+(B1.35), (Al-102)+(B1.36), (Al-102)+(B1.37), (Al-102)+(B1.38), (Al-102)+(B1.39), (Al-102)+(B1.40), (Al-102)+(B1.41), (Al-102)+(B1.42), (Al-102)+(B1.43), (Al-102)+(B1.44), (Al-102)+(B1.45), (Al-102)+(B1.46), (Al-102)+(B1.47), (Al-102)+(B1.48), (Al-102)+(B1.49), (Al-102)+(B1.50), (Al-102)+(B1.51), (Al-102)+(B1.52), (Al-102)+(B1.53), (Al-102)+(B1.54), (Al-102)+(B1.55), (Al-102)+(B1.56), (Al-102)+(B1.57), (Al-102)+(B1.58), (Al-102)+(B1.59), (Al-102)+(B1.60), (Al-102)+(B1.61), (Al-102)+(B1.62), (Al-102)+(B1.63), (Al-102)+(B1.64), (Al-102)+(B1.65), (Al-102)+(B1.66), (Al-102)+(B2.1), (Al-102)+(B2.2), (Al-102)+(B2.3), (Al-102)+(B2.4), (Al-102)+(B2.5), (Al-102)+(B2.6), (Al-102)+(B2.7), (Al-102)+(B2.8), (Al-102)+(B2.9), (Al-102)+(B2.10), (Al-102)+(B2.11), (Al-102)+(B2.12), (Al-102)+(B2.13), (Al-102)+(B2.14), (Al-102)+(B2.15), (Al-102)+(B2.16), (Al-102)+(B2.17), (Al-102)+(B2.18), (Al-102)+(B2.19), (Al-102)+(B2.20), (Al-102)+(B2.21), (Al-102)+(B2.22), (Al-102)+(B2.23), (Al-102)+(B2.24), (Al-102)+(B2.25), (Al-102)+

(B2.26), (Al-102)+(B2.27), (Al-102)+(B2.28), (Al-102)+(B2.29), (Al-102)+(B2.30), (Al-102)+(B2.31), (Al-102)+(B2.32), (Al-102)+(B2.33), (Al-102)+(B2.34), (Al-102)+(B2.35), (Al-102)+(B2.36), (Al-102)+(B2.37), (Al-102)+(B2.38), (Al-102)+(B2.39), (Al-102)+(B2.40), (Al-102)+(B2.41), (Al-102)+(B2.42), (Al-102)+(B2.43), (Al-102)+(B2.44), (Al-102)+(B2.45), (Al-102)+(B2.46), (Al-102)+(B2.47), (Al-102)+(B2.48), (Al-102)+(B2.49), (Al-102)+(B2.50), (Al-102)+(B3.1), (Al-102)+(B3.2.), (Al-102)+(B3.3), (Al-102)+(B3.4), (Al-102)+(B3.5), (Al-102)+(B3.6), (Al-102)+(B3.7), (Al-102)+(B3.8), (Al-102)+(B3.9), (Al-102)+(B3.10), (Al-102)+(B3.11), (Al-102)+(B3.12), (Al-102)+(B3.13), (Al-102)+(B3.14), (Al-102)+(B3.15), (Al-102)+(B3.16), (Al-102)+(B4.1), (Al-102)+(B4.2), (Al-102)+(B4.3), (Al-102)+(B4.4), (Al-102)+(B4.5), (Al-102)+(B4.6), (Al-102)+(B4.7).

(Al-103)+(B1.1), (Al-103)+(B1.2), (Al-103)+(B1.3), (Al-103)+(B1.4), (Al-103)+(B1.5), (Al-103)+(B1.6), (Al-103)+(B1.7), (Al-103)+(B1.8), (Al-103)+(B1.9), (Al-103)+(B1.10), (Al-103)+(B1.11), (Al-103)+(B1.12), (Al-103)+(B1.13), (Al-103)+(B1.14), (Al-103)+(B1.15), (Al-103)+(B1.16), (Al-103)+(B1.17), (Al-103)+(B1.18), (Al-103)+(B1.19), (Al-103)+(B1.20), (Al-103)+(B1.21), (Al-103)+(B1.22), (Al-103)+(B1.23), (Al-103)+(B1.24), (Al-103)+(B1.25), (Al-103)+(B1.26), (Al-103)+(B1.27), (Al-103)+(B1.28), (Al-103)+(B1.29), (Al-103)+(B1.30), (Al-103)+(B1.31), (Al-103)+(B1.32), (Al-103)+(B1.33), (Al-103)+(B1.34), (Al-103)+(B1.35), (Al-103)+(B1.36), (Al-103)+(B1.37), (Al-103)+(B1.38), (Al-103)+(B1.39), (Al-103)+(B1.40), (Al-103)+(B1.41), (Al-103)+(B1.42), (Al-103)+(B1.43), (Al-103)+(B1.44), (Al-103)+(B1.45), (Al-103)+(B1.46), (Al-103)+(B1.47), (Al-103)+(B1.48), (Al-103)+(B1.49), (Al-103)+(B1.50), (Al-103)+(B1.51), (Al-103)+(B1.52), (Al-103)+(B1.53), (Al-103)+(B1.54), (Al-103)+(B1.55), (Al-103)+(B1.56), (Al-103)+(B1.57), (Al-103)+(B1.58), (Al-103)+(B1.59), (Al-103)+(B1.60), (Al-103)+(B1.61), (Al-103)+(B1.62), (Al-103)+(B1.63), (Al-103)+(B1.64), (Al-103)+(B1.65), (Al-103)+(B1.66), (Al-103)+(B2.1), (Al-103)+(B2.2), (Al-103)+(B2.3), (Al-103)+(B2.4), (Al-103)+(B2.5), (Al-103)+(B2.6), (Al-103)+(B2.7), (Al-103)+(B2.8), (Al-103)+(B2.9), (Al-103)+(B2.10), (Al-103)+(B2.11), (Al-103)+(B2.12), (Al-103)+(B2.13), (Al-103)+(B2.14), (Al-103)+(B2.15), (Al-103)+(B2.16), (Al-103)+(B2.17), (Al-103)+(B2.18), (Al-103)+(B2.19), (Al-103)+(B2.20), (Al-103)+(B2.21), (Al-103)+(B2.22), (Al-103)+(B2.23), (Al-103)+(B2.24), (Al-103)+(B2.25), (Al-103)+(B2.26), (Al-103)+(B2.27), (Al-103)+(B2.28), (Al-103)+(B2.29), (Al-103)+(B2.30), (Al-103)+(B2.31), (Al-103)+(B2.32), (Al-103)+(B2.33), (Al-103)+(B2.34), (Al-103)+(B2.35), (Al-103)+(B2.36), (Al-103)+(B2.37), (Al-103)+(B2.38), (Al-103)+(B2.39), (Al-103)+(B2.40), (Al-103)+(B2.41), (Al-103)+(B2.42), (Al-103)+(B2.43), (Al-103)+(B2.44), (Al-103)+(B2.45), (Al-103)+(B2.46), (Al-103)+(B2.47), (Al-103)+(B2.48), (Al-103)+(B2.49), (Al-103)+(B2.50), (Al-103)+(B3.1), (Al-103)+(B3.2.), (Al-103)+(B3.3), (Al-103)+(B3.4), (Al-103)+(B3.5), (Al-103)+(B3.6), (Al-103)+(B3.7), (Al-103)+(B3.8), (Al-103)+(B3.9), (Al-103)+(B3.10), (Al-103)+(B3.11), (Al-103)+(B3.12), (Al-103)+(B3.13), (Al-103)+(B3.14), (Al-103)+(B3.15), (Al-103)+(B3.16), (Al-103)+(B4.1), (Al-103)+(B4.2), (Al-103)+(B4.3), (Al-103)+(B4.4), (Al-103)+(B4.5), (Al-103)+(B4.6), (Al-103)+(B4.7).

(Al-104)+(B1.1), (Al-104)+(B1.2), (Al-104)+(B1.3), (Al-104)+(B1.4), (Al-104)+(B1.5), (Al-104)+(B1.6), (Al-104)+(B1.7), (Al-104)+(B1.8), (Al-104)+(B1.9), (Al-104)+(B1.10), (Al-104)+(B1.11), (Al-104)+(B1.12), (Al-104)+(B1.13), (Al-104)+(B1.14), (Al-104)+(B1.15), (Al-104)+(B1.16), (Al-104)+(B1.17), (Al-104)+(B1.18), (Al-104)+(B1.19), (Al-104)+(B1.20), (Al-104)+(B1.21), (Al-104)+(B1.22), (Al-104)+(B1.23), (Al-104)+(B1.24), (Al-104)+(B1.25), (Al-104)+(B1.26), (Al-104)+(B1.27), (Al-104)+(B1.28), (Al-104)+(B1.29), (Al-104)+(B1.30), (Al-104)+(B1.31), (Al-104)+(B1.32), (Al-104)+(B1.33), (Al-104)+(B1.34), (Al-104)+(B1.35), (Al-104)+(B1.36), (Al-104)+(B1.37), (Al-104)+(B1.38), (Al-104)+(B1.39), (Al-104)+(B1.40), (Al-104)+(B1.41), (Al-104)+(B1.42), (Al-104)+(B1.43), (Al-104)+(B1.44), (Al-104)+(B1.45), (Al-104)+(B1.46), (Al-104)+(B1.47), (Al-104)+(B1.48), (Al-104)+(B1.49), (Al-104)+(B1.50), (Al-104)+(B1.51), (Al-104)+(B1.52), (Al-104)+(B1.53), (Al-104)+(B1.54), (Al-104)+(B1.55), (Al-104)+(B1.56), (Al-104)+(B1.57), (Al-104)+(B1.58), (Al-104)+(B1.59), (Al-104)+(B1.60), (Al-104)+(B1.61), (Al-104)+(B1.62), (Al-104)+(B1.63), (Al-104)+(B1.64), (Al-104)+(B1.65), (Al-104)+(B1.66), (Al-104)+(B2.1), (Al-104)+(B2.2), (Al-104)+(B2.3), (Al-104)+(B2.4), (Al-104)+(B2.5), (Al-104)+(B2.6), (Al-104)+(B2.7), (Al-104)+(B2.8), (Al-104)+(B2.9), (Al-104)+(B2.10), (Al-104)+(B2.11), (Al-104)+(B2.12), (Al-104)+(B2.13), (Al-104)+(B2.14), (Al-104)+(B2.15), (Al-104)+(B2.16), (Al-104)+(B2.17), (Al-104)+(B2.18), (Al-104)+(B2.19), (Al-104)+(B2.20), (Al-104)+(B2.21), (Al-104)+(B2.22), (Al-104)+(B2.23), (Al-104)+(B2.24), (Al-104)+(B2.25), (Al-104)+(B2.26), (Al-104)+(B2.27), (Al-104)+(B2.28), (Al-104)+(B2.29), (Al-104)+(B2.30), (Al-104)+(B2.31), (Al-104)+(B2.32), (Al-104)+(B2.33), (Al-104)+(B2.34), (Al-104)+(B2.35), (Al-104)+(B2.36), (Al-104)+(B2.37), (Al-104)+(B2.38), (Al-104)+(B2.39), (Al-104)+(B2.40), (Al-104)+(B2.41), (Al-104)+(B2.42), (Al-104)+(B2.43), (Al-104)+(B2.44), (Al-104)+(B2.45), (Al-104)+(B2.46), (Al-104)+(B2.47), (Al-104)+(B2.48), (Al-104)+(B2.49), (Al-104)+(B2.50), (Al-104)+(B3.1), (Al-104)+(B3.2.), (Al-104)+(B3.3), (Al-104)+(B3.4), (Al-104)+(B3.5), (Al-104)+(B3.6), (Al-104)+(B3.7), (Al-104)+(B3.8), (Al-104)+(B3.9), (Al-104)+(B3.10), (Al-104)+(B3.11), (Al-104)+(B3.12), (Al-104)+(B3.13), (Al-104)+(B3.14), (Al-104)+(B3.15), (Al-104)+(B3.16), (Al-104)+(B4.1), (Al-104)+(B4.2), (Al-104)+(B4.3), (Al-104)+(B4.4), (Al-104)+(B4.5), (Al-104)+(B4.6), (Al-104)+(B4.7).

(Al-105)+(B1.1), (Al-105)+(B1.2), (Al-105)+(B1.3), (Al-105)+(B1.4), (Al-105)+(B1.5), (Al-105)+(B1.6), (Al-105)+(B1.7), (Al-105)+(B1.8), (Al-105)+(B1.9), (Al-105)+(B1.10), (Al-105)+(B1.11), (Al-105)+(B1.12), (Al-105)+(B1.13), (Al-105)+(B1.14), (Al-105)+(B1.15), (Al-105)+(B1.16), (Al-105)+(B1.17), (Al-105)+(B1.18), (Al-105)+(B1.19), (Al-105)+(B1.20), (Al-105)+(B1.21), (Al-105)+(B1.22), (Al-105)+(B1.23), (Al-105)+(B1.24), (Al-105)+(B1.25), (Al-105)+(B1.26), (Al-105)+(B1.27), (Al-105)+(B1.28), (Al-105)+(B1.29), (Al-105)+(B1.30), (Al-105)+(B1.31), (Al-105)+(B1.32), (Al-105)+(B1.33), (Al-105)+(B1.34), (Al-105)+(B1.35), (Al-105)+(B1.36), (Al-105)+(B1.37), (Al-105)+(B1.38), (Al-105)+(B1.39), (Al-105)+(B1.40), (Al-105)+(B1.41), (Al-105)+(B1.42), (Al-105)+(B1.43), (Al-105)+(B1.44), (Al-105)+(B1.45), (Al-105)+(B1.46), (Al-105)+(B1.47), (Al-105)+(B1.48), (Al-105)+(B1.49), (Al-105)+(B1.50), (Al-105)+(B1.51), (Al-105)+(B1.52), (Al-105)+(B1.53), (Al-105)+(B1.54), (Al-105)+(B1.55), (Al-105)+(B1.56), (Al-105)+(B1.57), (Al-105)+(B1.58), (Al-105)+(B1.59), (Al-105)+(B1.60), (Al-105)+(B1.61), (Al-105)+(B1.62), (Al-105)+(B1.63), (Al-105)+(B1.64), (Al-105)+(B1.65), (Al-105)+(B1.66), (Al-105)+(B2.1), (Al-105)+(B2.2), (Al-105)+(B2.3), (Al-105)+(B2.4), (Al-105)+(B2.5), (Al-105)+(B2.6), (Al-105)+(B2.7), (Al-105)+(B2.8), (Al-105)+(B2.9), (Al-105)+(B2.10), (Al-105)+(B2.11), (Al-105)+(B2.12), (Al-105)+(B2.13), (Al-105)+

(B2.14), (Al-105)+(B2.15), (Al-105)+(B2.16), (Al-105)+(B2.17), (Al-105)+(B2.18), (Al-105)+(B2.19), (Al-105)+(B2.20), (Al-105)+(B2.21), (Al-105)+(B2.22), (Al-105)+(B2.23), (Al-105)+(B2.24), (Al-105)+(B2.25), (Al-105)+(B2.26), (Al-105)+(B2.27), (Al-105)+(B2.28), (Al-105)+(B2.29), (Al-105)+(B2.30), (Al-105)+(B2.31), (Al-105)+(B2.32), (Al-105)+(B2.33), (Al-105)+(B2.34), (Al-105)+(B2.35), (Al-105)+(B2.36), (Al-105)+(B2.37), (Al-105)+(B2.38), (Al-105)+(B2.39), (Al-105)+(B2.40), (Al-105)+(B2.41), (Al-105)+(B2.42), (Al-105)+(B2.43), (Al-105)+(B2.44), (Al-105)+(B2.45), (Al-105)+(B2.46), (Al-105)+(B2.47), (Al-105)+(B2.48), (Al-105)+(B2.49), (Al-105)+(B2.50), (Al-105)+(B3.1), (Al-105)+(B3.2.), (Al-105)+(B3.3), (Al-105)+(B3.4), (Al-105)+(B3.5), (Al-105)+(B3.6), (Al-105)+(B3.7), (Al-105)+(B3.8), (Al-105)+(B3.9), (Al-105)+(B3.10), (Al-105)+(B3.11), (Al-105)+(B3.12), (Al-105)+(B3.13), (Al-105)+(B3.14), (Al-105)+(B3.15), (Al-105)+(B3.16), (Al-105)+(B4.1), (Al-105)+(B4.2), (Al-105)+(B4.3), (Al-105)+(B4.4), (Al-105)+(B4.5), (Al-105)+(B4.6), (Al-105)+(B4.7).

(Al-106)+(B1.1), (Al-106)+(B1.2), (Al-106)+(B1.3), (Al-106)+(B1.4), (Al-106)+(B1.5), (Al-106)+(B1.6), (Al-106)+(B1.7), (Al-106)+(B1.8), (Al-106)+(B1.9), (Al-106)+(B1.10), (Al-106)+(B1.11), (Al-106)+(B1.12), (Al-106)+(B1.13), (Al-106)+(B1.14), (Al-106)+(B1.15), (Al-106)+(B1.16), (Al-106)+(B1.17), (Al-106)+(B1.18), (Al-106)+(B1.19), (Al-106)+(B1.20), (Al-106)+(B1.21), (Al-106)+(B1.22), (Al-106)+(B1.23), (Al-106)+(B1.24), (Al-106)+(B1.25), (Al-106)+(B1.26), (Al-106)+(B1.27), (Al-106)+(B1.28), (Al-106)+(B1.29), (Al-106)+(B1.30), (Al-106)+(B1.31), (Al-106)+(B1.32), (Al-106)+(B1.33), (Al-106)+(B1.34), (Al-106)+(B1.35), (Al-106)+(B1.36), (Al-106)+(B1.37), (Al-106)+(B1.38), (Al-106)+(B1.39), (Al-106)+(B1.40), (Al-106)+(B1.41), (Al-106)+(B1.42), (Al-106)+(B1.43), (Al-106)+(B1.44), (Al-106)+(B1.45), (Al-106)+(B1.46), (Al-106)+(B1.47), (Al-106)+(B1.48), (Al-106)+(B1.49), (Al-106)+(B1.50), (Al-106)+(B1.51), (Al-106)+(B1.52), (Al-106)+(B1.53), (Al-106)+(B1.54), (Al-106)+(B1.55), (Al-106)+(B1.56), (Al-106)+(B1.57), (Al-106)+(B1.58), (Al-106)+(B1.59), (Al-106)+(B1.60), (Al-106)+(B1.61), (Al-106)+(B1.62), (Al-106)+(B1.63), (Al-106)+(B1.64), (Al-106)+(B1.65), (Al-106)+(B1.66), (Al-106)+(B2.1), (Al-106)+(B2.2), (Al-106)+(B2.3), (Al-106)+(B2.4), (Al-106)+(B2.5), (Al-106)+(B2.6), (Al-106)+(B2.7), (Al-106)+(B2.8), (Al-106)+(B2.9), (Al-106)+(B2.10), (Al-106)+(B2.11), (Al-106)+(B2.12), (Al-106)+(B2.13), (Al-106)+(B2.14), (Al-106)+(B2.15), (Al-106)+(B2.16), (Al-106)+(B2.17), (Al-106)+(B2.18), (Al-106)+(B2.19), (Al-106)+(B2.20), (Al-106)+(B2.21), (Al-106)+(B2.22), (Al-106)+(B2.23), (Al-106)+(B2.24), (Al-106)+(B2.25), (Al-106)+(B2.26), (Al-106)+(B2.27), (Al-106)+(B2.28), (Al-106)+(B2.29), (Al-106)+(B2.30), (Al-106)+(B2.31), (Al-106)+(B2.32), (Al-106)+(B2.33), (Al-106)+(B2.34), (Al-106)+(B2.35), (Al-106)+(B2.36), (Al-106)+(B2.37), (Al-106)+(B2.38), (Al-106)+(B2.39), (Al-106)+(B2.40), (Al-106)+(B2.41), (Al-106)+(B2.42), (Al-106)+(B2.43), (Al-106)+(B2.44), (Al-106)+(B2.45), (Al-106)+(B2.46), (Al-106)+(B2.47), (Al-106)+(B2.48), (Al-106)+(B2.49), (Al-106)+(B2.50), (Al-106)+(B3.1), (Al-106)+(B3.2.), (Al-106)+(B3.3), (Al-106)+(B3.4), (Al-106)+(B3.5), (Al-106)+(B3.6), (Al-106)+(B3.7), (Al-106)+(B3.8), (Al-106)+(B3.9), (Al-106)+(B3.10), (Al-106)+(B3.11), (Al-106)+(B3.12), (Al-106)+(B3.13), (Al-106)+(B3.14), (Al-106)+(B3.15), (Al-106)+(B3.16), (Al-106)+(B4.1), (Al-106)+(B4.2), (Al-106)+(B4.3), (Al-106)+(B4.4), (Al-106)+(B4.5), (Al-106)+(B4.6), (Al-106)+(B4.7).

(Al-107)+(B1.1), (Al-107)+(B1.2), (Al-107)+(B1.3), (Al-107)+(B1.4), (Al-107)+(B1.5), (Al-107)+(B1.6), (Al-107)+(B1.7), (Al-107)+(B1.8), (Al-107)+(B1.9), (Al-107)+(B1.10), (Al-107)+(B1.11), (Al-107)+(B1.12), (Al-107)+(B1.13), (Al-107)+(B1.14), (Al-107)+(B1.15), (Al-107)+(B1.16), (Al-107)+(B1.17), (Al-107)+(B1.18), (Al-107)+(B1.19), (Al-107)+(B1.20), (Al-107)+(B1.21), (Al-107)+(B1.22), (Al-107)+(B1.23), (Al-107)+(B1.24), (Al-107)+(B1.25), (Al-107)+(B1.26), (Al-107)+(B1.27), (Al-107)+(B1.28), (Al-107)+(B1.29), (Al-107)+(B1.30), (Al-107)+(B1.31), (Al-107)+(B1.32), (Al-107)+(B1.33), (Al-107)+(B1.34), (Al-107)+(B1.35), (Al-107)+(B1.36), (Al-107)+(B1.37), (Al-107)+(B1.38), (Al-107)+(B1.39), (Al-107)+(B1.40), (Al-107)+(B1.41), (Al-107)+(B1.42), (Al-107)+(B1.43), (Al-107)+(B1.44), (Al-107)+(B1.45), (Al-107)+(B1.46), (Al-107)+(B1.47), (Al-107)+(B1.48), (Al-107)+(B1.49), (Al-107)+(B1.50), (Al-107)+(B1.51), (Al-107)+(B1.52), (Al-107)+(B1.53), (Al-107)+(B1.54), (Al-107)+(B1.55), (Al-107)+(B1.56), (Al-107)+(B1.57), (Al-107)+(B1.58), (Al-107)+(B1.59), (Al-107)+(B1.60), (Al-107)+(B1.61), (Al-107)+(B1.62), (Al-107)+(B1.63), (Al-107)+(B1.64), (Al-107)+(B1.65), (Al-107)+(B1.66), (Al-107)+(B2.1), (Al-107)+(B2.2), (Al-107)+(B2.3), (Al-107)+(B2.4), (Al-107)+(B2.5), (Al-107)+(B2.6), (Al-107)+(B2.7), (Al-107)+(B2.8), (Al-107)+(B2.9), (Al-107)+(B2.10), (Al-107)+(B2.11), (Al-107)+(B2.12), (Al-107)+(B2.13), (Al-107)+(B2.14), (Al-107)+(B2.15), (Al-107)+(B2.16), (Al-107)+(B2.17), (Al-107)+(B2.18), (Al-107)+(B2.19), (Al-107)+(B2.20), (Al-107)+(B2.21), (Al-107)+(B2.22), (Al-107)+(B2.23), (Al-107)+(B2.24), (Al-107)+(B2.25), (Al-107)+(B2.26), (Al-107)+(B2.27), (Al-107)+(B2.28), (Al-107)+(B2.29), (Al-107)+(B2.30), (Al-107)+(B2.31), (Al-107)+(B2.32), (Al-107)+(B2.33), (Al-107)+(B2.34), (Al-107)+(B2.35), (Al-107)+(B2.36), (Al-107)+(B2.37), (Al-107)+(B2.38), (Al-107)+(B2.39), (Al-107)+(B2.40), (Al-107)+(B2.41), (Al-107)+(B2.42), (Al-107)+(B2.43), (Al-107)+(B2.44), (Al-107)+(B2.45), (Al-107)+(B2.46), (Al-107)+(B2.47), (Al-107)+(B2.48), (Al-107)+(B2.49), (Al-107)+(B2.50), (Al-107)+(B3.1), (Al-107)+(B3.2.), (Al-107)+(B3.3), (Al-107)+(B3.4), (Al-107)+(B3.5), (Al-107)+(B3.6), (Al-107)+(B3.7), (Al-107)+(B3.8), (Al-107)+(B3.9), (Al-107)+(B3.10), (Al-107)+(B3.11), (Al-107)+(B3.12), (Al-107)+(B3.13), (Al-107)+(B3.14), (Al-107)+(B3.15), (Al-107)+(B3.16), (Al-107)+(B4.1), (Al-107)+(B4.2), (Al-107)+(B4.3), (Al-107)+(B4.4), (Al-107)+(B4.5), (Al-107)+(B4.6), (Al-107)+(B4.7).

(Al-108)+(B1.1), (Al-108)+(B1.2), (Al-108)+(B1.3), (Al-108)+(B1.4), (Al-108)+(B1.5), (Al-108)+(B1.6), (Al-108)+(B1.7), (Al-108)+(B1.8), (Al-108)+(B1.9), (Al-108)+(B1.10), (Al-108)+(B1.11), (Al-108)+(B1.12), (Al-108)+(B1.13), (Al-108)+(B1.14), (Al-108)+(B1.15), (Al-108)+(B1.16), (Al-108)+(B1.17), (Al-108)+(B1.18), (Al-108)+(B1.19), (Al-108)+(B1.20), (Al-108)+(B1.21), (Al-108)+(B1.22), (Al-108)+(B1.23), (Al-108)+(B1.24), (Al-108)+(B1.25), (Al-108)+(B1.26), (Al-108)+(B1.27), (Al-108)+(B1.28), (Al-108)+(B1.29), (Al-108)+(B1.30), (Al-108)+(B1.31), (Al-108)+(B1.32), (Al-108)+(B1.33), (Al-108)+(B1.34), (Al-108)+(B1.35), (Al-108)+(B1.36), (Al-108)+(B1.37), (Al-108)+(B1.38), (Al-108)+(B1.39), (Al-108)+(B1.40), (Al-108)+(B1.41), (Al-108)+(B1.42), (Al-108)+(B1.43), (Al-108)+(B1.44), (Al-108)+(B1.45), (Al-108)+(B1.46), (Al-108)+(B1.47), (Al-108)+(B1.48), (Al-108)+(B1.49), (Al-108)+(B1.50), (Al-108)+(B1.51), (Al-108)+(B1.52), (Al-108)+(B1.53), (Al-108)+(B1.54), (Al-108)+(B1.55), (Al-108)+(B1.56), (Al-108)+(B1.57), (Al-108)+(B1.58), (Al-108)+(B1.59), (Al-108)+(B1.60), (Al-108)+(B1.61), (Al-108)+(B1.62), (Al-108)+(B1.63), (Al-108)+

(B1.64), (Al-108)+(B1.65), (Al-108)+(B1.66), (Al-108)+ (B2.1), (Al-108)+(B2.2), (Al-108)+(B2.3), (Al-108)+(B2.4), (Al-108)+(B2.5), (Al-108)+(B2.6), (Al-108)+(B2.7), (Al-108)+(B2.8), (Al-108)+(B2.9), (Al-108)+(B2.10), (Al-108)+(B2.11), (Al-108)+(B2.12), (Al-108)+(B2.13), (Al-108)+(B2.14), (Al-108)+(B2.15), (Al-108)+(B2.16), (Al-108)+(B2.17), (Al-108)+(B2.18), (Al-108)+(B2.19), (Al-108)+(B2.20), (Al-108)+(B2.21), (Al-108)+(B2.22), (Al-108)+(B2.23), (Al-108)+(B2.24), (Al-108)+(B2.25), (Al-108)+(B2.26), (Al-108)+(B2.27), (Al-108)+(B2.28), (Al-108)+(B2.29), (Al-108)+(B2.30), (Al-108)+(B2.31), (Al-108)+(B2.32), (Al-108)+(B2.33), (Al-108)+(B2.34), (Al-108)+(B2.35), (Al-108)+(B2.36), (Al-108)+(B2.37), (Al-108)+(B2.38), (Al-108)+(B2.39), (Al-108)+(B2.40), (Al-108)+(B2.41), (Al-108)+(B2.42), (Al-108)+(B2.43), (Al-108)+(B2.44), (Al-108)+(B2.45), (Al-108)+(B2.46), (Al-108)+(B2.47), (Al-108)+(B2.48), (Al-108)+(B2.49), (Al-108)+(B2.50), (Al-108)+(B3.1), (Al-108)+(B3.2.), (Al-108)+(B3.3), (Al-108)+(B3.4), (Al-108)+(B3.5), (Al-108)+(B3.6), (Al-108)+(B3.7), (Al-108)+(B3.8), (Al-108)+(B3.9), (Al-108)+(B3.10), (Al-108)+(B3.11), (Al-108)+(B3.12), (Al-108)+(B3.13), (Al-108)+(B3.14), (Al-108)+(B3.15), (Al-108)+(B3.16), (Al-108)+(B4.1), (Al-108)+(B4.2), (Al-108)+(B4.3), (Al-108)+(B4.4), (Al-108)+(B4.5), (Al-108)+(B4.6), (Al-108)+(B4.7).

(Al-109)+(B1.1), (Al-109)+(B1.2), (Al-109)+(B1.3), (Al-109)+(B1.4), (Al-109)+(B1.5), (Al-109)+(B1.6), (Al-109)+(B1.7), (Al-109)+(B1.8), (Al-109)+(B1.9), (Al-109)+(B1.10), (Al-109)+(B1.11), (Al-109)+(B1.12), (Al-109)+(B1.13), (Al-109)+(B1.14), (Al-109)+(B1.15), (Al-109)+(B1.16), (Al-109)+(B1.17), (Al-109)+(B1.18), (Al-109)+(B1.19), (Al-109)+(B1.20), (Al-109)+(B1.21), (Al-109)+(B1.22), (Al-109)+(B1.23), (Al-109)+(B1.24), (Al-109)+(B1.25), (Al-109)+(B1.26), (Al-109)+(B1.27), (Al-109)+(B1.28), (Al-109)+(B1.29), (Al-109)+(B1.30), (Al-109)+(B1.31), (Al-109)+(B1.32), (Al-109)+(B1.33), (Al-109)+(B1.34), (Al-109)+(B1.35), (Al-109)+(B1.36), (Al-109)+(B1.37), (Al-109)+(B1.38), (Al-109)+(B1.39), (Al-109)+(B1.40), (Al-109)+(B1.41), (Al-109)+(B1.42), (Al-109)+(B1.43), (Al-109)+(B1.44), (Al-109)+(B1.45), (Al-109)+(B1.46), (Al-109)+(B1.47), (Al-109)+(B1.48), (Al-109)+(B1.49), (Al-109)+(B1.50), (Al-109)+(B1.51), (Al-109)+(B1.52), (Al-109)+(B1.53), (Al-109)+(B1.54), (Al-109)+(B1.55), (Al-109)+(B1.56), (Al-109)+(B1.57), (Al-109)+(B1.58), (Al-109)+(B1.59), (Al-109)+(B1.60), (Al-109)+(B1.61), (Al-109)+(B1.62), (Al-109)+(B1.63), (Al-109)+(B1.64), (Al-109)+(B1.65), (Al-109)+(B1.66), (Al-109)+(B2.1), (Al-109)+(B2.2), (Al-109)+(B2.3), (Al-109)+(B2.4), (Al-109)+(B2.5), (Al-109)+(B2.6), (Al-109)+(B2.7), (Al-109)+(B2.8), (Al-109)+(B2.9), (Al-109)+(B2.10), (Al-109)+(B2.11), (Al-109)+(B2.12), (Al-109)+(B2.13), (Al-109)+(B2.14), (Al-109)+(B2.15), (Al-109)+(B2.16), (Al-109)+(B2.17), (Al-109)+(B2.18), (Al-109)+(B2.19), (Al-109)+(B2.20), (Al-109)+(B2.21), (Al-109)+(B2.22), (Al-109)+(B2.23), (Al-109)+(B2.24), (Al-109)+(B2.25), (Al-109)+(B2.26), (Al-109)+(B2.27), (Al-109)+(B2.28), (Al-109)+(B2.29), (Al-109)+(B2.30), (Al-109)+(B2.31), (Al-109)+(B2.32), (Al-109)+(B2.33), (Al-109)+(B2.34), (Al-109)+(B2.35), (Al-109)+(B2.36), (Al-109)+(B2.37), (Al-109)+(B2.38), (Al-109)+(B2.39), (Al-109)+(B2.40), (Al-109)+(B2.41), (Al-109)+(B2.42), (Al-109)+(B2.43), (Al-109)+(B2.44), (Al-109)+(B2.45), (Al-109)+(B2.46), (Al-109)+(B2.47), (Al-109)+(B2.48), (Al-109)+(B2.49), (Al-109)+(B2.50), (Al-109)+(B3.1), (Al-109)+(B3.2.), (Al-109)+(B3.3), (Al-109)+(B3.4), (Al-109)+(B3.5), (Al-109)+(B3.6), (Al-109)+(B3.7), (Al-109)+(B3.8), (Al-109)+(B3.9), (Al-109)+(B3.10), (Al-109)+(B3.11), (Al-109)+(B3.12), (Al-109)+(B3.13), (Al-109)+(B3.14), (Al-109)+(B3.15), (Al-109)+(B3.16), (Al-109)+(B4.1), (Al-109)+(B4.2), (Al-109)+(B4.3), (Al-109)+(B4.4), (Al-109)+(B4.5), (Al-109)+(B4.6), (Al-109)+(B4.7).

(Al-110)+(B1.1), (Al-110)+(B1.2), (Al-110)+(B1.3), (Al-110)+(B1.4), (Al-110)+(B1.5), (Al-110)+(B1.6), (Al-110)+(B1.7), (Al-110)+(B1.8), (Al-110)+(B1.9), (Al-110)+(B1.10), (Al-110)+(B1.11), (Al-110)+(B1.12), (Al-110)+(B1.13), (Al-110)+(B1.14), (Al-110)+(B1.15), (Al-110)+(B1.16), (Al-110)+(B1.17), (Al-110)+(B1.18), (Al-110)+(B1.19), (Al-110)+(B1.20), (Al-110)+(B1.21), (Al-110)+(B1.22), (Al-110)+(B1.23), (Al-110)+(B1.24), (Al-110)+(B1.25), (Al-110)+(B1.26), (Al-110)+(B1.27), (Al-110)+(B1.28), (Al-110)+(B1.29), (Al-110)+(B1.30), (Al-110)+(B1.31), (Al-110)+(B1.32), (Al-110)+(B1.33), (Al-110)+(B1.34), (Al-110)+(B1.35), (Al-110)+(B1.36), (Al-110)+(B1.37), (Al-110)+(B1.38), (Al-110)+(B1.39), (Al-110)+(B1.40), (Al-110)+(B1.41), (Al-110)+(B1.42), (Al-110)+(B1.43), (Al-110)+(B1.44), (Al-110)+(B1.45), (Al-110)+(B1.46), (Al-110)+(B1.47), (Al-110)+(B1.48), (Al-110)+(B1.49), (Al-110)+(B1.50), (Al-110)+(B1.51), (Al-110)+(B1.52), (Al-110)+(B1.53), (Al-110)+(B1.54), (Al-110)+(B1.55), (Al-110)+(B1.56), (Al-110)+(B1.57), (Al-110)+(B1.58), (Al-110)+(B1.59), (Al-110)+(B1.60), (Al-110)+(B1.61), (Al-110)+(B1.62), (Al-110)+(B1.63), (Al-110)+(B1.64), (Al-110)+(B1.65), (Al-110)+(B1.66), (Al-110)+(B2.1), (Al-110)+(B2.2), (Al-110)+(B2.3), (Al-110)+(B2.4), (Al-110)+(B2.5), (Al-110)+(B2.6), (Al-110)+(B2.7), (Al-110)+(B2.8), (Al-110)+(B2.9), (Al-110)+(B2.10), (Al-110)+(B2.11), (Al-110)+(B2.12), (Al-110)+(B2.13), (Al-110)+(B2.14), (Al-110)+(B2.15), (Al-110)+(B2.16), (Al-110)+(B2.17), (Al-110)+(B2.18), (Al-110)+(B2.19), (Al-110)+(B2.20), (Al-110)+(B2.21), (Al-110)+(B2.22), (Al-110)+(B2.23), (Al-110)+(B2.24), (Al-110)+(B2.25), (Al-110)+(B2.26), (Al-110)+(B2.27), (Al-110)+(B2.28), (Al-110)+(B2.29), (Al-110)+(B2.30), (Al-110)+(B2.31), (Al-110)+(B2.32), (Al-110)+(B2.33), (Al-110)+(B2.34), (Al-110)+(B2.35), (Al-110)+(B2.36), (Al-110)+(B2.37), (Al-110)+(B2.38), (Al-110)+(B2.39), (Al-110)+(B2.40), (Al-110)+(B2.41), (Al-110)+(B2.42), (Al-110)+(B2.43), (Al-110)+(B2.44), (Al-110)+(B2.45), (Al-110)+(B2.46), (Al-110)+(B2.47), (Al-110)+(B2.48), (Al-110)+(B2.49), (Al-110)+(B2.50), (Al-110)+(B3.1), (Al-110)+(B3.2.), (Al-110)+(B3.3), (Al-110)+(B3.4), (Al-110)+(B3.5), (Al-110)+(B3.6), (Al-110)+(B3.7), (Al-110)+(B3.8), (Al-110)+(B3.9), (Al-110)+(B3.10), (Al-110)+(B3.11), (Al-110)+(B3.12), (Al-110)+(B3.13), (Al-110)+(B3.14), (Al-110)+(B3.15), (Al-110)+(B3.16), (Al-110)+(B4.1), (Al-110)+(B4.2), (Al-110)+(B4.3), (Al-110)+(B4.4), (Al-110)+(B4.5), (Al-110)+(B4.6), (Al-110)+(B4.7).

(Al-111)+(B1.1), (Al-111)+(B1.2), (Al-111)+(B1.3), (Al-111)+(B1.4), (Al-111)+(B1.5), (Al-111)+(B1.6), (Al-111)+(B1.7), (Al-111)+(B1.8), (Al-111)+(B1.9), (Al-111)+(B1.10), (Al-111)+(B1.11), (Al-111)+(B1.12), (Al-111)+(B1.13), (Al-111)+(B1.14), (Al-111)+(B1.15), (Al-111)+(B1.16), (Al-111)+(B1.17), (Al-111)+(B1.18), (Al-111)+(B1.19), (Al-111)+(B1.20), (Al-111)+(B1.21), (Al-111)+(B1.22), (Al-111)+(B1.23), (Al-111)+(B1.24), (Al-111)+(B1.25), (Al-111)+(B1.26), (Al-111)+(B1.27), (Al-111)+(B1.28), (Al-111)+(B1.29), (Al-111)+(B1.30), (Al-111)+(B1.31), (Al-111)+(B1.32), (Al-111)+(B1.33), (Al-111)+(B1.34), (Al-111)+(B1.35), (Al-111)+(B1.36), (Al-111)+(B1.37), (Al-111)+(B1.38), (Al-111)+(B1.39), (Al-111)+(B1.40), (Al-111)+(B1.41), (Al-111)+(B1.42), (Al-111)+(B1.43), (Al-111)+(B1.44), (Al-111)+(B1.45), (Al-111)+(B1.46), (Al-111)+(B1.47), (Al-111)+(B1.48), (Al-111)+(B1.49), (Al-111)+(B1.50), (Al-111)+(B1.51), (Al-111)+

(B1.52), (Al-111)+(B1.53), (Al-111)+(B1.54), (Al-111)+(B1.55), (Al-111)+(B1.56), (Al-111)+(B1.57), (Al-111)+(B1.58), (Al-111)+(B1.59), (Al-111)+(B1.60), (Al-111)+(B1.61), (Al-111)+(B1.62), (Al-111)+(B1.63), (Al-111)+(B1.64), (Al-111)+(B1.65), (Al-111)+(B1.66), (Al-111)+(B2.1), (Al-111)+(B2.2), (Al-111)+(B2.3), (Al-111)+(B2.4), (Al-111)+(B2.5), (Al-111)+(B2.6), (Al-111)+(B2.7), (Al-111)+(B2.8), (Al-111)+(B2.9), (Al-111)+(B2.10), (Al-111)+(B2.11), (Al-111)+(B2.12), (Al-111)+(B2.13), (Al-111)+(B2.14), (Al-111)+(B2.15), (Al-111)+(B2.16), (Al-111)+(B2.17), (Al-111)+(B2.18), (Al-111)+(B2.19), (Al-111)+(B2.20), (Al-111)+(B2.21), (Al-111)+(B2.22), (Al-111)+(B2.23), (Al-111)+(B2.24), (Al-111)+(B2.25), (Al-111)+(B2.26), (Al-111)+(B2.27), (Al-111)+(B2.28), (Al-111)+(B2.29), (Al-111)+(B2.30), (Al-111)+(B2.31), (Al-111)+(B2.32), (Al-111)+(B2.33), (Al-111)+(B2.34), (Al-111)+(B2.35), (Al-111)+(B2.36), (Al-111)+(B2.37), (Al-111)+(B2.38), (Al-111)+(B2.39), (Al-111)+(B2.40), (Al-111)+(B2.41), (Al-111)+(B2.42), (Al-111)+(B2.43), (Al-111)+(B2.44), (Al-111)+(B2.45), (Al-111)+(B2.46), (Al-111)+(B2.47), (Al-111)+(B2.48), (Al-111)+(B2.49), (Al-111)+(B2.50), (Al-111)+(B3.1), (Al-111)+(B3.2.), (Al-111)+(B3.3), (Al-111)+(B3.4), (Al-111)+(B3.5), (Al-111)+(B3.6), (Al-111)+(B3.7), (Al-111)+(B3.8), (Al-111)+(B3.9), (Al-111)+(B3.10), (Al-111)+(B3.11), (Al-111)+(B3.12), (Al-111)+(B3.13), (Al-111)+(B3.14), (Al-111)+(B3.15), (Al-111)+(B3.16), (Al-111)+(B4.1), (Al-111)+(B4.2), (Al-111)+(B4.3), (Al-111)+(B4.4), (Al-111)+(B4.5), (Al-111)+(B4.6), (Al-111)+(B4.7).

(Al-112)+(B1.1), (Al-112)+(B1.2), (Al-112)+(B1.3), (Al-112)+(B1.4), (Al-112)+(B1.5), (Al-112)+(B1.6), (Al-112)+(B1.7), (Al-112)+(B1.8), (Al-112)+(B1.9), (Al-112)+(B1.10), (Al-112)+(B1.11), (Al-112)+(B1.12), (Al-112)+(B1.13), (Al-112)+(B1.14), (Al-112)+(B1.15), (Al-112)+(B1.16), (Al-112)+(B1.17), (Al-112)+(B1.18), (Al-112)+(B1.19), (Al-112)+(B1.20), (Al-112)+(B1.21), (Al-112)+(B1.22), (Al-112)+(B1.23), (Al-112)+(B1.24), (Al-112)+(B1.25), (Al-112)+(B1.26), (Al-112)+(B1.27), (Al-112)+(B1.28), (Al-112)+(B1.29), (Al-112)+(B1.30), (Al-112)+(B1.31), (Al-112)+(B1.32), (Al-112)+(B1.33), (Al-112)+(B1.34), (Al-112)+(B1.35), (Al-112)+(B1.36), (Al-112)+(B1.37), (Al-112)+(B1.38), (Al-112)+(B1.39), (Al-112)+(B1.40), (Al-112)+(B1.41), (Al-112)+(B1.42), (Al-112)+(B1.43), (Al-112)+(B1.44), (Al-112)+(B1.45), (Al-112)+(B1.46), (Al-112)+(B1.47), (Al-112)+(B1.48), (Al-112)+(B1.49), (Al-112)+(B1.50), (Al-112)+(B1.51), (Al-112)+(B1.52), (Al-112)+(B1.53), (Al-112)+(B1.54), (Al-112)+(B1.55), (Al-112)+(B1.56), (Al-112)+(B1.57), (Al-112)+(B1.58), (Al-112)+(B1.59), (Al-112)+(B1.60), (Al-112)+(B1.61), (Al-112)+(B1.62), (Al-112)+(B1.63), (Al-112)+(B1.64), (Al-112)+(B1.65), (Al-112)+(B1.66), (Al-112)+(B2.1), (Al-112)+(B2.2), (Al-112)+(B2.3), (Al-112)+(B2.4), (Al-112)+(B2.5), (Al-112)+(B2.6), (Al-112)+(B2.7), (Al-112)+(B2.8), (Al-112)+(B2.9), (Al-112)+(B2.10), (Al-112)+(B2.11), (Al-112)+(B2.12), (Al-112)+(B2.13), (Al-112)+(B2.14), (Al-112)+(B2.15), (Al-112)+(B2.16), (Al-112)+(B2.17), (Al-112)+(B2.18), (Al-112)+(B2.19), (Al-112)+(B2.20), (Al-112)+(B2.21), (Al-112)+(B2.22), (Al-112)+(B2.23), (Al-112)+(B2.24), (Al-112)+(B2.25), (Al-112)+(B2.26), (Al-112)+(B2.27), (Al-112)+(B2.28), (Al-112)+(B2.29), (Al-112)+(B2.30), (Al-112)+(B2.31), (Al-112)+(B2.32), (Al-112)+(B2.33), (Al-112)+(B2.34), (Al-112)+(B2.35), (Al-112)+(B2.36), (Al-112)+(B2.37), (Al-112)+(B2.38), (Al-112)+(B2.39), (Al-112)+(B2.40), (Al-112)+(B2.41), (Al-112)+(B2.42), (Al-112)+(B2.43), (Al-112)+(B2.44), (Al-112)+(B2.45), (Al-112)+(B2.46), (Al-112)+(B2.47), (Al-112)+(B2.48), (Al-112)+(B2.49), (Al-112)+(B2.50), (Al-112)+(B3.1), (Al-112)+(B3.2.), (Al-112)+(B3.3), (Al-112)+(B3.4), (Al-112)+(B3.5), (Al-112)+(B3.6), (Al-112)+(B3.7), (Al-112)+(B3.8), (Al-112)+(B3.9), (Al-112)+(B3.10), (Al-112)+(B3.11), (Al-112)+(B3.12), (Al-112)+(B3.13), (Al-112)+(B3.14), (Al-112)+(B3.15), (Al-112)+(B3.16), (Al-112)+(B4.1), (Al-112)+(B4.2), (Al-112)+(B4.3), (Al-112)+(B4.4), (Al-112)+(B4.5), (Al-112)+(B4.6), (Al-112)+(B4.7).

(Al-113)+(B1.1), (Al-113)+(B1.2), (Al-113)+(B1.3), (Al-113)+(B1.4), (Al-113)+(B1.5), (Al-113)+(B1.6), (Al-113)+(B1.7), (Al-113)+(B1.8), (Al-113)+(B1.9), (Al-113)+(B1.10), (Al-113)+(B1.11), (Al-113)+(B1.12), (Al-113)+(B1.13), (Al-113)+(B1.14), (Al-113)+(B1.15), (Al-113)+(B1.16), (Al-113)+(B1.17), (Al-113)+(B1.18), (Al-113)+(B1.19), (Al-113)+(B1.20), (Al-113)+(B1.21), (Al-113)+(B1.22), (Al-113)+(B1.23), (Al-113)+(B1.24), (Al-113)+(B1.25), (Al-113)+(B1.26), (Al-113)+(B1.27), (Al-113)+(B1.28), (Al-113)+(B1.29), (Al-113)+(B1.30), (Al-113)+(B1.31), (Al-113)+(B1.32), (Al-113)+(B1.33), (Al-113)+(B1.34), (Al-113)+(B1.35), (Al-113)+(B1.36), (Al-113)+(B1.37), (Al-113)+(B1.38), (Al-113)+(B1.39), (Al-113)+(B1.40), (Al-113)+(B1.41), (Al-113)+(B1.42), (Al-113)+(B1.43), (Al-113)+(B1.44), (Al-113)+(B1.45), (Al-113)+(B1.46), (Al-113)+(B1.47), (Al-113)+(B1.48), (Al-113)+(B1.49), (Al-113)+(B1.50), (Al-113)+(B1.51), (Al-113)+(B1.52), (Al-113)+(B1.53), (Al-113)+(B1.54), (Al-113)+(B1.55), (Al-113)+(B1.56), (Al-113)+(B1.57), (Al-113)+(B1.58), (Al-113)+(B1.59), (Al-113)+(B1.60), (Al-113)+(B1.61), (Al-113)+(B1.62), (Al-113)+(B1.63), (Al-113)+(B1.64), (Al-113)+(B1.65), (Al-113)+(B1.66), (Al-113)+(B2.1), (Al-113)+(B2.2), (Al-113)+(B2.3), (Al-113)+(B2.4), (Al-113)+(B2.5), (Al-113)+(B2.6), (Al-113)+(B2.7), (Al-113)+(B2.8), (Al-113)+(B2.9), (Al-113)+(B2.10), (Al-113)+(B2.11), (Al-113)+(B2.12), (Al-113)+(B2.13), (Al-113)+(B2.14), (Al-113)+(B2.15), (Al-113)+(B2.16), (Al-113)+(B2.17), (Al-113)+(B2.18), (Al-113)+(B2.19), (Al-113)+(B2.20), (Al-113)+(B2.21), (Al-113)+(B2.22), (Al-113)+(B2.23), (Al-113)+(B2.24), (Al-113)+(B2.25), (Al-113)+(B2.26), (Al-113)+(B2.27), (Al-113)+(B2.28), (Al-113)+(B2.29), (Al-113)+(B2.30), (Al-113)+(B2.31), (Al-113)+(B2.32), (Al-113)+(B2.33), (Al-113)+(B2.34), (Al-113)+(B2.35), (Al-113)+(B2.36), (Al-113)+(B2.37), (Al-113)+(B2.38), (Al-113)+(B2.39), (Al-113)+(B2.40), (Al-113)+(B2.41), (Al-113)+(B2.42), (Al-113)+(B2.43), (Al-113)+(B2.44), (Al-113)+(B2.45), (Al-113)+(B2.46), (Al-113)+(B2.47), (Al-113)+(B2.48), (Al-113)+(B2.49), (Al-113)+(B2.50), (Al-113)+(B3.1), (Al-113)+(B3.2.), (Al-113)+(B3.3), (Al-113)+(B3.4), (Al-113)+(B3.5), (Al-113)+(B3.6), (Al-113)+(B3.7), (Al-113)+(B3.8), (Al-113)+(B3.9), (Al-113)+(B3.10), (Al-113)+(B3.11), (Al-113)+(B3.12), (Al-113)+(B3.13), (Al-113)+(B3.14), (Al-113)+(B3.15), (Al-113)+(B3.16), (Al-113)+(B4.1), (Al-113)+(B4.2), (Al-113)+(B4.3), (Al-113)+(B4.4), (Al-113)+(B4.5), (Al-113)+(B4.6), (Al-113)+(B4.7).

(Al-114)+(B1.1), (Al-114)+(B1.2), (Al-114)+(B1.3), (Al-114)+(B1.4), (Al-114)+(B1.5), (Al-114)+(B1.6), (Al-114)+(B1.7), (Al-114)+(B1.8), (Al-114)+(B1.9), (Al-114)+(B1.10), (Al-114)+(B1.11), (Al-114)+(B1.12), (Al-114)+(B1.13), (Al-114)+(B1.14), (Al-114)+(B1.15), (Al-114)+(B1.16), (Al-114)+(B1.17), (Al-114)+(B1.18), (Al-114)+(B1.19), (Al-114)+(B1.20), (Al-114)+(B1.21), (Al-114)+(B1.22), (Al-114)+(B1.23), (Al-114)+(B1.24), (Al-114)+(B1.25), (Al-114)+(B1.26), (Al-114)+(B1.27), (Al-114)+(B1.28), (Al-114)+(B1.29), (Al-114)+(B1.30), (Al-114)+(B1.31), (Al-114)+(B1.32), (Al-114)+(B1.33), (Al-114)+(B1.34), (Al-114)+(B1.35), (Al-114)+(B1.36), (Al-114)+(B1.37), (Al-114)+(B1.38), (Al-114)+(B1.39), (Al-114)+

(B1.40), (Al-114)+(B1.41), (Al-114)+(B1.42), (Al-114)+(B1.43), (Al-114)+(B1.44), (Al-114)+(B1.45), (Al-114)+(B1.46), (Al-114)+(B1.47), (Al-114)+(B1.48), (Al-114)+(B1.49), (Al-114)+(B1.50), (Al-114)+(B1.51), (Al-114)+(B1.52), (Al-114)+(B1.53), (Al-114)+(B1.54), (Al-114)+(B1.55), (Al-114)+(B1.56), (Al-114)+(B1.57), (Al-114)+(B1.58), (Al-114)+(B1.59), (Al-114)+(B1.60), (Al-114)+(B1.61), (Al-114)+(B1.62), (Al-114)+(B1.63), (Al-114)+(B1.64), (Al-114)+(B1.65), (Al-114)+(B1.66), (Al-114)+(B2.1), (Al-114)+(B2.2), (Al-114)+(B2.3), (Al-114)+(B2.4), (Al-114)+(B2.5), (Al-114)+(B2.6), (Al-114)+(B2.7), (Al-114)+(B2.8), (Al-114)+(B2.9), (Al-114)+(B2.10), (Al-114)+(B2.11), (Al-114)+(B2.12), (Al-114)+(B2.13), (Al-114)+(B2.14), (Al-114)+(B2.15), (Al-114)+(B2.16), (Al-114)+(B2.17), (Al-114)+(B2.18), (Al-114)+(B2.19), (Al-114)+(B2.20), (Al-114)+(B2.21), (Al-114)+(B2.22), (Al-114)+(B2.23), (Al-114)+(B2.24), (Al-114)+(B2.25), (Al-114)+(B2.26), (Al-114)+(B2.27), (Al-114)+(B2.28), (Al-114)+(B2.29), (Al-114)+(B2.30), (Al-114)+(B2.31), (Al-114)+(B2.32), (Al-114)+(B2.33), (Al-114)+(B2.34), (Al-114)+(B2.35), (Al-114)+(B2.36), (Al-114)+(B2.37), (Al-114)+(B2.38), (Al-114)+(B2.39), (Al-114)+(B2.40), (Al-114)+(B2.41), (Al-114)+(B2.42), (Al-114)+(B2.43), (Al-114)+(B2.44), (Al-114)+(B2.45), (Al-114)+(B2.46), (Al-114)+(B2.47), (Al-114)+(B2.48), (Al-114)+(B2.49), (Al-114)+(B2.50), (Al-114)+(B3.1), (Al-114)+(B3.2.), (Al-114)+(B3.3), (Al-114)+(B3.4), (Al-114)+(B3.5), (Al-114)+(B3.6), (Al-114)+(B3.7), (Al-114)+(B3.8), (Al-114)+(B3.9), (Al-114)+(B3.10), (Al-114)+(B3.11), (Al-114)+(B3.12), (Al-114)+(B3.13), (Al-114)+(B3.14), (Al-114)+(B3.15), (Al-114)+(B3.16), (Al-114)+(B4.1), (Al-114)+(B4.2), (Al-114)+(B4.3), (Al-114)+(B4.4), (Al-114)+(B4.5), (Al-114)+(B4.6), (Al-114)+(B4.7).

(Al-115)+(B1.1), (Al-115)+(B1.2), (Al-115)+(B1.3), (Al-115)+(B1.4), (Al-115)+(B1.5), (Al-115)+(B1.6), (Al-115)+(B1.7), (Al-115)+(B1.8), (Al-115)+(B1.9), (Al-115)+(B1.10), (Al-115)+(B1.11), (Al-115)+(B1.12), (Al-115)+(B1.13), (Al-115)+(B1.14), (Al-115)+(B1.15), (Al-115)+(B1.16), (Al-115)+(B1.17), (Al-115)+(B1.18), (Al-115)+(B1.19), (Al-115)+(B1.20), (Al-115)+(B1.21), (Al-115)+(B1.22), (Al-115)+(B1.23), (Al-115)+(B1.24), (Al-115)+(B1.25), (Al-115)+(B1.26), (Al-115)+(B1.27), (Al-115)+(B1.28), (Al-115)+(B1.29), (Al-115)+(B1.30), (Al-115)+(B1.31), (Al-115)+(B1.32), (Al-115)+(B1.33), (Al-115)+(B1.34), (Al-115)+(B1.35), (Al-115)+(B1.36), (Al-115)+(B1.37), (Al-115)+(B1.38), (Al-115)+(B1.39), (Al-115)+(B1.40), (Al-115)+(B1.41), (Al-115)+(B1.42), (Al-115)+(B1.43), (Al-115)+(B1.44), (Al-115)+(B1.45), (Al-115)+(B1.46), (Al-115)+(B1.47), (Al-115)+(B1.48), (Al-115)+(B1.49), (Al-115)+(B1.50), (Al-115)+(B1.51), (Al-115)+(B1.52), (Al-115)+(B1.53), (Al-115)+(B1.54), (Al-115)+(B1.55), (Al-115)+(B1.56), (Al-115)+(B1.57), (Al-115)+(B1.58), (Al-115)+(B1.59), (Al-115)+(B1.60), (Al-115)+(B1.61), (Al-115)+(B1.62), (Al-115)+(B1.63), (Al-115)+(B1.64), (Al-115)+(B1.65), (Al-115)+(B1.66), (Al-115)+(B2.1), (Al-115)+(B2.2), (Al-115)+(B2.3), (Al-115)+(B2.4), (Al-115)+(B2.5), (Al-115)+(B2.6), (Al-115)+(B2.7), (Al-115)+(B2.8), (Al-115)+(B2.9), (Al-115)+(B2.10), (Al-115)+(B2.11), (Al-115)+(B2.12), (Al-115)+(B2.13), (Al-115)+(B2.14), (Al-115)+(B2.15), (Al-115)+(B2.16), (Al-115)+(B2.17), (Al-115)+(B2.18), (Al-115)+(B2.19), (Al-115)+(B2.20), (Al-115)+(B2.21), (Al-115)+(B2.22), (Al-115)+(B2.23), (Al-115)+(B2.24), (Al-115)+(B2.25), (Al-115)+(B2.26), (Al-115)+(B2.27), (Al-115)+(B2.28), (Al-115)+(B2.29), (Al-115)+(B2.30), (Al-115)+(B2.31), (Al-115)+(B2.32), (Al-115)+(B2.33), (Al-115)+(B2.34), (Al-115)+(B2.35), (Al-115)+(B2.36), (Al-115)+(B2.37), (Al-115)+(B2.38), (Al-115)+(B2.39), (Al-115)+(B2.40), (Al-115)+(B2.41), (Al-115)+(B2.42), (Al-115)+(B2.43), (Al-115)+(B2.44), (Al-115)+(B2.45), (Al-115)+(B2.46), (Al-115)+(B2.47), (Al-115)+(B2.48), (Al-115)+(B2.49), (Al-115)+(B2.50), (Al-115)+(B3.1), (Al-115)+(B3.2.), (Al-115)+(B3.3), (Al-115)+(B3.4), (Al-115)+(B3.5), (Al-115)+(B3.6), (Al-115)+(B3.7), (Al-115)+(B3.8), (Al-115)+(B3.9), (Al-115)+(B3.10), (Al-115)+(B3.11), (Al-115)+(B3.12), (Al-115)+(B3.13), (Al-115)+(B3.14), (Al-115)+(B3.15), (Al-115)+(B3.16), (Al-115)+(B4.1), (Al-115)+(B4.2), (Al-115)+(B4.3), (Al-115)+(B4.4), (Al-115)+(B4.5), (Al-115)+(B4.6), (Al-115)+(B4.7).

(Al-116)+(B1.1), (Al-116)+(B1.2), (Al-116)+(B1.3), (Al-116)+(B1.4), (Al-116)+(B1.5), (Al-116)+(B1.6), (Al-116)+(B1.7), (Al-116)+(B1.8), (Al-116)+(B1.9), (Al-116)+(B1.10), (Al-116)+(B1.11), (Al-116)+(B1.12), (Al-116)+(B1.13), (Al-116)+(B1.14), (Al-116)+(B1.15), (Al-116)+(B1.16), (Al-116)+(B1.17), (Al-116)+(B1.18), (Al-116)+(B1.19), (Al-116)+(B1.20), (Al-116)+(B1.21), (Al-116)+(B1.22), (Al-116)+(B1.23), (Al-116)+(B1.24), (Al-116)+(B1.25), (Al-116)+(B1.26), (Al-116)+(B1.27), (Al-116)+(B1.28), (Al-116)+(B1.29), (Al-116)+(B1.30), (Al-116)+(B1.31), (Al-116)+(B1.32), (Al-116)+(B1.33), (Al-116)+(B1.34), (Al-116)+(B1.35), (Al-116)+(B1.36), (Al-116)+(B1.37), (Al-116)+(B1.38), (Al-116)+(B1.39), (Al-116)+(B1.40), (Al-116)+(B1.41), (Al-116)+(B1.42), (Al-116)+(B1.43), (Al-116)+(B1.44), (Al-116)+(B1.45), (Al-116)+(B1.46), (Al-116)+(B1.47), (Al-116)+(B1.48), (Al-116)+(B1.49), (Al-116)+(B1.50), (Al-116)+(B1.51), (Al-116)+(B1.52), (Al-116)+(B1.53), (Al-116)+(B1.54), (Al-116)+(B1.55), (Al-116)+(B1.56), (Al-116)+(B1.57), (Al-116)+(B1.58), (Al-116)+(B1.59), (Al-116)+(B1.60), (Al-116)+(B1.61), (Al-116)+(B1.62), (Al-116)+(B1.63), (Al-116)+(B1.64), (Al-116)+(B1.65), (Al-116)+(B1.66), (Al-116)+(B2.1), (Al-116)+(B2.2), (Al-116)+(B2.3), (Al-116)+(B2.4), (Al-116)+(B2.5), (Al-116)+(B2.6), (Al-116)+(B2.7), (Al-116)+(B2.8), (Al-116)+(B2.9), (Al-116)+(B2.10), (Al-116)+(B2.11), (Al-116)+(B2.12), (Al-116)+(B2.13), (Al-116)+(B2.14), (Al-116)+(B2.15), (Al-116)+(B2.16), (Al-116)+(B2.17), (Al-116)+(B2.18), (Al-116)+(B2.19), (Al-116)+(B2.20), (Al-116)+(B2.21), (Al-116)+(B2.22), (Al-116)+(B2.23), (Al-116)+(B2.24), (Al-116)+(B2.25), (Al-116)+(B2.26), (Al-116)+(B2.27), (Al-116)+(B2.28), (Al-116)+(B2.29), (Al-116)+(B2.30), (Al-116)+(B2.31), (Al-116)+(B2.32), (Al-116)+(B2.33), (Al-116)+(B2.34), (Al-116)+(B2.35), (Al-116)+(B2.36), (Al-116)+(B2.37), (Al-116)+(B2.38), (Al-116)+(B2.39), (Al-116)+(B2.40), (Al-116)+(B2.41), (Al-116)+(B2.42), (Al-116)+(B2.43), (Al-116)+(B2.44), (Al-116)+(B2.45), (Al-116)+(B2.46), (Al-116)+(B2.47), (Al-116)+(B2.48), (Al-116)+(B2.49), (Al-116)+(B2.50), (Al-116)+(B3.1), (Al-116)+(B3.2.), (Al-116)+(B3.3), (Al-116)+(B3.4), (Al-116)+(B3.5), (Al-116)+(B3.6), (Al-116)+(B3.7), (Al-116)+(B3.8), (Al-116)+(B3.9), (Al-116)+(B3.10), (Al-116)+(B3.11), (Al-116)+(B3.12), (Al-116)+(B3.13), (Al-116)+(B3.14), (Al-116)+(B3.15), (Al-116)+(B3.16), (Al-116)+(B4.1), (Al-116)+(B4.2), (Al-116)+(B4.3), (Al-116)+(B4.4), (Al-116)+(B4.5), (Al-116)+(B4.6), (Al-116)+(B4.7).

(Al-117)+(B1.1), (Al-117)+(B1.2), (Al-117)+(B1.3), (Al-117)+(B1.4), (Al-117)+(B1.5), (Al-117)+(B1.6), (Al-117)+(B1.7), (Al-117)+(B1.8), (Al-117)+(B1.9), (Al-117)+(B1.10), (Al-117)+(B1.11), (Al-117)+(B1.12), (Al-117)+(B1.13), (Al-117)+(B1.14), (Al-117)+(B1.15), (Al-117)+(B1.16), (Al-117)+(B1.17), (Al-117)+(B1.18), (Al-117)+(B1.19), (Al-117)+(B1.20), (Al-117)+(B1.21), (Al-117)+(B1.22), (Al-117)+(B1.23), (Al-117)+(B1.24), (Al-117)+(B1.25), (Al-117)+(B1.26), (Al-117)+(B1.27), (Al-117)+

(B1.28), (Al-117)+(B1.29), (Al-117)+(B1.30), (Al-117)+(B1.31), (Al-117)+(B1.32), (Al-117)+(B1.33), (Al-117)+(B1.34), (Al-117)+(B1.35), (Al-117)+(B1.36), (Al-117)+(B1.37), (Al-117)+(B1.38), (Al-117)+(B1.39), (Al-117)+(B1.40), (Al-117)+(B1.41), (Al-117)+(B1.42), (Al-117)+(B1.43), (Al-117)+(B1.44), (Al-117)+(B1.45), (Al-117)+(B1.46), (Al-117)+(B1.47), (Al-117)+(B1.48), (Al-117)+(B1.49), (Al-117)+(B1.50), (Al-117)+(B1.51), (Al-117)+(B1.52), (Al-117)+(B1.53), (Al-117)+(B1.54), (Al-117)+(B1.55), (Al-117)+(B1.56), (Al-117)+(B1.57), (Al-117)+(B1.58), (Al-117)+(B1.59), (Al-117)+(B1.60), (Al-117)+(B1.61), (Al-117)+(B1.62), (Al-117)+(B1.63), (Al-117)+(B1.64), (Al-117)+(B1.65), (Al-117)+(B1.66), (Al-117)+(B2.1), (Al-117)+(B2.2), (Al-117)+(B2.3), (Al-117)+(B2.4), (Al-117)+(B2.5), (Al-117)+(B2.6), (Al-117)+(B2.7), (Al-117)+(B2.8), (Al-117)+(B2.9), (Al-117)+(B2.10), (Al-117)+(B2.11), (Al-117)+(B2.12), (Al-117)+(B2.13), (Al-117)+(B2.14), (Al-117)+(B2.15), (Al-117)+(B2.16), (Al-117)+(B2.17), (Al-117)+(B2.18), (Al-117)+(B2.19), (Al-117)+(B2.20), (Al-117)+(B2.21), (Al-117)+(B2.22), (Al-117)+(B2.23), (Al-117)+(B2.24), (Al-117)+(B2.25), (Al-117)+(B2.26), (Al-117)+(B2.27), (Al-117)+(B2.28), (Al-117)+(B2.29), (Al-117)+(B2.30), (Al-117)+(B2.31), (Al-117)+(B2.32), (Al-117)+(B2.33), (Al-117)+(B2.34), (Al-117)+(B2.35), (Al-117)+(B2.36), (Al-117)+(B2.37), (Al-117)+(B2.38), (Al-117)+(B2.39), (Al-117)+(B2.40), (Al-117)+(B2.41), (Al-117)+(B2.42), (Al-117)+(B2.43), (Al-117)+(B2.44), (Al-117)+(B2.45), (Al-117)+(B2.46), (Al-117)+(B2.47), (Al-117)+(B2.48), (Al-117)+(B2.49), (Al-117)+(B2.50), (Al-117)+(B3.1), (Al-117)+(B3.2.), (Al-117)+(B3.3), (Al-117)+(B3.4), (Al-117)+(B3.5), (Al-117)+(B3.6), (Al-117)+(B3.7), (Al-117)+(B3.8), (Al-117)+(B3.9), (Al-117)+(B3.10), (Al-117)+(B3.11), (Al-117)+(B3.12), (Al-117)+(B3.13), (Al-117)+(B3.14), (Al-117)+(B3.15), (Al-117)+(B3.16), (Al-117)+(B4.1), (Al-117)+(B4.2), (Al-117)+(B4.3), (Al-117)+(B4.4), (Al-117)+(B4.5), (Al-117)+(B4.6), (Al-117)+(B4.7).

(Al-118)+(B1.1), (Al-118)+(B1.2), (Al-118)+(B1.3), (Al-118)+(B1.4), (Al-118)+(B1.5), (Al-118)+(B1.6), (Al-118)+(B1.7), (Al-118)+(B1.8), (Al-118)+(B1.9), (Al-118)+(B1.10), (Al-118)+(B1.11), (Al-118)+(B1.12), (Al-118)+(B1.13), (Al-118)+(B1.14), (Al-118)+(B1.15), (Al-118)+(B1.16), (Al-118)+(B1.17), (Al-118)+(B1.18), (Al-118)+(B1.19), (Al-118)+(B1.20), (Al-118)+(B1.21), (Al-118)+(B1.22), (Al-118)+(B1.23), (Al-118)+(B1.24), (Al-118)+(B1.25), (Al-118)+(B1.26), (Al-118)+(B1.27), (Al-118)+(B1.28), (Al-118)+(B1.29), (Al-118)+(B1.30), (Al-118)+(B1.31), (Al-118)+(B1.32), (Al-118)+(B1.33), (Al-118)+(B1.34), (Al-118)+(B1.35), (Al-118)+(B1.36), (Al-118)+(B1.37), (Al-118)+(B1.38), (Al-118)+(B1.39), (Al-118)+(B1.40), (Al-118)+(B1.41), (Al-118)+(B1.42), (Al-118)+(B1.43), (Al-118)+(B1.44), (Al-118)+(B1.45), (Al-118)+(B1.46), (Al-118)+(B1.47), (Al-118)+(B1.48), (Al-118)+(B1.49), (Al-118)+(B1.50), (Al-118)+(B1.51), (Al-118)+(B1.52), (Al-118)+(B1.53), (Al-118)+(B1.54), (Al-118)+(B1.55), (Al-118)+(B1.56), (Al-118)+(B1.57), (Al-118)+(B1.58), (Al-118)+(B1.59), (Al-118)+(B1.60), (Al-118)+(B1.61), (Al-118)+(B1.62), (Al-118)+(B1.63), (Al-118)+(B1.64), (Al-118)+(B1.65), (Al-118)+(B1.66), (Al-118)+(B2.1), (Al-118)+(B2.2), (Al-118)+(B2.3), (Al-118)+(B2.4), (Al-118)+(B2.5), (Al-118)+(B2.6), (Al-118)+(B2.7), (Al-118)+(B2.8), (Al-118)+(B2.9), (Al-118)+(B2.10), (Al-118)+(B2.11), (Al-118)+(B2.12), (Al-118)+(B2.13), (Al-118)+(B2.14), (Al-118)+(B2.15), (Al-118)+(B2.16), (Al-118)+(B2.17), (Al-118)+(B2.18), (Al-118)+(B2.19), (Al-118)+(B2.20), (Al-118)+(B2.21), (Al-118)+(B2.22), (Al-118)+(B2.23), (Al-118)+(B2.24), (Al-118)+(B2.25), (Al-118)+(B2.26), (Al-118)+(B2.27), (Al-118)+(B2.28), (Al-118)+(B2.29), (Al-118)+(B2.30), (Al-118)+(B2.31), (Al-118)+(B2.32), (Al-118)+(B2.33), (Al-118)+(B2.34), (Al-118)+(B2.35), (Al-118)+(B2.36), (Al-118)+(B2.37), (Al-118)+(B2.38), (Al-118)+(B2.39), (Al-118)+(B2.40), (Al-118)+(B2.41), (Al-118)+(B2.42), (Al-118)+(B2.43), (Al-118)+(B2.44), (Al-118)+(B2.45), (Al-118)+(B2.46), (Al-118)+(B2.47), (Al-118)+(B2.48), (Al-118)+(B2.49), (Al-118)+(B2.50), (Al-118)+(B3.1), (Al-118)+(B3.2.), (Al-118)+(B3.3), (Al-118)+(B3.4), (Al-118)+(B3.5), (Al-118)+(B3.6), (Al-118)+(B3.7), (Al-118)+(B3.8), (Al-118)+(B3.9), (Al-118)+(B3.10), (Al-118)+(B3.11), (Al-118)+(B3.12), (Al-118)+(B3.13), (Al-118)+(B3.14), (Al-118)+(B3.15), (Al-118)+(B3.16), (Al-118)+(B4.1), (Al-118)+(B4.2), (Al-118)+(B4.3), (Al-118)+(B4.4), (Al-118)+(B4.5), (Al-118)+(B4.6), (Al-118)+(B4.7).

(Al-119)+(B1.1), (Al-119)+(B1.2), (Al-119)+(B1.3), (Al-119)+(B1.4), (Al-119)+(B1.5), (Al-119)+(B1.6), (Al-119)+(B1.7), (Al-119)+(B1.8), (Al-119)+(B1.9), (Al-119)+(B1.10), (Al-119)+(B1.11), (Al-119)+(B1.12), (Al-119)+(B1.13), (Al-119)+(B1.14), (Al-119)+(B1.15), (Al-119)+(B1.16), (Al-119)+(B1.17), (Al-119)+(B1.18), (Al-119)+(B1.19), (Al-119)+(B1.20), (Al-119)+(B1.21), (Al-119)+(B1.22), (Al-119)+(B1.23), (Al-119)+(B1.24), (Al-119)+(B1.25), (Al-119)+(B1.26), (Al-119)+(B1.27), (Al-119)+(B1.28), (Al-119)+(B1.29), (Al-119)+(B1.30), (Al-119)+(B1.31), (Al-119)+(B1.32), (Al-119)+(B1.33), (Al-119)+(B1.34), (Al-119)+(B1.35), (Al-119)+(B1.36), (Al-119)+(B1.37), (Al-119)+(B1.38), (Al-119)+(B1.39), (Al-119)+(B1.40), (Al-119)+(B1.41), (Al-119)+(B1.42), (Al-119)+(B1.43), (Al-119)+(B1.44), (Al-119)+(B1.45), (Al-119)+(B1.46), (Al-119)+(B1.47), (Al-119)+(B1.48), (Al-119)+(B1.49), (Al-119)+(B1.50), (Al-119)+(B1.51), (Al-119)+(B1.52), (Al-119)+(B1.53), (Al-119)+(B1.54), (Al-119)+(B1.55), (Al-119)+(B1.56), (Al-119)+(B1.57), (Al-119)+(B1.58), (Al-119)+(B1.59), (Al-119)+(B1.60), (Al-119)+(B1.61), (Al-119)+(B1.62), (Al-119)+(B1.63), (Al-119)+(B1.64), (Al-119)+(B1.65), (Al-119)+(B1.66), (Al-119)+(B2.1), (Al-119)+(B2.2), (Al-119)+(B2.3), (Al-119)+(B2.4), (Al-119)+(B2.5), (Al-119)+(B2.6), (Al-119)+(B2.7), (Al-119)+(B2.8), (Al-119)+(B2.9), (Al-119)+(B2.10), (Al-119)+(B2.11), (Al-119)+(B2.12), (Al-119)+(B2.13), (Al-119)+(B2.14), (Al-119)+(B2.15), (Al-119)+(B2.16), (Al-119)+(B2.17), (Al-119)+(B2.18), (Al-119)+(B2.19), (Al-119)+(B2.20), (Al-119)+(B2.21), (Al-119)+(B2.22), (Al-119)+(B2.23), (Al-119)+(B2.24), (Al-119)+(B2.25), (Al-119)+(B2.26), (Al-119)+(B2.27), (Al-119)+(B2.28), (Al-119)+(B2.29), (Al-119)+(B2.30), (Al-119)+(B2.31), (Al-119)+(B2.32), (Al-119)+(B2.33), (Al-119)+(B2.34), (Al-119)+(B2.35), (Al-119)+(B2.36), (Al-119)+(B2.37), (Al-119)+(B2.38), (Al-119)+(B2.39), (Al-119)+(B2.40), (Al-119)+(B2.41), (Al-119)+(B2.42), (Al-119)+(B2.43), (Al-119)+(B2.44), (Al-119)+(B2.45), (Al-119)+(B2.46), (Al-119)+(B2.47), (Al-119)+(B2.48), (Al-119)+(B2.49), (Al-119)+(B2.50), (Al-119)+(B3.1), (Al-119)+(B3.2.), (Al-119)+(B3.3), (Al-119)+(B3.4), (Al-119)+(B3.5), (Al-119)+(B3.6), (Al-119)+(B3.7), (Al-119)+(B3.8), (Al-119)+(B3.9), (Al-119)+(B3.10), (Al-119)+(B3.11), (Al-119)+(B3.12), (Al-119)+(B3.13), (Al-119)+(B3.14), (Al-119)+(B3.15), (Al-119)+(B3.16), (Al-119)+(B4.1), (Al-119)+(B4.2), (Al-119)+(B4.3), (Al-119)+(B4.4), (Al-119)+(B4.5), (Al-119)+(B4.6), (Al-119)+(B4.7).

(Al-120)+(B1.1), (Al-120)+(B1.2), (Al-120)+(B1.3), (Al-120)+(B1.4), (Al-120)+(B1.5), (Al-120)+(B1.6), (Al-120)+(B1.7), (Al-120)+(B1.8), (Al-120)+(B1.9), (Al-120)+(B1.10), (Al-120)+(B1.11), (Al-120)+(B1.12), (Al-120)+(B1.13), (Al-120)+(B1.14), (Al-120)+(B1.15), (Al-120)+

(B1.16), (Al-120)+(B1.17), (Al-120)+(B1.18), (Al-120)+(B1.19), (Al-120)+(B1.20), (Al-120)+(B1.21), (Al-120)+(B1.22), (Al-120)+(B1.23), (Al-120)+(B1.24), (Al-120)+(B1.25), (Al-120)+(B1.26), (Al-120)+(B1.27), (Al-120)+(B1.28), (Al-120)+(B1.29), (Al-120)+(B1.30), (Al-120)+(B1.31), (Al-120)+(B1.32), (Al-120)+(B1.33), (Al-120)+(B1.34), (Al-120)+(B1.35), (Al-120)+(B1.36), (Al-120)+(B1.37), (Al-120)+(B1.38), (Al-120)+(B1.39), (Al-120)+(B1.40), (Al-120)+(B1.41), (Al-120)+(B1.42), (Al-120)+(B1.43), (Al-120)+(B1.44), (Al-120)+(B1.45), (Al-120)+(B1.46), (Al-120)+(B1.47), (Al-120)+(B1.48), (Al-120)+(B1.49), (Al-120)+(B1.50), (Al-120)+(B1.51), (Al-120)+(B1.52), (Al-120)+(B1.53), (Al-120)+(B1.54), (Al-120)+(B1.55), (Al-120)+(B1.56), (Al-120)+(B1.57), (Al-120)+(B1.58), (Al-120)+(B1.59), (Al-120)+(B1.60), (Al-120)+(B1.61), (Al-120)+(B1.62), (Al-120)+(B1.63), (Al-120)+(B1.64), (Al-120)+(B1.65), (Al-120)+(B1.66), (Al-120)+(B2.1), (Al-120)+(B2.2), (Al-120)+(B2.3), (Al-120)+(B2.4), (Al-120)+(B2.5), (Al-120)+(B2.6), (Al-120)+(B2.7), (Al-120)+(B2.8), (Al-120)+(B2.9), (Al-120)+(B2.10), (Al-120)+(B2.11), (Al-120)+(B2.12), (Al-120)+(B2.13), (Al-120)+(B2.14), (Al-120)+(B2.15), (Al-120)+(B2.16), (Al-120)+(B2.17), (Al-120)+(B2.18), (Al-120)+(B2.19), (Al-120)+(B2.20), (Al-120)+(B2.21), (Al-120)+(B2.22), (Al-120)+(B2.23), (Al-120)+(B2.24), (Al-120)+(B2.25), (Al-120)+(B2.26), (Al-120)+(B2.27), (Al-120)+(B2.28), (Al-120)+(B2.29), (Al-120)+(B2.30), (Al-120)+(B2.31), (Al-120)+(B2.32), (Al-120)+(B2.33), (Al-120)+(B2.34), (Al-120)+(B2.35), (Al-120)+(B2.36), (Al-120)+(B2.37), (Al-120)+(B2.38), (Al-120)+(B2.39), (Al-120)+(B2.40), (Al-120)+(B2.41), (Al-120)+(B2.42), (Al-120)+(B2.43), (Al-120)+(B2.44), (Al-120)+(B2.45), (Al-120)+(B2.46), (Al-120)+(B2.47), (Al-120)+(B2.48), (Al-120)+(B2.49), (Al-120)+(B2.50), (Al-120)+(B3.1), (Al-120)+(B3.2.), (Al-120)+(B3.3), (Al-120)+(B3.4), (Al-120)+(B3.5), (Al-120)+(B3.6), (Al-120)+(B3.7), (Al-120)+(B3.8), (Al-120)+(B3.9), (Al-120)+(B3.10), (Al-120)+(B3.11), (Al-120)+(B3.12), (Al-120)+(B3.13), (Al-120)+(B3.14), (Al-120)+(B3.15), (Al-120)+(B3.16), (Al-120)+(B4.1), (Al-120)+(B4.2), (Al-120)+(B4.3), (Al-120)+(B4.4), (Al-120)+(B4.5), (Al-120)+(B4.6), (Al-120)+(B4.7).

(Al-121)+(B1.1), (Al-121)+(B1.2), (Al-121)+(B1.3), (Al-121)+(B1.4), (Al-121)+(B1.5), (Al-121)+(B1.6), (Al-121)+(B1.7), (Al-121)+(B1.8), (Al-121)+(B1.9), (Al-121)+(B1.10), (Al-121)+(B1.11), (Al-121)+(B1.12), (Al-121)+(B1.13), (Al-121)+(B1.14), (Al-121)+(B1.15), (Al-121)+(B1.16), (Al-121)+(B1.17), (Al-121)+(B1.18), (Al-121)+(B1.19), (Al-121)+(B1.20), (Al-121)+(B1.21), (Al-121)+(B1.22), (Al-121)+(B1.23), (Al-121)+(B1.24), (Al-121)+(B1.25), (Al-121)+(B1.26), (Al-121)+(B1.27), (Al-121)+(B1.28), (Al-121)+(B1.29), (Al-121)+(B1.30), (Al-121)+(B1.31), (Al-121)+(B1.32), (Al-121)+(B1.33), (Al-121)+(B1.34), (Al-121)+(B1.35), (Al-121)+(B1.36), (Al-121)+(B1.37), (Al-121)+(B1.38), (Al-121)+(B1.39), (Al-121)+(B1.40), (Al-121)+(B1.41), (Al-121)+(B1.42), (Al-121)+(B1.43), (Al-121)+(B1.44), (Al-121)+(B1.45), (Al-121)+(B1.46), (Al-121)+(B1.47), (Al-121)+(B1.48), (Al-121)+(B1.49), (Al-121)+(B1.50), (Al-121)+(B1.51), (Al-121)+(B1.52), (Al-121)+(B1.53), (Al-121)+(B1.54), (Al-121)+(B1.55), (Al-121)+(B1.56), (Al-121)+(B1.57), (Al-121)+(B1.58), (Al-121)+(B1.59), (Al-121)+(B1.60), (Al-121)+(B1.61), (Al-121)+(B1.62), (Al-121)+(B1.63), (Al-121)+(B1.64), (Al-121)+(B1.65), (Al-121)+(B1.66), (Al-121)+(B2.1), (Al-121)+(B2.2), (Al-121)+(B2.3), (Al-121)+(B2.4), (Al-121)+(B2.5), (Al-121)+(B2.6), (Al-121)+(B2.7), (Al-121)+(B2.8), (Al-121)+(B2.9), (Al-121)+(B2.10), (Al-121)+(B2.11), (Al-121)+(B2.12), (Al-121)+(B2.13), (Al-121)+(B2.14), (Al-121)+(B2.15), (Al-121)+(B2.16), (Al-121)+(B2.17), (Al-121)+(B2.18), (Al-121)+(B2.19), (Al-121)+(B2.20), (Al-121)+(B2.21), (Al-121)+(B2.22), (Al-121)+(B2.23), (Al-121)+(B2.24), (Al-121)+(B2.25), (Al-121)+(B2.26), (Al-121)+(B2.27), (Al-121)+(B2.28), (Al-121)+(B2.29), (Al-121)+(B2.30), (Al-121)+(B2.31), (Al-121)+(B2.32), (Al-121)+(B2.33), (Al-121)+(B2.34), (Al-121)+(B2.35), (Al-121)+(B2.36), (Al-121)+(B2.37), (Al-121)+(B2.38), (Al-121)+(B2.39), (Al-121)+(B2.40), (Al-121)+(B2.41), (Al-121)+(B2.42), (Al-121)+(B2.43), (Al-121)+(B2.44), (Al-121)+(B2.45), (Al-121)+(B2.46), (Al-121)+(B2.47), (Al-121)+(B2.48), (Al-121)+(B2.49), (Al-121)+(B2.50), (Al-121)+(B3.1), (Al-121)+(B3.2.), (Al-121)+(B3.3), (Al-121)+(B3.4), (Al-121)+(B3.5), (Al-121)+(B3.6), (Al-121)+(B3.7), (Al-121)+(B3.8), (Al-121)+(B3.9), (Al-121)+(B3.10), (Al-121)+(B3.11), (Al-121)+(B3.12), (Al-121)+(B3.13), (Al-121)+(B3.14), (Al-121)+(B3.15), (Al-121)+(B3.16), (Al-121)+(B4.1), (Al-121)+(B4.2), (Al-121)+(B4.3), (Al-121)+(B4.4), (Al-121)+(B4.5), (Al-121)+(B4.6), (Al-121)+(B4.7).

(Al-122)+(B1.1), (Al-122)+(B1.2), (Al-122)+(B1.3), (Al-122)+(B1.4), (Al-122)+(B1.5), (Al-122)+(B1.6), (Al-122)+(B1.7), (Al-122)+(B1.8), (Al-122)+(B1.9), (Al-122)+(B1.10), (Al-122)+(B1.11), (Al-122)+(B1.12), (Al-122)+(B1.13), (Al-122)+(B1.14), (Al-122)+(B1.15), (Al-122)+(B1.16), (Al-122)+(B1.17), (Al-122)+(B1.18), (Al-122)+(B1.19), (Al-122)+(B1.20), (Al-122)+(B1.21), (Al-122)+(B1.22), (Al-122)+(B1.23), (Al-122)+(B1.24), (Al-122)+(B1.25), (Al-122)+(B1.26), (Al-122)+(B1.27), (Al-122)+(B1.28), (Al-122)+(B1.29), (Al-122)+(B1.30), (Al-122)+(B1.31), (Al-122)+(B1.32), (Al-122)+(B1.33), (Al-122)+(B1.34), (Al-122)+(B1.35), (Al-122)+(B1.36), (Al-122)+(B1.37), (Al-122)+(B1.38), (Al-122)+(B1.39), (Al-122)+(B1.40), (Al-122)+(B1.41), (Al-122)+(B1.42), (Al-122)+(B1.43), (Al-122)+(B1.44), (Al-122)+(B1.45), (Al-122)+(B1.46), (Al-122)+(B1.47), (Al-122)+(B1.48), (Al-122)+(B1.49), (Al-122)+(B1.50), (Al-122)+(B1.51), (Al-122)+(B1.52), (Al-122)+(B1.53), (Al-122)+(B1.54), (Al-122)+(B1.55), (Al-122)+(B1.56), (Al-122)+(B1.57), (Al-122)+(B1.58), (Al-122)+(B1.59), (Al-122)+(B1.60), (Al-122)+(B1.61), (Al-122)+(B1.62), (Al-122)+(B1.63), (Al-122)+(B1.64), (Al-122)+(B1.65), (Al-122)+(B1.66), (Al-122)+(B2.1), (Al-122)+(B2.2), (Al-122)+(B2.3), (Al-122)+(B2.4), (Al-122)+(B2.5), (Al-122)+(B2.6), (Al-122)+(B2.7), (Al-122)+(B2.8), (Al-122)+(B2.9), (Al-122)+(B2.10), (Al-122)+(B2.11), (Al-122)+(B2.12), (Al-122)+(B2.13), (Al-122)+(B2.14), (Al-122)+(B2.15), (Al-122)+(B2.16), (Al-122)+(B2.17), (Al-122)+(B2.18), (Al-122)+(B2.19), (Al-122)+(B2.20), (Al-122)+(B2.21), (Al-122)+(B2.22), (Al-122)+(B2.23), (Al-122)+(B2.24), (Al-122)+(B2.25), (Al-122)+(B2.26), (Al-122)+(B2.27), (Al-122)+(B2.28), (Al-122)+(B2.29), (Al-122)+(B2.30), (Al-122)+(B2.31), (Al-122)+(B2.32), (Al-122)+(B2.33), (Al-122)+(B2.34), (Al-122)+(B2.35), (Al-122)+(B2.36), (Al-122)+(B2.37), (Al-122)+(B2.38), (Al-122)+(B2.39), (Al-122)+(B2.40), (Al-122)+(B2.41), (Al-122)+(B2.42), (Al-122)+(B2.43), (Al-122)+(B2.44), (Al-122)+(B2.45), (Al-122)+(B2.46), (Al-122)+(B2.47), (Al-122)+(B2.48), (Al-122)+(B2.49), (Al-122)+(B2.50), (Al-122)+(B3.1), (Al-122)+(B3.2.), (Al-122)+(B3.3), (Al-122)+(B3.4), (Al-122)+(B3.5), (Al-122)+(B3.6), (Al-122)+(B3.7), (Al-122)+(B3.8), (Al-122)+(B3.9), (Al-122)+(B3.10), (Al-122)+(B3.11), (Al-122)+(B3.12), (Al-122)+(B3.13), (Al-122)+(B3.14), (Al-122)+(B3.15), (Al-122)+(B3.16), (Al-122)+(B4.1), (Al-122)+(B4.2), (Al-122)+(B4.3), (Al-122)+(B4.4), (Al-122)+(B4.5), (Al-122)+(B4.6), (Al-122)+(B4.7).

(Al-123)+(B1.1), (Al-123)+(B1.2), (Al-123)+(B1.3), (Al-123)+(B1.4), (Al-123)+(B1.5), (Al-123)+(B1.6), (Al-123)+(B1.7), (Al-123)+(B1.8), (Al-123)+(B1.9), (Al-123)+(B1.10), (Al-123)+(B1.11), (Al-123)+(B1.12), (Al-123)+(B1.13), (Al-123)+(B1.14), (Al-123)+(B1.15), (Al-123)+(B1.16), (Al-123)+(B1.17), (Al-123)+(B1.18), (Al-123)+(B1.19), (Al-123)+(B1.20), (Al-123)+(B1.21), (Al-123)+(B1.22), (Al-123)+(B1.23), (Al-123)+(B1.24), (Al-123)+(B1.25), (Al-123)+(B1.26), (Al-123)+(B1.27), (Al-123)+(B1.28), (Al-123)+(B1.29), (Al-123)+(B1.30), (Al-123)+(B1.31), (Al-123)+(B1.32), (Al-123)+(B1.33), (Al-123)+(B1.34), (Al-123)+(B1.35), (Al-123)+(B1.36), (Al-123)+(B1.37), (Al-123)+(B1.38), (Al-123)+(B1.39), (Al-123)+(B1.40), (Al-123)+(B1.41), (Al-123)+(B1.42), (Al-123)+(B1.43), (Al-123)+(B1.44), (Al-123)+(B1.45), (Al-123)+(B1.46), (Al-123)+(B1.47), (Al-123)+(B1.48), (Al-123)+(B1.49), (Al-123)+(B1.50), (Al-123)+(B1.51), (Al-123)+(B1.52), (Al-123)+(B1.53), (Al-123)+(B1.54), (Al-123)+(B1.55), (Al-123)+(B1.56), (Al-123)+(B1.57), (Al-123)+(B1.58), (Al-123)+(B1.59), (Al-123)+(B1.60), (Al-123)+(B1.61), (Al-123)+(B1.62), (Al-123)+(B1.63), (Al-123)+(B1.64), (Al-123)+(B1.65), (Al-123)+(B1.66), (Al-123)+(B2.1), (Al-123)+(B2.2), (Al-123)+(B2.3), (Al-123)+(B2.4), (Al-123)+(B2.5), (Al-123)+(B2.6), (Al-123)+(B2.7), (Al-123)+(B2.8), (Al-123)+(B2.9), (Al-123)+(B2.10), (Al-123)+(B2.11), (Al-123)+(B2.12), (Al-123)+(B2.13), (Al-123)+(B2.14), (Al-123)+(B2.15), (Al-123)+(B2.16), (Al-123)+(B2.17), (Al-123)+(B2.18), (Al-123)+(B2.19), (Al-123)+(B2.20), (Al-123)+(B2.21), (Al-123)+(B2.22), (Al-123)+(B2.23), (Al-123)+(B2.24), (Al-123)+(B2.25), (Al-123)+(B2.26), (Al-123)+(B2.27), (Al-123)+(B2.28), (Al-123)+(B2.29), (Al-123)+(B2.30), (Al-123)+(B2.31), (Al-123)+(B2.32), (Al-123)+(B2.33), (Al-123)+(B2.34), (Al-123)+(B2.35), (Al-123)+(B2.36), (Al-123)+(B2.37), (Al-123)+(B2.38), (Al-123)+(B2.39), (Al-123)+(B2.40), (Al-123)+(B2.41), (Al-123)+(B2.42), (Al-123)+(B2.43), (Al-123)+(B2.44), (Al-123)+(B2.45), (Al-123)+(B2.46), (Al-123)+(B2.47), (Al-123)+(B2.48), (Al-123)+(B2.49), (Al-123)+(B2.50), (Al-123)+(B3.1), (Al-123)+(B3.2.), (Al-123)+(B3.3), (Al-123)+(B3.4), (Al-123)+(B3.5), (Al-123)+(B3.6), (Al-123)+(B3.7), (Al-123)+(B3.8), (Al-123)+(B3.9), (Al-123)+(B3.10), (Al-123)+(B3.11), (Al-123)+(B3.12), (Al-123)+(B3.13), (Al-123)+(B3.14), (Al-123)+(B3.15), (Al-123)+(B3.16), (Al-123)+(B4.1), (Al-123)+(B4.2), (Al-123)+(B4.3), (Al-123)+(B4.4), (Al-123)+(B4.5), (Al-123)+(B4.6), (Al-123)+(B4.7).

(Al-124)+(B1.1), (Al-124)+(B1.2), (Al-124)+(B1.3), (Al-124)+(B1.4), (Al-124)+(B1.5), (Al-124)+(B1.6), (Al-124)+(B1.7), (Al-124)+(B1.8), (Al-124)+(B1.9), (Al-124)+(B1.10), (Al-124)+(B1.11), (Al-124)+(B1.12), (Al-124)+(B1.13), (Al-124)+(B1.14), (Al-124)+(B1.15), (Al-124)+(B1.16), (Al-124)+(B1.17), (Al-124)+(B1.18), (Al-124)+(B1.19), (Al-124)+(B1.20), (Al-124)+(B1.21), (Al-124)+(B1.22), (Al-124)+(B1.23), (Al-124)+(B1.24), (Al-124)+(B1.25), (Al-124)+(B1.26), (Al-124)+(B1.27), (Al-124)+(B1.28), (Al-124)+(B1.29), (Al-124)+(B1.30), (Al-124)+(B1.31), (Al-124)+(B1.32), (Al-124)+(B1.33), (Al-124)+(B1.34), (Al-124)+(B1.35), (Al-124)+(B1.36), (Al-124)+(B1.37), (Al-124)+(B1.38), (Al-124)+(B1.39), (Al-124)+(B1.40), (Al-124)+(B1.41), (Al-124)+(B1.42), (Al-124)+(B1.43), (Al-124)+(B1.44), (Al-124)+(B1.45), (Al-124)+(B1.46), (Al-124)+(B1.47), (Al-124)+(B1.48), (Al-124)+(B1.49), (Al-124)+(B1.50), (Al-124)+(B1.51), (Al-124)+(B1.52), (Al-124)+(B1.53), (Al-124)+(B1.54), (Al-124)+(B1.55), (Al-124)+(B1.56), (Al-124)+(B1.57), (Al-124)+(B1.58), (Al-124)+(B1.59), (Al-124)+(B1.60), (Al-124)+(B1.61), (Al-124)+(B1.62), (Al-124)+(B1.63), (Al-124)+(B1.64), (Al-124)+(B1.65), (Al-124)+(B1.66), (Al-124)+(B2.1), (Al-124)+(B2.2), (Al-124)+(B2.3), (Al-124)+(B2.4), (Al-124)+(B2.5), (Al-124)+(B2.6), (Al-124)+(B2.7), (Al-124)+(B2.8), (Al-124)+(B2.9), (Al-124)+(B2.10), (Al-124)+(B2.11), (Al-124)+(B2.12), (Al-124)+(B2.13), (Al-124)+(B2.14), (Al-124)+(B2.15), (Al-124)+(B2.16), (Al-124)+(B2.17), (Al-124)+(B2.18), (Al-124)+(B2.19), (Al-124)+(B2.20), (Al-124)+(B2.21), (Al-124)+(B2.22), (Al-124)+(B2.23), (Al-124)+(B2.24), (Al-124)+(B2.25), (Al-124)+(B2.26), (Al-124)+(B2.27), (Al-124)+(B2.28), (Al-124)+(B2.29), (Al-124)+(B2.30), (Al-124)+(B2.31), (Al-124)+(B2.32), (Al-124)+(B2.33), (Al-124)+(B2.34), (Al-124)+(B2.35), (Al-124)+(B2.36), (Al-124)+(B2.37), (Al-124)+(B2.38), (Al-124)+(B2.39), (Al-124)+(B2.40), (Al-124)+(B2.41), (Al-124)+(B2.42), (Al-124)+(B2.43), (Al-124)+(B2.44), (Al-124)+(B2.45), (Al-124)+(B2.46), (Al-124)+(B2.47), (Al-124)+(B2.48), (Al-124)+(B2.49), (Al-124)+(B2.50), (Al-124)+(B3.1), (Al-124)+(B3.2.), (Al-124)+(B3.3), (Al-124)+(B3.4), (Al-124)+(B3.5), (Al-124)+(B3.6), (Al-124)+(B3.7), (Al-124)+(B3.8), (Al-124)+(B3.9), (Al-124)+(B3.10), (Al-124)+(B3.11), (Al-124)+(B3.12), (Al-124)+(B3.13), (Al-124)+(B3.14), (Al-124)+(B3.15), (Al-124)+(B3.16), (Al-124)+(B4.1), (Al-124)+(B4.2), (Al-124)+(B4.3), (Al-124)+(B4.4), (Al-124)+(B4.5), (Al-124)+(B4.6), (Al-124)+(B4.7).

(Al-125)+(B1.1), (Al-125)+(B1.2), (Al-125)+(B1.3), (Al-125)+(B1.4), (Al-125)+(B1.5), (Al-125)+(B1.6), (Al-125)+(B1.7), (Al-125)+(B1.8), (Al-125)+(B1.9), (Al-125)+(B1.10), (Al-125)+(B1.11), (Al-125)+(B1.12), (Al-125)+(B1.13), (Al-125)+(B1.14), (Al-125)+(B1.15), (Al-125)+(B1.16), (Al-125)+(B1.17), (Al-125)+(B1.18), (Al-125)+(B1.19), (Al-125)+(B1.20), (Al-125)+(B1.21), (Al-125)+(B1.22), (Al-125)+(B1.23), (Al-125)+(B1.24), (Al-125)+(B1.25), (Al-125)+(B1.26), (Al-125)+(B1.27), (Al-125)+(B1.28), (Al-125)+(B1.29), (Al-125)+(B1.30), (Al-125)+(B1.31), (Al-125)+(B1.32), (Al-125)+(B1.33), (Al-125)+(B1.34), (Al-125)+(B1.35), (Al-125)+(B1.36), (Al-125)+(B1.37), (Al-125)+(B1.38), (Al-125)+(B1.39), (Al-125)+(B1.40), (Al-125)+(B1.41), (Al-125)+(B1.42), (Al-125)+(B1.43), (Al-125)+(B1.44), (Al-125)+(B1.45), (Al-125)+(B1.46), (Al-125)+(B1.47), (Al-125)+(B1.48), (Al-125)+(B1.49), (Al-125)+(B1.50), (Al-125)+(B1.51), (Al-125)+(B1.52), (Al-125)+(B1.53), (Al-125)+(B1.54), (Al-125)+(B1.55), (Al-125)+(B1.56), (Al-125)+(B1.57), (Al-125)+(B1.58), (Al-125)+(B1.59), (Al-125)+(B1.60), (Al-125)+(B1.61), (Al-125)+(B1.62), (Al-125)+(B1.63), (Al-125)+(B1.64), (Al-125)+(B1.65), (Al-125)+(B1.66), (Al-125)+(B2.1), (Al-125)+(B2.2), (Al-125)+(B2.3), (Al-125)+(B2.4), (Al-125)+(B2.5), (Al-125)+(B2.6), (Al-125)+(B2.7), (Al-125)+(B2.8), (Al-125)+(B2.9), (Al-125)+(B2.10), (Al-125)+(B2.11), (Al-125)+(B2.12), (Al-125)+(B2.13), (Al-125)+(B2.14), (Al-125)+(B2.15), (Al-125)+(B2.16), (Al-125)+(B2.17), (Al-125)+(B2.18), (Al-125)+(B2.19), (Al-125)+(B2.20), (Al-125)+(B2.21), (Al-125)+(B2.22), (Al-125)+(B2.23), (Al-125)+(B2.24), (Al-125)+(B2.25), (Al-125)+(B2.26), (Al-125)+(B2.27), (Al-125)+(B2.28), (Al-125)+(B2.29), (Al-125)+(B2.30), (Al-125)+(B2.31), (Al-125)+(B2.32), (Al-125)+(B2.33), (Al-125)+(B2.34), (Al-125)+(B2.35), (Al-125)+(B2.36), (Al-125)+(B2.37), (Al-125)+(B2.38), (Al-125)+(B2.39), (Al-125)+(B2.40), (Al-125)+(B2.41), (Al-125)+(B2.42), (Al-125)+(B2.43), (Al-125)+(B2.44), (Al-125)+(B2.45), (Al-125)+(B2.46), (Al-125)+(B2.47), (Al-125)+(B2.48), (Al-125)+(B2.49), (Al-125)+(B2.50), (Al-125)+(B3.1), (Al-125)+(B3.2.), (Al-125)+(B3.3), (Al-125)+(B3.4), (Al-125)+(B3.5), (Al-125)+(B3.6), (Al-125)+(B3.7), (Al-125)+(B3.8), (Al-125)+(B3.9), (Al-125)+(B3.10), (Al-125)+(B3.11), (Al-125)+(B3.12), (Al- (Al-125)+(B3.13), (Al-125)+(B3.14), (Al-125)+(B3.15), (Al-125)+(B3.16), (Al-125)+(B4.1), (Al-125)+(B4.2), (Al-125)+(B4.3), (Al-125)+(B4.4), (Al-125)+(B4.5), (Al-125)+(B4.6), (Al-125)+(B4.7).

(Al-126)+(B1.1), (Al-126)+(B1.2), (Al-126)+(B1.3), (Al-126)+(B1.4), (Al-126)+(B1.5), (Al-126)+(B1.6), (Al-126)+(B1.7), (Al-126)+(B1.8), (Al-126)+(B1.9), (Al-126)+(B1.10), (Al-126)+(B1.11), (Al-126)+(B1.12), (Al-126)+(B1.13), (Al-126)+(B1.14), (Al-126)+(B1.15), (Al-126)+(B1.16), (Al-126)+(B1.17), (Al-126)+(B1.18), (Al-126)+(B1.19), (Al-126)+(B1.20), (Al-126)+(B1.21), (Al-126)+(B1.22), (Al-126)+(B1.23), (Al-126)+(B1.24), (Al-126)+(B1.25), (Al-126)+(B1.26), (Al-126)+(B1.27), (Al-126)+(B1.28), (Al-126)+(B1.29), (Al-126)+(B1.30), (Al-126)+(B1.31), (Al-126)+(B1.32), (Al-126)+(B1.33), (Al-126)+(B1.34), (Al-126)+(B1.35), (Al-126)+(B1.36), (Al-126)+(B1.37), (Al-126)+(B1.38), (Al-126)+(B1.39), (Al-126)+(B1.40), (Al-126)+(B1.41), (Al-126)+(B1.42), (Al-126)+(B1.43), (Al-126)+(B1.44), (Al-126)+(B1.45), (Al-126)+(B1.46), (Al-126)+(B1.47), (Al-126)+(B1.48), (Al-126)+(B1.49), (Al-126)+(B1.50), (Al-126)+(B1.51), (Al-126)+(B1.52), (Al-126)+(B1.53), (Al-126)+(B1.54), (Al-126)+(B1.55), (Al-126)+(B1.56), (Al-126)+(B1.57), (Al-126)+(B1.58), (Al-126)+(B1.59), (Al-126)+(B1.60), (Al-126)+(B1.61), (Al-126)+(B1.62), (Al-126)+(B1.63), (Al-126)+(B1.64), (Al-126)+(B1.65), (Al-126)+(B1.66), (Al-126)+(B2.1), (Al-126)+(B2.2), (Al-126)+(B2.3), (Al-126)+(B2.4), (Al-126)+(B2.5), (Al-126)+(B2.6), (Al-126)+(B2.7), (Al-126)+(B2.8), (Al-126)+(B2.9), (Al-126)+(B2.10), (Al-126)+(B2.11), (Al-126)+(B2.12), (Al-126)+(B2.13), (Al-126)+(B2.14), (Al-126)+(B2.15), (Al-126)+(B2.16), (Al-126)+(B2.17), (Al-126)+(B2.18), (Al-126)+(B2.19), (Al-126)+(B2.20), (Al-126)+(B2.21), (Al-126)+(B2.22), (Al-126)+(B2.23), (Al-126)+(B2.24), (Al-126)+(B2.25), (Al-126)+(B2.26), (Al-126)+(B2.27), (Al-126)+(B2.28), (Al-126)+(B2.29), (Al-126)+(B2.30), (Al-126)+(B2.31), (Al-126)+(B2.32), (Al-126)+(B2.33), (Al-126)+(B2.34), (Al-126)+(B2.35), (Al-126)+(B2.36), (Al-126)+(B2.37), (Al-126)+(B2.38), (Al-126)+(B2.39), (Al-126)+(B2.40), (Al-126)+(B2.41), (Al-126)+(B2.42), (Al-126)+(B2.43), (Al-126)+(B2.44), (Al-126)+(B2.45), (Al-126)+(B2.46), (Al-126)+(B2.47), (Al-126)+(B2.48), (Al-126)+(B2.49), (Al-126)+(B2.50), (Al-126)+(B3.1), (Al-126)+(B3.2.), (Al-126)+(B3.3), (Al-126)+(B3.4), (Al-126)+(B3.5), (Al-126)+(B3.6), (Al-126)+(B3.7), (Al-126)+(B3.8), (Al-126)+(B3.9), (Al-126)+(B3.10), (Al-126)+(B3.11), (Al-126)+(B3.12), (Al-126)+(B3.13), (Al-126)+(B3.14), (Al-126)+(B3.15), (Al-126)+(B3.16), (Al-126)+(B4.1), (Al-126)+(B4.2), (Al-126)+(B4.3), (Al-126)+(B4.4), (Al-126)+(B4.5), (Al-126)+(B4.6), (Al-126)+(B4.7).

(Al-127)+(B1.1), (Al-127)+(B1.2), (Al-127)+(B1.3), (Al-127)+(B1.4), (Al-127)+(B1.5), (Al-127)+(B1.6), (Al-127)+(B1.7), (Al-127)+(B1.8), (Al-127)+(B1.9), (Al-127)+(B1.10), (Al-127)+(B1.11), (Al-127)+(B1.12), (Al-127)+(B1.13), (Al-127)+(B1.14), (Al-127)+(B1.15), (Al-127)+(B1.16), (Al-127)+(B1.17), (Al-127)+(B1.18), (Al-127)+(B1.19), (Al-127)+(B1.20), (Al-127)+(B1.21), (Al-127)+(B1.22), (Al-127)+(B1.23), (Al-127)+(B1.24), (Al-127)+(B1.25), (Al-127)+(B1.26), (Al-127)+(B1.27), (Al-127)+(B1.28), (Al-127)+(B1.29), (Al-127)+(B1.30), (Al-127)+(B1.31), (Al-127)+(B1.32), (Al-127)+(B1.33), (Al-127)+(B1.34), (Al-127)+(B1.35), (Al-127)+(B1.36), (Al-127)+(B1.37), (Al-127)+(B1.38), (Al-127)+(B1.39), (Al-127)+(B1.40), (Al-127)+(B1.41), (Al-127)+(B1.42), (Al-127)+(B1.43), (Al-127)+(B1.44), (Al-127)+(B1.45), (Al-127)+(B1.46), (Al-127)+(B1.47), (Al-127)+(B1.48), (Al-127)+(B1.49), (Al-127)+(B1.50), (Al-127)+(B1.51), (Al-127)+(B1.52), (Al-127)+(B1.53), (Al-127)+(B1.54), (Al-127)+(B1.55), (Al-127)+(B1.56), (Al-127)+(B1.57), (Al-127)+(B1.58), (Al-127)+(B1.59), (Al-127)+(B1.60), (Al-127)+(B1.61), (Al-127)+(B1.62), (Al-127)+(B1.63), (Al-127)+(B1.64), (Al-127)+(B1.65), (Al-127)+(B1.66), (Al-127)+(B2.1), (Al-127)+(B2.2), (Al-127)+(B2.3), (Al-127)+(B2.4), (Al-127)+(B2.5), (Al-127)+(B2.6), (Al-127)+(B2.7), (Al-127)+(B2.8), (Al-127)+(B2.9), (Al-127)+(B2.10), (Al-127)+(B2.11), (Al-127)+(B2.12), (Al-127)+(B2.13), (Al-127)+(B2.14), (Al-127)+(B2.15), (Al-127)+(B2.16), (Al-127)+(B2.17), (Al-127)+(B2.18), (Al-127)+(B2.19), (Al-127)+(B2.20), (Al-127)+(B2.21), (Al-127)+(B2.22), (Al-127)+(B2.23), (Al-127)+(B2.24), (Al-127)+(B2.25), (Al-127)+(B2.26), (Al-127)+(B2.27), (Al-127)+(B2.28), (Al-127)+(B2.29), (Al-127)+(B2.30), (Al-127)+(B2.31), (Al-127)+(B2.32), (Al-127)+(B2.33), (Al-127)+(B2.34), (Al-127)+(B2.35), (Al-127)+(B2.36), (Al-127)+(B2.37), (Al-127)+(B2.38), (Al-127)+(B2.39), (Al-127)+(B2.40), (Al-127)+(B2.41), (Al-127)+(B2.42), (Al-127)+(B2.43), (Al-127)+(B2.44), (Al-127)+(B2.45), (Al-127)+(B2.46), (Al-127)+(B2.47), (Al-127)+(B2.48), (Al-127)+(B2.49), (Al-127)+(B2.50), (Al-127)+(B3.1), (Al-127)+(B3.2.), (Al-127)+(B3.3), (Al-127)+(B3.4), (Al-127)+(B3.5), (Al-127)+(B3.6), (Al-127)+(B3.7), (Al-127)+(B3.8), (Al-127)+(B3.9), (Al-127)+(B3.10), (Al-127)+(B3.11), (Al-127)+(B3.12), (Al-127)+(B3.13), (Al-127)+(B3.14), (Al-127)+(B3.15), (Al-127)+(B3.16), (Al-127)+(B4.1), (Al-127)+(B4.2), (Al-127)+(B4.3), (Al-127)+(B4.4), (Al-127)+(B4.5), (Al-127)+(B4.6), (Al-127)+(B4.7).

(Al-128)+(B1.1), (Al-128)+(B1.2), (Al-128)+(B1.3), (Al-128)+(B1.4), (Al-128)+(B1.5), (Al-128)+(B1.6), (Al-128)+(B1.7), (Al-128)+(B1.8), (Al-128)+(B1.9), (Al-128)+(B1.10), (Al-128)+(B1.11), (Al-128)+(B1.12), (Al-128)+(B1.13), (Al-128)+(B1.14), (Al-128)+(B1.15), (Al-128)+(B1.16), (Al-128)+(B1.17), (Al-128)+(B1.18), (Al-128)+(B1.19), (Al-128)+(B1.20), (Al-128)+(B1.21), (Al-128)+(B1.22), (Al-128)+(B1.23), (Al-128)+(B1.24), (Al-128)+(B1.25), (Al-128)+(B1.26), (Al-128)+(B1.27), (Al-128)+(B1.28), (Al-128)+(B1.29), (Al-128)+(B1.30), (Al-128)+(B1.31), (Al-128)+(B1.32), (Al-128)+(B1.33), (Al-128)+(B1.34), (Al-128)+(B1.35), (Al-128)+(B1.36), (Al-128)+(B1.37), (Al-128)+(B1.38), (Al-128)+(B1.39), (Al-128)+(B1.40), (Al-128)+(B1.41), (Al-128)+(B1.42), (Al-128)+(B1.43), (Al-128)+(B1.44), (Al-128)+(B1.45), (Al-128)+(B1.46), (Al-128)+(B1.47), (Al-128)+(B1.48), (Al-128)+(B1.49), (Al-128)+(B1.50), (Al-128)+(B1.51), (Al-128)+(B1.52), (Al-128)+(B1.53), (Al-128)+(B1.54), (Al-128)+(B1.55), (Al-128)+(B1.56), (Al-128)+(B1.57), (Al-128)+(B1.58), (Al-128)+(B1.59), (Al-128)+(B1.60), (Al-128)+(B1.61), (Al-128)+(B1.62), (Al-128)+(B1.63), (Al-128)+(B1.64), (Al-128)+(B1.65), (Al-128)+(B1.66), (Al-128)+(B2.1), (Al-128)+(B2.2), (Al-128)+(B2.3), (Al-128)+(B2.4), (Al-128)+(B2.5), (Al-128)+(B2.6), (Al-128)+(B2.7), (Al-128)+(B2.8), (Al-128)+(B2.9), (Al-128)+(B2.10), (Al-128)+(B2.11), (Al-128)+(B2.12), (Al-128)+(B2.13), (Al-128)+(B2.14), (Al-128)+(B2.15), (Al-128)+(B2.16), (Al-128)+(B2.17), (Al-128)+(B2.18), (Al-128)+(B2.19), (Al-128)+(B2.20), (Al-128)+(B2.21), (Al-128)+(B2.22), (Al-128)+(B2.23), (Al-128)+(B2.24), (Al-128)+(B2.25), (Al-128)+(B2.26), (Al-128)+(B2.27), (Al-128)+(B2.28), (Al-128)+(B2.29), (Al-128)+(B2.30), (Al-128)+(B2.31), (Al-128)+(B2.32), (Al-128)+(B2.33), (Al-128)+(B2.34), (Al-128)+(B2.35), (Al-128)+(B2.36), (Al-128)+(B2.37), (Al-128)+(B2.38), (Al-128)+(B2.39), (Al-128)+(B2.40), (Al-128)+(B2.41), (Al-128)+(B2.42), (Al-128)+(B2.43), (Al-128)+(B2.44), (Al-128)+(B2.45), (Al-128)+(B2.46), (Al-128)+(B2.47), (Al-128)+(B2.48), (Al-128)+(B2.49), (Al-128)+

(B2.50), (Al-128)+(B3.1), (Al-128)+(B3.2.), (Al-128)+(B3.3), (Al-128)+(B3.4), (Al-128)+(B3.5), (Al-128)+(B3.6), (Al-128)+(B3.7), (Al-128)+(B3.8), (Al-128)+(B3.9), (Al-128)+(B3.10), (Al-128)+(B3.11), (Al-128)+(B3.12), (Al-128)+(B3.13), (Al-128)+(B3.14), (Al-128)+(B3.15), (Al-128)+(B3.16), (Al-128)+(B4.1), (Al-128)+(B4.2), (Al-128)+(B4.3), (Al-128)+(B4.4), (Al-128)+(B4.5), (Al-128)+(B4.6), (Al-128)+(B4.7).

(Al-129)+(B1.1), (Al-129)+(B1.2), (Al-129)+(B1.3), (Al-129)+(B1.4), (Al-129)+(B1.5), (Al-129)+(B1.6), (Al-129)+(B1.7), (Al-129)+(B1.8), (Al-129)+(B1.9), (Al-129)+(B1.10), (Al-129)+(B1.11), (Al-129)+(B1.12), (Al-129)+(B1.13), (Al-129)+(B1.14), (Al-129)+(B1.15), (Al-129)+(B1.16), (Al-129)+(B1.17), (Al-129)+(B1.18), (Al-129)+(B1.19), (Al-129)+(B1.20), (Al-129)+(B1.21), (Al-129)+(B1.22), (Al-129)+(B1.23), (Al-129)+(B1.24), (Al-129)+(B1.25), (Al-129)+(B1.26), (Al-129)+(B1.27), (Al-129)+(B1.28), (Al-129)+(B1.29), (Al-129)+(B1.30), (Al-129)+(B1.31), (Al-129)+(B1.32), (Al-129)+(B1.33), (Al-129)+(B1.34), (Al-129)+(B1.35), (Al-129)+(B1.36), (Al-129)+(B1.37), (Al-129)+(B1.38), (Al-129)+(B1.39), (Al-129)+(B1.40), (Al-129)+(B1.41), (Al-129)+(B1.42), (Al-129)+(B1.43), (Al-129)+(B1.44), (Al-129)+(B1.45), (Al-129)+(B1.46), (Al-129)+(B1.47), (Al-129)+(B1.48), (Al-129)+(B1.49), (Al-129)+(B1.50), (Al-129)+(B1.51), (Al-129)+(B1.52), (Al-129)+(B1.53), (Al-129)+(B1.54), (Al-129)+(B1.55), (Al-129)+(B1.56), (Al-129)+(B1.57), (Al-129)+(B1.58), (Al-129)+(B1.59), (Al-129)+(B1.60), (Al-129)+(B1.61), (Al-129)+(B1.62), (Al-129)+(B1.63), (Al-129)+(B1.64), (Al-129)+(B1.65), (Al-129)+(B1.66), (Al-129)+(B2.1), (Al-129)+(B2.2), (Al-129)+(B2.3), (Al-129)+(B2.4), (Al-129)+(B2.5), (Al-129)+(B2.6), (Al-129)+(B2.7), (Al-129)+(B2.8), (Al-129)+(B2.9), (Al-129)+(B2.10), (Al-129)+(B2.11), (Al-129)+(B2.12), (Al-129)+(B2.13), (Al-129)+(B2.14), (Al-129)+(B2.15), (Al-129)+(B2.16), (Al-129)+(B2.17), (Al-129)+(B2.18), (Al-129)+(B2.19), (Al-129)+(B2.20), (Al-129)+(B2.21), (Al-129)+(B2.22), (Al-129)+(B2.23), (Al-129)+(B2.24), (Al-129)+(B2.25), (Al-129)+(B2.26), (Al-129)+(B2.27), (Al-129)+(B2.28), (Al-129)+(B2.29), (Al-129)+(B2.30), (Al-129)+(B2.31), (Al-129)+(B2.32), (Al-129)+(B2.33), (Al-129)+(B2.34), (Al-129)+(B2.35), (Al-129)+(B2.36), (Al-129)+(B2.37), (Al-129)+(B2.38), (Al-129)+(B2.39), (Al-129)+(B2.40), (Al-129)+(B2.41), (Al-129)+(B2.42), (Al-129)+(B2.43), (Al-129)+(B2.44), (Al-129)+(B2.45), (Al-129)+(B2.46), (Al-129)+(B2.47), (Al-129)+(B2.48), (Al-129)+(B2.49), (Al-129)+(B2.50), (Al-129)+(B3.1), (Al-129)+(B3.2.), (Al-129)+(B3.3), (Al-129)+(B3.4), (Al-129)+(B3.5), (Al-129)+(B3.6), (Al-129)+(B3.7), (Al-129)+(B3.8), (Al-129)+(B3.9), (Al-129)+(B3.10), (Al-129)+(B3.11), (Al-129)+(B3.12), (Al-129)+(B3.13), (Al-129)+(B3.14), (Al-129)+(B3.15), (Al-129)+(B3.16), (Al-129)+(B4.1), (Al-129)+(B4.2), (Al-129)+(B4.3), (Al-129)+(B4.4), (Al-129)+(B4.5), (Al-129)+(B4.6), (Al-129)+(B4.7).

(Al-130)+(B1.1), (Al-130)+(B1.2), (Al-130)+(B1.3), (Al-130)+(B1.4), (Al-130)+(B1.5), (Al-130)+(B1.6), (Al-130)+(B1.7), (Al-130)+(B1.8), (Al-130)+(B1.9), (Al-130)+(B1.10), (Al-130)+(B1.11), (Al-130)+(B1.12), (Al-130)+(B1.13), (Al-130)+(B1.14), (Al-130)+(B1.15), (Al-130)+(B1.16), (Al-130)+(B1.17), (Al-130)+(B1.18), (Al-130)+(B1.19), (Al-130)+(B1.20), (Al-130)+(B1.21), (Al-130)+(B1.22), (Al-130)+(B1.23), (Al-130)+(B1.24), (Al-130)+(B1.25), (Al-130)+(B1.26), (Al-130)+(B1.27), (Al-130)+(B1.28), (Al-130)+(B1.29), (Al-130)+(B1.30), (Al-130)+(B1.31), (Al-130)+(B1.32), (Al-130)+(B1.33), (Al-130)+(B1.34), (Al-130)+(B1.35), (Al-130)+(B1.36), (Al-130)+(B1.37), (Al-130)+(B1.38), (Al-130)+(B1.39), (Al-130)+(B1.40), (Al-130)+(B1.41), (Al-130)+(B1.42), (Al-130)+(B1.43), (Al-130)+(B1.44), (Al-130)+(B1.45), (Al-130)+(B1.46), (Al-130)+(B1.47), (Al-130)+(B1.48), (Al-130)+(B1.49), (Al-130)+(B1.50), (Al-130)+(B1.51), (Al-130)+(B1.52), (Al-130)+(B1.53), (Al-130)+(B1.54), (Al-130)+(B1.55), (Al-130)+(B1.56), (Al-130)+(B1.57), (Al-130)+(B1.58), (Al-130)+(B1.59), (Al-130)+(B1.60), (Al-130)+(B1.61), (Al-130)+(B1.62), (Al-130)+(B1.63), (Al-130)+(B1.64), (Al-130)+(B1.65), (Al-130)+(B1.66), (Al-130)+(B2.1), (Al-130)+(B2.2), (Al-130)+(B2.3), (Al-130)+(B2.4), (Al-130)+(B2.5), (Al-130)+(B2.6), (Al-130)+(B2.7), (Al-130)+(B2.8), (Al-130)+(B2.9), (Al-130)+(B2.10), (Al-130)+(B2.11), (Al-130)+(B2.12), (Al-130)+(B2.13), (Al-130)+(B2.14), (Al-130)+(B2.15), (Al-130)+(B2.16), (Al-130)+(B2.17), (Al-130)+(B2.18), (Al-130)+(B2.19), (Al-130)+(B2.20), (Al-130)+(B2.21), (Al-130)+(B2.22), (Al-130)+(B2.23), (Al-130)+(B2.24), (Al-130)+(B2.25), (Al-130)+(B2.26), (Al-130)+(B2.27), (Al-130)+(B2.28), (Al-130)+(B2.29), (Al-130)+(B2.30), (Al-130)+(B2.31), (Al-130)+(B2.32), (Al-130)+(B2.33), (Al-130)+(B2.34), (Al-130)+(B2.35), (Al-130)+(B2.36), (Al-130)+(B2.37), (Al-130)+(B2.38), (Al-130)+(B2.39), (Al-130)+(B2.40), (Al-130)+(B2.41), (Al-130)+(B2.42), (Al-130)+(B2.43), (Al-130)+(B2.44), (Al-130)+(B2.45), (Al-130)+(B2.46), (Al-130)+(B2.47), (Al-130)+(B2.48), (Al-130)+(B2.49), (Al-130)+(B2.50), (Al-130)+(B3.1), (Al-130)+(B3.2.), (Al-130)+(B3.3), (Al-130)+(B3.4), (Al-130)+(B3.5), (Al-130)+(B3.6), (Al-130)+(B3.7), (Al-130)+(B3.8), (Al-130)+(B3.9), (Al-130)+(B3.10), (Al-130)+(B3.11), (Al-130)+(B3.12), (Al-130)+(B3.13), (Al-130)+(B3.14), (Al-130)+(B3.15), (Al-130)+(B3.16), (Al-130)+(B4.1), (Al-130)+(B4.2), (Al-130)+(B4.3), (Al-130)+(B4.4), (Al-130)+(B4.5), (Al-130)+(B4.6), (Al-130)+(B4.7).

(Al-131)+(B1.1), (Al-131)+(B1.2), (Al-131)+(B1.3), (Al-131)+(B1.4), (Al-131)+(B1.5), (Al-131)+(B1.6), (Al-131)+(B1.7), (Al-131)+(B1.8), (Al-131)+(B1.9), (Al-131)+(B1.10), (Al-131)+(B1.11), (Al-131)+(B1.12), (Al-131)+(B1.13), (Al-131)+(B1.14), (Al-131)+(B1.15), (Al-131)+(B1.16), (Al-131)+(B1.17), (Al-131)+(B1.18), (Al-131)+(B1.19), (Al-131)+(B1.20), (Al-131)+(B1.21), (Al-131)+(B1.22), (Al-131)+(B1.23), (Al-131)+(B1.24), (Al-131)+(B1.25), (Al-131)+(B1.26), (Al-131)+(B1.27), (Al-131)+(B1.28), (Al-131)+(B1.29), (Al-131)+(B1.30), (Al-131)+(B1.31), (Al-131)+(B1.32), (Al-131)+(B1.33), (Al-131)+(B1.34), (Al-131)+(B1.35), (Al-131)+(B1.36), (Al-131)+(B1.37), (Al-131)+(B1.38), (Al-131)+(B1.39), (Al-131)+(B1.40), (Al-131)+(B1.41), (Al-131)+(Al-131)+(B1.42), (Al-131)+(B1.43), (Al-131)+(B1.44), (Al-131)+(B1.45), (Al-131)+(B1.46), (Al-131)+(B1.47), (Al-131)+(B1.48), (Al-131)+(B1.49), (Al-131)+(B1.50), (Al-131)+(B1.51), (Al-131)+(B1.52), (Al-131)+(B1.53), (Al-131)+(B1.54), (Al-131)+(B1.55), (Al-131)+(B1.56), (Al-131)+(B1.57), (Al-131)+(B1.58), (Al-131)+(B1.59), (Al-131)+(B1.60), (Al-131)+(B1.61), (Al-131)+(B1.62), (Al-131)+(B1.63), (Al-131)+(B1.64), (Al-131)+(B1.65), (Al-131)+(B1.66), (Al-131)+(B2.1), (Al-131)+(B2.2), (Al-131)+(B2.3), (Al-131)+(B2.4), (Al-131)+(B2.5), (Al-131)+(B2.6), (Al-131)+(B2.7), (Al-131)+(B2.8), (Al-131)+(B2.9), (Al-131)+(B2.10), (Al-131)+(B2.11), (Al-131)+(B2.12), (Al-131)+(B2.13), (Al-131)+(B2.14), (Al-131)+(B2.15), (Al-131)+(B2.16), (Al-131)+(B2.17), (Al-131)+(B2.18), (Al-131)+(B2.19), (Al-131)+(B2.20), (Al-131)+(B2.21), (Al-131)+(B2.22), (Al-131)+(B2.23), (Al-131)+(B2.24), (Al-131)+(B2.25), (Al-131)+(B2.26), (Al-131)+(B2.27), (Al-131)+(B2.28), (Al-131)+(B2.29), (Al-131)+(B2.30), (Al-131)+(B2.31), (Al-131)+(B2.32), (Al-131)+(B2.33), (Al-131)+(B2.34), (Al-131)+(B2.35), (Al-131)+(B2.36), (Al-131)+

(B2.37), (Al-131)+(B2.38), (Al-131)+(B2.39), (Al-131)+(B2.40), (Al-131)+(B2.41), (Al-131)+(B2.42), (Al-131)+(B2.43), (Al-131)+(B2.44), (Al-131)+(B2.45), (Al-131)+(B2.46), (Al-131)+(B2.47), (Al-131)+(B2.48), (Al-131)+(B2.49), (Al-131)+(B2.50), (Al-131)+(B3.1), (Al-131)+(B3.2.), (Al-131)+(B3.3), (Al-131)+(B3.4), (Al-131)+(B3.5), (Al-131)+(B3.6), (Al-131)+(B3.7), (Al-131)+(B3.8), (Al-131)+(B3.9), (Al-131)+(B3.10), (Al-131)+(B3.11), (Al-131)+(B3.12), (Al-131)+(B3.13), (Al-131)+(B3.14), (Al-131)+(B3.15), (Al-131)+(B3.16), (Al-131)+(B4.1), (Al-131)+(B4.2), (Al-131)+(B4.3), (Al-131)+(B4.4), (Al-131)+(B4.5), (Al-131)+(B4.6), (Al-131)+(B4.7).

(Al-132)+(B1.1), (Al-132)+(B1.2), (Al-132)+(B1.3), (Al-132)+(B1.4), (Al-132)+(B1.5), (Al-132)+(B1.6), (Al-132)+(B1.7), (Al-132)+(B1.8), (Al-132)+(B1.9), (Al-132)+(B1.10), (Al-132)+(B1.11), (Al-132)+(B1.12), (Al-132)+(B1.13), (Al-132)+(B1.14), (Al-132)+(B1.15), (Al-132)+(B1.16), (Al-132)+(B1.17), (Al-132)+(B1.18), (Al-132)+(B1.19), (Al-132)+(B1.20), (Al-132)+(B1.21), (Al-132)+(B1.22), (Al-132)+(B1.23), (Al-132)+(B1.24), (Al-132)+(B1.25), (Al-132)+(B1.26), (Al-132)+(B1.27), (Al-132)+(B1.28), (Al-132)+(B1.29), (Al-132)+(B1.30), (Al-132)+(B1.31), (Al-132)+(B1.32), (Al-132)+(B1.33), (Al-132)+(B1.34), (Al-132)+(B1.35), (Al-132)+(B1.36), (Al-132)+(B1.37), (Al-132)+(B1.38), (Al-132)+(B1.39), (Al-132)+(B1.40), (Al-132)+(B1.41), (Al-132)+(B1.42), (Al-132)+(B1.43), (Al-132)+(B1.44), (Al-132)+(B1.45), (Al-132)+(B1.46), (Al-132)+(B1.47), (Al-132)+(B1.48), (Al-132)+(B1.49), (Al-132)+(B1.50), (Al-132)+(B1.51), (Al-132)+(B1.52), (Al-132)+(B1.53), (Al-132)+(B1.54), (Al-132)+(B1.55), (Al-132)+(B1.56), (Al-132)+(B1.57), (Al-132)+(B1.58), (Al-132)+(B1.59), (Al-132)+(B1.60), (Al-132)+(B1.61), (Al-132)+(B1.62), (Al-132)+(B1.63), (Al-132)+(B1.64), (Al-132)+(B1.65), (Al-132)+(B1.66), (Al-132)+(B2.1), (Al-132)+(B2.2), (Al-132)+(B2.3), (Al-132)+(B2.4), (Al-132)+(B2.5), (Al-132)+(B2.6), (Al-132)+(B2.7), (Al-132)+(B2.8), (Al-132)+(B2.9), (Al-132)+(B2.10), (Al-132)+(B2.11), (Al-132)+(B2.12), (Al-132)+(B2.13), (Al-132)+(B2.14), (Al-132)+(B2.15), (Al-132)+(B2.16), (Al-132)+(B2.17), (Al-132)+(B2.18), (Al-132)+(B2.19), (Al-132)+(B2.20), (Al-132)+(B2.21), (Al-132)+(B2.22), (Al-132)+(B2.23), (Al-132)+(B2.24), (Al-132)+(B2.25), (Al-132)+(B2.26), (Al-132)+(B2.27), (Al-132)+(B2.28), (Al-132)+(B2.29), (Al-132)+(B2.30), (Al-132)+(B2.31), (Al-132)+(B2.32), (Al-132)+(B2.33), (Al-132)+(B2.34), (Al-132)+(B2.35), (Al-132)+(B2.36), (Al-132)+(B2.37), (Al-132)+(B2.38), (Al-132)+(B2.39), (Al-132)+(B2.40), (Al-132)+(B2.41), (Al-132)+(B2.42), (Al-132)+(B2.43), (Al-132)+(B2.44), (Al-132)+(B2.45), (Al-132)+(B2.46), (Al-132)+(B2.47), (Al-132)+(B2.48), (Al-132)+(B2.49), (Al-132)+(B2.50), (Al-132)+(B3.1), (Al-132)+(B3.2.), (Al-132)+(B3.3), (Al-132)+(B3.4), (Al-132)+(B3.5), (Al-132)+(B3.6), (Al-132)+(B3.7), (Al-132)+(B3.8), (Al-132)+(B3.9), (Al-132)+(B3.10), (Al-132)+(B3.11), (Al-132)+(B3.12), (Al-132)+(B3.13), (Al-132)+(B3.14), (Al-132)+(B3.15), (Al-132)+(B3.16), (Al-132)+(B4.1), (Al-132)+(B4.2), (Al-132)+(B4.3), (Al-132)+(B4.4), (Al-132)+(B4.5), (Al-132)+(B4.6), (Al-132)+(B4.7).

(Al-133)+(B1.1), (Al-133)+(B1.2), (Al-133)+(B1.3), (Al-133)+(B1.4), (Al-133)+(B1.5), (Al-133)+(B1.6), (Al-133)+(B1.7), (Al-133)+(B1.8), (Al-133)+(B1.9), (Al-133)+(B1.10), (Al-133)+(B1.11), (Al-133)+(B1.12), (Al-133)+(B1.13), (Al-133)+(B1.14), (Al-133)+(B1.15), (Al-133)+(B1.16), (Al-133)+(B1.17), (Al-133)+(B1.18), (Al-133)+(B1.19), (Al-133)+(B1.20), (Al-133)+(B1.21), (Al-133)+(B1.22), (Al-133)+(B1.23), (Al-133)+(B1.24), (Al-133)+(B1.25), (Al-133)+(B1.26), (Al-133)+(B1.27), (Al-133)+(B1.28), (Al-133)+(B1.29), (Al-133)+(B1.30), (Al-133)+(B1.31), (Al-133)+(B1.32), (Al-133)+(B1.33), (Al-133)+(B1.34), (Al-133)+(B1.35), (Al-133)+(B1.36), (Al-133)+(B1.37), (Al-133)+(B1.38), (Al-133)+(B1.39), (Al-133)+(B1.40), (Al-133)+(B1.41), (Al-133)+(B1.42), (Al-133)+(B1.43), (Al-133)+(B1.44), (Al-133)+(B1.45), (Al-133)+(B1.46), (Al-133)+(B1.47), (Al-133)+(B1.48), (Al-133)+(B1.49), (Al-133)+(B1.50), (Al-133)+(B1.51), (Al-133)+(B1.52), (Al-133)+(B1.53), (Al-133)+(B1.54), (Al-133)+(B1.55), (Al-133)+(B1.56), (Al-133)+(B1.57), (Al-133)+(B1.58), (Al-133)+(B1.59), (Al-133)+(B1.60), (Al-133)+(B1.61), (Al-133)+(B1.62), (Al-133)+(B1.63), (Al-133)+(B1.64), (Al-133)+(B1.65), (Al-133)+(B1.66), (Al-133)+(B2.1), (Al-133)+(B2.2), (Al-133)+(B2.3), (Al-133)+(B2.4), (Al-133)+(B2.5), (Al-133)+(B2.6), (Al-133)+(B2.7), (Al-133)+(B2.8), (Al-133)+(B2.9), (Al-133)+(B2.10), (Al-133)+(B2.11), (Al-133)+(B2.12), (Al-133)+(B2.13), (Al-133)+(B2.14), (Al-133)+(B2.15), (Al-133)+(B2.16), (Al-133)+(B2.17), (Al-133)+(B2.18), (Al-133)+(B2.19), (Al-133)+(B2.20), (Al-133)+(B2.21), (Al-133)+(B2.22), (Al-133)+(B2.23), (Al-133)+(B2.24), (Al-133)+(B2.25), (Al-133)+(B2.26), (Al-133)+(B2.27), (Al-133)+(B2.28), (Al-133)+(B2.29), (Al-133)+(B2.30), (Al-133)+(B2.31), (Al-133)+(B2.32), (Al-133)+(B2.33), (Al-133)+(B2.34), (Al-133)+(B2.35), (Al-133)+(B2.36), (Al-133)+(B2.37), (Al-133)+(B2.38), (Al-133)+(B2.39), (Al-133)+(B2.40), (Al-133)+(B2.41), (Al-133)+(B2.42), (Al-133)+(B2.43), (Al-133)+(B2.44), (Al-133)+(B2.45), (Al-133)+(B2.46), (Al-133)+(B2.47), (Al-133)+(B2.48), (Al-133)+(B2.49), (Al-133)+(B2.50), (Al-133)+(B3.1), (Al-133)+(B3.2.), (Al-133)+(B3.3), (Al-133)+(B3.4), (Al-133)+(B3.5), (Al-133)+(B3.6), (Al-133)+(B3.7), (Al-133)+(B3.8), (Al-133)+(B3.9), (Al-133)+(B3.10), (Al-133)+(B3.11), (Al-133)+(B3.12), (Al-133)+(B3.13), (Al-133)+(B3.14), (Al-133)+(B3.15), (Al-133)+(B3.16), (Al-133)+(B4.1), (Al-133)+(B4.2), (Al-133)+(B4.3), (Al-133)+(B4.4), (Al-133)+(B4.5), (Al-133)+(B4.6), (Al-133)+(B4.7).

(Al-134)+(B1.1), (Al-134)+(B1.2), (Al-134)+(B1.3), (Al-134)+(B1.4), (Al-134)+(B1.5), (Al-134)+(B1.6), (Al-134)+(B1.7), (Al-134)+(B1.8), (Al-134)+(B1.9), (Al-134)+(B1.10), (Al-134)+(B1.11), (Al-134)+(B1.12), (Al-134)+(B1.13), (Al-134)+(B1.14), (Al-134)+(B1.15), (Al-134)+(B1.16), (Al-134)+(B1.17), (Al-134)+(B1.18), (Al-134)+(B1.19), (Al-134)+(B1.20), (Al-134)+(B1.21), (Al-134)+(B1.22), (Al-134)+(B1.23), (Al-134)+(B1.24), (Al-134)+(B1.25), (Al-134)+(B1.26), (Al-134)+(B1.27), (Al-134)+(B1.28), (Al-134)+(B1.29), (Al-134)+(B1.30), (Al-134)+(B1.31), (Al-134)+(B1.32), (Al-134)+(B1.33), (Al-134)+(B1.34), (Al-134)+(B1.35), (Al-134)+(B1.36), (Al-134)+(B1.37), (Al-134)+(B1.38), (Al-134)+(B1.39), (Al-134)+(B1.40), (Al-134)+(B1.41), (Al-134)+(B1.42), (Al-134)+(B1.43), (Al-134)+(B1.44), (Al-134)+(B1.45), (Al-134)+(B1.46), (Al-134)+(B1.47), (Al-134)+(B1.48), (Al-134)+(B1.49), (Al-134)+(B1.50), (Al-134)+(B1.51), (Al-134)+(B1.52), (Al-134)+(B1.53), (Al-134)+(B1.54), (Al-134)+(B1.55), (Al-134)+(B1.56), (Al-134)+(B1.57), (Al-134)+(B1.58), (Al-134)+(B1.59), (Al-134)+(B1.60), (Al-134)+(B1.61), (Al-134)+(B1.62), (Al-134)+(B1.63), (Al-134)+(B1.64), (Al-134)+(B1.65), (Al-134)+(B1.66), (Al-134)+(B2.1), (Al-134)+(B2.2), (Al-134)+(B2.3), (Al-134)+(B2.4), (Al-134)+(B2.5), (Al-134)+(B2.6), (Al-134)+(B2.7), (Al-134)+(B2.8), (Al-134)+(B2.9), (Al-134)+(B2.10), (Al-134)+(B2.11), (Al-134)+(B2.12), (Al-134)+(B2.13), (Al-134)+(B2.14), (Al-134)+(B2.15), (Al-134)+(B2.16), (Al-134)+(B2.17), (Al-134)+(B2.18), (Al-134)+(B2.19), (Al-134)+(B2.20), (Al-134)+(B2.21), (Al-134)+(B2.22), (Al-134)+(B2.23), (Al-134)+(B2.24), (Al-134)+(B2.25), (Al-134)+

(B2.26), (Al-134)+(B2.27), (Al-134)+(B2.28), (Al-134)+(B2.29), (Al-134)+(B2.30), (Al-134)+(B2.31), (Al-134)+(B2.32), (Al-134)+(B2.33), (Al-134)+(B2.34), (Al-134)+(B2.35), (Al-134)+(B2.36), (Al-134)+(B2.37), (Al-134)+(B2.38), (Al-134)+(B2.39), (Al-134)+(B2.40), (Al-134)+(B2.41), (Al-134)+(B2.42), (Al-134)+(B2.43), (Al-134)+(B2.44), (Al-134)+(B2.45), (Al-134)+(B2.46), (Al-134)+(B2.47), (Al-134)+(B2.48), (Al-134)+(B2.49), (Al-134)+(B2.50), (Al-134)+(B3.1), (Al-134)+(B3.2.), (Al-134)+(B3.3), (Al-134)+(B3.4), (Al-134)+(B3.5), (Al-134)+(B3.6), (Al-134)+(B3.7), (Al-134)+(B3.8), (Al-134)+(B3.9), (Al-134)+(B3.10), (Al-134)+(B3.11), (Al-134)+(B3.12), (Al-134)+(B3.13), (Al-134)+(B3.14), (Al-134)+(B3.15), (Al-134)+(B3.16), (Al-134)+(B4.1), (Al-134)+(B4.2), (Al-134)+(B4.3), (Al-134)+(B4.4), (Al-134)+(B4.5), (Al-134)+(B4.6), (Al-134)+(B4.7).

(Al-135)+(B1.1), (Al-135)+(B1.2), (Al-135)+(B1.3), (Al-135)+(B1.4), (Al-135)+(B1.5), (Al-135)+(B1.6), (Al-135)+(B1.7), (Al-135)+(B1.8), (Al-135)+(B1.9), (Al-135)+(B1.10), (Al-135)+(B1.11), (Al-135)+(B1.12), (Al-135)+(B1.13), (Al-135)+(B1.14), (Al-135)+(B1.15), (Al-135)+(B1.16), (Al-135)+(B1.17), (Al-135)+(B1.18), (Al-135)+(B1.19), (Al-135)+(B1.20), (Al-135)+(B1.21), (Al-135)+(B1.22), (Al-135)+(B1.23), (Al-135)+(B1.24), (Al-135)+(B1.25), (Al-135)+(B1.26), (Al-135)+(B1.27), (Al-135)+(B1.28), (Al-135)+(B1.29), (Al-135)+(B1.30), (Al-135)+(B1.31), (Al-135)+(B1.32), (Al-135)+(B1.33), (Al-135)+(B1.34), (Al-135)+(B1.35), (Al-135)+(B1.36), (Al-135)+(B1.37), (Al-135)+(B1.38), (Al-135)+(B1.39), (Al-135)+(B1.40), (Al-135)+(B1.41), (Al-135)+(B1.42), (Al-135)+(B1.43), (Al-135)+(B1.44), (Al-135)+(B1.45), (Al-135)+(B1.46), (Al-135)+(B1.47), (Al-135)+(B1.48), (Al-135)+(B1.49), (Al-135)+(B1.50), (Al-135)+(B1.51), (Al-135)+(B1.52), (Al-135)+(B1.53), (Al-135)+(B1.54), (Al-135)+(B1.55), (Al-135)+(B1.56), (Al-135)+(B1.57), (Al-135)+(B1.58), (Al-135)+(B1.59), (Al-135)+(B1.60), (Al-135)+(B1.61), (Al-135)+(B1.62), (Al-135)+(B1.63), (Al-135)+(B1.64), (Al-135)+(B1.65), (Al-135)+(B1.66), (Al-135)+(B2.1), (Al-135)+(B2.2), (Al-135)+(B2.3), (Al-135)+(B2.4), (Al-135)+(B2.5), (Al-135)+(B2.6), (Al-135)+(B2.7), (Al-135)+(B2.8), (Al-135)+(B2.9), (Al-135)+(B2.10), (Al-135)+(B2.11), (Al-135)+(B2.12), (Al-135)+(B2.13), (Al-135)+(B2.14), (Al-135)+(B2.15), (Al-135)+(B2.16), (Al-135)+(B2.17), (Al-135)+(B2.18), (Al-135)+(B2.19), (Al-135)+(B2.20), (Al-135)+(B2.21), (Al-135)+(B2.22), (Al-135)+(B2.23), (Al-135)+(B2.24), (Al-135)+(B2.25), (Al-135)+(B2.26), (Al-135)+(B2.27), (Al-135)+(B2.28), (Al-135)+(B2.29), (Al-135)+(B2.30), (Al-135)+(B2.31), (Al-135)+(B2.32), (Al-135)+(B2.33), (Al-135)+(B2.34), (Al-135)+(B2.35), (Al-135)+(B2.36), (Al-135)+(B2.37), (Al-135)+(B2.38), (Al-135)+(B2.39), (Al-135)+(B2.40), (Al-135)+(B2.41), (Al-135)+(B2.42), (Al-135)+(B2.43), (Al-135)+(B2.44), (Al-135)+(B2.45), (Al-135)+(B2.46), (Al-135)+(B2.47), (Al-135)+(B2.48), (Al-135)+(B2.49), (Al-135)+(B2.50), (Al-135)+(B3.1), (Al-135)+(B3.2.), (Al-135)+(B3.3), (Al-135)+(B3.4), (Al-135)+(B3.5), (Al-135)+(B3.6), (Al-135)+(B3.7), (Al-135)+(B3.8), (Al-135)+(B3.9), (Al-135)+(B3.10), (Al-135)+(B3.11), (Al-135)+(B3.12), (Al-135)+(B3.13), (Al-135)+(B3.14), (Al-135)+(B3.15), (Al-135)+(B3.16), (Al-135)+(B4.1), (Al-135)+(B4.2), (Al-135)+(B4.3), (Al-135)+(B4.4), (Al-135)+(B4.5), (Al-135)+(B4.6), (Al-135)+(B4.7).

(Al-136)+(B1.1), (Al-136)+(B1.2), (Al-136)+(B1.3), (Al-136)+(B1.4), (Al-136)+(B1.5), (Al-136)+(B1.6), (Al-136)+(B1.7), (Al-136)+(B1.8), (Al-136)+(B1.9), (Al-136)+(B1.10), (Al-136)+(B1.11), (Al-136)+(B1.12), (Al-136)+(B1.13), (Al-136)+(B1.14), (Al-136)+(B1.15), (Al-136)+(B1.16), (Al-136)+(B1.17), (Al-136)+(B1.18), (Al-136)+(B1.19), (Al-136)+(B1.20), (Al-136)+(B1.21), (Al-136)+(B1.22), (Al-136)+(B1.23), (Al-136)+(B1.24), (Al-136)+(B1.25), (Al-136)+(B1.26), (Al-136)+(B1.27), (Al-136)+(B1.28), (Al-136)+(B1.29), (Al-136)+(B1.30), (Al-136)+(B1.31), (Al-136)+(B1.32), (Al-136)+(B1.33), (Al-136)+(B1.34), (Al-136)+(B1.35), (Al-136)+(B1.36), (Al-136)+(B1.37), (Al-136)+(B1.38), (Al-136)+(B1.39), (Al-136)+(B1.40), (Al-136)+(B1.41), (Al-136)+(B1.42), (Al-136)+(B1.43), (Al-136)+(B1.44), (Al-136)+(B1.45), (Al-136)+(B1.46), (Al-136)+(B1.47), (Al-136)+(B1.48), (Al-136)+(B1.49), (Al-136)+(B1.50), (Al-136)+(B1.51), (Al-136)+(B1.52), (Al-136)+(B1.53), (Al-136)+(B1.54), (Al-136)+(B1.55), (Al-136)+(B1.56), (Al-136)+(B1.57), (Al-136)+(B1.58), (Al-136)+(B1.59), (Al-136)+(B1.60), (Al-136)+(B1.61), (Al-136)+(B1.62), (Al-136)+(B1.63), (Al-136)+(B1.64), (Al-136)+(B1.65), (Al-136)+(B1.66), (Al-136)+(B2.1), (Al-136)+(B2.2), (Al-136)+(B2.3), (Al-136)+(B2.4), (Al-136)+(B2.5), (Al-136)+(B2.6), (Al-136)+(B2.7), (Al-136)+(B2.8), (Al-136)+(B2.9), (Al-136)+(B2.10), (Al-136)+(B2.11), (Al-136)+(B2.12), (Al-136)+(B2.13), (Al-136)+(B2.14), (Al-136)+(B2.15), (Al-136)+(B2.16), (Al-136)+(B2.17), (Al-136)+(B2.18), (Al-136)+(B2.19), (Al-136)+(B2.20), (Al-136)+(B2.21), (Al-136)+(B2.22), (Al-136)+(B2.23), (Al-136)+(B2.24), (Al-136)+(B2.25), (Al-136)+(B2.26), (Al-136)+(B2.27), (Al-136)+(B2.28), (Al-136)+(B2.29), (Al-136)+(B2.30), (Al-136)+(B2.31), (Al-136)+(B2.32), (Al-136)+(B2.33), (Al-136)+(B2.34), (Al-136)+(B2.35), (Al-136)+(B2.36), (Al-136)+(B2.37), (Al-136)+(B2.38), (Al-136)+(B2.39), (Al-136)+(B2.40), (Al-136)+(B2.41), (Al-136)+(B2.42), (Al-136)+(B2.43), (Al-136)+(B2.44), (Al-136)+(B2.45), (Al-136)+(B2.46), (Al-136)+(B2.47), (Al-136)+(B2.48), (Al-136)+(B2.49), (Al-136)+(B2.50), (Al-136)+(B3.1), (Al-136)+(B3.2.), (Al-136)+(B3.3), (Al-136)+(B3.4), (Al-136)+(B3.5), (Al-136)+(B3.6), (Al-136)+(B3.7), (Al-136)+(B3.8), (Al-136)+(B3.9), (Al-136)+(B3.10), (Al-136)+(B3.11), (Al-136)+(B3.12), (Al-136)+(B3.13), (Al-136)+(B3.14), (Al-136)+(B3.15), (Al-136)+(B3.16), (Al-136)+(B4.1), (Al-136)+(B4.2), (Al-136)+(B4.3), (Al-136)+(B4.4), (Al-136)+(B4.5), (Al-136)+(B4.6), (Al-136)+(B4.7).

(Al-137)+(B1.1), (Al-137)+(B1.2), (Al-137)+(B1.3), (Al-137)+(B1.4), (Al-137)+(B1.5), (Al-137)+(B1.6), (Al-137)+(B1.7), (Al-137)+(B1.8), (Al-137)+(B1.9), (Al-137)+(B1.10), (Al-137)+(B1.11), (Al-137)+(B1.12), (Al-137)+(B1.13), (Al-137)+(B1.14), (Al-137)+(B1.15), (Al-137)+(B1.16), (Al-137)+(B1.17), (Al-137)+(B1.18), (Al-137)+(B1.19), (Al-137)+(B1.20), (Al-137)+(B1.21), (Al-137)+(B1.22), (Al-137)+(B1.23), (Al-137)+(B1.24), (Al-137)+(B1.25), (Al-137)+(B1.26), (Al-137)+(B1.27), (Al-137)+(B1.28), (Al-137)+(B1.29), (Al-137)+(B1.30), (Al-137)+(B1.31), (Al-137)+(B1.32), (Al-137)+(B1.33), (Al-137)+(B1.34), (Al-137)+(B1.35), (Al-137)+(B1.36), (Al-137)+(B1.37), (Al-137)+(B1.38), (Al-137)+(B1.39), (Al-137)+(B1.40), (Al-137)+(B1.41), (Al-137)+(B1.42), (Al-137)+(B1.43), (Al-137)+(B1.44), (Al-137)+(B1.45), (Al-137)+(B1.46), (Al-137)+(B1.47), (Al-137)+(B1.48), (Al-137)+(B1.49), (Al-137)+(B1.50), (Al-137)+(B1.51), (Al-137)+(B1.52), (Al-137)+(B1.53), (Al-137)+(B1.54), (Al-137)+(B1.55), (Al-137)+(B1.56), (Al-137)+(B1.57), (Al-137)+(B1.58), (Al-137)+(B1.59), (Al-137)+(B1.60), (Al-137)+(B1.61), (Al-137)+(B1.62), (Al-137)+(B1.63), (Al-137)+(B1.64), (Al-137)+(B1.65), (Al-137)+(B1.66), (Al-137)+(B2.1), (Al-137)+(B2.2), (Al-137)+(B2.3), (Al-137)+(B2.4), (Al-137)+(B2.5), (Al-137)+(B2.6), (Al-137)+(B2.7), (Al-137)+(B2.8), (Al-137)+(B2.9), (Al-137)+(B2.10), (Al-137)+(B2.11), (Al-137)+(B2.12), (Al-137)+(B2.13), (Al-137)+

(B2.14), (Al-137)+(B2.15), (Al-137)+(B2.16), (Al-137)+(B2.17), (Al-137)+(B2.18), (Al-137)+(B2.19), (Al-137)+(B2.20), (Al-137)+(B2.21), (Al-137)+(B2.22), (Al-137)+(B2.23), (Al-137)+(B2.24), (Al-137)+(B2.25), (Al-137)+(B2.26), (Al-137)+(B2.27), (Al-137)+(B2.28), (Al-137)+(B2.29), (Al-137)+(B2.30), (Al-137)+(B2.31), (Al-137)+(B2.32), (Al-137)+(B2.33), (Al-137)+(B2.34), (Al-137)+(B2.35), (Al-137)+(B2.36), (Al-137)+(B2.37), (Al-137)+(B2.38), (Al-137)+(B2.39), (Al-137)+(B2.40), (Al-137)+(B2.41), (Al-137)+(B2.42), (Al-137)+(B2.43), (Al-137)+(B2.44), (Al-137)+(B2.45), (Al-137)+(B2.46), (Al-137)+(B2.47), (Al-137)+(B2.48), (Al-137)+(B2.49), (Al-137)+(B2.50), (Al-137)+(B3.1), (Al-137)+(B3.2.), (Al-137)+(B3.3), (Al-137)+(B3.4), (Al-137)+(B3.5), (Al-137)+(B3.6), (Al-137)+(B3.7), (Al-137)+(B3.8), (Al-137)+(B3.9), (Al-137)+(B3.10), (Al-137)+(B3.11), (Al-137)+(B3.12), (Al-137)+(B3.13), (Al-137)+(B3.14), (Al-137)+(B3.15), (Al-137)+(B3.16), (Al-137)+(B4.1), (Al-137)+(B4.2), (Al-137)+(B4.3), (Al-137)+(B4.4), (Al-137)+(B4.5), (Al-137)+(B4.6), (Al-137)+(B4.7).

(Al-138)+(B1.1), (Al-138)+(B1.2), (Al-138)+(B1.3), (Al-138)+(B1.4), (Al-138)+(B1.5), (Al-138)+(B1.6), (Al-138)+(B1.7), (Al-138)+(B1.8), (Al-138)+(B1.9), (Al-138)+(B1.10), (Al-138)+(B1.11), (Al-138)+(B1.12), (Al-138)+(B1.13), (Al-138)+(B1.14), (Al-138)+(B1.15), (Al-138)+(B1.16), (Al-138)+(B1.17), (Al-138)+(B1.18), (Al-138)+(B1.19), (Al-138)+(B1.20), (Al-138)+(B1.21), (Al-138)+(B1.22), (Al-138)+(B1.23), (Al-138)+(B1.24), (Al-138)+(B1.25), (Al-138)+(B1.26), (Al-138)+(B1.27), (Al-138)+(B1.28), (Al-138)+(B1.29), (Al-138)+(B1.30), (Al-138)+(B1.31), (Al-138)+(B1.32), (Al-138)+(B1.33), (Al-138)+(B1.34), (Al-138)+(B1.35), (Al-138)+(B1.36), (Al-138)+(B1.37), (Al-138)+(B1.38), (Al-138)+(B1.39), (Al-138)+(B1.40), (Al-138)+(B1.41), (Al-138)+(B1.42), (Al-138)+(B1.43), (Al-138)+(B1.44), (Al-138)+(B1.45), (Al-138)+(B1.46), (Al-138)+(B1.47), (Al-138)+(B1.48), (Al-138)+(B1.49), (Al-138)+(B1.50), (Al-138)+(B1.51), (Al-138)+(B1.52), (Al-138)+(B1.53), (Al-138)+(B1.54), (Al-138)+(B1.55), (Al-138)+(B1.56), (Al-138)+(B1.57), (Al-138)+(B1.58), (Al-138)+(B1.59), (Al-138)+(B1.60), (Al-138)+(B1.61), (Al-138)+(B1.62), (Al-138)+(B1.63), (Al-138)+(B1.64), (Al-138)+(B1.65), (Al-138)+(B1.66), (Al-138)+(B2.1), (Al-138)+(B2.2), (Al-138)+(B2.3), (Al-138)+(B2.4), (Al-138)+(B2.5), (Al-138)+(B2.6), (Al-138)+(B2.7), (Al-138)+(B2.8), (Al-138)+(B2.9), (Al-138)+(B2.10), (Al-138)+(B2.11), (Al-138)+(B2.12), (Al-138)+(B2.13), (Al-138)+(B2.14), (Al-138)+(B2.15), (Al-138)+(B2.16), (Al-138)+(B2.17), (Al-138)+(B2.18), (Al-138)+(B2.19), (Al-138)+(B2.20), (Al-138)+(B2.21), (Al-138)+(B2.22), (Al-138)+(B2.23), (Al-138)+(B2.24), (Al-138)+(B2.25), (Al-138)+(B2.26), (Al-138)+(B2.27), (Al-138)+(B2.28), (Al-138)+(B2.29), (Al-138)+(B2.30), (Al-138)+(B2.31), (Al-138)+(B2.32), (Al-138)+(B2.33), (Al-138)+(B2.34), (Al-138)+(B2.35), (Al-138)+(B2.36), (Al-138)+(B2.37), (Al-138)+(B2.38), (Al-138)+(B2.39), (Al-138)+(B2.40), (Al-138)+(B2.41), (Al-138)+(B2.42), (Al-138)+(B2.43), (Al-138)+(B2.44), (Al-138)+(B2.45), (Al-138)+(B2.46), (Al-138)+(B2.47), (Al-138)+(B2.48), (Al-138)+(B2.49), (Al-138)+(B2.50), (Al-138)+(B3.1), (Al-138)+(B3.2.), (Al-138)+(B3.3), (Al-138)+(B3.4), (Al-138)+(B3.5), (Al-138)+(B3.6), (Al-138)+(B3.7), (Al-138)+(B3.8), (Al-138)+(B3.9), (Al-138)+(B3.10), (Al-138)+(B3.11), (Al-138)+(B3.12), (Al-138)+(B3.13), (Al-138)+(B3.14), (Al-138)+(B3.15), (Al-138)+(B3.16), (Al-138)+(B4.1), (Al-138)+(B4.2), (Al-138)+(B4.3), (Al-138)+(B4.4), (Al-138)+(B4.5), (Al-138)+(B4.6), (Al-138)+(B4.7).

(Al-139)+(B1.1), (Al-139)+(B1.2), (Al-139)+(B1.3), (Al-139)+(B1.4), (Al-139)+(B1.5), (Al-139)+(B1.6), (Al-139)+(B1.7), (Al-139)+(B1.8), (Al-139)+(B1.9), (Al-139)+(B1.10), (Al-139)+(B1.11), (Al-139)+(B1.12), (Al-139)+(B1.13), (Al-139)+(B1.14), (Al-139)+(B1.15), (Al-139)+(B1.16), (Al-139)+(B1.17), (Al-139)+(B1.18), (Al-139)+(B1.19), (Al-139)+(B1.20), (Al-139)+(B1.21), (Al-139)+(B1.22), (Al-139)+(B1.23), (Al-139)+(B1.24), (Al-139)+(B1.25), (Al-139)+(B1.26), (Al-139)+(B1.27), (Al-139)+(B1.28), (Al-139)+(B1.29), (Al-139)+(B1.30), (Al-139)+(B1.31), (Al-139)+(B1.32), (Al-139)+(B1.33), (Al-139)+(B1.34), (Al-139)+(B1.35), (Al-139)+(B1.36), (Al-139)+(B1.37), (Al-139)+(B1.38), (Al-139)+(B1.39), (Al-139)+(B1.40), (Al-139)+(B1.41), (Al-139)+(B1.42), (Al-139)+(B1.43), (Al-139)+(B1.44), (Al-139)+(B1.45), (Al-139)+(B1.46), (Al-139)+(B1.47), (Al-139)+(B1.48), (Al-139)+(B1.49), (Al-139)+(B1.50), (Al-139)+(B1.51), (Al-139)+(B1.52), (Al-139)+(B1.53), (Al-139)+(B1.54), (Al-139)+(B1.55), (Al-139)+(B1.56), (Al-139)+(B1.57), (Al-139)+(B1.58), (Al-139)+(B1.59), (Al-139)+(B1.60), (Al-139)+(B1.61), (Al-139)+(B1.62), (Al-139)+(B1.63), (Al-139)+(B1.64), (Al-139)+(B1.65), (Al-139)+(B1.66), (Al-139)+(B2.1), (Al-139)+(B2.2), (Al-139)+(B2.3), (Al-139)+(B2.4), (Al-139)+(B2.5), (Al-139)+(B2.6), (Al-139)+(B2.7), (Al-139)+(B2.8), (Al-139)+(B2.9), (Al-139)+(B2.10), (Al-139)+(B2.11), (Al-139)+(B2.12), (Al-139)+(B2.13), (Al-139)+(B2.14), (Al-139)+(B2.15), (Al-139)+(B2.16), (Al-139)+(B2.17), (Al-139)+(B2.18), (Al-139)+(B2.19), (Al-139)+(B2.20), (Al-139)+(B2.21), (Al-139)+(B2.22), (Al-139)+(B2.23), (Al-139)+(B2.24), (Al-139)+(B2.25), (Al-139)+(B2.26), (Al-139)+(B2.27), (Al-139)+(B2.28), (Al-139)+(B2.29), (Al-139)+(B2.30), (Al-139)+(B2.31), (Al-139)+(B2.32), (Al-139)+(B2.33), (Al-139)+(B2.34), (Al-139)+(B2.35), (Al-139)+(B2.36), (Al-139)+(B2.37), (Al-139)+(B2.38), (Al-139)+(B2.39), (Al-139)+(B2.40), (Al-139)+(B2.41), (Al-139)+(B2.42), (Al-139)+(B2.43), (Al-139)+(B2.44), (Al-139)+(B2.45), (Al-139)+(B2.46), (Al-139)+(B2.47), (Al-139)+(B2.48), (Al-139)+(B2.49), (Al-139)+(B2.50), (Al-139)+(B3.1), (Al-139)+(B3.2.), (Al-139)+(B3.3), (Al-139)+(B3.4), (Al-139)+(B3.5), (Al-139)+(B3.6), (Al-139)+(B3.7), (Al-139)+(B3.8), (Al-139)+(B3.9), (Al-139)+(B3.10), (Al-139)+(B3.11), (Al-139)+(B3.12), (Al-139)+(B3.13), (Al-139)+(B3.14), (Al-139)+(B3.15), (Al-139)+(B3.16), (Al-139)+(B4.1), (Al-139)+(B4.2), (Al-139)+(B4.3), (Al-139)+(B4.4), (Al-139)+(B4.5), (Al-139)+(B4.6), (Al-139)+(B4.7).

(Al-140)+(B1.1), (Al-140)+(B1.2), (Al-140)+(B1.3), (Al-140)+(B1.4), (Al-140)+(B1.5), (Al-140)+(B1.6), (Al-140)+(B1.7), (Al-140)+(B1.8), (Al-140)+(B1.9), (Al-140)+(B1.10), (Al-140)+(B1.11), (Al-140)+(B1.12), (Al-140)+(B1.13), (Al-140)+(B1.14), (Al-140)+(B1.15), (Al-140)+(B1.16), (Al-140)+(B1.17), (Al-140)+(B1.18), (Al-140)+(B1.19), (Al-140)+(B1.20), (Al-140)+(B1.21), (Al-140)+(B1.22), (Al-140)+(B1.23), (Al-140)+(B1.24), (Al-140)+(B1.25), (Al-140)+(B1.26), (Al-140)+(B1.27), (Al-140)+(B1.28), (Al-140)+(B1.29), (Al-140)+(B1.30), (Al-140)+(B1.31), (Al-140)+(B1.32), (Al-140)+(B1.33), (Al-140)+(B1.34), (Al-140)+(B1.35), (Al-140)+(B1.36), (Al-140)+(B1.37), (Al-140)+(B1.38), (Al-140)+(B1.39), (Al-140)+(B1.40), (Al-140)+(B1.41), (Al-140)+(B1.42), (Al-140)+(B1.43), (Al-140)+(B1.44), (Al-140)+(B1.45), (Al-140)+(B1.46), (Al-140)+(B1.47), (Al-140)+(B1.48), (Al-140)+(B1.49), (Al-140)+(B1.50), (Al-140)+(B1.51), (Al-140)+(B1.52), (Al-140)+(B1.53), (Al-140)+(B1.54), (Al-140)+(B1.55), (Al-140)+(B1.56), (Al-140)+(B1.57), (Al-140)+(B1.58), (Al-140)+(B1.59), (Al-140)+(B1.60), (Al-140)+(B1.61), (Al-140)+(B1.62), (Al-140)+(B1.63), (Al-140)+

(B1.64), (Al-140)+(B1.65), (Al-140)+(B1.66), (Al-140)+(B2.1), (Al-140)+(B2.2), (Al-140)+(B2.3), (Al-140)+(B2.4), (Al-140)+(B2.5), (Al-140)+(B2.6), (Al-140)+(B2.7), (Al-140)+(B2.8), (Al-140)+(B2.9), (Al-140)+(B2.10), (Al-140)+(B2.11), (Al-140)+(B2.12), (Al-140)+(B2.13), (Al-140)+(B2.14), (Al-140)+(B2.15), (Al-140)+(B2.16), (Al-140)+(B2.17), (Al-140)+(B2.18), (Al-140)+(B2.19), (Al-140)+(B2.20), (Al-140)+(B2.21), (Al-140)+(B2.22), (Al-140)+(B2.23), (Al-140)+(B2.24), (Al-140)+(B2.25), (Al-140)+(B2.26), (Al-140)+(B2.27), (Al-140)+(B2.28), (Al-140)+(B2.29), (Al-140)+(B2.30), (Al-140)+(B2.31), (Al-140)+(B2.32), (Al-140)+(B2.33), (Al-140)+(B2.34), (Al-140)+(B2.35), (Al-140)+(B2.36), (Al-140)+(B2.37), (Al-140)+(B2.38), (Al-140)+(B2.39), (Al-140)+(B2.40), (Al-140)+(B2.41), (Al-140)+(B2.42), (Al-140)+(B2.43), (Al-140)+(B2.44), (Al-140)+(B2.45), (Al-140)+(B2.46), (Al-140)+(B2.47), (Al-140)+(B2.48), (Al-140)+(B2.49), (Al-140)+(B2.50), (Al-140)+(B3.1), (Al-140)+(B3.2.), (Al-140)+(B3.3), (Al-140)+(B3.4), (Al-140)+(B3.5), (Al-140)+(B3.6), (Al-140)+(B3.7), (Al-140)+(B3.8), (Al-140)+(B3.9), (Al-140)+(B3.10), (Al-140)+(B3.11), (Al-140)+(B3.12), (Al-140)+(B3.13), (Al-140)+(B3.14), (Al-140)+(B3.15), (Al-140)+(B3.16), (Al-140)+(B4.1), (Al-140)+(B4.2), (Al-140)+(B4.3), (Al-140)+(B4.4), (Al-140)+(B4.5), (Al-140)+(B4.6), (Al-140)+(B4.7).

(Al-141)+(B1.1), (Al-141)+(B1.2), (Al-141)+(B1.3), (Al-141)+(B1.4), (Al-141)+(B1.5), (Al-141)+(B1.6), (Al-141)+(B1.7), (Al-141)+(B1.8), (Al-141)+(B1.9), (Al-141)+(B1.10), (Al-141)+(B1.11), (Al-141)+(B1.12), (Al-141)+(B1.13), (Al-141)+(B1.14), (Al-141)+(B1.15), (Al-141)+(B1.16), (Al-141)+(B1.17), (Al-141)+(B1.18), (Al-141)+(B1.19), (Al-141)+(B1.20), (Al-141)+(B1.21), (Al-141)+(B1.22), (Al-141)+(B1.23), (Al-141)+(B1.24), (Al-141)+(B1.25), (Al-141)+(B1.26), (Al-141)+(B1.27), (Al-141)+(B1.28), (Al-141)+(B1.29), (Al-141)+(B1.30), (Al-141)+(B1.31), (Al-141)+(B1.32), (Al-141)+(B1.33), (Al-141)+(B1.34), (Al-141)+(B1.35), (Al-141)+(B1.36), (Al-141)+(B1.37), (Al-141)+(B1.38), (Al-141)+(B1.39), (Al-141)+(B1.40), (Al-141)+(B1.41), (Al-141)+(B1.42), (Al-141)+(B1.43), (Al-141)+(B1.44), (Al-141)+(B1.45), (Al-141)+(B1.46), (Al-141)+(B1.47), (Al-141)+(B1.48), (Al-141)+(B1.49), (Al-141)+(B1.50), (Al-141)+(B1.51), (Al-141)+(B1.52), (Al-141)+(B1.53), (Al-141)+(B1.54), (Al-141)+(B1.55), (Al-141)+(B1.56), (Al-141)+(B1.57), (Al-141)+(B1.58), (Al-141)+(B1.59), (Al-141)+(B1.60), (Al-141)+(B1.61), (Al-141)+(B1.62), (Al-141)+(B1.63), (Al-141)+(B1.64), (Al-141)+(B1.65), (Al-141)+(B1.66), (Al-141)+(B2.1), (Al-141)+(B2.2), (Al-141)+(B2.3), (Al-141)+(B2.4), (Al-141)+(B2.5), (Al-141)+(B2.6), (Al-141)+(B2.7), (Al-141)+(B2.8), (Al-141)+(B2.9), (Al-141)+(B2.10), (Al-141)+(B2.11), (Al-141)+(B2.12), (Al-141)+(B2.13), (Al-141)+(B2.14), (Al-141)+(B2.15), (Al-141)+(B2.16), (Al-141)+(B2.17), (Al-141)+(B2.18), (Al-141)+(B2.19), (Al-141)+(B2.20), (Al-141)+(B2.21), (Al-141)+(B2.22), (Al-141)+(B2.23), (Al-141)+(B2.24), (Al-141)+(B2.25), (Al-141)+(B2.26), (Al-141)+(B2.27), (Al-141)+(B2.28), (Al-141)+(B2.29), (Al-141)+(B2.30), (Al-141)+(B2.31), (Al-141)+(B2.32), (Al-141)+(B2.33), (Al-141)+(B2.34), (Al-141)+(B2.35), (Al-141)+(B2.36), (Al-141)+(B2.37), (Al-141)+(B2.38), (Al-141)+(B2.39), (Al-141)+(B2.40), (Al-141)+(B2.41), (Al-141)+(B2.42), (Al-141)+(B2.43), (Al-141)+(B2.44), (Al-141)+(B2.45), (Al-141)+(B2.46), (Al-141)+(B2.47), (Al-141)+(B2.48), (Al-141)+(B2.49), (Al-141)+(B2.50), (Al-141)+(B3.1), (Al-141)+(B3.2.), (Al-141)+(B3.3), (Al-141)+(B3.4), (Al-141)+(B3.5), (Al-141)+(B3.6), (Al-141)+(B3.7), (Al-141)+(B3.8), (Al-141)+(B3.9), (Al-141)+(B3.10), (Al-141)+(B3.11), (Al-141)+(B3.12), (Al-141)+(B3.13), (Al-141)+(B3.14), (Al-141)+(B3.15), (Al-141)+(B3.16), (Al-141)+(B4.1), (Al-141)+(B4.2), (Al-141)+(B4.3), (Al-141)+(B4.4), (Al-141)+(B4.5), (Al-141)+(B4.6), (Al-141)+(B4.7).

(Al-142)+(B1.1), (Al-142)+(B1.2), (Al-142)+(B1.3), (Al-142)+(B1.4), (Al-142)+(B1.5), (Al-142)+(B1.6), (Al-142)+(B1.7), (Al-142)+(B1.8), (Al-142)+(B1.9), (Al-142)+(B1.10), (Al-142)+(B1.11), (Al-142)+(B1.12), (Al-142)+(B1.13), (Al-142)+(B1.14), (Al-142)+(B1.15), (Al-142)+(B1.16), (Al-142)+(B1.17), (Al-142)+(B1.18), (Al-142)+(B1.19), (Al-142)+(B1.20), (Al-142)+(B1.21), (Al-142)+(B1.22), (Al-142)+(B1.23), (Al-142)+(B1.24), (Al-142)+(B1.25), (Al-142)+(B1.26), (Al-142)+(B1.27), (Al-142)+(B1.28), (Al-142)+(B1.29), (Al-142)+(B1.30), (Al-142)+(B1.31), (Al-142)+(B1.32), (Al-142)+(B1.33), (Al-142)+(B1.34), (Al-142)+(B1.35), (Al-142)+(B1.36), (Al-142)+(B1.37), (Al-142)+(B1.38), (Al-142)+(B1.39), (Al-142)+(B1.40), (Al-142)+(B1.41), (Al-142)+(B1.42), (Al-142)+(B1.43), (Al-142)+(B1.44), (Al-142)+(B1.45), (Al-142)+(B1.46), (Al-142)+(B1.47), (Al-142)+(B1.48), (Al-142)+(B1.49), (Al-142)+(B1.50), (Al-142)+(B1.51), (Al-142)+(B1.52), (Al-142)+(B1.53), (Al-142)+(B1.54), (Al-142)+(B1.55), (Al-142)+(B1.56), (Al-142)+(B1.57), (Al-142)+(B1.58), (Al-142)+(B1.59), (Al-142)+(B1.60), (Al-142)+(B1.61), (Al-142)+(B1.62), (Al-142)+(B1.63), (Al-142)+(B1.64), (Al-142)+(B1.65), (Al-142)+(B1.66), (Al-142)+(B2.1), (Al-142)+(B2.2), (Al-142)+(B2.3), (Al-142)+(B2.4), (Al-142)+(B2.5), (Al-142)+(B2.6), (Al-142)+(B2.7), (Al-142)+(B2.8), (Al-142)+(B2.9), (Al-142)+(B2.10), (Al-142)+(B2.11), (Al-142)+(B2.12), (Al-142)+(B2.13), (Al-142)+(B2.14), (Al-142)+(B2.15), (Al-142)+(B2.16), (Al-142)+(B2.17), (Al-142)+(B2.18), (Al-142)+(B2.19), (Al-142)+(B2.20), (Al-142)+(B2.21), (Al-142)+(B2.22), (Al-142)+(B2.23), (Al-142)+(B2.24), (Al-142)+(B2.25), (Al-142)+(B2.26), (Al-142)+(B2.27), (Al-142)+(B2.28), (Al-142)+(B2.29), (Al-142)+(B2.30), (Al-142)+(B2.31), (Al-142)+(B2.32), (Al-142)+(B2.33), (Al-142)+(B2.34), (Al-142)+(B2.35), (Al-142)+(B2.36), (Al-142)+(B2.37), (Al-142)+(B2.38), (Al-142)+(B2.39), (Al-142)+(B2.40), (Al-142)+(B2.41), (Al-142)+(B2.42), (Al-142)+(B2.43), (Al-142)+(B2.44), (Al-142)+(B2.45), (Al-142)+(B2.46), (Al-142)+(B2.47), (Al-142)+(B2.48), (Al-142)+(B2.49), (Al-142)+(B2.50), (Al-142)+(B3.1), (Al-142)+(B3.2.), (Al-142)+(B3.3), (Al-142)+(B3.4), (Al-142)+(B3.5), (Al-142)+(B3.6), (Al-142)+(B3.7), (Al-142)+(B3.8), (Al-142)+(B3.9), (Al-142)+(B3.10), (Al-142)+(B3.11), (Al-142)+(B3.12), (Al-142)+(B3.13), (Al-142)+(B3.14), (Al-142)+(B3.15), (Al-142)+(B3.16), (Al-142)+(B4.1), (Al-142)+(B4.2), (Al-142)+(B4.3), (Al-142)+(B4.4), (Al-142)+(B4.5), (Al-142)+(B4.6), (Al-142)+(B4.7).

(Al-143)+(B1.1), (Al-143)+(B1.2), (Al-143)+(B1.3), (Al-143)+(B1.4), (Al-143)+(B1.5), (Al-143)+(B1.6), (Al-143)+(B1.7), (Al-143)+(B1.8), (Al-143)+(B1.9), (Al-143)+(B1.10), (Al-143)+(B1.11), (Al-143)+(B1.12), (Al-143)+(B1.13), (Al-143)+(B1.14), (Al-143)+(B1.15), (Al-143)+(B1.16), (Al-143)+(B1.17), (Al-143)+(B1.18), (Al-143)+(B1.19), (Al-143)+(B1.20), (Al-143)+(B1.21), (Al-143)+(B1.22), (Al-143)+(B1.23), (Al-143)+(B1.24), (Al-143)+(B1.25), (Al-143)+(B1.26), (Al-143)+(B1.27), (Al-143)+(B1.28), (Al-143)+(B1.29), (Al-143)+(B1.30), (Al-143)+(B1.31), (Al-143)+(B1.32), (Al-143)+(B1.33), (Al-143)+(B1.34), (Al-143)+(B1.35), (Al-143)+(B1.36), (Al-143)+(B1.37), (Al-143)+(B1.38), (Al-143)+(B1.39), (Al-143)+(B1.40), (Al-143)+(B1.41), (Al-143)+(B1.42), (Al-143)+(B1.43), (Al-143)+(B1.44), (Al-143)+(B1.45), (Al-143)+(B1.46), (Al-143)+(B1.47), (Al-143)+(B1.48), (Al-143)+(B1.49), (Al-143)+(B1.50), (Al-143)+(B1.51), (Al-143)+

(B1.52), (Al-143)+(B1.53), (Al-143)+(B1.54), (Al-143)+ (B1.55), (Al-143)+(B1.56), (Al-143)+(B1.57), (Al-143)+ (B1.58), (Al-143)+(B1.59), (Al-143)+(B1.60), (Al-143)+ (B1.61), (Al-143)+(B1.62), (Al-143)+(B1.63), (Al-143)+ (B1.64), (Al-143)+(B1.65), (Al-143)+(B1.66), (Al-143)+ (B2.1), (Al-143)+(B2.2), (Al-143)+(B2.3), (Al-143)+(B2.4), (Al-143)+(B2.5), (Al-143)+(B2.6), (Al-143)+(B2.7), (Al-143)+(B2.8), (Al-143)+(B2.9), (Al-143)+(B2.10), (Al-143)+(B2.11), (Al-143)+(B2.12), (Al-143)+(B2.13), (Al-143)+(B2.14), (Al-143)+(B2.15), (Al-143)+(B2.16), (Al-143)+(B2.17), (Al-143)+(B2.18), (Al-143)+(B2.19), (Al-143)+(B2.20), (Al-143)+(B2.21), (Al-143)+(B2.22), (Al-143)+(B2.23), (Al-143)+(B2.24), (Al-143)+(B2.25), (Al-143)+(B2.26), (Al-143)+(B2.27), (Al-143)+(B2.28), (Al-143)+(B2.29), (Al-143)+(B2.30), (Al-143)+(B2.31), (Al-143)+(B2.32), (Al-143)+(B2.33), (Al-143)+(B2.34), (Al-143)+(B2.35), (Al-143)+(B2.36), (Al-143)+(B2.37), (Al-143)+(B2.38), (Al-143)+(B2.39), (Al-143)+(B2.40), (Al-143)+(B2.41), (Al-143)+(B2.42), (Al-143)+(B2.43), (Al-143)+(B2.44), (Al-143)+(B2.45), (Al-143)+(B2.46), (Al-143)+(B2.47), (Al-143)+(B2.48), (Al-143)+(B2.49), (Al-143)+(B2.50), (Al-143)+(B3.1), (Al-143)+(B3.2.), (Al-143)+(B3.3), (Al-143)+(B3.4), (Al-143)+(B3.5), (Al-143)+(B3.6), (Al-143)+(B3.7), (Al-143)+(B3.8), (Al-143)+(B3.9), (Al-143)+(B3.10), (Al-143)+(B3.11), (Al-143)+(B3.12), (Al-143)+(B3.13), (Al-143)+(B3.14), (Al-143)+(B3.15), (Al-143)+(B3.16), (Al-143)+(B4.1), (Al-143)+(B4.2), (Al-143)+(B4.3), (Al-143)+(B4.4), (Al-143)+(B4.5), (Al-143)+(B4.6), (Al-143)+(B4.7).

(Al-144)+(B1.1), (Al-144)+(B1.2), (Al-144)+(B1.3), (Al-144)+(B1.4), (Al-144)+(B1.5), (Al-144)+(B1.6), (Al-144)+(B1.7), (Al-144)+(B1.8), (Al-144)+(B1.9), (Al-144)+(B1.10), (Al-144)+(B1.11), (Al-144)+(B1.12), (Al-144)+(B1.13), (Al-144)+(B1.14), (Al-144)+(B1.15), (Al-144)+(B1.16), (Al-144)+(B1.17), (Al-144)+(B1.18), (Al-144)+(B1.19), (Al-144)+(B1.20), (Al-144)+(B1.21), (Al-144)+(B1.22), (Al-144)+(B1.23), (Al-144)+(B1.24), (Al-144)+(B1.25), (Al-144)+(B1.26), (Al-144)+(B1.27), (Al-144)+(B1.28), (Al-144)+(B1.29), (Al-144)+(B1.30), (Al-144)+(B1.31), (Al-144)+(B1.32), (Al-144)+(B1.33), (Al-144)+(B1.34), (Al-144)+(B1.35), (Al-144)+(B1.36), (Al-144)+(B1.37), (Al-144)+(B1.38), (Al-144)+(B1.39), (Al-144)+(B1.40), (Al-144)+(B1.41), (Al-144)+(B1.42), (Al-144)+(B1.43), (Al-144)+(B1.44), (Al-144)+(B1.45), (Al-144)+(B1.46), (Al-144)+(B1.47), (Al-144)+(B1.48), (Al-144)+(B1.49), (Al-144)+(B1.50), (Al-144)+(B1.51), (Al-144)+(B1.52), (Al-144)+(B1.53), (Al-144)+(B1.54), (Al-144)+(B1.55), (Al-144)+(B1.56), (Al-144)+(B1.57), (Al-144)+(B1.58), (Al-144)+(B1.59), (Al-144)+(B1.60), (Al-144)+(B1.61), (Al-144)+(B1.62), (Al-144)+(B1.63), (Al-144)+(B1.64), (Al-144)+(B1.65), (Al-144)+(B1.66), (Al-144)+(B2.1), (Al-144)+(B2.2), (Al-144)+(B2.3), (Al-144)+(B2.4), (Al-144)+(B2.5), (Al-144)+(B2.6), (Al-144)+(B2.7), (Al-144)+(B2.8), (Al-144)+(B2.9), (Al-144)+(B2.10), (Al-144)+(B2.11), (Al-144)+(B2.12), (Al-144)+(B2.13), (Al-144)+(B2.14), (Al-144)+(B2.15), (Al-144)+(B2.16), (Al-144)+(B2.17), (Al-144)+(B2.18), (Al-144)+(B2.19), (Al-144)+(B2.20), (Al-144)+(B2.21), (Al-144)+(B2.22), (Al-144)+(B2.23), (Al-144)+(B2.24), (Al-144)+(B2.25), (Al-144)+(B2.26), (Al-144)+(B2.27), (Al-144)+(B2.28), (Al-144)+(B2.29), (Al-144)+(B2.30), (Al-144)+(B2.31), (Al-144)+(B2.32), (Al-144)+(B2.33), (Al-144)+(B2.34), (Al-144)+(B2.35), (Al-144)+(B2.36), (Al-144)+(B2.37), (Al-144)+(B2.38), (Al-144)+(B2.39), (Al-144)+(B2.40), (Al-144)+(B2.41), (Al-144)+(B2.42), (Al-144)+(B2.43), (Al-144)+(B2.44), (Al-144)+(B2.45), (Al-144)+(B2.46), (Al-144)+(B2.47), (Al-144)+(B2.48), (Al-144)+(B2.49), (Al-144)+(B2.50), (Al-144)+(B3.1), (Al-144)+(B3.2.), (Al-144)+(B3.3), (Al-144)+(B3.4), (Al-144)+(B3.5), (Al-144)+(B3.6), (Al-144)+(B3.7), (Al-144)+(B3.8), (Al-144)+(B3.9), (Al-144)+(B3.10), (Al-144)+(B3.11), (Al-144)+(B3.12), (Al-144)+(B3.13), (Al-144)+(B3.14), (Al-144)+(B3.15), (Al-144)+(B3.16), (Al-144)+(B4.1), (Al-144)+(B4.2), (Al-144)+(B4.3), (Al-144)+(B4.4), (Al-144)+(B4.5), (Al-144)+(B4.6), (Al-144)+(B4.7).

(Al-145)+(B1.1), (Al-145)+(B1.2), (Al-145)+(B1.3), (Al-145)+(B1.4), (Al-145)+(B1.5), (Al-145)+(B1.6), (Al-145)+(B1.7), (Al-145)+(B1.8), (Al-145)+(B1.9), (Al-145)+(B1.10), (Al-145)+(B1.11), (Al-145)+(B1.12), (Al-145)+(B1.13), (Al-145)+(B1.14), (Al-145)+(B1.15), (Al-145)+(B1.16), (Al-145)+(B1.17), (Al-145)+(B1.18), (Al-145)+(B1.19), (Al-145)+(B1.20), (Al-145)+(B1.21), (Al-145)+(B1.22), (Al-145)+(B1.23), (Al-145)+(B1.24), (Al-145)+(B1.25), (Al-145)+(B1.26), (Al-145)+(B1.27), (Al-145)+(B1.28), (Al-145)+(B1.29), (Al-145)+(B1.30), (Al-145)+(B1.31), (Al-145)+(B1.32), (Al-145)+(B1.33), (Al-145)+(B1.34), (Al-145)+(B1.35), (Al-145)+(B1.36), (Al-145)+(B1.37), (Al-145)+(B1.38), (Al-145)+(B1.39), (Al-145)+(B1.40), (Al-145)+(B1.41), (Al-145)+(B1.42), (Al-145)+(B1.43), (Al-145)+(B1.44), (Al-145)+(B1.45), (Al-145)+(B1.46), (Al-145)+(B1.47), (Al-145)+(B1.48), (Al-145)+(B1.49), (Al-145)+(B1.50), (Al-145)+(B1.51), (Al-145)+(B1.52), (Al-145)+(B1.53), (Al-145)+(B1.54), (Al-145)+(B1.55), (Al-145)+(B1.56), (Al-145)+(B1.57), (Al-145)+(B1.58), (Al-145)+(B1.59), (Al-145)+(B1.60), (Al-145)+(B1.61), (Al-145)+(B1.62), (Al-145)+(B1.63), (Al-145)+(B1.64), (Al-145)+(B1.65), (Al-145)+(B1.66), (Al-145)+(B2.1), (Al-145)+(B2.2), (Al-145)+(B2.3), (Al-145)+(B2.4), (Al-145)+(B2.5), (Al-145)+(B2.6), (Al-145)+(B2.7), (Al-145)+(B2.8), (Al-145)+(B2.9), (Al-145)+(B2.10), (Al-145)+(B2.11), (Al-145)+(B2.12), (Al-145)+(B2.13), (Al-145)+(B2.14), (Al-145)+(B2.15), (Al-145)+(B2.16), (Al-145)+(B2.17), (Al-145)+(B2.18), (Al-145)+(B2.19), (Al-145)+(B2.20), (Al-145)+(B2.21), (Al-145)+(B2.22), (Al-145)+(B2.23), (Al-145)+(B2.24), (Al-145)+(B2.25), (Al-145)+(B2.26), (Al-145)+(B2.27), (Al-145)+(B2.28), (Al-145)+(B2.29), (Al-145)+(B2.30), (Al-145)+(B2.31), (Al-145)+(B2.32), (Al-145)+(B2.33), (Al-145)+(B2.34), (Al-145)+(B2.35), (Al-145)+(B2.36), (Al-145)+(B2.37), (Al-145)+(B2.38), (Al-145)+(B2.39), (Al-145)+(B2.40), (Al-145)+(B2.41), (Al-145)+(B2.42), (Al-145)+(B2.43), (Al-145)+(B2.44), (Al-145)+(B2.45), (Al-145)+(B2.46), (Al-145)+(B2.47), (Al-145)+(B2.48), (Al-145)+(B2.49), (Al-145)+(B2.50), (Al-145)+(B3.1), (Al-145)+(B3.2.), (Al-145)+(B3.3), (Al-145)+(B3.4), (Al-145)+(B3.5), (Al-145)+(B3.6), (Al-145)+(B3.7), (Al-145)+(B3.8), (Al-145)+(B3.9), (Al-145)+(B3.10), (Al-145)+(B3.11), (Al-145)+(B3.12), (Al-145)+(B3.13), (Al-145)+(B3.14), (Al-145)+(B3.15), (Al-145)+(B3.16), (Al-145)+(B4.1), (Al-145)+(B4.2), (Al-145)+(B4.3), (Al-145)+(B4.4), (Al-145)+(B4.5), (Al-145)+(B4.6), (Al-145)+(B4.7).

The ranges of application rates and the ratios mentioned above are in each case preferred.

It may also be advantageous to combine one or more, preferably one, of the herbicides (A) with one or more herbicides (B), in particular from the groups (B1), (B2), (B3) and (B4).

Furthermore, the herbicide combinations according to the invention can comprise various agrochemically active compounds, for example from the group of the safeners, fungicides, insecticides and plant growth regulators, or from the group of the formulation auxiliaries and additives customary in crop protection. Additives are, for example, fertilizers and colorants.

The combinations according to the invention (=herbicidal compositions) have outstanding herbicidal activity against a broad spectrum of economically important monocotyledonous and dicotyledonous harmful plants such as weeds, including species which are resistant to herbicidally active compounds such as glyphosate, glufosinate, atrazine or imidazolinone herbicides. The active compounds also act efficiently on perennial weeds which produce shoots from rhizomes, rootstocks or other perennial organs and which are difficult to control. The substances can be applied, for example, by the pre-sowing, the pre-emergence or the post-emergence method, for example jointly or separately. Preferred is, for example, the application by the post-emergence method, in particular to the emerged harmful plants prior to emergence of unwanted crop plants.

Specifically, examples which may be mentioned are some representatives of the monocotyledonous and dicotyledonous weed flora which can be controlled by the compounds according to the invention, without the enumeration being a restriction to certain species.

The compositions act efficiently against, from amongst the monocotyledonous weed species, for example *Avena* spp., *Alopecurus* spp., *Brachiaria* spp., *Digitaria* spp, *Lolium* spp., *Echinochloa* spp., *Panicum* spp., *Phalaris* spp., *Poa* spp., *Setaria* spp. and also *Cyperus* species from the annual group and, from amongst the perennial species, *Agropyron, Cynodon, Imperata* and *Sorghum* and also perennial *Cyperus* species.

In the case of the dicotyledonous weed species, the spectrum of action extends to species such as, for example, *Abutilon* spp., *Amaranthus* spp., *Chenopodium* spp., *Chrysanthemum* spp., *Galium* spp., *Ipomoea* spp., *Kochia* spp., *Lamium* spp., *Matricaria* spp., *Pharbitis* spp., *Polygonum* spp., *Sida* spp., *Sinapis* spp., *Solanum* spp., *Stellaria* spp., *Veronica* spp. and *Viola* spp., *Xanthium* spp., amongst the annuals, and *Convolvulus, Cirsium, Rumex* and *Artemisia* in the case of the perennial weeds.

If the compounds according to the invention are applied to the soil surface before germination, then the weed seedlings are either prevented completely from emerging, or the weeds grow until they have reached the cotyledon stage but then their growth stops, and, eventually, after three to four weeks have elapsed, they die completely.

If the active compounds are applied post-emergence to the green parts of the plants, growth likewise stops drastically a very short time after the treatment and the weed plants remain at the growth stage of the point of time of application, or they die completely after a certain time, so that in this manner competition by the weeds, which is harmful to the crop plants, is eliminated at a very early point in time and in a sustained manner.

The herbicidal compositions according to the invention are distinguished by a rapidly commencing and long-lasting herbicidal action. As a rule, the rainfastness of the active compounds in the combination according to the invention is advantageous. A particular advantage is that the dosages of the compounds (A) and (B), which are used in the combinations and are effective, can be adjusted to such a low quantity that their soil action is optimally low. Not only does this allow them to be employed in sensitive crops in the first place, but ground water contaminations are also virtually avoided. The active compound combinations according to the invention allow the application rate of the active compounds required to be reduced considerably.

When herbicides of the type (A)+(B) are used jointly, superadditive (=synergistic) effects are preferably observed. This means that the effect in the combinations exceeds the expected total of the effects of the individual herbicides employed. The synergistic effects allow the application rate to be reduced, a broader spectrum of broad-leaved weeds and weed grasses to be controlled, the herbicidal action to take place more rapidly, the duration of action to be longer, the harmful plants to be controlled better while using only one, or few, applications, and the application period which is possible to be extended. To some extent, using the compositions also reduces the amount of harmful ingredients, such as nitrogen or oleic acid, and their introduction into the soil.

The abovementioned properties and advantages are of benefit for weed control practice to keep agricultural crops free from undesired competing plants and thus to safeguard and/or increase the yields from the qualitative and quantitative point of view. These novel combinations markedly exceed the technical state of the art with a view to the properties described.

Owing to their herbicidal and plant-growth-regulatory properties, the compositions according to the invention can be employed for controlling harmful plants in known crop plants or still to be developed tolerant or genetically modified crop plants. These transgenic plants are distinguished as a rule by particular, advantageous properties, such as, in addition to resistances to compositions according to the invention, for example resistances to plant diseases or causative agents of plant diseases such as particular insects or microorganisms such as fungi, bacteria or viruses. Other particular properties relate, for example, to the harvested material with regard to quantity, quality, storability, composition and specific constituents. Thus, for example, transgenic plants are known whose starch content is increased or whose starch quality is altered, or those where the harvested material has a different fatty acid composition.

Conventional methods of generating novel plants which have modified properties in comparison to plants occurring to date consist, for example, in traditional breeding method and the generation of mutants. Alternatively, novel plants with altered properties can be generated with the aid of recombinant methods (see, for exaple, EP-A-0221044, EP-A-0131624). For example, the following have been described in several cases:

the modification, by recombinant technology, of crop plants with the aim of modifying the starch synthesized in the plants (for example WO 92/11376, WO92/14827, WO 91/19806), transgenic crop plants which exhibit resistances to other herbicides, for example to sulfonylureas (EP-A-0257993, U.S. Pat. No. 5,013,659), transgenic crop plants with the capability of producing *Bacillus thuringiensis* toxins (Bt toxins), which make the plants resistant to certain pests (EP-A-0142924, EP-A-0193259), transgenic crop plants with a modified fatty acid composition (WO 91/13972).

A large number of techniques in molecular biology are known in principle with the aid of which novel transgenic plants with modified properties can be generated; see, for example, Sambrook et al., 1989, Molecular Cloning, A Laboratory Manual, $2^{nd}$ Edition, Cold Spring Harbor Laboratory Press, Cold Spring Harbor, N.Y.; or Winnacker "Gene und Klone", VCH Weinheim $2^{nd}$ Edition 1996 or Christou, "Trends in Plant Science" 1 (1996) 423-431).

To carry out such recombinant manipulations, nucleic acid molecules which allow mutagenesis or sequence changes by recombination of DNA sequences can be introduced into plasmids. For example, the abovementioned standard methods allow base exchanges to be carried out, subsequences to be removed, or natural or synthetic sequences to be added. To connect the DNA fragments to each other, adapters or linkers may be added to the fragments.

For example, the generation of plant cells with a reduced activity of a gene product can be achieved by expressing at least one corresponding antisense RNA, a sense RNA for achieving a cosuppression effect or by expressing at least one suitably constructed ribosome which specifically cleaves transcripts of the above-mentioned gene product.

To this end, it is possible to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. The use of DNA sequences which have a high degree of homology to the coding sequences of a gene product, but are not completely identical to them, is also possible.

When expressing nucleic acid molecules in plants, the protein synthesized can be localized in any desired compartment of the plant cell. However, to achieve localization in a particular compartment, it is possible, for example, to link the coding region with DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J.1 (1991), 95-106).

The transgenic plant cells can be regenerated by known techniques to give rise to entire plants. In principle, the transgenic plants can be plants of any desired plant species, i.e. not only monocotyledonous, but also dicotyledonous, plants. Thus, transgenic plants can be obtained whose properties are altered by overexpression, suppression or inhibition of homologous (=natural) genes or gene sequences or the expression of heterologous (=foreign) genes or gene sequences.

The present invention furthermore provides a process for controlling unwanted plants (for example for the non-selective control of harmful plants or for the selective control of harmful plants in crop plants such as leguminous plants), preferably in crop plants, which comprises applying the herbicides (A) and (B) of the herbicide combination according to the invention to the plants (for example harmful plants, such as monocotyledonous or dicotyledonous weeds or unwanted crop plants), the seed (for example grains, seeds or vegetative propagation organs, such as tubers or shoot parts with buds) or to the area in which the plants grow (for example the area under cultivation), for example together or separately. One or more herbicides (A) may be applied before, after or simultaneously with the herbicide(s) (B) to the plants, the seed or the area in which the plants grow (for example the area under cultivation).

Unwanted plants are to be understood as meaning all plants which grow in locations where they are unwanted. This can, for example, be harmful plants (for example monocotyledonous or dicotyledonous weeds or unwanted crop plants), including, for example, those which are resistant to certain herbicidally active compounds, such as glyphosate, atrazine, glufosinate or imidazolinone herbicides.

In the process according to the invention, an effective amount of the herbicides (A) and (B) is preferably employed for controlling harmful plants, preferably for the selective control of harmful plants and crop plants, for example in economically important farm crops, for example monocotyledonous farm crops, for example cereals (for example wheat, barley, rye, oats), rice, corn, millet, or dicotyledonous farm crops, such as sugar beet, oilseed rape, cotton, sunflowers and leguminous plants, for example of the genera *Glycine* (for example *Glycine max.* such as non-transgenic *Glycine max.* (for example conventional cultivars, such as STS cultivars) or transgenic *Glycine max.* (for example RR-soybean or LL-soybean) and crossbreeds thereof), *Phaseolus, Pisum, Vicia* and *Arachis*, or vegetable crops from various botanical groups, such as potato, leek, cabbage, carrot, tomato, onion, and also permanent crops and plantation crops, such as pome fruit and stone fruit, berry fruit, grapevine, Hevea, bananas, sugar cane, coffee, tea, citrus fruits, nut plantations, lawn, palm plantations and forest plantations.

The herbicidal combinations according to the invention can also be employed non-selectively for controlling unwanted vegetation, for example in permanent crops and plantation crops (for example pome fruit and stone fruit, berry fruit, grapevine, Hevea, bananas, sugar cane, coffee, tea, citrus fruits, nut plantations, roses, palm plantations and forest plantations), on roadsides, squares, industrial plants, airports or railway tracks, or for the burn-down application, for example in crop plants such as farm crops, for example monocotyledonous farm crops, such as cereals (for example wheat, barley, rye, oats), rice, corn, millet, or dicotyledonous farm crops, such as sugar beet, oilseed rape, cotton, sunflowers and leguminous plants, for example of the genera *Glycine* (for example *Glycine max.* (soybean), such as non-transgenic *Glycine max.* (for example conventional cultivars, such as STS cultivars) or transgenic *Glycine max.* (for example RR-soybean or LL-soybean) and crossbreeds thereof), *Phaseolus, Pisum, Vicia* and *Arachis*, or vegetable crops from various botanical groups, such as potato, leek, cabbage, carrot, tomato, onion. The application is preferably carried out to the emerged harmful plants (for example weeds or unwanted crop plants), in particular prior to the emergence of (wanted) crop plants.

Preferred for the selective application is an application to emerged plants, in particular emerged harmful plants (for example weeds or unwanted crop plants), preferably prior to the emergence of the (wanted) crop plants. Preferred for the non-selective application is the application to the emerged harmful plants (for example weeds or unwanted crop plants), in particular in the case of the burn-down application prior to the emergence of the (want) crop plants.

A preferred use in the non-selective field is the burn-down application in crop plants where at least one of the components of the herbicide combination according to the invention, in particular the herbicides (A), if appropriate in combination with the herbicides (B), is applied prior to the emergence of the crop plants to the emerged harmful plants (for example weeds or unwanted crop plants); preference is given here to the application to the emerged harmful plants prior to sowing of the crop plants or during sowing of the crop plants.

The invention also provides the use of the herbicide combinations according to the invention for controlling unwanted vegetation, preferably in crop plants.

The herbicide combinations according to the invention can be prepared by known processes, for example as mixed formulations of the individual components, if appropriate with further active compounds, additives and/or customary formulation auxiliaries, which combinations are then applied in a customary manner diluted with water, or as tank mixes by joint dilution of the components, formulated separately or formulated partially separately, with water. Also possible is the split application of the separately formulated or partially separately formulated individual components.

It is also possible to apply the herbicides or the herbicide combinations in a plurality of portions (sequential application) using for example, pre-emergence applications followed by post-emergence applications or using early post-emergence applications followed by medium or late post-emergence applications. Preference is given here to the joint or almost simultaneous application of the active compounds of the combination in question.

The herbicides (A) and (B) can be converted jointly or separately into customary formulations, such as solutions, emulsions suspensions, powders, foams, pastes, granules, aerosols, natural and synthetic materials impregnated with active compound and microencapsulations in polymeric materials. The formulations may comprise the customary auxiliaries and additives.

The formulations are produced in a known manner, for example by mixing the active compounds with extenders, that is liquid solvents, pressurized liquefied gases and/or solid carriers, if appropriate with the use of surfactants, that is emulsifiers and/or dispersants, and/or foam formers.

If the extender used is water, it is also possible to use, for example, organic solvents as auxiliary solvents. Suitable liquid solvents are essentially: aromatics, such as xylene, toluene, alkylnaphthalenes, chlorinated aromatics or chlorinated aliphatic hydrocarbons, such as chlorobenzenes, chloroethylenes, or methylene chloride, aliphatic hydrocarbons, such as cyclohexane or paraffins, for example mineral oil fractions, mineral and vegetable oils, alcohols, such as butanol or glycol, and ethers and esters thereof, ketones, such as acetone, methyl ethyl ketone, methyl isobutyl ketone or cyclohexanone, strongly polar solvents, such as dimethylformamide or dimethyl sulfoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite and dolomite, and also synthetic granules of inorganic and organic meals, and granules of organic material, such as sawdust, coconut shells, corn cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers alkylsulfonates, alkyl sulfates, arylsulfonates and also protein, hydrolysates; suitable dispersants are: for example lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins and synthetic phospholipids, can be used in the formulations. Other possible additives are mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients, such as salts of iron, manganese, boron, copper, cobalt, molybdenum and zinc.

The formulations generally comprise between 0.1 and 95% by weight of active compound, preferably between 0.5 and 90% by weight.

The herbicides (A) and (B) can be used as such or in their formulations, including as a mixture with other agrochemically active compounds, such as known herbicides, for controlling unwanted vegetation, for example for controlling weeds or for controlling unwanted crop plants, ready mixes and tank mixes being possible.

Also possible are mixtures with other known active compounds, such as fungicides, insecticides, acaricides, nematicides, safeners, bird repellents, plant nutrients and soil conditioners.

The herbicides (A) and (B) can be applied as such, in the form of their formulations or the use forms prepared therefrom by further dilution, such as ready-to-use solutions, suspensions, emulsions, powders, pastes and granules. Application is effected in a customary manner, for example by watering, spraying, atomizing, broadcasting.

The active compounds can be applied to the plants (for example harmful plants, such as monocotyledonous or dicotyledonous weeds or unwanted crop plants), the seed (for example grains, seeds or vegetative propagation organs, such as tubers or shoot parts with buds) or the area under cultivation (for example the soil), preferably to the green plants and parts of plants and, if appropriate, additionally the soil. One possible use is the joint application of the active compounds in the form of tank mixers, where the optimally formulated concentrated formulations of the individual active compounds are, together, mixed in tank with water, and the spray liquor obtained is applied.

A joint herbicidal formulation of the combination according to the invention of herbicides (A) and (B) has the advantage that it is easier to apply, since the amounts of the components are already in an optimum ratio. Moreover, the auxiliaries in the formulation can be adjusted optimally to one another.

BIOLOGICAL EXAMPLES

1. Pre-emergence Action against Weeds

Seeds or rhizome pieces of monocotyledonous and dicotyledonous weed plants were placed in sandy loam soil in cardboard pots and covered with soil. The active compounds (A) and (B), formulated as wettable powders or emulsion concentrates, were then applied to the surface of the covering soil as aqueous suspensions or emulsions in different dosages at a water application rate of 600 to 800 l/ha (converted).

After the treatment, the pots were placed in the greenhouse and kept under good growth conditions for the weeds. Visual scoring of the plant damage or emergence damage was carried out after the test plants had emerged after a test period of 3 to 4 weeks, in comparison to untreated controls. The results show that the tested herbicide combinations have good herbicidal pre-emergence activity against a broad spectrum of weed grasses and broad-leaved weeds. The herbicide combinations of the compounds Nos. I-1, I-3, I-8, I-9, I-10, I-11, I-12, I-14, I-21, I-22, I-23, I-29, I-30, I-51, I-52, I-60, I-70, I-142, I-143, I-145 and other compounds from table 1 with herbicides (B1.1) to (B1.66), (B2.1) to (B2.50), (B3.1) to (B3.16) and (B4.1) to (B4.7), for example, have very good herbicidal activity against harmful plants such as *Sinapis alba, Chrysanthemum segetum, Avena sativa, Stellaria media, Echinochloa crus-galli, Lolium multiflorum, Setaria viridis, Abutilon theophrasti, Amaranthus retroflexus* and *Panicum miliaceum* when applied by the pre-emergence method at an application rate of 100 g or less of active substance per hectare.

2. Post-emergence Action against Weeds

Seeds or rhizome pieces of monocotyledonous and dicotyledonous weeds were placed in sandy loam soil in plastic pots, covered with soil and cultivated in the greenhouse under good growth conditions. Three weeks after sowing, the test plants were treated at the three-leaf stage. The compounds according to the invention, formulated as sprayable powders or as emulsion concentrates, were sprayed onto the green parts of the plants in various dosages at a water application rate of 600 to 800 I/ha (converted). After the test plants had been left to stand in the greenhouse for about 3 to 4 weeks under optimum growth conditions, the effect of the preparations was scored visually in comparison to untreated controls. The herbicide combinations according to the invention also have good herbicidal post-emergence activity against a broad spectrum of economically important weed grasses and broad-leaved weeds. Herbicide combinations of compounds Nos. 1-1, I-3, I-8, I-9, I-10, I-11, I-12, I-14, I-21, I-22, I-23, I-29, I-30, I-51, I-52, I-60, I-70, I-142, I-143, I-145 and other compounds from table 1 with herbicides (B1.1) to (B1.66), (B2.1) to (B2.50), (B3.1) to (B3.16) and (B4.1) to (B4.7), for example, have very good herbicidal activity against harmful plants such as *Sinapis alba, Echinochloa crus-galli, Lolium multiflorum, Chrysanthemum segetum, Setaria viridis, Abutilon theophrasti, Amaranthus retroflexus, Panicum miliaceum* and *Avena sativa* when applied by the post emergence method at an application rate of 100 g or less of active substance per hectare.

The invention claimed is:

1. A herbicide combination, comprising components (A) and (B), where
   (A) is one or more herbicides from the group of the compounds of the formula (I) or salts thereof

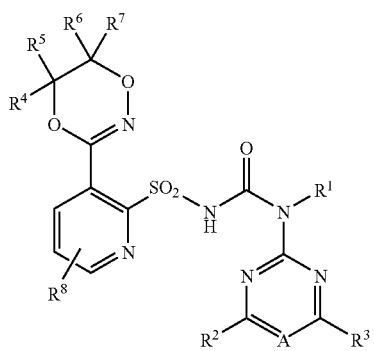

in which
A is a CH grouping,
$R^1$ is hydrogen or methyl,
$R^2$ is methoxy, ethoxy, methyl, ethyl, trifluoromethyl, difluoromethoxy, methylamino, dimethylamino or chloro,
$R^3$ is methoxy, ethoxy, methyl, ethyl, trifluoromethyl, difluoromethoxy, methylamino, dimethylamino, chloro or trifluoroethoxy
$R^4$-$R^7$ independently of one another are hydrogen,
$R^8$ is hydrogen; and
(B) is one or more herbicides selected from the group consisting of thifensulfhron-methyl, fenoxaprop-P-ethyl, lactofen, chioransulam, glyphosate, and glufosinate-ammonium.

2. The herbicide combination as claimed in claim 1 which comprises an effective amount of components (A) and (B) and one or more further components selected from the group consisting of agrochemically active compounds of a different type, formulation auxiliaries and additives customary in crop protection.

3. A method for controlling unwanted plants which comprises applying the herbicides (A) and (B) of the herbicide combination as defined in claim 1 together or separately to the plants, one or more seeds of the plants or the area in which the plants grow.

4. The method as claimed in claim 3 for the selective control of harmful plants in crop plants or for the non-selective control of harmful plants.

5. The method as claimed in claim 4 for the control of harmful plants in leguminous crop plants.

6. A method of using the herbicide combination as claimed in claim 1 for controlling unwanted plants comprising the step of applying said combination to the plants, one or more seeds of the plants or to the area in which the plants grow.

7. The method as claimed in claim 5, wherein said leguminous crop plants are Glycine.

8. The herbicide combination of claim 1 wherein said component (A) is the compound of formula I wherein A is a CH grouping, $R^1$ is hydrogen, $R^2$ is methoxy, $R^3$ is methoxy, $R^4$-$R^7$ are each hydrogen and $R^8$ is hydrogen, or sodium salt thereof.

* * * * *

UNITED STATES PATENT AND TRADEMARK OFFICE
CERTIFICATE OF CORRECTION

| | |
|---|---|
| PATENT NO. | : 7,648,945 B2 |
| APPLICATION NO. | : 11/090374 |
| DATED | : January 19, 2010 |
| INVENTOR(S) | : Hills et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 847 days.

Signed and Sealed this

Twenty-third Day of November, 2010

David J. Kappos
*Director of the United States Patent and Trademark Office*